(12) United States Patent
Wu

(10) Patent No.: US 11,912,754 B2
(45) Date of Patent: Feb. 27, 2024

(54) VEGFR-ANTIBODY LIGHT CHAIN FUSION PROTEIN

(71) Applicant: IMMUNOWAKE INC., Birmingham, AL (US)

(72) Inventor: Xiaoyun Wu, Birmingham, AL (US)

(73) Assignee: IMMUNOWAKE INC., Birmingham, AL (US)

( * ) Notice: Subject to any disclaimer, the term of this patent is extended or adjusted under 35 U.S.C. 154(b) by 75 days.

(21) Appl. No.: 16/755,134

(22) PCT Filed: Oct. 11, 2018

(86) PCT No.: PCT/US2018/055512
§ 371 (c)(1),
(2) Date: Apr. 9, 2020

(87) PCT Pub. No.: WO2019/075270
PCT Pub. Date: Apr. 18, 2019

(65) Prior Publication Data
US 2020/0325208 A1   Oct. 15, 2020

Related U.S. Application Data

(60) Provisional application No. 62/571,773, filed on Oct. 12, 2017.

(51) Int. Cl.
| | |
|---|---|
| *C07K 16/00* | (2006.01) |
| *C07K 14/71* | (2006.01) |
| *C07K 16/24* | (2006.01) |
| *C07K 16/28* | (2006.01) |
| *C07K 16/32* | (2006.01) |
| *A61K 38/00* | (2006.01) |

(52) U.S. Cl.
CPC ............ *C07K 14/71* (2013.01); *C07K 16/244* (2013.01); *C07K 16/2818* (2013.01); *C07K 16/2827* (2013.01); *C07K 16/32* (2013.01); *A61K 38/00* (2013.01); *C07K 2317/565* (2013.01); *C07K 2317/732* (2013.01); *C07K 2317/92* (2013.01); *C07K 2319/00* (2013.01)

(58) Field of Classification Search
CPC ........... C07K 16/2818; C07K 16/2827; C07K 16/32; C07K 2317/565; C07K 2317/732; C07K 2317/92; C07K 2319/00; A61K 38/00
See application file for complete search history.

(56) References Cited

U.S. PATENT DOCUMENTS

| | | |
|---|---|---|
| 3,691,016 A | 9/1972 | Patel |
| 3,773,919 A | 11/1973 | Boswell |
| 3,969,287 A | 7/1976 | Jaworek |
| 4,195,128 A | 3/1980 | Gribnau |
| 4,229,537 A | 10/1980 | Hodgins |
| 4,247,642 A | 1/1981 | Hirohara |
| 4,330,440 A | 5/1982 | Ayers |
| RE30,985 E | 6/1982 | Cartaya |
| 4,419,446 A | 12/1983 | Howley et al. |
| 4,485,045 A | 11/1984 | Regen |
| 4,544,545 A | 10/1985 | Ryan |
| 4,560,655 A | 12/1985 | Baker |
| 4,601,978 A | 7/1986 | Karia |
| 4,657,866 A | 4/1987 | Kumar |
| 4,676,980 A | 6/1987 | Segal et al. |
| 4,767,704 A | 8/1988 | Cleveland |
| 4,816,567 A | 3/1989 | Cabilly |
| 4,927,762 A | 5/1990 | Darfler |
| 4,965,199 A | 10/1990 | Capon et al. |
| 4,968,603 A | 11/1990 | Slamon |
| 5,013,556 A | 5/1991 | Woodle |
| 5,122,469 A | 6/1992 | Mather et al. |
| 5,264,365 A | 11/1993 | Georgiou |
| 5,500,362 A | 3/1996 | Robinson |
| 5,508,192 A | 4/1996 | Georgiou |
| 5,545,806 A | 8/1996 | Lonberg |
| 5,545,807 A | 8/1996 | Surani et al. |
| 5,569,825 A | 10/1996 | Lonberg |
| 5,591,828 A | 1/1997 | Bosslet |
| 5,624,821 A | 4/1997 | Winter |
| 5,625,126 A | 4/1997 | Lonberg |
| 5,633,425 A | 5/1997 | Lonberg |
| 5,639,635 A | 6/1997 | Joly |
| 5,641,870 A | 6/1997 | Rinderknecht |
| 5,648,237 A | 7/1997 | Carter |
| 5,648,260 A | 7/1997 | Winter |
| 5,661,016 A | 8/1997 | Lonberg |

(Continued)

FOREIGN PATENT DOCUMENTS

| | | |
|---|---|---|
| CN | 101575379 A | 11/2009 |
| CN | 102134277 A | 7/2011 |

(Continued)

OTHER PUBLICATIONS

Zhang et al Cancer Research, 70:2495-2503, 2010 (Year: 2010).*
Aasland, R. et al. (Apr. 1988). "Expression Of Oncogenes In Thyroid Tumours: Coexpression Of C-Erbb2/Neu And C-Erbb," British Journal Of Cancer 57(4):358-363.
Adelman, J.P. et al. (Sep. 1983). "In Vitro Deletional Mutagenesis For Bacterial Production Of The 20,000-Dalton Form Of Human Pituitary Growth Hormone," DNA 2(3):183-193. (Abstract only).

(Continued)

*Primary Examiner* — Lei Yao

(74) *Attorney, Agent, or Firm* — MORRISON & FOERSTER LLP

(57) ABSTRACT

The present application provides an antibody fusion protein comprising a vascular endothelial growth factor receptor (VEGFR) fused to the C-terminus of the antibody light chain. Also provided are methods of making and using these antibody fusion proteins.

17 Claims, 5 Drawing Sheets

Specification includes a Sequence Listing.

(56) References Cited

U.S. PATENT DOCUMENTS

| | | |
|---|---|---|
| 5,730,977 A | 3/1998 | Ooka |
| 5,731,168 A | 3/1998 | Carter |
| 5,821,337 A | 10/1998 | Carter |
| 5,840,523 A | 11/1998 | Simmons et al. |
| 5,869,046 A | 2/1999 | Presta et al. |
| 6,027,888 A | 2/2000 | Georgiou |
| 6,075,181 A | 6/2000 | Kucherlapati |
| 6,083,715 A | 7/2000 | Georgiou |
| 6,100,071 A | 8/2000 | Davis-smyth |
| 6,150,584 A | 11/2000 | Kucherlapati |
| 6,166,185 A | 12/2000 | Davis |
| 6,194,551 B1 | 2/2001 | Idusogie |
| 6,602,684 B1 | 8/2003 | Umana et al. |
| 6,737,056 B1 | 5/2004 | Presta |
| 6,884,879 B1 | 4/2005 | Baca et al. |
| 6,982,321 B2 | 1/2006 | Winter |
| 7,087,409 B2 | 8/2006 | Barbas, III |
| 7,087,411 B2 | 8/2006 | Daly |
| 7,214,775 B2 | 5/2007 | Hanai |
| 7,332,581 B2 | 2/2008 | Presta |
| 7,371,826 B2 | 5/2008 | Presta |
| 7,521,049 B2 | 4/2009 | Wiegand |
| 7,521,053 B2 | 4/2009 | Oliner |
| 7,521,541 B2 | 4/2009 | Eigenbrot |
| 7,973,140 B2 | 7/2011 | Green |
| 8,975,381 B2 | 3/2015 | Fuh |
| 9,605,043 B2 * | 3/2017 | Hong ............ A61P 35/00 |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0259150 A1 | 12/2004 | Nakamura |
| 2005/0014934 A1 | 1/2005 | Hinton |
| 2005/0031613 A1 | 2/2005 | Nakamura |
| 2005/0059639 A1 | 3/2005 | Wei |
| 2005/0096257 A1 | 5/2005 | Shima et al. |
| 2005/0123546 A1 | 6/2005 | Umana et al. |
| 2006/0025576 A1 | 2/2006 | Miller |
| 2007/0134759 A1 | 6/2007 | Imai |
| 2008/0241884 A1 | 10/2008 | Shitara |
| 2009/0220572 A1 | 9/2009 | Deschatelets |
| 2010/0087632 A1 * | 4/2010 | Daly ............ A61P 27/00 530/391.1 |
| 2013/0236467 A1 | 9/2013 | Griggs |
| 2013/0323204 A1 * | 12/2013 | Rossi ............ A61K 47/6813 424/85.7 |
| 2014/0294758 A1 | 10/2014 | Gillies |
| 2015/0030603 A1 | 1/2015 | Kim |
| 2015/0044216 A1 | 2/2015 | Wu |
| 2016/0177276 A1 * | 6/2016 | Lo ............ C12N 9/16 435/328 |
| 2017/0275353 A1 | 9/2017 | Sheng |

FOREIGN PATENT DOCUMENTS

| | | |
|---|---|---|
| EP | 0075444 A2 | 3/1983 |
| EP | 0404097 A2 | 12/1990 |
| EP | 2314685 B1 | 4/2011 |
| EP | 2329821 B1 | 8/2012 |
| WO | 198700195 A1 | 1/1987 |
| WO | 199003430 A1 | 4/1990 |
| WO | 199110741 A1 | 7/1991 |
| WO | 199308829 A1 | 5/1993 |
| WO | 199311161 A1 | 6/1993 |
| WO | 199411026 A2 | 5/1994 |
| WO | 199429351 A2 | 12/1994 |
| WO | 199633735 A1 | 10/1996 |
| WO | 199634096 A1 | 10/1996 |
| WO | 199634103 A1 | 10/1996 |
| WO | 199730087 A1 | 8/1997 |
| WO | 1998024893 A2 | 6/1998 |
| WO | 199858964 A1 | 12/1998 |
| WO | 199922764 A1 | 5/1999 |
| WO | 199951642 A1 | 10/1999 |
| WO | 199954440 A1 | 10/1999 |
| WO | 200061739 A1 | 10/2000 |
| WO | 2002031140 A1 | 4/2002 |
| WO | 2003011878 A2 | 2/2003 |
| WO | 2003084570 A1 | 10/2003 |
| WO | 2003085107 A1 | 10/2003 |
| WO | 2003085119 A1 | 10/2003 |
| WO | 2004056312 A2 | 7/2004 |
| WO | 2005035586 A1 | 4/2005 |
| WO | 2005035778 A1 | 4/2005 |
| WO | 2005053742 A1 | 6/2005 |
| WO | 2005100402 A1 | 10/2005 |
| WO | 2006029879 A2 | 3/2006 |
| WO | 2007048022 A2 | 4/2007 |
| WO | 2007109254 A2 | 9/2007 |
| WO | 2008077546 A1 | 7/2008 |
| WO | 2009015345 A1 | 1/2009 |
| WO | 2009089004 A1 | 7/2009 |
| WO | 2010148321 A1 | 12/2010 |
| WO | WO2012178137 * | 12/2012 |
| WO | 2014055836 A2 | 4/2014 |
| WO | 2014144600 A2 | 9/2014 |
| WO | WO2015109898 * | 7/2015 |
| WO | 2015149708 A1 | 10/2015 |
| WO | 2017001990 A1 | 1/2017 |
| WO | 2019075270 A1 | 4/2019 |

OTHER PUBLICATIONS

Aiello, L. et al. (1994). "Vascular Endothellal Growth Factor in Ocular Fluid of Patients with Diabetic Retinopathy and Other Retinal Disorders," New Engl. J. Med. 331(22):1480-1487.

Aiello, L.P. et al. (Nov. 1995). "Suppression Of Retinal Neovascularization In Vivo By Inhibition Of Vascular Endothelial Growth Factor (VEGF) Using Soluble VEGF-Receptor Chimeric Proteins," Proc Natl Acad Sci USA 92(23):10457-10461.

Arie, J-P. et al. (Jan. 1, 2001). "Chaperone Function of FkpA, A Heat Shock Prolyl Isomerase, in the Periplasm of *Escherichia Coll*," Molecular Micorbiology 39(1):199-210.

Barbas, C.F. et al. (Apr. 1994). "In vitro Evolution of a Neutralizing Human Antibody to Human Immunodeficiency Virus Type 1 to Enhance Affinity and Broaden Strain Cross-Reactivity," Proc. Nat. Acad. Sci. USA 91:3809-3813.

Barnes, D. et al. (Mar. 1, 1980). "Methods for Growth of Cultured Cells In Serum-Free Medium," Anal. Biochem. 102(2):255-270.

Bass, S. et al. (1990). "Hormone Phage: An Enrichment Method for Variant Proteins With Altered Binding Properties," Proteins 8:309-314.

Berkman, R.A. et al. (Jan. 1993). "Expression Of The Vascular Permeability Factor/Vascular Endothelial Growth Factor Gene In Central Nervous System Neoplasms," The Journal Of Clinical Investigation 91(1):153-159.

Boerner, P. et al. (Jul. 1, 1991). "Production of a Antigen-Specific Human Monoclonal Antibodies from In Vitro-Primed Human Splenocytes," J. Immunol. 147(1):86-95.

Borst, M.P. et al. (1990). "Oncogene Alterations In Endometrial Carcinoma," Gynecologic Oncology 38(3):364-366. (Abstract only).

Bothmann, H. et al., (Jun. 2, 2000). "The Periplasmic *Escherichia coli* Peptidylprolyl cis,trans-Isomerase FkpA," The Journal of Biological Chemistry 275(22):17100-17105.

Bourges, J-L. et al. (Aug. 2003). "Ocular Drug Delivery Targeting The Retina And Retinal Pigment Epithelium Using Polylactide Nanoparticles," Investigative Ophthalmology & Visual Science 44(8):3562-3569.

Brennan, M. et al. (Jul. 5, 1985). "Preparation of Bispecific Antibodies by Chemical Recombination of Monoclonal Immunoglobulin G1 Fragments," Science 229:81-83.

Brown, L.F. et al. (Jan. 1995). "Expression Of Vascular Permeability Factor (Vascular Endothelial Growth Factor) And Its Receptors In Breast Cancer," Human Pathology 26(1):86-91.

Brown, L.F. et al. (Oct. 1, 1993). "Expression Of Vascular Permeability Factor (Vascular Endothelial Growth Factor) And Its Receptors In Adenocarcinomas Of The Gastrointestinal Tract," Cancer Research 53(19):4727-4735.

(56) References Cited

OTHER PUBLICATIONS

Brüggemann, M. et al. (1993). "Designer Mice: The Production of Human Antibody Repertoires in Transgenic Animals," Year in Immuno. 7:33-40.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Bunone, G. et al. (Dec. 1999). "Expression of Angiogenesis Stimulators and Inhibitors in Human Thyroid Tumors and Correlation With Clinical Pathological Features," American Journal of Pathology 155(6):1967-1976.

Calfa, C.I. et al. (Jun. 2006). "Antibodies And Antibody-Fusion Proteins As Anti-Angiogenic, Anti-Tumor Agents," Update on Cancer Therapeutics I 1(2):159-173.

Carmeliet, P. et al. (May 19, 2011). "Molecular Mechanisms And Clinical Applications Of Angiogenesis," Nature 473(7347):298-307, 28 pages.

Carter, P. et al. (Feb. 1992). "High Level *Escherichia coli* Expression and Production of a Bivalent Humanized Antibody Fragment," BioTechnology 10:163-167.

Cheadle, C. et al. (Jan. 1992). "Cloning And Expression Of The Variable Regions Of Mouse Myeloma Protein MOPC315 In *E. Coli*: Recovery Of Active FV Fragments," Mol Immunol (1992) 29(1):21-30.

Chen, J. et al. (Jul. 9, 1999). "Chaperone Activity of DsbC*," The Journal of Biological Chemistry 274 (28):19601-19605.

Chothia, C. et al. (Aug. 20, 1987). "Canonical Structures for the Hypervariable Regions of Immunoglobulins," J. Mol. Biol. 196(4):901-917.

Chowdhury, P.S. (2008). "Engineering Hot Spots for Affinity Enhancement of Antibodies," Methods Mol. Biol. 207:179-196.

Clackson, T. et al. (Aug. 15, 1991). "Making Antibody Fragments Using Phage Display Libraries," Nature 352:624-628.

Clynes, R. et al. (Jan. 1998). "Fc Receptors are Required in Passive and Active Immunity to Melanoma," Proc. Natl. Acad. Sci. U.S.A. 95:652-656.

Cohen, J.A. et al. (Jan. 1989). "Expression Pattern Of The Neu (NGL) Gene-Encoded Growth Fa ctor Receptor Protein (P185neu) In Normal And Transformed Epithelial Tissues Of The Digestive Tract," Oncogene 4(1):81-88. (Abstract only).

Cole, S.P.C. et al. (1985). "The EBV-Hybridoma Technique and Its Application to Human Lung Cancer," in Monoclonal Antibodies and Cancer Therapy, Alan R. Liss, p. 77-96.

Cragg, M.S. et al. (2004). "Antibody Specificity Controls In Vivo Effector Mechanisms Of Anti-CD20 Reagents," Blood 103:2738-2743.

Crea, R. et al. (Dec. 1978). "Chemical Synthesis Of Genes For Human Insulin," Proceedings of the National Academy of Sciences 75(12):5765-5769.

Creighton, T.E. et al. (1983). Proteins: Structure and Molecular Properties, W.H. Freeman & OC.:San Francisco, CA, pp. 70-87, 24 pages.

Cunningham, B.C. et al. (Jun. 2, 1989). "High-Resolution Epitope Mapping of hGH-Receptor Interactions by Alanine-Scanning Mutagenesis," Science 244:1081-1085.

Dall'Acqua, W. et al. (1998). "Contribution of Domain Interface Residues to the Stability of Antibody CH3 Domain Homodimers", Biochemistry37:9266-9273.

De Vries, C. et al. (Feb. 21, 1992). "The fms-Like Tyrosine Kinase, A Receptor For Vascular Endothelial Growth Factor," Science 255:989-991.

Duncan, A.R. et al. (Apr. 21, 1988). "The Binding Site for C1q on IgG," Nature 322:738-740.

Dvorak, H.F. et al. (Jan. 1979). "Induction Of A Fibrin-Gel Investment: An Early Event In Line 10 Hepatocarcinoma Growth Mediated By Tumor-Secreted Products," The Journal of Immunology 122(1):166-174.

Dvorak, H.F. et al. (May 1995). "Vascular Permeability Factor/Vascular Endothellal Growth Factor, Microvascular Hyperpermeability, And Angiogenesis," The American Journal of Pathology 146(5): 1029-1039.

Einmahl, S. et al. (May 2002). "Evaluation of a Novel Biomaterial in the Suprachoroidal Space of the Rabbit Eye," Investigative Ophthalmology & Visual Science 43(5):1533-1539.

Elicciri, B.P. (Dec. 7, 2001). "Integrin And Growth Factor Receptor Crosstalk," Circ. Res 89(12):1104-1110.

Elshabrawy, H.A. et al. (Oct. 2015). "The Pathogenic Role Of Angiogenesis In Rheumatoid Arthritis," Angiogenesis 18(4):433-448.

Epstein, D.A. et al. (Jun. 1985). "Biological Activity of Lipsome-Encapsulated Murine Interferon γ is Mediated by Cell Membrane Receptor," Proc. Natl. Acad. Sci. USA, 82:3688-3692.

Etoh, T. et al. (Mar. 1, 2001). "Angiopoietin-2 Is Related to Tumor Angiogenesis in Gastric Carcinoma: Possible in Vivo Regulation via Induction of Proteases," Cancer Research 61(5):2145-2153.

Fellouse, F.A. et al. (Aug. 24, 2004). "Synthetic Antibodies from a Four-Amino-Acid Code: A Dominant Role for Tyrosine in Antigen Recognition," Proc. Natl. Acad. Sci. USA 101(34):12467-12472.

Ferrara, N. et al. (Feb. 1997). "The Biology of Vascular Endothelial Growth Factor," Endocrine Rev. 18(1):4-25.

Fishwild, D.M. et al. (Jul. 1996). "High-Avidity Human IgGK Monoclonal Antibodies from a Novel Strain of Minilocus Transgenic Mice," Nature Biotechnol. 14:845-851.

Folkman J. et al. (Jan. 23, 1987). "Angiogenic Factors," Science 235(4787):442-447. (Abstract only).

Fukushige, S.I. et al. (Mar. 1986). "Localization Of A Novel V-Erbb-Related Gene, C-Erbb-2, On Human Chromosome 17 And Its Amplification In A Gastric Cancer Cell Line," Molecular and Cellular Biology 6(3):955-958.

Gazzano-Santoro, H. et al. (1996). "A Non-Radioactive Complement-Dependent Cytotoxicity Assay Anti-CD20 Monoclonal Antibody," J. Immunol. Methods 202:163-171.

Geering, B. et al. (Feb. 2015). "Synthetic Immunology: Modulating The Human Immune System," Trends in Biotechnology 33(2):65-79. (Abstract only).

Graham, F.L. et al. (1977). "Characteristics Of A Human Cell Line Transformed By DNA From Human Adenovirus Type 5," Journal General Virology 36(1):59-74.

Gu, K. et al. (Feb. 6, 1996). "Overexpression Of Her-2/Neu In Human Prostate Cancer And Benign Hyperplasia," Cancer Letters 99(2):185-189.

Guerin, M. et al. (1988). "Overexpression Of Either C-Myc Or C-Erbb-2/Neu Proto-Oncogenes In Human Breast Carcinomas: Correlation With Poor Prognosis," Oncogene Research 3(1):21-31. (Abstract only).

Guerrin, M. et al. (1995). "Vasculotropin/Vascular Endothellal Growth Factor is an Autocrine Growth Factor for Human Retinal Pigment Epithelial Cells Cultured in Vitro," J. Cell Physiol. 164:385-394.

Guss, B. et al. (Jul. 1986). "Structure of the IgG-Binding Regions of Streptococcal Protein G," Embo J. 5(7):1567-1575.

Guyer, R.L. et al. (Aug. 1976). "Immunoglobulin Binding By Mouse Intestinal Epithelial Cell Receptors," J. Immunol. 117(2):587-593.

Ham, R.J. et al. (1979). "Media and Growth Requirements," Meth. Enz. 58:44-93.

Hamers-Casterman, C. et al. (Jun. 3, 1993). "Naturally Occurring Antibodies Devoid Of Light Chains," Nature 363(6428):446-448.

Hammerling, G. et al. (1981). "Monoclonal Antibodies and T-Cell Hybridomas," in Monoclonal Antibodies and T-Cell Hybridomas, pp. 563-681.

Hangai, M. et al. (Jun. 2001). "Angiopoietin-1 Upregulation By Vascular Endothelial Growth Factor In Human Retinal Pigment Epithelial Cells," Investigative Ophthalmology & Visual Science 42(7):1617-1625.

Hara, H. et al. (1996) "Overproduction Of Penicillin-Binding Protein 7 Suppresses Thermosensitive Grovvth Defect At Low Osmolarity Due To An Spr Mutation Of *Escherichia Coli*," Microhial Drug Resistance 2(1):63-72.

(56) References Cited

OTHER PUBLICATIONS

Harding, T.C. et al. (Mar. 27, 2013, e-pub Jul. 21, 2014). "Blockade Of Nonhormonal Fibroblast Growth Factors By FP-1039 Inhibits Growth Of Multiple Types Of Cancer," Science Translational Medicine 5(178):178ra39, 10 pages.
Harris, W.J. (1995). "Production of Humanized Monoclonal Antibodies for in vivo Imaging and Therapy," Biochem. Soc. Transactions 23:1035-1038.
Hawkins, R.E. et al. (1992). "Selection of Phage Antibodies by Binding Affinity: Mimicking Affinity Maturations," J. Mol. Biol. 226:889-896.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Holash, J. et al. (Aug. 20, 2009). "VEGF-Trap: A VEGF Blocker With Potent Antitumor Effects," PNAS 99(17):11393-11398.
Hollinger, P. et al. (Jul. 1993). "Diabodies": Small Bivalent And Bispecific Antibody Fragments, Proc. Natl. Acad. Sci. Usa 90:6444-6448.
Hongo, J.A. S. et al. (1995). "Development and Characterization of Murine Monoclonal Antibodies to the Latency- Associated Peptide of Transforming Growth Factor Beta1," Hybridoma, 14(3):253-260.
Hoogenboom, H.R. et al. (2001). "Overview of Antibody Phage-Display Technology and Its Applications," Chapter 1 in Methods in Molecular Biology, O'Brien et al. ed., Humana Press, Totowa, NJ, 178:1-37.
Hoogenboom, -H.R et al. (Sep. 1991). "By-Passing Immunisation: Human Antibodies from Synthetic Repertoires of Germline VH Gene Segments Rearranged in vitro," Journal of Molecular Biology 227(2):381-388.
Hudson, P.J. et al. (Jan. 2003). "Engineered Antibodies," Nature Medicine 9(1):129-134.
Hurle, M.R. et al. (1994). "Protein Engineering Techniques for Antibody Humanization," Curr. Op. Biotech. 5(4):428-433.
Hwang, K.J. et al. (Jul. 1980). "Hepatic Uptake and Degradation of Unilamellar Sphingomyelin/Cholesterol Liposomes: A Kinetic Study." Proc. Natl. Acad. Sci. USA 77:4030-4034.
Idusogic, E.E. et al. (Apr. 15, 2000). "Mapping of the C1q Binding Site on Rituxan, a Chimeric Antibody With a Human IgG1 Fc," J. Immunol. 164(8): 4178-4184.
International Preliminary Report on Patentability dated Apr. 14, 2020 for International Application No. PCT/US2018/055512, filed Oct. 11, 2018, seven pages.
International Search Report and Written Opinion dated Dec. 3, 2018 for International Application No. PCT/US2018/055512, filed Oct. 11, 2018, thirteen pages.
Iwai, Y. et al. (Feb. 2005, e-pub. Dec. 20, 2004). "PD-1 Blockade Inhibits Hematogenous Spread of Poorly Immunogenic Tumor Cells by Enhanced Recruitment of Effector T Cells," International Immunology 17(2):133-144.
Jackson, J.R. et al. (1995). "In Vitro Antibody Maturation," J. Immunol. 154(7):3310-3319.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90(6):2551-2555.
Jansen, F.K. et al. (1982). "Immunotoxins: Hybrid Molecules Combining High Specificity and Potent Cytotoxicity," Immunol. Rev. 62:185-216.
Joly, J.C. et al. (Mar. 1998). "Overexpression of *Escherichia coli* Oxidoreductases Increases Recombinant Insulin-like Growth Factor-I Accumulation," Proc. Natl. Acad. Sci. USA 95:2773-2777.
Jones, A.J.S. (1993). "Analysis of Polypeptides and Proteins," Adv. Drug Delivery Rev. 10:29-90.
Jones, P. et al. (May 29, 1986). "Replacing The Complementarity-Determining Regions In A Human Antibody With Those From A Mouse," Nature 321:522-525.

Kanda, Y. et al. (2006, e-pub. Apr. 11, 2006). "Comparison of Cell Line for Stable Production of Fucose-Negative Antibodies with Enhanced ADCC," Biotechnol. Bioeng. 94(4):680-688.
Kern, J.A. et al (Aug. 15, 1990). "P185neu Expression In Human Lung Adenocarcinomas Predicts Shortened Survival," Cancer Research 50(16):5184-5191.
Killen, J. A. et al. (Nov. 1, 1984). "Specific Killing Of Lymphocytes That Cause Experimental Autoimmune Myasthenia Gravis By Ricin Toxin-Acetylcholine Receptor Conjugates," The Journal of Immunology 133(5):2549-2553. (Abstract only).
Kim, J-K. et al. (1994). "Localization of the Site of the Murine IgG1 Molecule That is Involved in Binding to the Murine Intestinal Fc Receptor," Eur. J. Immunol. 24:2429-2434.
King, C.R. et al. (Sep. 6, 1985). "Amplification of a Novel v-erbB-related Gene in a Human Mammary Carcinoma," Science 229(4717):974-976. (Abstract only).
Kohler, G. et al. (Aug. 7, 1975) "Continuous Cultures Of Fused Cells Secreting Antibody Of Predefined Specificity," Nature 256:495-497.
Kostelny, S.A. et al. (Mar. 1, 1992). "Formation of a Bispecific Antibody By The Use of Leucine Zippers," J. Immunol. 148(5):1547-1553.
Kuroda, K. et al. (May 2001). "Altered Expression of Angiopoietins and Tie2 Endothelium Receptor in Psoriasis," Journal of Investigative Dermatology 116(5):713-720.
Lee, C.V. et al. (2004). "Bivalent Antibody Phage Display Mimics Natural Immunoglobulin," .J. Immunol. Methods 284(1-2):119-132.
Lee, C.V. et al. (2004). "High-affinity Human Antibodies From Phage-Displayed Synthetic Fab Libraries With A Single Framework Scaffold," J. Mol. Biol. 340:1073-1093.
Li, J. et al. (Mar. 7, 2006). "Human Antibodies for Immunotherapy Development Generated via a Human B Cell Hybridoma Technology," Proc. Natl. Acad. Sci. USA 103:3557-3562.
Lindmark, R. et al. (1983). "Binding of Immunoglobulins to Protein A and Immunoglobulin Levels in Mammalian Sera," J. Immunol. Meth. 62:1-13.
Lonberg, N. (1995). "Human Antibodies From Transgenic Mice," Int. Rev. Immunol. 13(1):65-93.
Lonberg, N. et al. (Apr. 28, 1994). "Antigen-Specific Human Antibodies From Mice Comprising Four Distinct Genetic Modifications," Nature 368(6474):856-859.
Lopez, P. et al. (1996). "Transdifferentiated Retinal Pigment Epithelial Cells Are Immunoreactive for Vascular Endothelial Growth Factor in Surgically Excised Age-Related Macular Degeneration-Related Choroidal Neovascular Membranes," Invest. Opththalmol. Vis. Sci. 37(5):855-868.
Maisonpierre, P.C. et al. (Jul. 4, 1997). "Angiopoietin-2, A Natural Antagonist For Tie2 That Disrupts In Vivo Angiogenesis," Science 277(5322):55-60.
Major, T.C. et al. (Oct. 1997). "Inhibition Of Cell Growth: Effects Of The Tyrosine Kinase Inhibitor CGP 53716," Journal of Pharmacology and Experimental Therapeutics 283(1):402-410. (Abstract only).
Marks, J.D. et al. (1991). "By-Passing Immunization Human Antibodies from V-gene Libraries Displayed on Phage," J. Mol. Biol. 222:581-597.
Marks, J.D. et al. (Jul. 1992). "By-Passing Immunization: Building High Affinity Human Antibodies by Chain Shuffling," Bio/Technology 10:779-783.
Mather, J.P. et al. (1980). "Establishment and Characterization Of Two Distinct Mouse Testicular Epithelial Cell Lines," Biology of Reproduction 23:243-252.
Mather, J.P. et al. (1982) "Culture of Testicular Cells in Hormone-Supplemented Serum-Free Medium," Annals New York Academy of Sciences pp. 44-68.
Mattern, J. et al. (Apr. 1996). "Association of Vascular Endothellal Growth Factor Expression With Intratumoral Microvessel Density and Tumour Cell Proliferation in Human Epidermoid Lung Carcinoma," Brit. J. Cancer. 73 (7):931-934.
McCann. A. et al. (Jan. 1990). "C-Erbb-2 Oncoprotein Expression In Primary Human Tumors," Cancer 65 (1):88-92.

(56) References Cited

OTHER PUBLICATIONS

Mezquita, J. et al. (Jul. 5, 1999). "Characterization of a Novel Form of angiopoietin-2 (Ang-2B) and Expression of VEGF and angiopoietin-2 During Chicken Testicular Development and Regression," Biochemical and Biophysical Research Communications 260(2):492-498.

Milstein. C. et al. (Oct. 6, 1983). "Hybrid Hybridomas and Their Use in Immunohistochemistry," Nature 305:537-539.

Mordenti, J. et al. (1989). "The Use of Interspecies Scaling in Toxicokinetics," Chapter 4 in Toxicokinetics and New Drug Development, Yacobi A. ed et al.; Pergamon Press, New York, pp. 42-96.

Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.

Morrison, S.L. (Apr. 28, 1994). "Success in Specification," Nature 368:812-813.

Neuberger, M. (Jul. 1996). "Generating High-Avidity Human Mabs in Mice," Nature Biotechnol. 14:826.

Oberg-Welsh, C. et al. (Feb. 7, 1997). "Effects of Vascular Endothelial Growth Factor on Pancreatic Duct Cell Replication and the Insulin Production of Fetal Islet-like Cell Clusters in Vitro," Mol. Cell. Endocrinol. 126(2):125-132.

Okazaki, A. et al. (Mar. 5, 2004). "Fucose Depletion From Human IgG1 Oligosaccharide Enhances Binding Enthalpy And Association Rate Between IgG1 and FcγRIIIa," J. Mol. Biol. 336(5):1239-1249.

Otani, A. et al. (Aug. 1999). "Expressions Of Angiopoletins And Tie2 In Human Choroidal Neovascular Membranes," Investigative Ophthalmology & Visual Science 40(9):1912-1920.

Papadopoulos, N. et al. (2012). "Binding And Neutralization Of Vascular Endothelial Growth Factor (VEGF) And Related Ligands By VEGF Trap, Ranibizumab And Bevacizumab," Angiogenesis 15(2): 171-185.

Pardoll, D.M. (Apr. 2012). "The Blockade Of Immune Checkpoints In Cancer Immunotherapy," Nat. Rev. Cancer 12 (4): 252-264.

Park, J-B., et al. (Dec. 1, 1989). "Amplification, Overexpression, And Rearrangement Of The Erbb-2 Protooncogene In Primary Human Stomach Carcinomas," Cancer Research 49(23):6605-6609.

Park, J.E et al. (Oct. 14, 1994). "Placenta Growth Factor. Potentiation Of Vascular Endothelial Growth Factor Bioactivity, In Vitro And In Vivo, And High Affinity Binding To Fit-1 But Not To Flk-1/KDR," Journal of Biological Chemistry 269(41):2546-25654.

Pearlman, R. et al. (1991). "6: Analysis of Protein Drugs," in Peptide and Protein Drug Delivery, Vincent H. L Lee Ed., Marcel Dekker, Inc., New York, N.Y., Pubs., pp. 247-301.

Petkova, S.B. et al. (Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18 (12):1759-1769.

Plückthun, A. (1994). "Antibodies from Escherichia coli," in Chapter 11 The Pharmacology of Monoclonal Antibodies, vol. 113, Rosenburg and Moore eds., SpringerVerlag, New York, pp. 269-315.

Polverini, P.J. (1995). "The Pathophysiology of Angiogenesis," Crit Rev Oral Biol Med. 6(3):230-247.

Presta, L.G. (1992). "Antibody Engineering," Current Opinion in Structural Biology 2:593-596.

Proba, K. et al. (1995). "Functional Antibody Single-chain Fragments From The Cytoplasm of Escherichia Coli: Influence of Thioredoxin Reductase (trxb)," Gene 159(2):203-207.

Raag, R. et al. (Jan. 1995). "Single-chain Fvs," The FASEB Journal 9:73-80.

Ramakrishnan, S. et al. (Jan. 1984), "Comparison of the Selective Cytotoxic Effects of Immunotoxins Containing Ricin A Chain or Pokeweed Antiviral Protein and Anti-Thy 1.1 Monoclonal Antibodies," Cancer Res. 44:201-208.

Ramm, K. et al. (2000). "The Periplasmic *Escherichia Coli* Peptidylprolyl cis, Trans-Isomerase FkpA," The Journal of Biological Chemistry 275(22):17106-17113.

Ravetch, J.V. et al. (1991). "Fc Receptors," Annu. Rev. Immunol. 9:457-492.

Reyes, G.R. et al. (Jun. 17, 1982) "Expression of Human β-interferon cDNA Under the Control of a Thymidine Kinase Promoter from Herpes Simplex Virus," Nature 297:598-601.

Riechmann, L. et al. (Mar. 24, 1988). "Reshaping Human Antibodies for Therapy," Nature 332:323-329.

Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.

Rosenberg, S.A. et al. (Dec. 22, 1988). "Use Of Tumor-Infiltrating Lymphocytes And Interleukin-2 In The Immunotherapy Of Patients With Metastatic Melanoma. A Preliminary Report," N Engl J Med. 319:1676-1680.

Ross, J.S. et al. (Jul. 1997). "HER-2/Neu Gene Amplification Status In Prostate Cancer By Fluorescence In Situ Hybridization," Human Pathology 28(7):827-833.

Ross, J.S. et al. (Jun. 1997). "Prognostic Significance Of HER-2/Neu Gene Amplification Status By Fluorescence In Situ Hybridization Of Prostate Carcinoma," Cancer: Interdisciplinary International Journal of the American Cancer Society 79(11): 2162-2170.

Sadasivan, R. et al. (Jul. 1993). "Overexpression of Her-2/neu May Be an Indicator of Poor Prognosis in Prostate Cancer," J. Urol. 150(1):126-131. (Abstract only).

Sarabipour, S. et al. (Apr. 7, 2016). "VEGFR-2 Conformational Switch In Response To Ligand Binding," Elife: e13876, 23 pages.

Scheraga, H.A. (Jan. 1992). "Predicting Three-Dimensional Structures Of Oligopeptides," Reviews in Computational Chemistry 3:73-142. (Abstract only).

Schier, R. et al. (1995). "Identification of Functional and Structural Amino-Acid Residues by Parsimonious Mutagenesis," Gene 169:147-155.

Senger, D.R. et al. (Feb. 25, 1983). "Tumor Cells Secrete a Vascular Permeability Factor That Promotes Accumulation of Ascites Fluid," Science 219(4587):983-985.

Senger, D.R. et al. (Nov. 1986). "A Highly Conserved Vascular Permeability Factor Secreted By A Variety Of Human And Rodent Tumor Cell Lines," Cancer Research 46(11):5629-5632.

Sheriff, S. et al. (Sep. 1996). "Redefining the Minimal Antigen-Binding Fragment," Nature Struct. Biol. 3(9):733-736.

Shields, R.L. et al. (Mar. 2, 2001). "High Resolution Mapping of the Binding Site on Human IgG1 for FcγRI, FcγII. FoyIII, and FcRn and Design of IgG1 Variants With Improved Binding to the FcγR," J. Biol.Chem. 276(9):6591-6604.

Shinkawa, T. et al. (Jan. 31, 2003). "The Absence Of Fucose But Not The Presence Of Galactose Or Bisecting N-Acetylglucosamine Of Human IgG1 Complex-Type Oligosaccharides Shows The Critical Role Of Enhancing Antibody-Dependent Cellular Cytotoxicity," Journal of Biological Chemistry 278(5):3466-3473.

Sidhu, S.S. et al. (2004). "Phage-Displayed Antibody Libraries of Synthetic Heavy Chain Complementarity Determining Regions," J. Mol. Biol. 338(2):299-310.

Siebenlist, U. et al. (Jun. 1980). "*E. Coli* RNA Polymerase Interacts Homologously With Two Different Promoters," Cell 20(2):269-281.

Simmons, L.C. et al. (May 1, 2002). "Expression of Full-Length Immunoglobulins in *Escherichia Coli*: Rapid and Efficient Production of Aglycosylaled Antibodies," J. Immunol. Meth. 263(1-2): 133-147.

Slamon, D.J. et al. (Jan. 9, 1987). "Human Breast Cancer: Correlation Of Relapse And Survival With Amplification Of The HER-2/Neu Oncogene," Science 235(4785):177-182.

Slamon, D.J. et al. (May 12, 1989). "Studies Of The HER-2/Neu Proto-Oncogene In Human Breast And Ovarian Cancer," Science 244(4905):707-712.

Sondell, M. et al. (Jul. 15, 1999). "Vascular Endothellal Growth Factor Has Neurotrophic Activity and Stimulates Axonal Outgrowth, Enhancing Cell Survival and Schwann Cell Proliferation in the Periflheral Nervous System," J. Neurosci. 19(14):5731-5740.

Spiess, C. et al. (2015, e-pub. Jan. 27, 2015). "Alternative Molecular Formats and Therapeutic Applications For Bispecific Antibodies," Mol. Immunol. 67:95-106.

Stamova, S. et al. (May 24, 2012), "Cancer Immunotherapy by Retargeting of Immune Effector Cells via Recombinant Bispecific Antibody Constructs," Antibodies, 1(2):172-198.

(56) References Cited

OTHER PUBLICATIONS

Stratmann, A. et al. (Nov. 1998). "Cell Type-Specific Expression Of Angiopoietin-1 And Angiopoietin-2 Suggests A Role In Glioblastoma Angiogenesis," The American Journal Of Pathology 153(5):1459-1466.
Sullivan, L.A. et al. (2010). "The VEGF Family In Cancer And Antibody-Based Strategies For Their Inhibition," MAbs 2(2), pp. 165-175.
Tanaka, S. et al. (Feb. 1999). "Biologic Significance of angiopoietin-2 Expression in Human Hepatocellular Carcinoma," J Clin Invest. 103(3):341-345.
Terman, B.I. et al. (Sep. 1991). "Identification Of A New Endothelial Cell Growth Factor Receptor Tyrosine Kinase," Oncogene 6(9):1677-1683. (Abstract only).
Traunecker, A. et al. (1991). "Bispecific Single Chain Molecules (Janusins) Target Cytotoxic Lymphocytes on HIV Infected Cells," EMBO J. 10(12):3655-3659.
Turnis, M.E. (e-pub. Oct. 1, 2012). "Combinatorial Immunotherapy PD-1 May Not Be LAG-ing Behind Any More," Combinatorial Immunotherapy, OncoImmunology, 1(7):1172-1174.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.
Urlaub, G. et al. (Jul. 1980). "Isolation of Chinese hamster cell mutants deficient in dihydrofolate reductase activity," Proc. Natl. Acad. Sci. USA 77(7):4216-4220.
Van Dijk, M.A. et al. (2001). "Human Antibodies as Next Generation Therapeutics," Curr. Opin. Pharmacol 5:368-374.
Vaswani, S.K. et al. (Aug. 1998) "Humanized Antibodies as Potential Therapeutic Drugs," Annals of Allergy, Asthma, & Immunology 81:105-115.
Meira, J. et al. (1987). "Production of Single-Stranded Plasmid DNA," Meth. Enzymol. 153:3-11.
Vitetta, E.S. et al. (Nov. 20, 1987). "Redesigning Nature's Poisons to Create Anti-tumor Reagents," Science 238:1098-1104.
Weidle, U.H. et al. (Jan.-Feb. 2013). "The Intriguing Options Of Multispecific Antibody Formats For Treatment Of Cancer," Cancer Genomics Proteomics 10(1):1-18.
Weiner, D.B. et al. (Jan. 15, 1990). "Expression Of The Neu Gene-Encoded Protein (P185neu) In Human Non-Small Cell Carcinomas Of The Lung," Cancer Research 50(2):421-425.
West, H.J. (Apr. 2015). "Immune Checkpoint Inhibitors," JAMA Oncol. 1(1):115.
Wiesmann, C. et al. (Nov. 28, 1997). "Crystal Structure At 1.7 Å Resolution Of VEGF In Complex With Domain 2 Of The Flt-1 Receptor," Cell 91(5):695-704.
Willet, C.G. et al. (Feb. 2004). "Direct Evidence That the VEGF-specific Antibody Bevacizumab Has Antivascular Effects in Human Rectal Cancer," Nat. Med. 10(2):145-147.
Williams, T. M. et al. (1991). "Expression Of C-Erbb-2 In Human Pancreatic Adenocarcinomas," Pathobiology 59(1):46-52. (Abstract only).
Wright, A. et al. (Jan. 1997). "Effect of Glycosylation on Antibody Function: Implications for Genetics Engineering." Trends Biotechnol. 15:26-32.
Yamane-Ohnuki, N. et al. (Sep. 5, 2004, e-pub Aug. 6, 2004). "Establishment Of FUT8 Knockout Chinese Hamster Ovary Cells: An Ideal Host Cell Line For Producing Completely Defucosylated Antibodies With Enhanced Antibody-Dependent Cellular Cytotoxicity." Biotechnology and Bioengineering 87(5):614-622.
Yaniv, M. (May 6, 1982). "Enhancing Elements for Activation of Eukaryotic Promoters," Nature 297:17-18.
Yansura, D.G. et al. (1992). "Nucleotide Sequence Selection for Increased Expression of Heterologous Genes in *Escherichia Coli*," Methods: A Companion to Methods in Enzymol 4:151-158.
Yelton, D.E. et al. (1995). "Affinity Maturation of the BR96 Anti-Carcinoma Antibody by Codon-Based Mutagenesis," J. Immunol. 155:1994-2004.
Yokota, J. et al. (Apr. 5, 1986). "Amplification Of C-Erbb-2 Oncogene In Human Adenocarcinomas In Vivo," The Lancet 327(8484):765-767. (Abstract only).
Yonemura, Y. et al. (Feb. 1, 1991). "Evaluation Of Immunoreactivity For Erbb-2 Protein As A Marker Of Poor Short Term Prognosis In Gastric Cancer," Cancer Research 51(3):1034-1038.
Yoshida, Y. et al. (Dec. 1991). "Expression Of Angiostatic Factors In Colorectal Cancer," International Journal Of Oncology 15(6):1221-1226. (Abstract only).
Yuan, K. et al. (Jun. 2000). "Expression Of Tie-2, Angiopoietin-1, Angiopoietin-2, Ephrinb2 And Ephb4 In Pyogenic Granuloma Of Human Gingiva Implicates Their Roles In Inflammatory Angiogenesis," Journal Of Periodontal Research 35(3):165-171. (Abstract only).
Zagzag, D. et al. (Oct. 1, 1999). "In Situ Expression Of Angiopoietins In Astrocytomas Identifies Angiopoietin-2 As An Early Marker Of Tumor Angiogenesis," Experimental Neurology 159(2):391-400.
Zapata, G. et al. (1995). "Engineering Linear F(ab')2 Fragments For Efficient Production In *Escherichia coli* And Enhanced Antiproliferative Activity," Protein Engineering 8(10):1057-1062.
Zhang, D. et al. (Mar. 2010). "Suppression of Tumor Growth and Metastasis by Simultaneously Blocking Vascular Endothelial Growth Factor (VEGF)-A and VEGF-C with a Receptor-Immunoglobulin Fusion Protein," Cancer Research 70(6):2495-2503.
Zhau, H.E. al. (1990). "Amplification and Expression of the C-Erb B-2/neu Proto-Oncogene in Human Bladder Cancer," Mot Carcinog. 3(5):254-257. (Abstract only).
Lafleur, D. et al. (Mar./Apr. 2013). "Monoclonal Antibody Therapeutics With Up To Five Specificities: Functional Enhancement Through Fusion Of Target-Specific Peptides," Mabs 5(2):208-2018.

\* cited by examiner

```
                        SEQUENCE LISTING

<160> NUMBER OF SEQ ID NOS: 44

<210> SEQ ID NO 1
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Can be present in repeats of at least one

<400> SEQUENCE: 1

Gly
1

<210> SEQ ID NO 2
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(2)
<223> OTHER INFORMATION: Can be present in repeats of at least one

<400> SEQUENCE: 2

Gly Ser
1

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(5)
<223> OTHER INFORMATION: Can be present in repeats of at least one

<400> SEQUENCE: 3

Gly Ser Gly Gly Ser
1               5
```

```
<210> SEQ ID NO 4
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(5)
<223> OTHER INFORMATION: Can be present in repeats of at least one

<400> SEQUENCE: 4

Gly Gly Gly Gly Ser
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(4)
<223> OTHER INFORMATION: Can be present in repeats of at least one

<400> SEQUENCE: 5

Gly Gly Gly Ser
1

<210> SEQ ID NO 6
<211> LENGTH: 15
<212> TYPE: PRT
<213> ORGANISM: Artificial Sequence
<220> FEATURE:
<223> OTHER INFORMATION: Synthetic Construct

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 30
<212> TYPE: PRT
<213> ORGANISM: Artificial Sequence
<220> FEATURE:
<223> OTHER INFORMATION: Synthetic Construct

<400> SEQUENCE: 7

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 8
<211> LENGTH: 211
<212> TYPE: PRT
<213> ORGANISM: Artificial Sequence
<220> FEATURE:
<223> OTHER INFORMATION: Synthetic Construct

<400> SEQUENCE: 8

Thr Gly Ser Asp Thr Gly Arg Pro Phe Val Glu Met Tyr Ser Glu Ile
1               5                   10                  15

Pro Glu Ile Ile His Met Thr Glu Gly Arg Glu Leu Val Ile Pro Cys
            20                  25                  30
```

```
Arg Val Thr Ser Pro Asn Ile Thr Val Thr Leu Lys Lys Phe Pro Leu
         35                  40                  45

Asp Thr Leu Ile Pro Asp Gly Lys Arg Ile Ile Trp Asp Ser Arg Lys
 50                  55                  60

Gly Phe Ile Ile Ser Asn Ala Thr Tyr Lys Glu Ile Gly Leu Leu Thr
 65                  70                  75                  80

Cys Glu Ala Thr Val Asn Gly His Leu Tyr Lys Thr Asn Tyr Leu Thr
                 85                  90                  95

His Arg Gln Thr Asn Thr Ile Ile Asp Val Val Leu Ser Pro Ser His
             100                 105                 110

Gly Ile Glu Leu Ser Val Gly Glu Lys Leu Val Leu Asn Cys Thr Ala
         115                 120                 125

Arg Thr Glu Leu Asn Val Gly Ile Asp Phe Asn Trp Glu Tyr Pro Ser
130                 135                 140

Ser Lys His Gln His Lys Lys Leu Val Leu Ser Pro Val Asn Arg Asp
145                 150                 155                 160

Leu Lys Thr Gln Ser Gly Ser Glu Met Lys Lys Phe Leu Ser Thr Leu
                165                 170                 175

Thr Ile Asp Gly Val Thr Arg Ser Asp Gln Gly Leu Tyr Thr Cys Ala
            180                 185                 190

Ala Ser Ser Gly Leu Met Thr Lys Lys Asn Ser Thr Phe Val Arg Val
        195                 200                 205

His Glu Lys
210

<210> SEQ ID NO 9
<211> LENGTH: 448
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Val Glu Ser Gly Gly Gly Val Val Gln Pro Gly Arg
1               5                  10                  15

Ser Leu Arg Leu Ser Cys Ala Ala Ser Gly Phe Thr Phe Ser Ser Tyr
             20                  25                  30

Thr Met His Trp Val Arg Gln Ala Pro Gly Lys Gly Leu Glu Trp Val
         35                  40                  45

Thr Phe Ile Ser Tyr Asp Gly Asn Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Thr Gly Trp Leu Gly Pro Phe Asp Tyr Trp Gly Gln Gly Thr
             100                 105                 110

Leu Val Thr Val Ser Ser Ala Ser Thr Lys Gly Pro Ser Val Phe Pro
         115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

-continued

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 10
<211> LENGTH: 215
<212> TYPE: PRT
<213> ORGANISM: Artificial Sequence
<220> FEATURE:
<223> OTHER INFORMATION: Synthetic Construct

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
            85                  90                  95

```
Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 11
<211> LENGTH: 457
<212> TYPE: PRT
<213> ORGANISM: Artificial Sequence
<220> FEATURE:
<223> OTHER INFORMATION: Synthetic Construct

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Thr Gly Gly Gly Ser Gly Gly Gly
    210                 215                 220

Gly Ser Gly Gly Gly Gly Ser Gly Gly Gly Gly Ser Gly Gly Gly Gly
225                 230                 235                 240
```

```
Ser Gly Gly Gly Gly Ser Thr Gly Ser Asp Thr Gly Arg Pro Phe Val
            245                 250                 255

Glu Met Tyr Ser Glu Ile Pro Glu Ile Ile His Met Thr Glu Gly Arg
        260                 265                 270

Glu Leu Val Ile Pro Cys Arg Val Thr Ser Pro Asn Ile Thr Val Thr
    275                 280                 285

Leu Lys Lys Phe Pro Leu Asp Thr Leu Ile Pro Asp Gly Lys Arg Ile
290                 295                 300

Ile Trp Asp Ser Arg Lys Gly Phe Ile Ile Ser Asn Ala Thr Tyr Lys
305                 310                 315                 320

Glu Ile Gly Leu Leu Thr Cys Glu Ala Thr Val Asn Gly His Leu Tyr
                325                 330                 335

Lys Thr Asn Tyr Leu Thr His Arg Gln Thr Asn Thr Ile Ile Asp Val
            340                 345                 350

Val Leu Ser Pro Ser His Gly Ile Glu Leu Ser Val Gly Glu Lys Leu
        355                 360                 365

Val Leu Asn Cys Thr Ala Arg Thr Glu Leu Asn Val Gly Ile Asp Phe
    370                 375                 380

Asn Trp Glu Tyr Pro Ser Ser Lys His Gln His Lys Lys Leu Val Leu
385                 390                 395                 400

Ser Pro Val Asn Arg Asp Leu Lys Thr Gln Ser Gly Ser Glu Met Lys
                405                 410                 415

Lys Phe Leu Ser Thr Leu Thr Ile Asp Gly Val Thr Arg Ser Asp Gln
            420                 425                 430

Gly Leu Tyr Thr Cys Ala Ala Ser Ser Gly Leu Met Thr Lys Lys Asn
        435                 440                 445

Ser Thr Phe Val Arg Val His Glu Lys
    450                 455

<210> SEQ ID NO 12
<211> LENGTH: 447
<212> TYPE: PRT
<213> ORGANISM: Artificial Sequence
<220> FEATURE:
<223> OTHER INFORMATION: Synthetic Construct

<400> SEQUENCE: 12

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
    195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Arg Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 13
<211> LENGTH: 218
<212> TYPE: PRT
<213> ORGANISM: Artificial Sequence
<220> FEATURE:
<223> OTHER INFORMATION: Synthetic Construct

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60
```

```
Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 14
<211> LENGTH: 460
<212> TYPE: PRT
<213> ORGANISM: Artificial Sequence
<220> FEATURE:
<223> OTHER INFORMATION: Synthetic Construct

<400> SEQUENCE: 14

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Lys Gly Val Ser Thr Ser
                 20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
```

Val Thr Lys Ser Phe Asn Arg Gly Glu Cys Thr Gly Gly Gly Gly Ser
    210                 215                 220
Gly Gly Gly Gly Ser Gly Gly Gly Ser Gly Gly Gly Ser Gly
225                 230                 235                 240
Gly Gly Gly Ser Gly Gly Gly Ser Thr Gly Ser Asp Thr Gly Arg
                245                 250                 255
Pro Phe Val Glu Met Tyr Ser Glu Ile Pro Glu Ile Ile His Met Thr
                260                 265                 270
Glu Gly Arg Glu Leu Val Ile Pro Cys Arg Val Thr Ser Pro Asn Ile
            275                 280                 285
Thr Val Thr Leu Lys Lys Phe Pro Leu Asp Thr Leu Ile Pro Asp Gly
    290                 295                 300
Lys Arg Ile Ile Trp Asp Ser Arg Lys Gly Phe Ile Ile Ser Asn Ala
305                 310                 315                 320
Thr Tyr Lys Glu Ile Gly Leu Leu Thr Cys Glu Ala Thr Val Asn Gly
                325                 330                 335
His Leu Tyr Lys Thr Asn Tyr Leu Thr His Arg Gln Thr Asn Thr Ile
                340                 345                 350
Ile Asp Val Val Leu Ser Pro Ser His Gly Ile Glu Leu Ser Val Gly
            355                 360                 365
Glu Lys Leu Val Leu Asn Cys Thr Ala Arg Thr Glu Leu Asn Val Gly
    370                 375                 380
Ile Asp Phe Asn Trp Glu Tyr Pro Ser Ser Lys His Gln His Lys Lys
385                 390                 395                 400
Leu Val Leu Ser Pro Val Asn Arg Asp Leu Lys Thr Gln Ser Gly Ser
                405                 410                 415
Glu Met Lys Lys Phe Leu Ser Thr Leu Thr Ile Asp Gly Val Thr Arg
            420                 425                 430
Ser Asp Gln Gly Leu Tyr Thr Cys Ala Ala Ser Ser Gly Leu Met Thr
    435                 440                 445
Lys Lys Asn Ser Thr Phe Val Arg Val His Glu Lys
    450                 455                 460

<210> SEQ ID NO 15
<211> LENGTH: 440
<212> TYPE: PRT
<213> ORGANISM: Artificial Sequence
<220> FEATURE:
<223> OTHER INFORMATION: Synthetic Construct

<400> SEQUENCE: 15

Gln Val Gln Leu Val Glu Ser Gly Gly Val Val Gln Pro Gly Arg
1               5                   10                  15
Ser Leu Arg Leu Asp Cys Lys Ala Ser Gly Ile Thr Phe Ser Asn Ser
                20                  25                  30
Gly Met His Trp Val Arg Gln Ala Pro Gly Lys Gly Leu Glu Trp Val
            35                  40                  45
Ala Val Ile Trp Tyr Asp Gly Ser Lys Arg Tyr Tyr Ala Asp Ser Val
    50                  55                  60
Lys Gly Arg Phe Thr Ile Ser Arg Asp Asn Ser Lys Asn Thr Leu Phe
65                  70                  75                  80
Leu Gln Met Asn Ser Leu Arg Ala Glu Asp Thr Ala Val Tyr Tyr Cys
                85                  90                  95
Ala Thr Asn Asp Asp Tyr Trp Gly Gln Gly Thr Leu Val Thr Val Ser
                100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Arg
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 16
<211> LENGTH: 214
<212> TYPE: PRT
<213> ORGANISM: Artificial Sequence
<220> FEATURE:
<223> OTHER INFORMATION: Synthetic Construct

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

```
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 17
<211> LENGTH: 456
<212> TYPE: PRT
<213> ORGANISM: Artificial Sequence
<220> FEATURE:
<223> OTHER INFORMATION: Synthetic Construct

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Gly Gly Gly Ser Gly Gly Gly Gly
    210                 215                 220

Ser Gly Gly Gly Ser Gly Gly Gly Gly Ser Gly Gly Gly Gly Ser
225                 230                 235                 240

Gly Gly Gly Gly Ser Thr Gly Ser Asp Thr Gly Arg Pro Phe Val Glu
                245                 250                 255

Met Tyr Ser Glu Ile Pro Glu Ile Ile His Met Thr Glu Gly Arg Glu
            260                 265                 270

Leu Val Ile Pro Cys Arg Val Thr Ser Pro Asn Ile Thr Val Thr Leu
        275                 280                 285

Lys Lys Phe Pro Leu Asp Thr Leu Ile Pro Asp Gly Lys Arg Ile Ile
    290                 295                 300

Trp Asp Ser Arg Lys Gly Phe Ile Ile Ser Asn Ala Thr Tyr Lys Glu
305                 310                 315                 320

Ile Gly Leu Leu Thr Cys Glu Ala Thr Val Asn Gly His Leu Tyr Lys
                325                 330                 335

Thr Asn Tyr Leu Thr His Arg Gln Thr Asn Thr Ile Ile Asp Val Val
            340                 345                 350

Leu Ser Pro Ser His Gly Ile Glu Leu Ser Val Gly Glu Lys Leu Val
        355                 360                 365

Leu Asn Cys Thr Ala Arg Thr Glu Leu Asn Val Gly Ile Asp Phe Asn
    370                 375                 380

Trp Glu Tyr Pro Ser Ser Lys His Gln His Lys Lys Leu Val Leu Ser
385                 390                 395                 400

Pro Val Asn Arg Asp Leu Lys Thr Gln Ser Gly Ser Glu Met Lys Lys
                405                 410                 415

Phe Leu Ser Thr Leu Thr Ile Asp Gly Val Thr Arg Ser Asp Gln Gly
            420                 425                 430

Leu Tyr Thr Cys Ala Ala Ser Ser Gly Leu Met Thr Lys Lys Asn Ser
        435                 440                 445

Thr Phe Val Arg Val His Glu Lys
    450                 455

<210> SEQ ID NO 18
<211> LENGTH: 448
<212> TYPE: PRT
<213> ORGANISM: Artificial Sequence
<220> FEATURE:
<223> OTHER INFORMATION: Synthetic Construct

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 19
<211> LENGTH: 214
<212> TYPE: PRT
<213> ORGANISM: Artificial Sequence
<220> FEATURE:
<223> OTHER INFORMATION: Synthetic Construct

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 456
<212> TYPE: PRT
<213> ORGANISM: Artificial Sequence
<220> FEATURE:
<223> OTHER INFORMATION: Synthetic Construct

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Gly Gly Gly Ser Gly Gly Gly Gly
    210                 215                 220

Ser Gly Gly Gly Ser Gly Gly Gly Ser Gly Gly Gly Ser
225                 230                 235                 240

Gly Gly Gly Ser Thr Gly Ser Asp Thr Gly Arg Pro Phe Val Glu
            245                 250                 255

Met Tyr Ser Glu Ile Pro Glu Ile Ile His Met Thr Glu Gly Arg Glu
                260                 265                 270

Leu Val Ile Pro Cys Arg Val Thr Ser Pro Asn Ile Thr Val Thr Leu
            275                 280                 285

Lys Lys Phe Pro Leu Asp Thr Leu Ile Pro Asp Gly Lys Arg Ile Ile
            290                 295                 300

Trp Asp Ser Arg Lys Gly Phe Ile Ile Ser Asn Ala Thr Tyr Lys Glu
305                 310                 315                 320

Ile Gly Leu Leu Thr Cys Glu Ala Thr Val Asn Gly His Leu Tyr Lys
                325                 330                 335

Thr Asn Tyr Leu Thr His Arg Gln Thr Asn Thr Ile Ile Asp Val Val
            340                 345                 350

Leu Ser Pro Ser His Gly Ile Glu Leu Ser Val Gly Glu Lys Leu Val
            355                 360                 365

Leu Asn Cys Thr Ala Arg Thr Glu Leu Asn Val Gly Ile Asp Phe Asn
370                 375                 380

Trp Glu Tyr Pro Ser Ser Lys His Gln His Lys Lys Leu Val Leu Ser
385                 390                 395                 400

Pro Val Asn Arg Asp Leu Lys Thr Gln Ser Gly Ser Glu Met Lys Lys
                405                 410                 415

Phe Leu Ser Thr Leu Thr Ile Asp Gly Val Thr Arg Ser Asp Gln Gly
                420                 425                 430

Leu Tyr Thr Cys Ala Ala Ser Ser Gly Leu Met Thr Lys Lys Asn Ser
            435                 440                 445

Thr Phe Val Arg Val His Glu Lys
            450                 455

<210> SEQ ID NO 21
<211> LENGTH: 451
<212> TYPE: PRT
<213> ORGANISM: Artificial Sequence
<220> FEATURE:
<223> OTHER INFORMATION: Synthetic Construct

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
                20                  25                  30

Trp Met Ser Trp Val Arg Gln Ala Pro Gly Lys Gly Leu Glu Trp Val
            35                  40                  45
```

-continued

```
Ala Asn Ile Lys Gln Asp Gly Ser Glu Lys Tyr Tyr Val Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Glu Gly Gly Trp Phe Gly Glu Leu Ala Phe Asp Tyr Trp Gly
                100                 105                 110
Gln Gly Thr Leu Val Thr Val Ser Ala Ser Thr Lys Gly Pro Ser
            115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Phe Glu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Ser Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450
```

```
<210> SEQ ID NO 22
<211> LENGTH: 215
<212> TYPE: PRT
<213> ORGANISM: Artificial Sequence
<220> FEATURE:
<223> OTHER INFORMATION: Synthetic Construct

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 23
<211> LENGTH: 457
<212> TYPE: PRT
<213> ORGANISM: Artificial Sequence
<220> FEATURE:
<223> OTHER INFORMATION: Synthetic Construct

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95
```

Trp Thr Phe Gly Gln Gly Thr Lys Val Glu Ile Lys Arg Thr Val Ala
                100                 105                 110

Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Thr Gly Gly Gly Ser Gly Gly Gly
    210                 215                 220

Gly Ser Gly Gly Gly Ser Gly Gly Gly Ser Gly Gly Gly Gly
225                 230                 235                 240

Ser Gly Gly Gly Ser Thr Gly Ser Asp Thr Gly Arg Pro Phe Val
                245                 250                 255

Glu Met Tyr Ser Glu Ile Pro Glu Ile Ile His Met Thr Glu Gly Arg
            260                 265                 270

Glu Leu Val Ile Pro Cys Arg Val Thr Ser Pro Asn Ile Thr Val Thr
        275                 280                 285

Leu Lys Lys Phe Pro Leu Asp Thr Leu Ile Pro Asp Gly Lys Arg Ile
    290                 295                 300

Ile Trp Asp Ser Arg Lys Gly Phe Ile Ile Ser Asn Ala Thr Tyr Lys
305                 310                 315                 320

Glu Ile Gly Leu Leu Thr Cys Glu Ala Thr Val Asn Gly His Leu Tyr
                325                 330                 335

Lys Thr Asn Tyr Leu Thr His Arg Gln Thr Asn Thr Ile Ile Asp Val
            340                 345                 350

Val Leu Ser Pro Ser His Gly Ile Glu Leu Ser Val Gly Glu Lys Leu
        355                 360                 365

Val Leu Asn Cys Thr Ala Arg Thr Glu Leu Asn Val Gly Ile Asp Phe
    370                 375                 380

Asn Trp Glu Tyr Pro Ser Ser Lys His Gln His Lys Lys Leu Val Leu
385                 390                 395                 400

Ser Pro Val Asn Arg Asp Leu Lys Thr Gln Ser Gly Ser Glu Met Lys
                405                 410                 415

Lys Phe Leu Ser Thr Leu Thr Ile Asp Gly Val Thr Arg Ser Asp Gln
            420                 425                 430

Gly Leu Tyr Thr Cys Ala Ala Ser Ser Gly Leu Met Thr Lys Lys Asn
        435                 440                 445

Ser Thr Phe Val Arg Val His Glu Lys
    450                 455

<210> SEQ ID NO 24
<211> LENGTH: 450
<212> TYPE: PRT
<213> ORGANISM: Artificial Sequence
<220> FEATURE:
<223> OTHER INFORMATION: Synthetic Construct

<400> SEQUENCE: 24

-continued

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415
```

-continued

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 25
<211> LENGTH: 214
<212> TYPE: PRT
<213> ORGANISM: Artificial Sequence
<220> FEATURE:
<223> OTHER INFORMATION: Synthetic Construct

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 456
<212> TYPE: PRT
<213> ORGANISM: Artificial Sequence
<220> FEATURE:
<223> OTHER INFORMATION: Synthetic Construct

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Gly Gly Gly Ser Gly Gly Gly Gly
    210                 215                 220

Ser Gly Gly Gly Gly Ser Gly Gly Gly Ser Gly Gly Gly Gly Ser
225                 230                 235                 240

Gly Gly Gly Gly Ser Thr Gly Ser Asp Thr Gly Arg Pro Phe Val Glu
            245                 250                 255

Met Tyr Ser Glu Ile Pro Glu Ile Ile His Met Thr Glu Gly Arg Glu
        260                 265                 270

Leu Val Ile Pro Cys Arg Val Thr Ser Pro Asn Ile Thr Val Thr Leu
        275                 280                 285

Lys Lys Phe Pro Leu Asp Thr Leu Ile Pro Asp Gly Lys Arg Ile Ile
        290                 295                 300

Trp Asp Ser Arg Lys Gly Phe Ile Ile Ser Asn Ala Thr Tyr Lys Glu
305                 310                 315                 320

Ile Gly Leu Leu Thr Cys Glu Ala Thr Val Asn Gly His Leu Tyr Lys
                325                 330                 335

Thr Asn Tyr Leu Thr His Arg Gln Thr Asn Thr Ile Ile Asp Val Val
            340                 345                 350

Leu Ser Pro Ser His Gly Ile Glu Leu Ser Val Gly Glu Lys Leu Val
        355                 360                 365

Leu Asn Cys Thr Ala Arg Thr Glu Leu Asn Val Gly Ile Asp Phe Asn
    370                 375                 380

Trp Glu Tyr Pro Ser Ser Lys His Gln His Lys Lys Leu Val Leu Ser
385                 390                 395                 400

Pro Val Asn Arg Asp Leu Lys Thr Gln Ser Gly Ser Glu Met Lys Lys
                405                 410                 415

Phe Leu Ser Thr Leu Thr Ile Asp Gly Val Thr Arg Ser Asp Gln Gly
            420                 425                 430

Leu Tyr Thr Cys Ala Ala Ser Ser Gly Leu Met Thr Lys Lys Asn Ser
        435                 440                 445

Thr Phe Val Arg Val His Glu Lys
450                 455
```

-continued

```
<210> SEQ ID NO 27
<211> LENGTH: 441
<212> TYPE: PRT
<213> ORGANISM: Artificial Sequence
<220> FEATURE:
<223> OTHER INFORMATION: Synthetic Construct

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Gly Gly Gly Ser Gly Gly Gly Gly
    210                 215                 220

Ser Gly Gly Gly Ser Thr Gly Ser Asp Thr Gly Arg Pro Phe Val
225                 230                 235                 240

Glu Met Tyr Ser Glu Ile Pro Glu Ile Ile His Met Thr Glu Gly Arg
                245                 250                 255

Glu Leu Val Ile Pro Cys Arg Val Thr Ser Pro Asn Ile Thr Val Thr
            260                 265                 270

Leu Lys Lys Phe Pro Leu Asp Thr Leu Ile Pro Asp Gly Lys Arg Ile
        275                 280                 285

Ile Trp Asp Ser Arg Lys Gly Phe Ile Ile Ser Asn Ala Thr Tyr Lys
    290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
                325                 330                 335

Val Leu Ser Pro Ser His Gly Ile Glu Leu Ser Val Gly Glu Lys Leu
            340                 345                 350

Val Leu Asn Cys Thr Ala Arg Thr Glu Leu Asn Val Gly Ile Asp Phe
        355                 360                 365
```

```
Asn Trp Glu Tyr Pro Ser Ser Lys His Gln His Lys Lys Leu Val Leu
    370             375                 380

Ser Pro Val Asn Arg Asp Leu Lys Thr Gln Ser Gly Ser Glu Met Lys
385             390                 395                 400

Lys Phe Leu Ser Thr Leu Thr Ile Asp Gly Val Thr Arg Ser Asp Gln
            405                 410                 415

Gly Leu Tyr Thr Cys Ala Ala Ser Ser Gly Leu Met Thr Lys Lys Asn
            420                 425                 430

Ser Thr Phe Val Arg Val His Glu Lys
            435                 440
```

<210> SEQ ID NO 28
<211> LENGTH: 426
<212> TYPE: PRT
<213> ORGANISM: Artificial Sequence
<220> FEATURE:
<223> OTHER INFORMATION: Synthetic Construct

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Thr Gly Ser Asp Thr Gly Arg Pro Phe
    210                 215                 220

Val Glu Met Tyr Ser Glu Ile Pro Glu Ile Ile His Met Thr Glu Gly
225                 230                 235                 240

Arg Glu Leu Val Ile Pro Cys Arg Val Thr Ser Pro Asn Ile Thr Val
                245                 250                 255

Thr Leu Lys Lys Phe Pro Leu Asp Thr Leu Ile Pro Asp Gly Lys Arg
            260                 265                 270

Ile Ile Trp Asp Ser Arg Lys Gly Phe Ile Ile Ser Asn Ala Thr Tyr
        275                 280                 285
```

```
Lys Glu Ile Gly Leu Leu Thr Cys Glu Ala Thr Val Asn Gly His Leu
    290                 295                 300

Tyr Lys Thr Asn Tyr Leu Thr His Arg Gln Thr Asn Thr Ile Ile Asp
305                 310                 315                 320

Val Val Leu Ser Pro Ser His Gly Ile Glu Leu Ser Val Gly Glu Lys
                325                 330                 335

Leu Val Leu Asn Cys Thr Ala Arg Thr Glu Leu Asn Val Gly Ile Asp
                340                 345                 350

Phe Asn Trp Glu Tyr Pro Ser Ser Lys His Gln His Lys Lys Leu Val
            355                 360                 365

Leu Ser Pro Val Asn Arg Asp Leu Lys Thr Gln Ser Gly Ser Glu Met
    370                 375                 380

Lys Lys Phe Leu Ser Thr Leu Thr Ile Asp Gly Val Thr Arg Ser Asp
385                 390                 395                 400

Gln Gly Leu Tyr Thr Cys Ala Ala Ser Ser Gly Leu Met Thr Lys Lys
                405                 410                 415

Asn Ser Thr Phe Val Arg Val His Glu Lys
                420                 425

<210> SEQ ID NO 29
<211> LENGTH: 449
<212> TYPE: PRT
<213> ORGANISM: Artificial Sequence
<220> FEATURE:
<223> OTHER INFORMATION: Synthetic Construct

<400> SEQUENCE: 29

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 30
<211> LENGTH: 214
<212> TYPE: PRT
<213> ORGANISM: Artificial Sequence
<220> FEATURE:
<223> OTHER INFORMATION: Synthetic Construct

<400> SEQUENCE: 30

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 31
<211> LENGTH: 456
<212> TYPE: PRT
<213> ORGANISM: Artificial Sequence
<220> FEATURE:
<223> OTHER INFORMATION: Synthetic Construct

<400> SEQUENCE: 31

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys Thr Gly Gly Gly Ser Gly Gly Gly
            210                 215                 220

Ser Gly Gly Gly Ser Gly Gly Gly Ser Gly Gly Gly Ser
225                 230                 235                 240

Gly Gly Gly Gly Ser Thr Gly Ser Asp Thr Gly Arg Pro Phe Val Glu
                245                 250                 255

Met Tyr Ser Glu Ile Pro Glu Ile Ile His Met Thr Glu Gly Arg Glu
                260                 265                 270

Leu Val Ile Pro Cys Arg Val Thr Ser Pro Asn Ile Thr Val Thr Leu

```
                275                 280                 285
Lys Lys Phe Pro Leu Asp Thr Leu Ile Pro Asp Gly Lys Arg Ile Ile
    290                 295                 300

Trp Asp Ser Arg Lys Gly Phe Ile Ile Ser Asn Ala Thr Tyr Lys Glu
305                 310                 315                 320

Ile Gly Leu Leu Thr Cys Glu Ala Thr Val Asn Gly His Leu Tyr Lys
                325                 330                 335

Thr Asn Tyr Leu Thr His Arg Gln Thr Asn Thr Ile Ile Asp Val Val
            340                 345                 350

Leu Ser Pro Ser His Gly Ile Glu Leu Ser Val Gly Glu Lys Leu Val
        355                 360                 365

Leu Asn Cys Thr Ala Arg Thr Glu Leu Asn Val Gly Ile Asp Phe Asn
    370                 375                 380

Trp Glu Tyr Pro Ser Ser Lys His Gln His Lys Lys Leu Val Leu Ser
385                 390                 395                 400

Pro Val Asn Arg Asp Leu Lys Thr Gln Ser Gly Ser Glu Met Lys Lys
                405                 410                 415

Phe Leu Ser Thr Leu Thr Ile Asp Gly Val Thr Arg Ser Asp Gln Gly
            420                 425                 430

Leu Tyr Thr Cys Ala Ala Ser Ser Gly Leu Met Thr Lys Lys Asn Ser
        435                 440                 445

Thr Phe Val Arg Val His Glu Lys
    450                 455

<210> SEQ ID NO 32
<211> LENGTH: 451
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
            245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
            325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
            405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
Pro Gly Lys
    450

<210> SEQ ID NO 33
<211> LENGTH: 214
<212> TYPE: PRT
<213> ORGANISM: Artificial Sequence
<220> FEATURE:
<223> OTHER INFORMATION: Synthetic Construct

<400> SEQUENCE: 33

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Tyr
            20                  25                  30
Leu Ala Trp Tyr Gln Gln Lys Pro Gly Lys Ala Pro Lys Leu Leu Ile
        35                  40                  45
Tyr Ala Ala Ser Thr Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Arg Tyr Asn Arg Ala Pro Tyr

```
            85                    90                    95
Thr Phe Gly Gln Gly Thr Lys Val Glu Ile Lys Arg Thr Val Ala Ala
            100                   105                   110

Pro Ser Val Phe Ile Phe Pro Pro Ser Asp Glu Gln Leu Lys Ser Gly
            115                   120                   125

Thr Ala Ser Val Val Cys Leu Leu Asn Asn Phe Tyr Pro Arg Glu Ala
            130                   135                   140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 34
<211> LENGTH: 456
<212> TYPE: PRT
<213> ORGANISM: Artificial Sequence
<220> FEATURE:
<223> OTHER INFORMATION: Synthetic Construct

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                   105                   110

Pro Ser Val Phe Ile Phe Pro Pro Ser Asp Glu Gln Leu Lys Ser Gly
            115                   120                   125

Thr Ala Ser Val Val Cys Leu Leu Asn Asn Phe Tyr Pro Arg Glu Ala
            130                   135                   140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys Thr Gly Gly Gly Ser Gly Gly Gly Gly
            210                   215                   220

Ser Gly Gly Gly Gly Ser Gly Gly Gly Gly Ser Gly Gly Gly Gly Ser
```

```
                225                 230                 235                 240
Gly Gly Gly Gly Ser Thr Gly Ser Asp Thr Gly Arg Pro Phe Val Glu
            245                 250                 255

Met Tyr Ser Glu Ile Pro Glu Ile Ile His Met Thr Glu Gly Arg Glu
            260                 265                 270

Leu Val Ile Pro Cys Arg Val Thr Ser Pro Asn Ile Thr Val Thr Leu
            275                 280                 285

Lys Lys Phe Pro Leu Asp Thr Leu Ile Pro Asp Gly Lys Arg Ile Ile
            290                 295                 300

Trp Asp Ser Arg Lys Gly Phe Ile Ile Ser Asn Ala Thr Tyr Lys Glu
305                 310                 315                 320

Ile Gly Leu Leu Thr Cys Glu Ala Thr Val Asn Gly His Leu Tyr Lys
            325                 330                 335

Thr Asn Tyr Leu Thr His Arg Gln Thr Asn Thr Ile Ile Asp Val Val
            340                 345                 350

Leu Ser Pro Ser His Gly Ile Glu Leu Ser Val Gly Glu Lys Leu Val
            355                 360                 365

Leu Asn Cys Thr Ala Arg Thr Glu Leu Asn Val Gly Ile Asp Phe Asn
            370                 375                 380

Trp Glu Tyr Pro Ser Ser Lys His Gln His Lys Lys Leu Val Leu Ser
385                 390                 395                 400

Pro Val Asn Arg Asp Leu Lys Thr Gln Ser Gly Ser Glu Met Lys Lys
            405                 410                 415

Phe Leu Ser Thr Leu Thr Ile Asp Gly Val Thr Arg Ser Asp Gln Gly
            420                 425                 430

Leu Tyr Thr Cys Ala Ala Ser Ser Gly Leu Met Thr Lys Lys Asn Ser
            435                 440                 445

Thr Phe Val Arg Val His Glu Lys
            450                 455

<210> SEQ ID NO 35
<211> LENGTH: 452
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Thr Gly Lys Gly Leu Glu Trp Val
            35                  40                  45

Ser Ala Ile Gly Pro Ala Gly Asp Thr Tyr Tyr Pro Gly Ser Val Lys
        50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
            85                  90                  95

Arg Gly Leu Ile Thr Phe Gly Gly Leu Ile Ala Pro Phe Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
```

```
            130                 135                 140
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
            450

<210> SEQ ID NO 36
<211> LENGTH: 214
<212> TYPE: PRT
<213> ORGANISM: Artificial Sequence
<220> FEATURE:
<223> OTHER INFORMATION: Synthetic Construct

<400> SEQUENCE: 36

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
```

```
            35                  40                  45
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Asp Asn Ser Gln
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 37
<211> LENGTH: 456
<212> TYPE: PRT
<213> ORGANISM: Artificial Sequence
<220> FEATURE:
<223> OTHER INFORMATION: Synthetic Construct

<400> SEQUENCE: 37

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Thr
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Asp Asn Ser Gln
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
                180               185                190
Ala Cys Glu Val Thr His Gln Gly Leu Ser Ser Pro Val Thr Lys Ser
            195                 200                 205
Phe Asn Arg Gly Glu Cys Thr Gly Gly Gly Ser Gly Gly Gly Gly
        210                 215                 220
Ser Gly Gly Gly Ser Gly Gly Gly Ser Gly Gly Gly Ser
225                 230                 235                 240
Gly Gly Gly Ser Thr Gly Ser Asp Thr Gly Arg Pro Phe Val Glu
                245                 250                 255
Met Tyr Ser Glu Ile Pro Glu Ile Ile His Met Thr Glu Gly Arg Glu
            260                 265                 270
Leu Val Ile Pro Cys Arg Val Thr Ser Pro Asn Ile Thr Val Thr Leu
        275                 280                 285
Lys Lys Phe Pro Leu Asp Thr Leu Ile Pro Asp Gly Lys Arg Ile Ile
        290                 295                 300
Trp Asp Ser Arg Lys Gly Phe Ile Ile Ser Asn Ala Thr Tyr Lys Glu
305                 310                 315                 320
Ile Gly Leu Leu Thr Cys Glu Ala Thr Val Asn Gly His Leu Tyr Lys
                325                 330                 335
Thr Asn Tyr Leu Thr His Arg Gln Thr Asn Thr Ile Ile Asp Val Val
            340                 345                 350
Leu Ser Pro Ser His Gly Ile Glu Leu Ser Val Gly Glu Lys Leu Val
        355                 360                 365
Leu Asn Cys Thr Ala Arg Thr Glu Leu Asn Val Gly Ile Asp Phe Asn
        370                 375                 380
Trp Glu Tyr Pro Ser Ser Lys His Gln His Lys Lys Leu Val Leu Ser
385                 390                 395                 400
Pro Val Asn Arg Asp Leu Lys Thr Gln Ser Gly Ser Glu Met Lys Lys
                405                 410                 415
Phe Leu Ser Thr Leu Thr Ile Asp Gly Val Thr Arg Ser Asp Gln Gly
            420                 425                 430
Leu Tyr Thr Cys Ala Ala Ser Ser Gly Leu Met Thr Lys Lys Asn Ser
        435                 440                 445
Thr Phe Val Arg Val His Glu Lys
    450                 455

<210> SEQ ID NO 38
<211> LENGTH: 445
<212> TYPE: PRT
<213> ORGANISM: Artificial Sequence
<220> FEATURE:
<223> OTHER INFORMATION: Synthetic Construct

<400> SEQUENCE: 38

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ser Phe Thr Asp Tyr
            20                  25                  30
His Ile His Trp Val Arg Gln Ala Pro Gly Gln Gly Leu Glu Trp Met
        35                  40                  45
Gly Val Ile Asn Pro Met Tyr Gly Thr Thr Asp Tyr Asn Gln Arg Phe
    50                  55                  60
Lys Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
```

```
                85                  90                  95
Ala Arg Tyr Asp Tyr Phe Thr Gly Thr Gly Val Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
            435                 440                 445

<210> SEQ ID NO 39
<211> LENGTH: 219
<212> TYPE: PRT
<213> ORGANISM: Artificial Sequence
<220> FEATURE:
<223> OTHER INFORMATION: Synthetic Construct

<400> SEQUENCE: 39

Asp Ile Val Met Thr Gln Thr Pro Leu Ser Leu Ser Val Thr Pro Gly
```

```
1               5                   10                  15
Gln Pro Ala Ser Ile Ser Cys Arg Ser Ser Arg Ser Leu Val His Ser
                20                  25                  30

Arg Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ile Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 40
<211> LENGTH: 461
<212> TYPE: PRT
<213> ORGANISM: Artificial Sequence
<220> FEATURE:
<223> OTHER INFORMATION: Synthetic Construct

<400> SEQUENCE: 40

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
                20                  25                  30

Arg Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ile Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
```

```
            145                 150                 155                 160
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys Thr Gly Gly Gly Gly
    210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gly Gly Ser Thr Gly Ser Asp Thr Gly
                245                 250                 255

Arg Pro Phe Val Glu Met Tyr Ser Glu Ile Pro Glu Ile Ile His Met
                260                 265                 270

Thr Glu Gly Arg Glu Leu Val Ile Pro Cys Arg Val Thr Ser Pro Asn
                275                 280                 285

Ile Thr Val Thr Leu Lys Lys Phe Pro Leu Asp Thr Leu Ile Pro Asp
                290                 295                 300

Gly Lys Arg Ile Ile Trp Asp Ser Arg Lys Gly Phe Ile Ile Ser Asn
305                 310                 315                 320

Ala Thr Tyr Lys Glu Ile Gly Leu Leu Thr Cys Glu Ala Thr Val Asn
                325                 330                 335

Gly His Leu Tyr Lys Thr Asn Tyr Leu Thr His Arg Gln Thr Asn Thr
                340                 345                 350

Ile Ile Asp Val Val Leu Ser Pro Ser His Gly Ile Glu Leu Ser Val
                355                 360                 365

Gly Glu Lys Leu Val Leu Asn Cys Thr Ala Arg Thr Glu Leu Asn Val
                370                 375                 380

Gly Ile Asp Phe Asn Trp Glu Tyr Pro Ser Ser Lys His Gln His Lys
385                 390                 395                 400

Lys Leu Val Leu Ser Pro Val Asn Arg Asp Leu Lys Thr Gln Ser Gly
                405                 410                 415

Ser Glu Met Lys Lys Phe Leu Ser Thr Leu Thr Ile Asp Gly Val Thr
                420                 425                 430

Arg Ser Asp Gln Gly Leu Tyr Thr Cys Ala Ala Ser Ser Gly Leu Met
                435                 440                 445

Thr Lys Lys Asn Ser Thr Phe Val Arg Val His Glu Lys
    450                 455                 460

<210> SEQ ID NO 41
<211> LENGTH: 19
<212> TYPE: PRT
<213> ORGANISM: Artificial Sequence
<220> FEATURE:
<223> OTHER INFORMATION: Synthetic Construct

<400> SEQUENCE: 41

Met Glu Phe Gly Leu Ser Trp Leu Phe Leu Val Ala Ile Leu Lys Gly
1               5                   10                  15

Val Gln Cys

<210> SEQ ID NO 42
<211> LENGTH: 22
<212> TYPE: PRT
<213> ORGANISM: Artificial Sequence
```

```
<220> FEATURE:
<223> OTHER INFORMATION: Synthetic Construct

<400> SEQUENCE: 42

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic Construct

<400> SEQUENCE: 43

Met Glu Thr Asp Thr Leu Leu Leu Trp Val Leu Leu Leu Trp Val Pro
1               5                   10                  15

Gly Ser Thr Gly
            20

<210> SEQ ID NO 44
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(15)
<223> OTHER INFORMATION: Can be present in repeats of at least one

<400> SEQUENCE: 44

Gly Ser Thr Ser Gly Ser Gly Lys Pro Gly Ser Gly Glu Gly Ser
1               5                   10                  15
```

VEGFR-ANTIBODY LIGHT CHAIN FUSION PROTEIN

CROSS REFERENCE TO RELATED APPLICATIONS

This application is a National Phase application under 35 U.S.C § 371 of International Patent Application No. PCT/US2018/055512, filed Oct. 11, 2018, which claims priority benefit of U.S. Provisional Patent Application No. 62/571,773, filed Oct. 12, 2017, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 754392000200SEQLIST.txt, date recorded: Mar. 19, 2020, size: 106 KB).

FIELD OF THE INVENTION

The present invention relates to antibody fusion proteins comprising a vascular endothelial growth factor receptor (VEGFR) component fused to the C-terminus of the antibody light chain, and methods of making and using thereof.

BACKGROUND OF THE INVENTION

Vascular endothelial growth factor (VEGF) plays an important role in angiogenesis. The binding of VEGF to its tyrosine kinase receptors (VEGFR) expressed on vascular endothelial cells triggers cellular responses involved in vascular endothelial cell proliferation and new blood vessel growth. However, overexpression of VEGF contributes to diseases. Tumor tissues tend to have higher VEGF expression level, which stimulates tumor angiogenesis to provide nourishment to the growing solid tumor. Angiogenesis also allows tumors to be in contact with the vascular bed of the host, which may provide a route for metastasis of tumor cells. Overexpression of VEGF can also causes non-neoplastic conditions such as rheumatoid arthritis, psoriasis, atherosclerosis, hemangiomas, immune rejection of transplanted corneal tissue and other tissues, chronic inflammation, and ocular neovascular disorders (e.g. diabetic retinopathy, retrolental fibroplasia, neovascular glaucoma, and age-related macular degeneration (AMD)). Thus, one possible mechanism for the effective treatment of neoplastic tumors and non-neoplastic disorders (such as ocular neovascular disorders) is to inhibit or substantially reduce the endothelial proliferative and angiogenic activity of the VEGF protein.

The interaction between ligand and its receptor often possesses high affinity, reaching nanomolar to picomolar range. The extra-cellular domain (ECD) of a receptor, or a functional portion of the ECD, has been used successfully as a "ligand trap" for therapeutic purposes (Claesson-Welsh L., Nat Med. 2008 November; 14(11):1147-1148; Wiesmann C. et al., Cell. 1997 Nov. 28; 91(5):695-704; Harding T C et al., Sci Transl Med. 2013 Mar. 27; 5(178):178ra39).

Recombinant fusion protein comprising VEGFR components has been developed to treat diseases associated with VEGF expression, such as cancer and AMD. These fusion proteins are generated by fusing VEGFR fragments to the N-terminus of an immunoglobulin fc fragment, or a portion of the immunoglobulin Fc fragment, and are recognized as "VEGF trap." See, e.g. U.S. Pat. Nos. 6,100,071, 7,087,411, and 7,521,049. The VEGFR fragments will bind to and inactivate endogenous VEGF, thereby providing a means for reducing or inhibiting endogenous VEGF activity and, in turn, reducing or inhibiting endothelial cell proliferation and angiogenesis. The VEGF-trap (Aflibercept) can capture VEGF with higher affinity (0.5 pM) than bevacizumab (VEGF neutralizing antibody, 50 pM).

The disclosures of all publications, patents, patent applications and published patent applications referred to herein are hereby incorporated herein by reference in their entirety.

BRIEF SUMMARY OF THE INVENTION

The present invention relates to antibody fusion protein comprising a VEGFR component fused to the C-terminus of the antibody light chain (such as C-terminus of antibody light chain constant domain (CL domain)), and methods of making and using thereof.

One aspect of the present application provides an antibody fusion protein comprising 1) an antibody comprising a light chain, and 2) a VEGFR component, wherein the VEGFR component is fused to the C-terminus of the antibody light chain (such as C-terminus of antibody $V_L$-$C_L$ domain). In some embodiments, the antibody fusion protein comprises a first VEGFR component fused to the C-terminus of a first antibody light chain, and a second VEGFR component fused to the C-terminus of a second antibody light chain. In some embodiments, the first VEGFR component and the second VEGFR component are the same. In some embodiments, the first VEGFR component and the second VEGFR component are different.

In some embodiments according to any one of the antibody fusion protein described above, the VEGFR component comprises an immunoglobulin-like (Ig-like) domain 2 of a first VEGFR Flt1 (Flt1d2). In some embodiments, the VEGFR component further comprises an Ig-like domain 3 of a second VEGFR Flk1 (Flk1d3). In some embodiments, the VEGFR component comprises an amino acid sequence of SEQ ID NO: 8. In some embodiments, the VEGFR component further comprises an Ig-like domain 4 of a third VEGFR Flk1 (Flk1d4).

In some embodiments according to any one of the antibody fusion protein described above, the VEGFR component is at least about 4 kDa (such as at least about any of 4 kDa, 8 kDa, 12 kDa, 17 kDa, 20 kDa, 25 kDa, 27 kDa, or 30 kDa).

In some embodiments according to any one of the antibody fusion protein described above, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about 10–12 M, about $10^{-10}$ M to about $10^{-12}$ M).

In some embodiments according to any one of the antibody fusion protein described above, the VEGFR component and the C-terminus of the antibody light chain are connected by a linker. In some embodiments, the linker is a peptide linker, such as a peptide linker comprising an amino acid sequence of SEQ ID NO: 6 or 7.

In some embodiments according to any one of the antibody fusion protein described above, the antibody is selected from the group consisting of IgA, IgD, IgE, IgG, IgM, IgG-derived molecules, Fab, Fab', F(ab')2, Fab-scFv, F(ab')2-scFv2, Fab-scFv-Fc, Dock and Lock, scFv, di-scFv, diabody, Diabody-Fc, Diabody-CH$_3$, and intrabody. In some embodiments, the antibody comprises a light chain constant domain (C_L domain), and the VEGFR component is fused to the C-terminus of the antibody C_L domain (e.g., C-terminus of antibody V_L-C_L domain). In some embodiments, the antibody is a full length antibody. In some embodiments, the antibody is an IgG antibody, such as an IgG1 or IgG4 antibody, or variants thereof.

In some embodiments according to any one of the antibody fusion protein described above, the antibody is monospecific.

In some embodiments according to any one of the antibody fusion protein described above, the antibody is multispecific (e.g., bispecific).

In some embodiments according to any one of the antibody fusion protein described above, the antibody specifically recognizes an immune checkpoint molecule. In some embodiments, the immune checkpoint molecule is a stimulatory immune checkpoint molecule. In some embodiments, the immune checkpoint molecule is an inhibitory immune checkpoint molecule. In some embodiments, the inhibitory immune checkpoint molecule is selected from the group consisting of PD-1, PD-L1, PD-L2, CD47, CXCR4, CSF1R, LAG-3. TIM-3, HHLA2, BTLA, CTLA-4, TIGIT, VISTA, B7-H4, CD160, 2B4, and CD73. In some embodiments, the inhibitory immune checkpoint molecule is PD-1. In some embodiments, the antibody comprises heavy chain-CDR1 (HC-CDR1), HC-CDR2, and HC-CDR3 of a heavy chain comprising the amino acid sequence of SEQ ID NO: 12; and/or light chain-CDR1 (LC-CDR1), LC-CDR2, and LC-CDR3 of a light chain comprising the amino acid sequence of SEQ ID NO: 13. In some embodiments, the antibody comprises a heavy chain comprising the amino acid sequence of SEQ ID NO: 12, and a light chain comprising the amino acid sequence of SEQ ID NO: 13. In some embodiments, the antibody is pembrolizumab (e.g., Keytruda®) or antigen-binding fragments thereof. In some embodiments, the antibody fusion protein comprises a heavy chain comprising the amino acid sequence of SEQ ID NO: 12, and a light chain fusion polypeptide comprising the amino acid sequence of SEQ ID NO: 14. In some embodiments, the antibody comprises HC-CDR1, HC-CDR2, and HC-CDR3 of a heavy chain comprising the amino acid sequence of SEQ ID NO: 15; and/or LC-CDR1, LC-CDR2, and LC-CDR3 of a light chain comprising the amino acid sequence of SEQ ID NO: 16. In some embodiments, the antibody comprises a heavy chain comprising the amino acid sequence of SEQ ID NO: 15, and a light chain comprising the amino acid sequence of SEQ ID NO: 16. In some embodiments, the antibody is nivolumab (e.g., Opdivo®) or antigen-binding fragments thereof. In some embodiments, the antibody fusion protein comprises a heavy chain comprising the amino acid sequence of SEQ ID NO: 15, and a light chain fusion polypeptide comprising the amino acid sequence of SEQ ID NO: 17. In some embodiments, the inhibitory immune checkpoint molecule is PD-L1. In some embodiments, the antibody comprises HC-CDR1, HC-CDR2, and HC-CDR3 of a heavy chain comprising the amino acid sequence of SEQ ID NO: 18; and/or LC-CDR1, LC-CDR2, and LC-CDR3 of a light chain comprising the amino acid sequence of SEQ ID NO: 19. In some embodiments, the antibody comprises a heavy chain comprising the amino acid sequence of SEQ ID NO: 18, and a light chain comprising the amino acid sequence of SEQ ID NO: 19. In some embodiments, the antibody is atezolizumab (e.g., Tecentriq®) or antigen-binding fragments thereof. In some embodiments, the antibody fusion protein comprises a heavy chain comprising the amino acid sequence of SEQ ID NO: 18, and a light chain fusion polypeptide comprising the amino acid sequence of SEQ ID NO: 20. In some embodiments, the antibody comprises HC-CDR1, HC-CDR2, and HC-CDR3 of a heavy chain comprising the amino acid sequence of SEQ ID NO: 21; and/or LC-CDR1, LC-CDR2, and LC-CDR3 of a light chain comprising the amino acid sequence of SEQ ID NO: 22. In some embodiments, the antibody comprises a heavy chain comprising the amino acid sequence of SEQ ID NO: 21, and a light chain comprising the amino acid sequence of SEQ ID NO: 22. In some embodiments, the antibody is Durvalumab (e.g., Imfinzi®) or antigen-binding fragments thereof. In some embodiments, the antibody fusion protein comprises a heavy chain comprising the amino acid sequence of SEQ ID NO: 21, and a light chain fusion polypeptide comprising the amino acid sequence of SEQ ID NO: 23. In some embodiments, the inhibitory immune checkpoint molecule is CTLA-4. In some embodiments, the antibody comprises HC-CDR1, HC-CDR2, and HC-CDR3 of a heavy chain comprising the amino acid sequence of SEQ ID NO: 9; and/or LC-CDR1, LC-CDR2, and LC-CDR3 of a light chain comprising the amino acid sequence of SEQ ID NO: 10. In some embodiments, the antibody comprises a heavy chain comprising the amino acid sequence of SEQ ID NO: 9, and a light chain comprising the amino acid sequence of SEQ ID NO: 10. In some embodiments, the antibody is ipilimumab (e.g., Yervoy®) or antigen-binding fragments thereof. In some embodiments, the antibody fusion protein comprises a heavy chain comprising the amino acid sequence of SEQ ID NO: 9, and a light chain fusion polypeptide comprising the amino acid sequence of SEQ ID NO: 11.

In some embodiments according to any one of the antibody fusion protein described above, the antibody specifically recognizes a tumor antigen. In some embodiments, the tumor antigen is HER2. In some embodiments, the antibody comprises HC-CDR1, HC-CDR2, and HC-CDR3 of a heavy chain comprising the amino acid sequence of SEQ ID NO: 24; and/or LC-CDR1, LC-CDR2, and LC-CDR3 of a light chain comprising the amino acid sequence of SEQ ID NO: 25. In some embodiments, the antibody comprises a heavy chain comprising the amino acid sequence of SEQ ID NO: 24, and a light chain comprising the amino acid sequence of SEQ ID NO: 25. In some embodiments, the antibody is trastuzumab (e.g., Herceptin®) or antigen-binding fragments thereof. In some embodiments, the antibody fusion protein comprises a heavy chain comprising the amino acid sequence of SEQ ID NO: 24, and a light chain fusion polypeptide comprising the amino acid sequence of SEQ ID NO: 26, 27, or 28. In some embodiments, the tumor antigen is EGFR (HER1). In some embodiments, the antibody comprises HC-CDR1. HC-CDR2, and HC-CDR3 of a heavy chain comprising the amino acid sequence of SEQ ID NO: 29 and/or LC-CDR1, LC-CDR2, and LC-CDR3 of a light chain comprising the amino acid sequence of SEQ ID NO: 30. In some embodiments, the antibody comprises a heavy chain comprising the amino acid sequence of SEQ ID NO: 29, and a light chain comprising the amino acid sequence of SEQ ID NO: 30. In some embodiments, the antibody is Cetuximab (e.g., Erbitux®) or antigen-binding fragments thereof. In some embodiments, the antibody fusion protein comprises a heavy chain comprising the amino acid sequence of SEQ ID NO: 29, and a light chain fusion polypeptide comprising the amino acid sequence of SEQ ID NO: 31.

In some embodiments according to any one of the antibody fusion protein described above, the antibody specifically recognizes an angiogenic factor. In some embodiments, the angiogenic factor is Angiopoietin-2 (Ang2). In some embodiments, the antibody comprises HC-CDR1, HC-CDR2, and HC-CDR3 of a heavy chain comprising the amino acid sequence of SEQ ID NO: 35; and/or LC-CDR1, LC-CDR2, and LC-CDR3 of a light chain comprising the amino acid sequence of SEQ ID NO: 36. In some embodiments, the antibody comprises a heavy chain comprising the amino acid sequence of SEQ ID NO: 35, and a light chain comprising the amino acid sequence of SEQ ID NO: 36. In some embodiments, the antibody is Nesvacumab or antigen-binding fragments thereof. In some embodiments, the antibody fusion protein comprises a heavy chain comprising the amino acid sequence of SEQ ID NO: 35, and a light chain fusion polypeptide comprising the amino acid sequence of SEQ ID NO: 37. In some embodiments, the angiogenic factor is TNFα. In some embodiments, the antibody comprises HC-CDR1, HC-CDR2, and HC-CDR3 of a heavy chain comprising the amino acid sequence of SEQ ID NO: 32; and/or LC-CDR1, LC-CDR2, and LC-CDR3 of a light chain comprising the amino acid sequence of SEQ ID NO: 33. In some embodiments, the antibody comprises a heavy chain comprising the amino acid sequence of SEQ ID NO: 32, and a light chain comprising the amino acid sequence of SEQ ID NO: 33. In some embodiments, the antibody is Adalimumab (e.g., Humira®) or antigen-binding fragments thereof. In some embodiments, the antibody fusion protein comprises a heavy chain comprising the amino acid sequence of SEQ ID NO: 32, and a light chain fusion polypeptide comprising the amino acid sequence of SEQ ID NO: 34. In some embodiments, the angiogenic factor is IL-17a. In some embodiments, the antibody comprises HC-CDR1, HC-CDR2, and HC-CDR3 of a heavy chain comprising the amino acid sequence of SEQ ID NO: 38; and/or LC-CDR1, LC-CDR2, and LC-CDR3 of a light chain comprising the amino acid sequence of SEQ ID NO: 39. In some embodiments, the antibody comprises a heavy chain comprising the amino acid sequence of SEQ ID NO: 38, and a light chain comprising the amino acid sequence of SEQ ID NO: 39. In some embodiments, the antibody is Ixekizumab (e.g., Taltz®) or antigen-binding fragments thereof. In some embodiments, the antibody fusion protein comprises a heavy chain comprising the amino acid sequence of SEQ ID NO: 38, and a light chain fusion polypeptide comprising the amino acid sequence of SEQ ID NO: 40.

Further provided is a pharmaceutical composition comprising any one of the antibody fusion protein described above, and an optional pharmaceutical acceptable carrier.

Another aspect of the present application provides a method of treating an individual having cancer, comprising administering to the individual an effective amount of any one of the pharmaceutical composition or antibody fusion protein described above. In some embodiments, the cancer is a solid tumor. In some embodiments, the cancer is lung cancer, liver cancer, skin cancer (e.g., melanoma), breast cancer, ovarian cancer, prostate cancer, colorectal cancer, or bladder cancer. In some embodiments, the method further comprises subjecting the individual to an additional cancer therapy. In some embodiments, the pharmaceutical composition or antibody fusion protein is administered systemically, such as intravenously (i.v.). In some embodiments, the pharmaceutical composition or antibody fusion protein is administered locally, such as intratumorally. In some embodiments, the individual is a human.

Another aspect of the present application provides a method of treating an individual having non-neoplastic disorders, comprising administering to the individual an effective amount of any one of the pharmaceutical composition or antibody fusion protein described above. In some embodiments, the non-neoplastic disorder is associated with VEGF overexpression. In some embodiments, the non-neoplastic disorder is selected from rheumatoid arthritis, psoriasis, atherosclerosis, hemangiomas, immune rejection of transplanted corneal tissue and other tissues, chronic inflammation, and ocular neovascular disorders. In some embodiments, the pharmaceutical composition is administered systemically, such as intravenously (i.v.). In some embodiments, the non-neoplastic disorder is an ocular neovascular disorder, such as AMD or diabetic retinopathy. In some embodiments, the ocular neovascular disorder is associated with choroidal neovascularization, vascular leak, and/or retinal edema. In some embodiments, the administration of the pharmaceutical composition or antibody fusion protein is selected from one of eye drops, subconjunctival injection, subconjunctival implant, intravitreal injection, intravitreal implant, sub-Tenon's injection, and sub-Tenon's implant, such as intravitreal injection. In some embodiments, the individual is a human.

Further provided is an isolated nucleic acid encoding any one of the antibody fusion protein described above; a vector comprising any one of the isolated nucleic acid described above; an isolated host cell comprising any one of the isolated nucleic acid or vector described above: a kit comprising any one of the antibody fusion protein, isolated nucleic acid, vector, or isolated host cell described above.

Another aspect of the present application provides a method of producing any one of the antibody fusion protein described above, comprising culturing a host cell comprising any one of the isolated nucleic acid or vector described above, or culturing any one of the isolated host cell described above, under conditions effective to express the encoded antibody fusion protein; and obtaining the expressed antibody fusion protein from said host cell. In some embodiments, the method further comprises producing a host cell comprising any one of the isolated nucleic acid or vector described above.

DETAILED DESCRIPTION OF THE INVENTION

Figure 1:
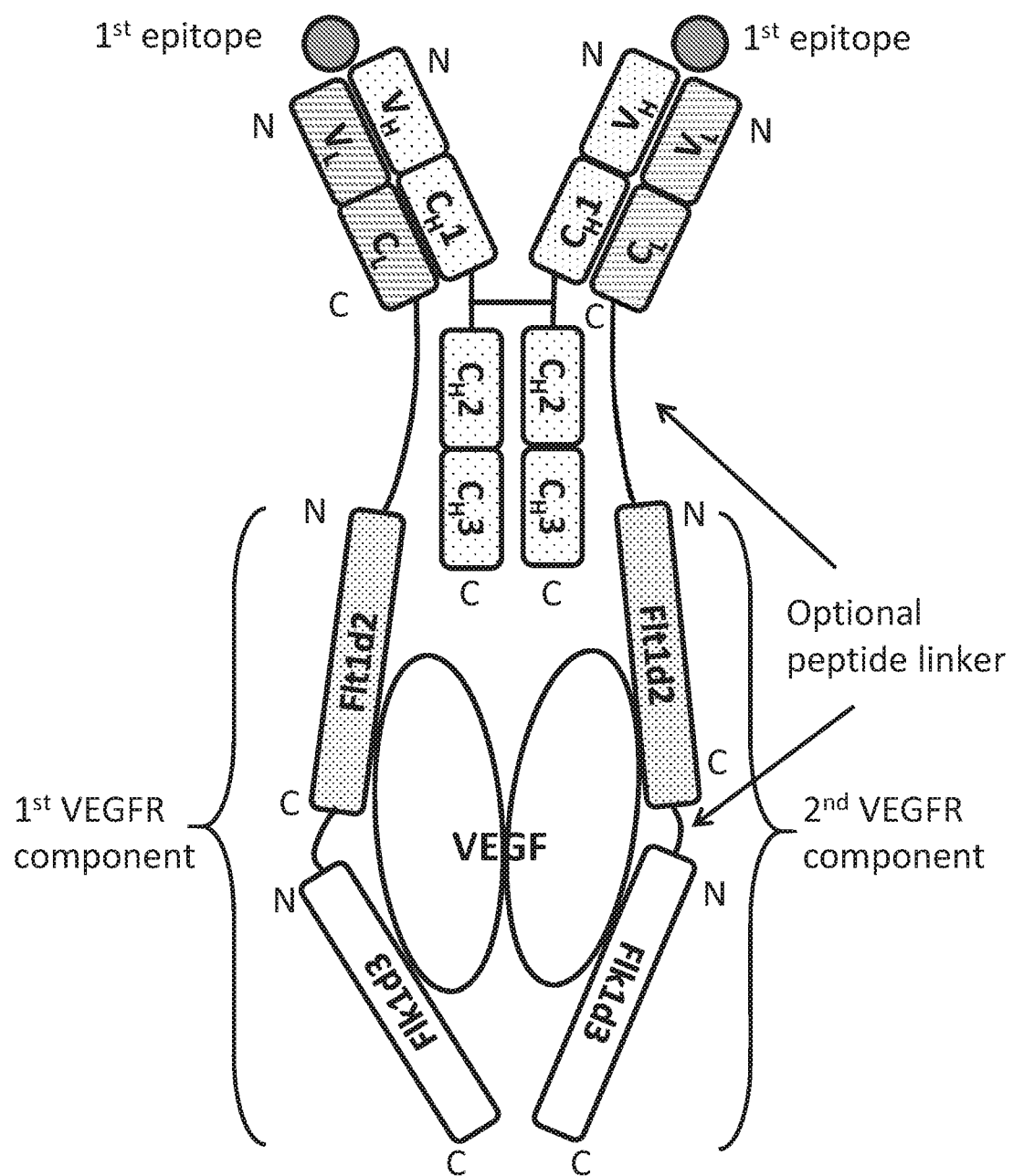
FIG. 1 depicts an exemplary VEGFR-antibody light chain fusion protein, comprising a monospecific full-length antibody and two VEGFR components, wherein each VEGFR component is fused to the C-terminus of each light chain of the antibody light chain. In alternative formats, the two VEGFR components can be different, can comprise three or more Ig-like domains, and/or can comprise any Ig-like domains of either Flt-1 or Flk-1.

The present invention provides an antibody fusion protein comprising a VEGFR component fused to the C-terminus of the antibody light chain (referred to hereinafter as "VEGFR-antibody light chain fusion protein"), methods of making, and uses thereof for treating diseases such as cancer and non-neoplastic disorders (such as ocular neovascular disorder, e.g. diabetic retinopathy and AMD).

The VEGFR-antibody light chain fusion protein described herein can have high stability with substantially no aggregation, increased serum half-life and subcutaneous bioavailability, retains ADCC and CDC activities, which enables delivery of an antibody fusion protein more effectively and at lower dosages, for example, compared to antibodies having a C-terminal fusion on the heavy chain. The VEGFR-antibody light chain fusion protein described herein can also retain high binding affinity to both VEGF and the antigen recognized by the parental antibody.

Accordingly, one aspect of the present application provides an antibody fusion protein comprising 1) an antibody comprising a light chain, and 2) a VEGFR component, wherein the VEGFR component is fused to the C-terminus of the antibody light chain (e.g., C-terminus of antibody $V_L$-$C_L$ domain).

Also provided are compositions (such as pharmaceutical compositions), kits and articles of manufacture comprising the VEGFR-antibody light chain fusion protein, methods of making thereof, and methods of treating disease (such as cancer, non-neoplastic disorders, e.g. ocular neovascular disorders) using the VEGFR-antibody light chain fusion protein.

I. Definitions

As used herein, "angiogenesis," "angiogenic," or "neovascularization" refers to formation, growth, and/or development of new blood vessels.

The term "neovascular disorder" used herein refers to a disorder characterized by altered or unregulated angiogenesis other than one accompanying oncogenic or neoplastic transformation, i.e., cancer. Examples of neovascular disorders include psoriasis, rheumatoid arthritis, and ocular neovascular disorders such as diabetic retinopathy and AMD.

The term "ocular neovascular disorder" used herein refers to a disorder characterized by altered or unregulated angiogenesis in the eye of a patient. Exemplary ocular neovascular disorders include optic disc neovascularization, iris neovascularization, retinal neovascularization (RNV), choroidal neovascularization (CNV), corneal neovascularization, vitreal neovascularization, glaucoma, pannus, pterygium, macular edema, diabetic retinopathy, diabetic macular edema, AMD, vascular retinopathy, retinal degeneration, uveitis, inflammatory diseases of the retina, and proliferative vitreoretinopathy.

"Choroidal neovascularization" (CNV) refers to the abnormal development, proliferation, and/or growth of blood vessels arising from the choriocapillaris. The blood vessels typically extend through Bruch's membrane, RPE layer, and/or subretinal space.

"Macular degeneration related condition" refers to any of a number of disorders and conditions in which the macula degenerates or loses functional activity. The degeneration or loss of functional activity can arise as a result of, for example, cell death, decreased cell proliferation, and/or loss of normal biological function. Macular degeneration can lead to and/or manifest as alterations in the structural integrity of the cells and/or extracellular matrix of the macula, alteration in normal cellular and/or extracellular matrix architecture, and/or the loss of function of macular cells. The cells can be any cell type normally present in or near the macula including RPE cells, photoreceptors, and/or capillary endothelial cells. AMD is the major macular degeneration related condition. Others include Best macular dystrophy, Sorsby fundus dystrophy, Mallatia Leventinese and Doyne honeycomb retinal dystrophy.

"Ocular implant" refers to a device or structure that has appropriate dimensions, shape, and/or configuration and is made of appropriate materials so that it may be placed in the eye without causing unacceptable interference with the physiology or functioning of the eye. Preferably placement of an ocular implant does not significantly disrupt vision. An ocular implant is typically a solid or semi-solid article of manufacture and is typically macroscopic, i.e., visible with the naked eye.

The terms "angiogenesis inhibitor" and "antiangiogenic agent" are used interchangeably herein to refer to agents that are capable of inhibiting or reducing one or more processes associated with angiogenesis including, but not limited to, endothelial cell proliferation, endothelial cell survival, endothelial cell migration, differentiation of precursor cells into endothelial cells, and capillary tube formation.

As used herein, the term "immune checkpoint inhibitor" refers to a molecule that totally or partially reduces, inhibits or interferes with one or more inhibitory immune checkpoint molecules, which can inhibit T-cell activation and function.

As used herein, the term "activator of a stimulatory immune checkpoint molecule" refers to a molecule that stimulates, activates, or increases the intensity of an immune response mediated by stimulatory immune checkpoint molecules.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer or ocular neovascular disorder. The methods of the invention contemplate any one or more of these aspects of treatment.

The term "prevent," and similar words such as "prevented," "preventing" etc., indicate an approach for preventing, inhibiting, or reducing the likelihood of the recurrence of, a disease or condition, e.g., cancer, neovascular disorder (such as ocular neovascular disorder). It also refers to delaying the recurrence of a disease or condition or delaying the recurrence of the symptoms of a disease or condition. As used herein, "prevention" and similar words also includes reducing the intensity, effect, symptoms and/or burden of a disease or condition prior to recurrence of the disease or condition.

As used herein. "delaying" the development of cancer or neovascular disorder (such as ocular neovascular disorder) means to defer, hinder, slow, retard, stabilize, and/or postpone development of the disease. This delay can be of varying lengths of time, depending on the history of the disease and/or individual being treated. A method that "delays" development of cancer or neovascular disorder (such as ocular neovascular disorder) is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer or neovascular disorder (such as ocular neovascular disorder) progression that may be initially undetectable and includes occurrence, recurrence, and onset.

The term "effective amount" used herein refers to an amount of an agent or a combination of agents, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. In reference to ocular neovascular disorder, an effective amount comprises an amount sufficient to treat, suppress, delay and/or prevent a neovascular disorder or symptom thereof, e.g., an amount sufficient to achieve one or more of the following: (i) inhibit or prevent drusen formation; (ii) cause a reduction in drusen number and/or size (drusen regression); (iii) cause a reduction in or prevent lipofuscin deposits; (iv) inhibit or prevent visual loss or slow the rate of visual loss; (v) inhibit choroidal neovascularization or slow the rate of choroidal neovascularization; (vi) cause a reduction in size and/or number of lesions characterized by choroidal neovascularization; (vii) inhibit choroidal neovascularization or slow the rate of retinal neovascularization; (viii) cause a reduction in size and/or number of lesions characterized by retinal neovascularization; (ix) improve visual acuity and/or contrast sensitivity; (x) reduce macular edema and/or reduce abnormal macular thickness; (xi) inhibit or prevent photoreceptor or RPE cell atrophy or apoptosis, or reduce the rate of photoreceptor or RPE cell atrophy or apoptosis; (xii) inhibit or prevent progression of non-exudative macular degeneration to exudative macular degeneration.

As used herein, an "individual" or a "subject" refers to a mammal, including, but not limited to, human, bovine, horse, feline, canine, rodent, or primate. In some embodiments, the individual is a human.

The term "antibody" or "antibody moiety" is used in the broadest sense and encompasses various antibody structures, including but not limited to monoclonal antibodies, multispecific antibodies (e.g., bispecific antibodies), full-length antibodies and antigen-binding fragments thereof, so long as they exhibit the desired antigen-binding activity.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen-binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The V is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgA2.

An "isolated" antibody (or construct) is one that has been identified, separated and/or recovered from a component of its production environment (e.g., natural or recombinant). Preferably, the isolated polypeptide is free of association with all other components from its production environment.

Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator; or (3) to homogeneity by SDS-PAGE under non-reducing or reducing conditions using Coomassie Blue or, preferably, silver stain. Isolated antibody (or construct) includes the antibody in situ within recombinant cells since at least one component of the antibody's natural environment will not be present. Ordinarily, however, an isolated polypeptide, antibody, or construct will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called complementary determining regions (CDRs) or hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press. $2^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al, *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The terms "full-length antibody", "intact antibody", or "whole antibody" are used interchangeably to refer to an antibody in its substantially intact form, as opposed to an antibody fragment. Specifically, full-length 4-chain antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include, but are not limited to Fab, Fab', F(ab')$_2$ and Fv fragments; diabodies; DART; linear antibodies (see U.S. Pat. No. 5,641,870, Example 2; Zapata et al., *Protein Eng.* 8(10): 1057-1062 (1995)); single-chain antibody molecules (such as scFv), and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy-terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

The term "constant domain" refers to the portion of an immunoglobulin molecule having a more conserved amino acid sequence relative to the other portion of the immunoglobulin, the variable domain, which contains the antigen-binding site. The constant domain contains the $C_H1$, $C_H2$ and $C_H3$ domains (collectively, CH) of the heavy chain and the CHL (or $C_L$) domain of the light chain.

The "light chains" of antibodies (immunoglobulins) from any mammalian species can be assigned to one of two clearly distinct types, called kappa ("κ") and lambda ("λ"), based on the amino acid sequences of their constant domains.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies described herein comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*. 81:6851-6855 (1984)). "Humanized antibody" is used as a subset of "chimeric antibodies".

"Humanized" forms of non-human (e.g., llama or camelid) antibodies are chimeric antibodies that contain minimal sequence derived from non-human immunoglobulin. In some embodiments, a humanized antibody is a human immunoglobulin (recipient antibody) in which residues from an CDR (hereinafter defined) of the recipient are replaced by residues from an CDR of a non-human species (donor antibody) such as mouse, rat, rabbit, camel, llama, alpaca, or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy. Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.* 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE® technology). See also, for example, Li et al., *Proc. Natl. Acad.*

Sci. USA, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, single-domain antibodies comprise three HVRs (or CDRs): HVR1 (or CDR1), HVR2 (or CDR2), and HVR3 (or CDR3). HVR3 (or CDR3) displays the most diversity of the three HVRs, and is believed to play a unique role in conferring fine specificity to antibodies. See, e.g., Hamers-Casterman et al., *Nature* 363:446-448 (1993): Sheriff et al., *Nature Struct. Biol.* 3:733-736 (1996).

The term "Complementarity Determining Region" or "CDR" are used to refer to hypervariable regions as defined by the Kabat system. See Kabat et al., *Sequences of Proteins of Immunological Interest*, 5th Ed. Public Health Service, National Institutes of Health, Bethesda, Md. (1991).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below in Table 1.

TABLE 1

HVR delineations.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
|  |  | (Kabat Numbering) |  |  |
| H1 | H31-H35 | H26-H35 | H26-H32 | H30-H35 |
|  |  | (Chothia Numbering) |  |  |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The expression "variable-domain residue-numbering as in Kabat" or "amino-acid-position numbering as in Kabat." and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al. *Sequences of Proteins of Immunological Interest.* 5$^{th}$ Ed. Public Health Service, National Institutes of Health, Bethesda, Md. (1991). Examples include for the $V_L$, the subgroup may be subgroup kappa 1, kappa II, kappa III or kappa IV as in Kabat et al., supra. Additionally, for the VH, the subgroup may be subgroup I, subgroup II, or subgroup III as in Kabat et al. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less. 7 or less. 6 or less, 5 or less, 4 or less, 3 or less, or 2 or less.

An "affinity-matured" antibody is one with one or more alterations in one or more CDRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by $V_H$- and $V_L$-domain shuffling. Random mutagenesis of CDR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds," "specifically recognizes," or is "specific for" refers to measurable and reproducible interactions such as binding between a target and an antigen binding protein, which is determinative of the presence of the target in the presence of a heterogeneous population of molecules including biological molecules. For example, an antigen binding protein that specifically binds a target (which can be an epitope) is an antigen binding protein that binds this target with greater affinity, avidity, more readily, and/or with greater duration than it binds other targets. In some embodiments, the extent of binding of an antigen binding protein to an unrelated target is less than about 10% of the binding of the antigen binding protein to the target as measured, e.g., by a radioimmunoassay (RIA). In some embodiments, an antigen binding protein that specifically binds a target, or the VEGFR component that specifically binds VEGF, has a dissociation constant ($K_d$) of ≤$10^{-5}$ M, ≤$10^{-6}$ M, ≤$10^{-7}$ M, ≤$10^{-8}$ M, ≤$10^{-9}$ M, ≤$10^{-10}$ M, ≤$10^{-11}$ M, or $10^{-12}$ M. In some embodiments, an antigen binding protein specifically binds an epitope on a protein that is conserved among the protein from different species. In some embodiments, specific binding can include, but does not require exclusive binding.

The term "specificity" refers to selective recognition of an antigen binding protein for a particular epitope of an antigen. Natural antibodies, for example, are monospecific. The term "multispecific" as used herein denotes that an antigen binding protein has polyepitopic specificity (i.e., is capable of specifically binding to two, three, or more, different epitopes on one biological molecule or is capable of specifically binding to epitopes on two, three, or more, different biological molecules). "Bispecific" as used herein denotes that an antigen binding protein has two different antigen-binding specificities. Unless otherwise indicated, the order in which the antigens bound by a bispecific antibody listed is arbitrary. The term "monospecific" as used herein denotes an antigen binding protein that has one or more binding sites each of which bind the same epitope of the same antigen.

The term "valent" as used herein denotes the presence of a specified number of binding sites in an antigen binding protein. A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein.

"Antibody effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%. 96%, 97%, 98%, 99%) from the wild type or unmodified antibody. The determination of antibody effector function is readily determinable and measurable by one of ordinary skill in the art. In a preferred embodiment, the antibody effector functions of complement binding, complement dependent cytotoxicity and antibody dependent cytotoxicity are affected. In some embodiments, effector function is eliminated through a mutation in the constant region that eliminated glycosylation, e.g., "effector-less mutation." In one aspect, the effector-less mutation is an N297A or DANA mutation (D265A+N297A) in the $C_H2$ region. Shields et al., *J. Biol. Chem.* 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., *E. coli.*) or in which result in an altered glycosylation pattern that is ineffective or less effective at promoting effector function (e.g., Shinkawa et al., *J. Biol. Chem.* 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202: 163 (1996), may be performed. Antibody variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

"Binding affinity" generally refers to the strength of the sum total of non-covalent interactions between a single binding site of a molecule (e.g., an antibody, VEGFR) and its binding partner (e.g., an antigen, VEGF). Unless indicated otherwise, as used herein, "binding affinity" refers to intrinsic binding affinity that reflects a 1:1 interaction between members of a binding pair. Binding affinity can be indicated by $K_d$, $K_{off}$, $K_{on}$, or $K_a$. The term as used herein, is intended to refer to the off rate constant for dissociation of an antibody (or antigen-binding domain) from the antibody/antigen complex (or for dissociation of VEGFR from the VEGF/VEGFR complex), as determined from a kinetic selection set up, expressed in units of $s^{-1}$. The term "$K_{on}$", as used herein, is intended to refer to the on rate constant for association of an antibody (or antigen-binding domain) to the antigen to form the antibody/antigen complex (or for association of VEGFR to VEGF to form the VEGFR/VEGF complex), expressed in units of $M^{-1}s^{-1}$. The term equilibrium dissociation constant "$K_D$" or "$K_d$", as used herein, refers to the dissociation constant of a particular antibody-antigen interaction (or VEGFR-VEGF interaction), and describes the concentration of antigen required to occupy one half of all of the antibody-binding domains present in a solution of antibody molecules at equilibrium (or the concentration of VEGF required to occupy one half of all of the VEGFR present in a solution of VEGFR at equilibrium), and is equal to $K_{off}/K_{on}$, expressed in units of M. The measurement of $K_d$ presupposes that all binding agents are in solution. In the case where the antibody is tethered to a cell wall, e.g., in a yeast expression system, the corresponding equilibrium rate constant is expressed as EC50, which gives a good approximation of $K_d$. The affinity constant, $K_a$, is the inverse of the dissociation constant. $K_d$, expressed in units of $M^{-1}$.

The dissociation constant ($K_D$ or $K_d$) is used as an indicator showing affinity of antibodies to antigens (or VEGFR to VEGF). For example, easy analysis is possible by the Scatchard method using antibodies marked with a variety of marker agents, as well as by using BiacoreX (made by Amersham Biosciences), which is an over-the-counter, measuring kit, or similar kit, according to the users manual and experiment operation method attached with the kit. The $K_D$ value that can be derived using these methods is expressed in units of M (Mols). An antibody or antigen-binding fragment thereof that specifically binds to a target (or a VEGFR component described herein that specifically binds to VEGF) may have a dissociation constant ($K_d$) of, for example, $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M.

Binding specificity of the antibody or antigen-binding domain (or VEGFR component described herein) can be determined experimentally by methods known in the art. Such methods comprise, but are not limited to Western blots, ELISA-, RIA-, ECL-, IRMA-, EIA-, BiAcore-tests and peptide scans.

Half maximal inhibitory concentration ($IC_{50}$) is a measure of the effectiveness of a substance (such as an antibody or VEGFR) in inhibiting a specific biological or biochemical function. It indicates how much of a particular drug or other substance (inhibitor, such as an antibody or VEGFR) is needed to inhibit a given biological process, or component of a process, i.e. an enzyme, cell, cell receptor or microorganism) by half. The values are typically expressed as molar concentration. $IC_{50}$ is comparable to an $EC_{50}$ for agonist drug or other substance (such as an antibody). $EC_{50}$ also represents the plasma concentration required for obtaining 50% of a maximum effect in vivo. As used herein, an "$IC_{50}$" is used to indicate the effective concentration of an antibody needed to neutralize 50% of the antigen bioactivity (or the effective concentration of VEGFR component needed to neutralize 50% of the VEGF bioactivity) in vitro. $IC_{50}$ or $EC_{50}$ can be measured by bioassays such as inhibition of ligand binding by FACS analysis (competition binding assay), cell based cytokine release assay, or amplified luminescent proximity homogeneous assay (AlphaLISA).

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

"Biocompatible" refers to a material that is substantially nontoxic to a recipient's cells in the quantities and at the location used, and does not elicit or cause a significant deleterious or untoward effect on the recipient's body at the location used, e.g., an unacceptable immunological or inflammatory reaction, unacceptable scar tissue formation, etc. For example, a material that is biocompatible with the eye does not substantially interfere with the physiology or function of the eye.

"Bioerodible" or "biodegradable" means that a material is capable of being broken down physically and/or chemically within cells or within the body of a subject, e.g., by hydrolysis under physiological conditions and/or by natural biological processes such as the action of enzymes present within cells or within the body, and/or by processes such as dissolution, dispersion, etc., to form smaller chemical species which can typically be metabolized and, optionally, used by the body, and/or excreted or otherwise disposed of. Preferably a biodegradable compound is biocompatible. A polymer whose molecular weight decreases over time in vivo due to a reduction in the number of monomers is considered biodegradable.

The term "pharmaceutical formulation" of "pharmaceutical composition" refers to a preparation that is in such form as to permit the biological activity of the active ingredient to be effective, and that contains no additional components that are unacceptably toxic to a subject to which the formulation would be administered. Such formulations are sterile. A "sterile" formulation is aseptic or free from all living microorganisms and their spores.

It is understood that embodiments of the invention described herein (such as "comprising" embodiments) include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Antibody Fusion Protein Comprising VEGFR Component Fused to the C-Terminus of Antibody Light Chain The antibody fusion protein described herein comprises 1) an antibody comprising a light chain, and 2) a VEGFR component, wherein the VEGFR component is fused to the C-terminus of the antibody light chain (e.g., C-terminus of antibody $V_L$-$C_L$ domain).

In some embodiments, there is provided an antibody fusion protein comprising 1) an antibody (such as a full length antibody) comprising a light chain, and 2) a VEGFR component fused to the C-terminus of the antibody light chain (e.g., C-terminus of antibody $V_L$-$C_L$ domain). In some embodiments, the VEGFR component comprises an immunoglobulin-like (Ig-like) domain 2 of a first VEGFR Flt-1 (Flt1d2). In some embodiments, the VEGFR component further comprises an Ig-like domain 3 of a second VEGFR Flk-1 (Flk1d3). In some embodiments, the VEGFR component further comprises an Ig-like domain 4 of a third VEGFR Flk1 (Flk1d4). In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component consists essentially of from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component consists essentially of from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the $K_D$ of the binding between the VEGFR component and VEGF is about $10^{-8}$ M to about $10^{-13}$ M (such as about 10–8 M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the VEGFR component and the C-terminus of the antibody light chain are connected by a linker (such as a peptide linker comprising amino acid sequence of SEQ ID NO: 6 or 7). In some embodiments, the antibody is selected from the group consisting of IgA, IgD, IgE, IgG, IgM, IgG-derived molecules, Fab, Fab', F(ab')2, Fab-scFv, F(ab')2-scFv2, Fab-scFv-Fc, Dock and Lock, scFv, di-scFv, diabody, Diabody-Fc, Diabody-$CH_3$, and intrabody. In some embodiments, the antibody comprises a light chain constant domain ($C_L$ domain), and the VEGFR component is fused to the C-terminus of the antibody $C_L$ domain (e.g., C-terminus of antibody $V_L$-$C_L$ domain). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (such as bispecific). In some embodiments, the antibody specifically recognizes an immune checkpoint molecule. In some embodiments, the immune checkpoint molecule is a stimulatory immune checkpoint molecule. In some embodiments, the immune checkpoint molecule is an inhibitory immune checkpoint molecule (such as PD-1, PD-L, PD-L2, CD47, CXCR4, CSF1R, LAG-3, TIM-3, HHLA2, BTLA, CTLA-4, TIGIT, VISTA, B7-H4, CD160, 2B4, and CD73). In some embodiments, the antibody specifically recognizes PD-1. In some embodiments, the antibody comprises HC-CDR1 HC-CDR2, and HC-CDR3 of a heavy chain comprising the amino acid sequence of SEQ ID NO: 12; and/or LC-CDR1, LC-CDR2, and LC-CDR3 of a light chain comprising the amino acid sequence of SEQ ID NO: 13. In some embodiments, the antibody comprises a heavy chain comprising the amino acid sequence of SEQ ID NO: 12, and a light chain comprising the amino acid sequence of SEQ ID NO: 13. In some embodiments, the antibody is pembrolizumab (e.g., Keytruda®) or antigen-binding fragments thereof. In some embodiments, the antibody binds to PD-1 competitively with pembrolizumab (e.g., Keytruda®). In some embodiments, the antibody fusion protein comprises a heavy chain comprising the amino acid sequence of SEQ ID NO: 12, and a light chain fusion polypeptide comprising the amino acid sequence of SEQ ID NO: 14. In some embodiments, the antibody comprises HC-CDR1, HC-CDR2, and HC-CDR3 of a heavy chain comprising the amino acid sequence of SEQ ID NO: 15; and/or LC-CDR1, LC-CDR2, and LC-CDR3 of a light chain comprising the amino acid sequence of SEQ ID NO: 16. In some embodiments, the antibody comprises a heavy chain comprising the amino acid sequence of SEQ ID NO: 15, and a light chain comprising the amino acid sequence of SEQ ID NO: 16. In some embodiments, the antibody is nivolumab (e.g., Opdivo®) or antigen-binding fragments thereof. In some embodiments, the antibody binds to PD-1 competitively with nivolumab (e.g., Opdivo®). In some embodiments, the antibody fusion protein comprises a heavy chain comprising the amino acid sequence of SEQ ID NO: 15, and a light chain fusion polypeptide comprising the amino acid sequence of SEQ ID NO: 17. In some embodiments, the antibody specifically recognizes PD-L1. In some embodiments, the antibody comprises HC-CDR1, HC-CDR2, and HC-CDR3 of a heavy chain comprising the amino acid sequence of SEQ ID NO: 18; and/or LC-CDR1, LC-CDR2, and LC-CDR3 of a light chain comprising the amino acid sequence of SEQ ID NO: 19. In some embodiments, the antibody comprises a heavy chain comprising the amino acid sequence of SEQ ID NO: 18, and a light chain comprising the amino acid sequence of SEQ ID NO: 19. In some embodiments, the antibody is atezolizumab (e.g., Tecentriq®) or antigen-binding fragments thereof. In some embodiments, the antibody binds to PD-L1 competitively with atezolizumab (e.g., Tecentriq®). In some embodiments, the antibody fusion protein comprises a heavy chain comprising the amino acid sequence of SEQ ID NO: 18, and a light chain fusion polypeptide comprising the amino acid sequence of SEQ ID NO: 20. In some embodiments, the antibody comprises HC-CDR1, HC-CDR2, and HC-CDR3 of a heavy chain comprising the amino acid sequence of SEQ ID NO: 21; and/or LC-CDR, LC-CDR2, and LC-CDR3 of a light chain comprising the amino acid sequence of SEQ ID NO: 22. In some embodiments, the antibody comprises a heavy chain comprising the amino acid sequence of SEQ ID NO: 21, and a light chain comprising the amino acid sequence of SEQ ID NO: 22. In some embodiments, the antibody is Durvalumab (e.g., Imfinzi®) or antigen-binding fragments thereof. In some embodiments, the antibody binds to PD-L1 competitively with Durvalumab (e.g., Imfinzi®). In some embodiments, the antibody fusion protein comprises a heavy chain comprising the amino acid sequence of SEQ ID NO: 21, and a light chain fusion polypeptide comprising the amino acid sequence of SEQ ID NO: 23. In some embodiments, the antibody specifically recognizes CTLA-4. In some embodiments, the antibody comprises HC-CDR1, HC-CDR2, and HC-CDR3 of a heavy chain comprising the amino acid sequence of SEQ ID NO: 9; and/or LC-CDR1, LC-CDR2, and LC-CDR3 of a light chain comprising the amino acid sequence of SEQ ID NO: 10. In some embodiments, the antibody comprises a heavy chain comprising the amino acid sequence of SEQ ID NO: 9, and a light chain comprising the amino acid sequence of SEQ ID NO: 10. In some embodiments, the antibody is ipilimumab (e.g., Yervoy®) or antigen-binding fragments thereof. In some embodiments, the antibody binds to CTLA-4 competitively with ipilimumab (e.g., Yervoy®). In some embodiments, the antibody fusion protein comprises a heavy chain comprising the amino acid sequence of SEQ ID NO: 9, and a light chain fusion polypeptide comprising the amino acid sequence of SEQ ID NO: 11. In some embodiments, the antibody specifically recognizes a tumor antigen. In some embodiments, the tumor antigen is HER2. In some embodiments, the antibody comprises HC-CDR1, HC-CDR2, and HC-CDR3 of a heavy chain comprising the amino acid sequence of SEQ ID NO: 24; and/or LC-CDR1, LC-CDR2, and LC-CDR3 of a light chain comprising the amino acid sequence of SEQ ID NO: 25. In some embodiments, the antibody comprises a heavy chain comprising the amino acid sequence of SEQ ID NO: 24, and a light chain comprising the amino acid sequence of SEQ ID NO: 25. In some embodiments, the antibody is trastuzumab (e.g., Herceptin®) or antigen-binding fragments thereof. In some embodiments, the antibody binds to HER2 competitively with trastuzumab (e.g., Herceptin®). In some embodiments, the antibody fusion protein comprises a heavy chain comprising the amino acid sequence of SEQ ID NO: 24, and a light chain fusion polypeptide comprising the amino acid sequence of SEQ ID NO: 26, 27, or 28. In some embodiments, the tumor antigen is EGFR (HER1). In some embodiments, the antibody comprises HC-CDR1, HC-CDR2, and HC-CDR3 of a heavy chain comprising the amino acid sequence of SEQ ID NO: 29; and/or LC-CDR, LC-CDR2, and LC-CDR3 of a light chain comprising the amino acid sequence of SEQ ID NO: 30. In some embodiments, the antibody comprises a heavy chain comprising the amino acid sequence of SEQ ID NO: 29, and a light chain comprising the amino acid sequence of SEQ ID NO: 30. In some embodiments, the antibody is Cetuximab (e.g., Erbitux®) or antigen-binding fragments thereof. In some embodiments, the antibody binds to EGFR competitively with Cetuximab (e.g., Erbitux®). In some embodiments, the antibody fusion protein comprises a heavy chain comprising the amino acid sequence of SEQ ID NO: 29, and a light chain fusion polypeptide comprising the amino acid sequence of SEQ ID NO: 31. In some embodiments, the antibody specifically recognizes an angiogenic factor. In some embodiments, the angiogenic factor is Ang2. In some embodiments, the antibody comprises HC-CDR1, HC-CDR2, and HC-CDR3 of a heavy chain comprising the amino acid sequence of SEQ ID NO: 35; and/or LC-CDR1. LC-CDR2, and LC-CDR3 of a light chain comprising the amino acid sequence of SEQ ID NO: 36. In some embodiments, the antibody comprises a heavy chain comprising the amino acid sequence of SEQ ID NO: 35, and a light chain comprising the amino acid sequence of SEQ ID NO: 36. In some embodiments, the antibody is Nesvacumab or antigen-binding fragments thereof. In some embodiments, the antibody binds to Ang2 competitively with Nesvacumab. In some embodiments, the antibody fusion protein comprises a heavy chain comprising the amino acid sequence of SEQ ID NO: 35, and a light chain fusion polypeptide comprising the amino acid sequence of SEQ ID NO: 37. In some embodiments, the angiogenic factor is TNFα. In some embodiments, the antibody comprises HC-CDR1, HC-CDR2, and HC-CDR3 of a heavy chain comprising the amino acid sequence of SEQ ID NO: 32; and/or LC-CDR1, LC-CDR2, and LC-CDR3 of a light chain comprising the amino acid sequence of SEQ ID NO: 33. In some embodiments, the antibody comprises a heavy chain comprising the amino acid sequence of SEQ ID NO: 32, and a light chain comprising the amino acid sequence of SEQ ID NO: 33. In some embodiments, the antibody is Adalimumab (e.g., Humira®) or antigen-binding fragments thereof. In some embodiments, the antibody binds to TNFα competitively with Adalimumab (e.g., Humira®). In some embodiments, the antibody fusion protein comprises a heavy chain comprising the amino acid sequence of SEQ ID NO: 32, and a light chain fusion polypeptide comprising the amino acid sequence of SEQ ID NO: 34. In some embodiments, the angiogenic factor is IL-17A. In some embodiments, the antibody comprises HC-CDR1, HC-CDR2, and HC-CDR3 of a heavy chain comprising the amino acid sequence of SEQ ID NO: 38; and/or LC-CDR1, LC-CDR2, and LC-CDR3 of a light chain comprising the amino acid sequence of SEQ ID NO: 39. In some embodiments, the antibody comprises a heavy chain comprising the amino acid sequence of SEQ ID NO: 38, and a light chain comprising the amino acid sequence of SEQ ID NO: 39. In some embodiments, the antibody is Ixekizumab (e.g., Taltz®) or antigen-binding fragments thereof. In some embodiments, the antibody binds to IL-17A competitively with Ixekizumab (e.g., Taltz®). In some embodiments, the antibody fusion protein comprises a heavy chain comprising the amino acid sequence of SEQ ID NO: 38, and a light chain fusion polypeptide comprising the amino acid sequence of SEQ ID NO: 40.

In some embodiments, the VEGFR-antibody light chain fusion protein described herein comprises only one VEGFR component.

In some embodiments, there is provided an antibody fusion protein comprising 1) an antibody (such as a full length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain), and the second VEGFR component is fused to the C-terminus of the second antibody light chain (e.g., C-terminus of antibody $V_L$-$C_L$ domain). In some embodiments, the first VEGFR component and the second VEGFR component are the same. In some embodiments, the first VEGFR component and the second VEGFR component are different. In some embodiments, the first and/or second VEGFR component comprises an Flt1d2. In some embodiments, the first and/or second VEGFR component further comprises an Flk1d3. In some embodiments, the first and/or second VEGFR component further comprises an Flk1d4. In some embodiments, the first and/or second VEGFR component comprises from N-terminus to C-terminus: Flt1d2-Flk1d3, wherein the N-terminus of the VEGFR component is fused to the C-terminus of antibody light chain. In some embodiments, the first and/or second VEGFR component consists essentially of from N-terminus to C-terminus: Flt1d2-Flk1d3, wherein the N-terminus of the VEGFR component is fused to the C-terminus of antibody light chain. In some embodiments, the first and/or second VEGFR component comprises an amino acid sequence of SEQ ID NO: 8. In some embodiments, the first and/or second VEGFR component comprises from N-terminus to C-terminus: Flt1d2-Flk1d3-Flk1d4, wherein the N-terminus of the VEGFR component is fused to the C-terminus of antibody light chain. In some embodiments, the first and/or second VEGFR component consists essentially of from N-terminus to C-terminus: Flt1d2-Flk1d3-Flk1d4, wherein the N-terminus of the VEGFR component is fused to the C-terminus of antibody light chain. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, at least one of the VEGFR components and the C-terminus of the antibody light chain are connected by a linker (such as a peptide linker comprising amino acid sequence of SEQ ID NO: 6 or 7). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody specifically recognizes an immune checkpoint molecule (e.g., inhibitory immune checkpoint molecule). In some embodiments, the antibody specifically recognizes PD-1 (e.g., pembrolizumab or nivolumab). In some embodiments, the antibody specifically recognizes PD-L1 (e.g., atezolizumab or durvalumab). In some embodiments, the antibody specifically recognizes CTLA-4 (e.g., ipilimumab). In some embodiments, the antibody specifically recognizes a tumor antigen. In some embodiments, the antibody specifically recognizes HER2 (e.g., trastuzumab). In some embodiments, the antibody specifically recognizes EGFR (HER1) (e.g., cetuximab). In some embodiments, the antibody specifically recognizes an angiogenic factor. In some embodiments, the antibody specifically recognizes Ang2 (e.g., nesvacumab). In some embodiments, the antibody specifically recognizes TNFα (e.g., adalimumab). In some embodiments, the antibody specifically recognizes IL-17A (e.g., ixekizumab).

In some embodiments, there is provided an antibody fusion protein comprising 1) an antibody (such as a full length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain), and the second VEGFR component is fused to the C-terminus of the second antibody light chain (e.g., C-terminus of antibody $V_L$-$C_L$ domain), wherein the first and second VEGFR component each comprises an amino acid sequence of SEQ ID NO: 8. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, at least one of the VEGFR components and the C-terminus of the antibody light chain are connected by a linker (such as a peptide linker comprising amino acid sequence of SEQ ID NO: 6 or 7). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody specifically recognizes an immune checkpoint molecule (e.g., inhibitory immune checkpoint molecule). In some embodiments, the antibody specifically recognizes PD-1 (e.g., pembrolizumab or nivolumab). In some embodiments, the antibody specifically recognizes PD-L1 (e.g., atezolizumab or durvalumab). In some embodiments, the antibody specifically recognizes CTLA-4 (e.g., ipilimumab). In some embodiments, the antibody specifically recognizes a tumor antigen. In some embodiments, the antibody specifically recognizes HER2 (e.g., trastuzumab). In some embodiments, the antibody specifically recognizes EGFR (HER1) (e.g., cetuximab). In some embodiments, the antibody specifically recognizes an angiogenic factor. In some embodiments, the antibody specifically recognizes Ang2 (e.g., nesvacumab). In some embodiments, the antibody specifically recognizes TNFα (e.g., adalimumab). In some embodiments, the antibody specifically recognizes IL-17A (e.g., ixekizumab).

In some embodiments, the VEGFR component and the C-terminus of the antibody light chain are connected by a linker. In some embodiments, the linker is a peptide linker (e.g., any one of SEQ ID NOs: 1-7 and 44). In some embodiments, the linker comprises an amino acid sequence of SEQ ID NO: 6 or 7. In some embodiments, at least one of the two VEGFR components and the two C-terminus of the antibody light chains are connected by a linker. In some embodiments, both VEGFR components and the two C-terminus of the antibody light chains are connected by linkers. In some embodiments, the two linkers are the same. In some embodiments, the two linkers are different.

In some embodiments, the VEGFR-antibody light chain fusion protein described herein comprises an antibody that specifically recognizes an immune checkpoint molecule. In some embodiments, the antibody specifically recognizes a stimulatory immune checkpoint molecule. In some embodiments, the antibody specifically recognizes an inhibitory immune checkpoint molecule (such as PD-1, PD-L1, PD-L2, CD47, CXCR4, CSF1R, LAG-3, TIM-3, HHLA2, BTLA, CTLA-4, TIGIT, VISTA, B7-H4, CD160, 2B4, and CD73) (the antibody is hereinafter referred to as "immune checkpoint inhibitor" or "inhibitor of inhibitory immune checkpoint molecule"). In some embodiments, the antibody specifically recognizes PD-1 (e.g., pembrolizumab or nivolumab). In some embodiments, the antibody specifically recognizes PD-L1 (e.g., atezolizumab or durvalumab). In some embodiments, the antibody specifically recognizes CTLA-4 (e.g., ipilimumab).

For example, in some embodiments, there is provided an antibody fusion protein comprising 1) an antibody (such as a full length antibody) specifically recognizing an immune checkpoint molecule (such as PD-1, PD-L1, or CTLA-4) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7). In some embodiments, linker X and linker Y are the same. In some embodiments, linker X and linker Y are different. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, there is provided an antibody fusion protein comprising 1) an antibody (such as a full length antibody) specifically recognizing an immune checkpoint molecule (such as PD-1, PD-L1, or CTLA-4) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8. In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-13}$ M, about $10^{-10}$ M to about $10^{-12}$ M). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody specifically recognizes PD-1 (e.g., pembrolizumab or nivolumab). In some embodiments, the antibody specifically recognizes PD-L1 (e.g., atezolizumab or durvalumab). In some embodiments, the antibody specifically recognizes CTLA-4 (e.g., ipilimumab).

In some embodiments, there is provided an antibody fusion protein comprising 1) an antibody (such as a full-length antibody) specifically recognizing PD-1 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7). In some embodiments, linker X and linker Y are the same. In some embodiments, linker X and linker Y are different. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody comprises HC-CDR1, HC-CDR2, and HC-CDR3 of a heavy chain comprising the amino acid sequence of SEQ ID NO: 12; and/or LC-CDR1, LC-CDR2, and LC-CDR3 of a light chain comprising the amino acid sequence of SEQ ID NO: 13. Thus in some embodiments, there is provided an antibody fusion protein comprising 1) an antibody (such as a full-length antibody) specifically recognizing PD-1 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); and wherein the antibody comprises HC-CDR1, HC-CDR2, and HC-CDR3 of a heavy chain comprising the amino acid sequence of SEQ ID NO: 12; and/or LC-CDR1, LC-CDR2, and LC-CDR3 of a light chain comprising the amino acid sequence of SEQ ID NO: 13. In some embodiments, the antibody comprises a heavy chain comprising the amino acid sequence of SEQ ID NO: 12, and a light chain comprising the amino acid sequence of SEQ ID NO: 13. In some embodiments, the antibody is pembrolizumab (e.g., Keytruda®) or antigen-binding fragments thereof. In some embodiments, the antibody binds to PD-1 competitively with pembrolizumab. In some embodiments, the antibody fusion protein comprises a heavy chain comprising the amino acid sequence of SEQ ID NO: 12, and a light chain fusion polypeptide comprising the amino acid sequence of SEQ ID NO: 14. In some embodiments, the antibody comprises HC-CDR1, HC-CDR2, and HC-CDR3 of a heavy chain comprising the amino acid sequence of SEQ ID NO: 15; and/or LC-CDR1, LC-CDR2, and LC-CDR3 of a light chain comprising the amino acid sequence of SEQ ID NO: 16. Thus in some embodiments, there is provided an antibody fusion protein comprising 1) an antibody (such as a full-length antibody) specifically recognizing PD-1 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); and wherein the antibody comprises HC-CDR1, HC-CDR2, and HC-CDR3 of a heavy chain comprising the amino acid sequence of SEQ ID NO: 15; and/or LC-CDR1, LC-CDR2, and LC-CDR3 of a light chain comprising the amino acid sequence of SEQ ID NO: 16. In some embodiments, the antibody comprises a heavy chain comprising the amino acid sequence of SEQ ID NO: 15, and a light chain comprising the amino acid sequence of SEQ ID NO: 16. In some embodiments, the antibody is nivolumab (e.g., Opdivo®) or antigen-binding fragments thereof. In some embodiments, the antibody binds to PD-1 competitively with nivolumab. In some embodiments, the antibody fusion protein comprises a heavy chain comprising the amino acid sequence of SEQ ID NO: 15, and a light chain fusion polypeptide comprising the amino acid sequence of SEQ ID NO: 17.

In some embodiments, there is provided an antibody fusion protein comprising 1) an antibody (such as a full-length antibody) specifically recognizing PD-1 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the antibody is a full length antibody. In some embodiments, the antibody is an IgG antibody (such as IgG1 or IgG4 antibody, or variants thereof). In some embodiments, linker X and linker Y are the same. In some embodiments, linker X and linker Y are different. In some embodiments, the $K_D$ of the binding between the VEGFR component and VEGF is about $10^{-8}$ M to about $10^{-9}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the antibody is monospecific. In some embodiments, the antibody is multispecific (e.g., bispecific). In some embodiments, the antibody is pembrolizumab (e.g., Keytruda®) or antigen-binding fragments thereof. In some embodiments, the antibody is nivolumab (e.g., Opdivo®) or antigen-binding fragments thereof. In some embodiments, there is provided an antibody fusion protein comprising 1) an antibody (such as a full-length antibody) specifically recognizing PD-1 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8; wherein the antibody comprises HC-CDR1, HC-CDR2, and HC-CDR3 of a heavy chain comprising the amino acid sequence of SEQ ID NO: 12; and/or LC-CDR1, LC-CDR2, and LC-CDR3 of a light chain comprising the amino acid sequence of SEQ ID NO: 13. In some embodiments, the antibody comprises a heavy chain comprising the amino acid sequence of SEQ ID NO: 12, and a light chain comprising the amino acid sequence of SEQ ID NO: 13. In some embodiments, the antibody is pembrolizumab (e.g., Keytruda®) or antigen-binding fragments thereof. In some embodiments, the antibody binds to PD-1 competitively with pembrolizumab. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the antibody fusion protein comprises a heavy chain comprising the amino acid sequence of SEQ ID NO: 12, and a light chain fusion polypeptide comprising the amino acid sequence of SEQ ID NO: 14. In some embodiments, there is provided an antibody fusion protein comprising 1) an antibody (such as a full-length antibody) specifically recognizing PD-1 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8; wherein the antibody comprises HC-CDR1, HC-CDR2, and HC-CDR3 of a heavy chain comprising the amino acid sequence of SEQ ID NO: 15; and/or LC-CDR1, LC-CDR2, and LC-CDR3 of a light chain comprising the amino acid sequence of SEQ ID NO: 16. In some embodiments, the antibody comprises a heavy chain comprising the amino acid sequence of SEQ ID NO: 15, and a light chain comprising the amino acid sequence of SEQ ID NO: 16. In some embodiments, the antibody is nivolumab (e.g., Opdivo®) or antigen-binding fragments thereof. In some embodiments, the antibody binds to PD-1 competitively with nivolumab. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the antibody fusion protein comprises a heavy chain comprising the amino acid sequence of SEQ ID NO: 15, and a light chain fusion polypeptide comprising the amino acid sequence of SEQ ID NO: 17.

In some embodiments, there is provided an antibody fusion protein comprising 1) an antibody (such as a full-length antibody) specifically recognizing PD-L1 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7). In some embodiments, linker X and linker Y are the same. In some embodiments, linker X and linker Y are different. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M about $10^{-9}$ M to about $10^{-12}$ M, about $10^{-10}$ M to about $10^{-12}$ M). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody comprises HC-CDR1, HC-CDR2, and HC-CDR3 of a heavy chain comprising the amino acid sequence of SEQ ID NO: 18; and/or LC-CDR1, LC-CDR2, and LC-CDR3 of a light chain comprising the amino acid sequence of SEQ ID NO: 19. Thus in some embodiments, there is provided an antibody fusion protein comprising 1) an antibody (such as a full-length antibody) specifically recognizing PD-L1 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); and wherein the antibody comprises HC-CDR1, HC-CDR2, and HC-CDR3 of a heavy chain comprising the amino acid sequence of SEQ ID NO: 18; and/or LC-CDR1. LC-CDR2, and LC-CDR3 of a light chain comprising the amino acid sequence of SEQ ID NO: 19. In some embodiments, the antibody comprises a heavy chain comprising the amino acid sequence of SEQ ID NO: 18, and a light chain comprising the amino acid sequence of SEQ ID NO: 19. In some embodiments, the antibody is atezolizumab (e.g., Tecentriq®) or antigen-binding fragments thereof. In some embodiments, the antibody binds to PD-L1 competitively with atezolizumab. In some embodiments, the antibody fusion protein comprises a heavy chain comprising the amino acid sequence of SEQ ID NO: 18, and a light chain fusion polypeptide comprising the amino acid sequence of SEQ ID NO: 20. In some embodiments, the antibody comprises HC-CDR1, HC-CDR2, and HC-CDR3 of a heavy chain comprising the amino acid sequence of SEQ ID NO: 21; and/or LC-CDR1, LC-CDR2, and LC-CDR3 of a light chain comprising the amino acid sequence of SEQ ID NO: 22. Thus in some embodiments, there is provided an antibody fusion protein comprising 1) an antibody (such as a full-length antibody) specifically recognizing PD-L1 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); and wherein the antibody comprises HC-CDR1, HC-CDR2, and HC-CDR3 of a heavy chain comprising the amino acid sequence of SEQ ID NO: 21; and/or LC-CDR1. LC-CDR2, and LC-CDR3 of a light chain comprising the amino acid sequence of SEQ ID NO: 22. In some embodiments, the antibody comprises a heavy chain comprising the amino acid sequence of SEQ ID NO: 21, and a light chain comprising the amino acid sequence of SEQ ID NO: 22. In some embodiments, the antibody is Durvalumab or antigen-binding fragments thereof. In some embodiments, the antibody binds to PD-L1 competitively with Durvalumab. In some embodiments, the antibody fusion protein comprises a heavy chain comprising the amino acid sequence of SEQ ID NO: 21, and a light chain fusion polypeptide comprising the amino acid sequence of SEQ ID NO: 23.

In some embodiments, there is provided an antibody fusion protein comprising 1) an antibody (such as a full-length antibody) specifically recognizing PD-L1 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, linker X and linker Y are the same. In some embodiments, linker X and linker Y are different. In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody is atezolizumab (e.g., Tecentriq®) or antigen-binding fragments thereof. In some embodiments, the antibody is Durvalumab or antigen-binding fragments thereof. In some embodiments, there is provided an antibody fusion protein comprising 1) an antibody (such as a full-length antibody) specifically recognizing PD-L1 comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7); wherein each VEGFR component comprises an amino acid sequence of SEQ ID NO: 8; wherein the antibody comprises HC-CDR1, HC-CDR2, and HC-CDR3 of a heavy chain comprising the amino acid sequence of SEQ ID NO: 18; and/or LC-CDR1, LC-CDR2, and LC-CDR3 of a light chain comprising the amino acid sequence of SEQ ID NO: 19. In some embodiments, the antibody comprises a heavy chain comprising the amino acid sequence of SEQ ID NO: 18, and a light chain comprising the amino acid sequence of SEQ ID NO: 19. In some embodiments, the antibody is atezolizumab (e.g., Tecentriq®) or antigen-binding fragments thereof. In some embodiments, the antibody binds to PD-L1 competitively with atezolizumab. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the antibody fusion protein comprises a heavy chain comprising the amino acid sequence of SEQ ID NO: 18, and a light chain fusion polypeptide comprising the amino acid sequence of SEQ ID NO: 20. In some embodiments, there is provided an antibody fusion protein comprising 1) an antibody (such as a full-length antibody) specifically recognizing PD-L1 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8; wherein the antibody comprises HC-CDR1, HC-CDR2, and HC-CDR3 of a heavy chain comprising the amino acid sequence of SEQ ID NO: 21; and/or LC-CDR1, LC-CDR2, and LC-CDR3 of a light chain comprising the amino acid sequence of SEQ ID NO: 22. In some embodiments, the antibody comprises a heavy chain comprising the amino acid sequence of SEQ ID NO: 21, and a light chain comprising the amino acid sequence of SEQ ID NO: 22. In some embodiments, the antibody is Durvalumab (e.g., Imfinzi®) or antigen-binding fragments thereof. In some embodiments, the antibody binds to PD-L1 competitively with Durvalumab. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the antibody fusion protein comprises a heavy chain comprising the amino acid sequence of SEQ ID NO: 21, and a light chain fusion polypeptide comprising the amino acid sequence of SEQ ID NO: 23.

In some embodiments, there is provided an antibody fusion protein comprising 1) an antibody (such as a full-length antibody) specifically recognizing CTLA-4 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7). In some embodiments, linker X and linker Y are the same. In some embodiments, linker X and linker Y are different. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody comprises HC-CDR1, HC-CDR2, and HC-CDR3 of a heavy chain comprising the amino acid sequence of SEQ ID NO: 9; and/or LC-CDR1, LC-CDR2, and LC-CDR3 of a light chain comprising the amino acid sequence of SEQ ID NO: 10. Thus in some embodiments, there is provided an antibody fusion protein comprising 1) an antibody (such as a full-length antibody) specifically recognizing CTLA-4 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); and wherein the antibody comprises HC-CDR1, HC-CDR2, and HC-CDR3 of a heavy chain comprising the amino acid sequence of SEQ ID NO: 9; and/or LC-CDR1, LC-CDR2, and LC-CDR3 of a light chain comprising the amino acid sequence of SEQ ID NO: 10. In some embodiments, the antibody comprises a heavy chain comprising the amino acid sequence of SEQ ID NO: 9, and a light chain comprising the amino acid sequence of SEQ ID NO: 10. In some embodiments, the antibody is ipilimumab (e.g., Yervoy®) or antigen-binding fragments thereof. In some embodiments, the antibody binds to CTLA-4 competitively with ipilimumab. In some embodiments, the antibody fusion protein comprises a heavy chain comprising the amino acid sequence of SEQ ID NO: 9, and a light chain fusion polypeptide comprising the amino acid sequence of SEQ ID NO: 11.

In some embodiments, there is provided an antibody fusion protein comprising 1) an antibody (such as a full-length antibody) specifically recognizing CTLA-4 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, linker X and linker Y are the same. In some embodiments, linker X and linker Y are different. In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody is ipilimumab (e.g., Yervoy®) or antigen-binding fragments thereof. In some embodiments, the antibody binds to CTLA-4 competitively with ipilimumab. In some embodiments, there is provided an antibody fusion protein comprising 1) an antibody (such as a full-length antibody) specifically recognizing CTLA-4 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8; wherein the antibody comprises HC-CDR1, HC-CDR2, and HC-CDR3 of a heavy chain comprising the amino acid sequence of SEQ ID NO: 9; and/or LC-CDR1. LC-CDR2, and LC-CDR3 of a light chain comprising the amino acid sequence of SEQ ID NO: 10. In some embodiments, the antibody comprises a heavy chain comprising the amino acid sequence of SEQ ID NO: 9, and a light chain comprising the amino acid sequence of SEQ ID NO: 10. In some embodiments, the antibody is ipilimumab (e.g., Yervoy®) or antigen-binding fragments thereof. In some embodiments, the antibody binds to CTLA-4 competitively with ipilimumab. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the antibody fusion protein comprises a heavy chain comprising the amino acid sequence of SEQ ID NO: 9, and a light chain fusion polypeptide comprising the amino acid sequence of SEQ ID NO: 11.

In some embodiments, the VEGFR-antibody light chain fusion protein described herein comprises an antibody that specifically recognizes a tumor antigen (such as HER2, EGFR).

Thus, in some embodiments, there is provided an antibody fusion protein comprising 1) an antibody (such as a full-length antibody) specifically recognizing a tumor antigen (such as HER2, EGFR) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7). In some embodiments, linker X and linker Y are the same. In some embodiments, linker X and linker Y are different. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa).

In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$, about $10^{-10}$ M to about $10^{-12}$ M). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the tumor antigen is HER2. Thus in some embodiments, there is provided an antibody fusion protein comprising 1) an antibody specifically recognizing HER2 (such as a full-length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7). In some embodiments, the antibody comprises HC-CDR1, HC-CDR2, and HC-CDR3 of a heavy chain comprising the amino acid sequence of SEQ ID NO: 24; and/or LC-CDR1, LC-CDR2, and LC-CDR3 of a light chain comprising the amino acid sequence of SEQ ID NO: 25. Thus, in some embodiments, there is provided an antibody fusion protein comprising 1) an antibody (such as a full-length antibody) specifically recognizing HER2 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); and wherein the antibody comprises HC-CDR1, HC-CDR2, and HC-CDR3 of a heavy chain comprising the amino acid sequence of SEQ ID NO: 24; and/or LC-CDR1, LC-CDR2, and LC-CDR3 of a light chain comprising the amino acid sequence of SEQ ID NO: 25. In some embodiments, the antibody comprises a heavy chain comprising the amino acid sequence of SEQ ID NO: 24, and a light chain comprising the amino acid sequence of SEQ ID NO: 25. In some embodiments, the antibody is trastuzumab (e.g., Herceptin®) or antigen-binding fragments thereof. In some embodiments, the antibody binds to HER2 competitively with trastuzumab. In some embodiments, the antibody fusion protein comprises a heavy chain comprising the amino acid sequence of SEQ ID NO: 24, and a light chain fusion polypeptide comprising the amino acid sequence of SEQ ID NO: 26, 27, or 28. In some embodiments, the tumor antigen is EGFR (HER1). Thus in some embodiments, there is provided an antibody fusion protein comprising 1) an antibody specifically recognizing HER (such as a full-length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7). In some embodiments, the antibody comprises HC-CDR1. HC-CDR2, and HC-CDR3 of a heavy chain comprising the amino acid sequence of SEQ ID NO: 29; and/or LC-CDR1 LC-CDR2, and LC-CDR3 of a light chain comprising the amino acid sequence of SEQ ID NO: 30. Thus, in some embodiments, there is provided an antibody fusion protein comprising 1) an antibody (such as a full-length antibody) specifically recognizing HER1 comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); and wherein the antibody comprises HC-CDR1, HC-CDR2, and HC-CDR3 of a heavy chain comprising the amino acid sequence of SEQ ID NO: 29; and/or LC-CDR1, LC-CDR2, and LC-CDR3 of a light chain comprising the amino acid sequence of SEQ ID NO: 30. In some embodiments, the antibody comprises a heavy chain comprising the amino acid sequence of SEQ ID NO: 29, and a light chain comprising the amino acid sequence of SEQ ID NO: 30. In some embodiments, the antibody is Cetuximab or antigen-binding fragments thereof. In some embodiments, the antibody binds to EGFR competitively with Cetuximab. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the antibody fusion protein comprises a heavy chain comprising the amino acid sequence of SEQ ID NO: 29, and a light chain fusion polypeptide comprising the amino acid sequence of SEQ ID NO: 31.

In some embodiments, there is provided an antibody fusion protein comprising 1) an antibody (such as a full-length antibody) specifically recognizing a tumor antigen (such as HER2, EGFR) comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7); wherein each VEGFR component comprises an amino acid sequence of SEQ ID NO: 8. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, linker X and linker Y are the same. In some embodiments, linker X and linker Y are different. In some embodiments, the $K_L$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g. bispecific). In some embodiments, the tumor antigen is HER2. Thus in some embodiments, there is provided an antibody fusion protein comprising 1) an antibody specifically recognizing HER2 (such as a full-length antibody) comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7); wherein each VEGFR component comprises an amino acid sequence of SEQ ID NO: 8. In some embodiments, the antibody comprises HC-CDR1, HC-CDR2, and HC-CDR3 of a heavy chain comprising the amino acid sequence of SEQ ID NO: 24 and/or LC-CDR LC-CDR2, and LC-CDR3 of a light chain comprising the amino acid sequence of SEQ ID NO: 25. Thus in some embodiments, there is provided an antibody fusion protein comprising 1) an antibody specifically recognizing HER2 (such as a full-length antibody) comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7); wherein each VEGFR component comprises an amino acid sequence of SEQ ID NO: 8; and wherein the antibody comprises HC-CDR1, HC-CDR2, and HC-CDR3 of a heavy chain comprising the amino acid sequence of SEQ ID NO: 24; and/or LC-CDR1, LC-CDR2, and LC-CDR3 of a light chain comprising the amino acid sequence of SEQ ID NO: 25. In some embodiments, the antibody comprises a heavy chain comprising the amino acid sequence of SEQ ID NO: 24, and a light chain comprising the amino acid sequence of SEQ ID NO: 25. In some embodiments, the antibody is trastuzumab (e.g., Herceptin®) or antigen-binding fragments thereof. In some embodiments, the antibody binds to HER2 competitively with trastuzumab. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the antibody fusion protein comprises a heavy chain comprising the amino acid sequence of SEQ ID NO: 24, and a light chain fusion polypeptide comprising the amino acid sequence of SEQ ID NO: 26, 27, or 28. In some embodiments, the tumor antigen is EGFR (HER1). Thus in some embodiments, there is provided an antibody fusion protein comprising 1) an antibody specifically recognizing HER1 (such as a full-length antibody) comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7); wherein each VEGFR component comprises an amino acid sequence of SEQ ID NO: 8. In some embodiments, the antibody comprises HC-CDR1, HC-CDR2, and HC-CDR3 of a heavy chain comprising the amino acid sequence of SEQ ID NO: 29; and/or LC-CDR1, LC-CDR2, and LC-CDR3 of a light chain comprising the amino acid sequence of SEQ ID NO: 30. Thus in some embodiments, there is provided an antibody fusion protein comprising 1) an antibody specifically recognizing EGFR (such as a full-length antibody) comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7); wherein each VEGFR component comprises an amino acid sequence of SEQ ID NO: 8; wherein the antibody comprises HC-CDR1. HC-CDR2, and HC-CDR3 of a heavy chain comprising the amino acid sequence of SEQ ID NO: 29; and/or LC-CDR1 LC-CDR2, and LC-CDR3 of a light chain comprising the amino acid sequence of SEQ ID NO: 30. In some embodiments, the antibody comprises a heavy chain comprising the amino acid sequence of SEQ ID NO: 29, and a light chain comprising the amino acid sequence of SEQ ID NO: 30. In some embodiments, the antibody is Cetuximab (e.g., Erbitux®) or antigen-binding fragments thereof. In some embodiments, the antibody binds to EGFR competitively with Cetuximab. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the antibody fusion protein comprises a heavy chain comprising the amino acid sequence of SEQ ID NO: 29, and a light chain fusion polypeptide comprising the amino acid sequence of SEQ ID NO: 31.

In some embodiments, the VEGFR-antibody light chain fusion protein described herein comprises an antibody that specifically recognizes an angiogenic factor. In some embodiments, the antibody specifically recognizes Ang2. In some embodiments, the antibody specifically recognizes TNFα. In some embodiments, the antibody specifically recognizes IL-17A.

Thus, in some embodiments, there is provided an antibody fusion protein comprising 1) an antibody (such as a full-length antibody) specifically recognizing an angiogenic factor (such as Ang2, TNFα. IL-17A) comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7). In some embodiments, linker X and linker Y are the same. In some embodiments, linker X and linker Y are different. In some embodiments, the first VEGFR component and the second VEGFR component are the same.

In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, there is provided an antibody fusion protein comprising 1) an antibody (such as a full-length antibody) specifically recognizing an angiogenic factor (such as Ang2, TNFα, IL-17A) comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7); wherein each VEGFR component comprises an amino acid sequence of SEQ ID NO: 8. In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$M, about $10^{-8}$M to about $10^{-12}$ M, about $10^{-9}$ M to about $10^{-11}$ M, about $10^{-10}$ M to about $10^{-12}$ M). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific).

In some embodiments, there is provided an antibody fusion protein comprising 1) an antibody (such as a full-length antibody) specifically recognizing Ang2 comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7). In some embodiments, linker X and linker Y are the same. In some embodiments, linker X and linker Y are different. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. Thus in some embodiments, there is provided an antibody fusion protein comprising 1) an antibody (such as a full-length antibody) specifically recognizing Ang2 comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7): wherein each VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa. 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody comprises HC-CDR1, HC-CDR2, and HC-CDR3 of a heavy chain comprising the amino acid sequence of SEQ ID NO: 35; and/or LC-CDR1, LC-CDR2, and LC-CDR3 of a light chain comprising the amino acid sequence of SEQ ID NO: 36. Thus in some embodiments, there is provided an antibody fusion protein comprising 1) an antibody (such as a full-length antibody) specifically recognizing Ang2 comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7); wherein each VEGFR component comprises an amino acid sequence of SEQ ID NO: 8; wherein the antibody comprises HC-CDR1. HC-CDR2, and HC-CDR3 of a heavy chain comprising the amino acid sequence of SEQ ID NO: 35; and/or LC-CDR1, LC-CDR2, and LC-CDR3 of a light chain comprising the amino acid sequence of SEQ ID NO: 36. In some embodiments, the antibody comprises a heavy chain comprising the amino acid sequence of SEQ ID NO: 35, and a light chain comprising the amino acid sequence of SEQ ID NO: 36. In some embodiments, the antibody is Nesvacumab or antigen-binding fragments thereof. In some embodiments, the antibody binds to Ang2 competitively with Nesvacumab. In some embodiments, the antibody fusion protein comprises a heavy chain comprising the amino acid sequence of SEQ ID NO: 35, and a light chain fusion polypeptide comprising the amino acid sequence of SEQ ID NO: 37.

In some embodiments, there is provided an antibody fusion protein comprising 1) an antibody (such as a full-length antibody) specifically recognizing TNFα comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7). In some embodiments, linker X and linker Y are the same. In some embodiments, linker X and linker Y are different. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. Thus in some embodiments, there is provided an antibody fusion protein comprising 1) an antibody (such as a full-length antibody) specifically recognizing TNFα comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7): wherein each VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa. 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody comprises HC-CDR1, HC-CDR2, and HC-CDR3 of a heavy chain comprising the amino acid sequence of SEQ ID NO: 32; and/or LC-CDR1, LC-CDR2, and LC-CDR3 of a light chain comprising the amino acid sequence of SEQ ID NO: 33. Thus in some embodiments, there is provided an antibody fusion protein comprising 1) an antibody (such as a full-length antibody) specifically recognizing TNFα comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7); wherein each VEGFR component comprises an amino acid sequence of SEQ ID NO: 8; wherein the antibody comprises HC-CDR1. HC-CDR2, and HC-CDR3 of a heavy chain comprising the amino acid sequence of SEQ ID NO: 32; and/or LC-CDR1, LC-CDR2, and LC-CDR3 of a light chain comprising the amino acid sequence of SEQ ID NO: 33. In some embodiments, the antibody comprises a heavy chain comprising the amino acid sequence of SEQ ID NO: 32, and a light chain comprising the amino acid sequence of SEQ ID NO: 33. In some embodiments, the antibody is Adalimumab (e.g., Humira®) or antigen-binding fragments thereof. In some embodiments, the antibody binds to TNFα competitively with Adalimumab. In some embodiments, the antibody fusion protein comprises a heavy chain comprising the amino acid sequence of SEQ ID NO: 32, and a light chain fusion polypeptide comprising the amino acid sequence of SEQ ID NO: 34.

In some embodiments, there is provided an antibody fusion protein comprising 1) an antibody (such as a full-length antibody) specifically recognizing IL-17A comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7). In some embodiments, linker X and linker Y are the same. In some embodiments, linker X and linker Y are different. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. Thus in some embodiments, there is provided an antibody fusion protein comprising 1) an antibody (such as a full-length antibody) specifically recognizing IL-17A comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7): wherein each VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa. 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody comprises HC-CDR1, HC-CDR2, and HC-CDR3 of a heavy chain comprising the amino acid sequence of SEQ ID NO: 38; and/or LC-CDR1, LC-CDR2, and LC-CDR3 of a light chain comprising the amino acid sequence of SEQ ID NO: 39. Thus in some embodiments, there is provided an antibody fusion protein comprising 1) an antibody (such as a full-length antibody) specifically recognizing IL-17A comprising a first light chain and a second light chain, and 2) a first VEGFR component and a second VEGFR component, wherein the first VEGFR component is fused to the C-terminus of the first antibody light chain (e.g., C-terminus of antibody VL-CL domain) optionally via a linker X (such as peptide linker of SEQ ID NO: 6 or 7), and the second VEGFR component is fused to the C-terminus of the second antibody light chain (e.g., C-terminus of antibody VL-CL domain) optionally via a linker Y (such as peptide linker of SEQ ID NO: 6 or 7); wherein each VEGFR component comprises an amino acid sequence of SEQ ID NO: 8; wherein the antibody comprises HC-CDR1, HC-CDR2, and HC-CDR3 of a heavy chain comprising the amino acid sequence of SEQ ID NO: 38; and/or LC-CDR1, LC-CDR2, and LC-CDR3 of a light chain comprising the amino acid sequence of SEQ ID NO: 39. In some embodiments, the antibody comprises a heavy chain comprising the amino acid sequence of SEQ ID NO: 38, and a light chain comprising the amino acid sequence of SEQ ID NO: 39. In some embodiments, the antibody is Ixekizumab (e.g., Taltz®) or antigen-binding fragments thereof. In some embodiments, the antibody binds to IL-17A competitively with Ixekizumab. In some embodiments, the antibody fusion protein comprises a heavy chain comprising the amino acid sequence of SEQ ID NO: 38, and a light chain fusion polypeptide comprising the amino acid sequence of SEQ ID NO: 40.

Antibody Fusion Protein Properties
Antibody Fusion Protein Stability

The VEGFR-antibody light chain fusion protein of the present invention may exhibit high levels of stability.

The term "stable," as used herein in reference to the VEGFR-antibody light chain fusion protein, means that the VEGFR-antibody light chain fusion protein retain an acceptable degree of chemical structure or biological function after storage under defined conditions. VEGFR-antibody light chain fusion protein may be stable even if it does not maintain 100% of its chemical structure or biological function after storage for a defined amount of time. In some embodiments, maintenance of about 90%, about 95%, about 96%, about 97%, about 98% or about 99% of structure or function of a VEGFR-antibody light chain fusion protein after storage for a defined amount of time may be regarded as "stable."

Stability can be measured, inter alia, by determining the percentage of native (non-aggregated or degraded) VEGFR-antibody light chain fusion protein that remains in the formulation (liquid or reconstituted) after storage for a defined amount of time at a defined temperature. The percentage of native VEGFR-antibody light chain fusion protein can be determined by, inter alia, size exclusion chromatography (e.g., size exclusion high performance liquid chromatography [SE-HPLC]), such that native means non-aggregated and non-degraded. In some embodiments, at least about 90% (such as at least about 90%, 91%, 92%. 93%. 94%, 95%, 96%, 97%, 98%, 99% or 100%) of the native form of the VEGFR-antibody light chain fusion protein can be detected in the formulation after storage for a defined amount of time at a given temperature. In some embodiments, at least about 90% (such as at least about 90%, 91%, 92%, 93%. 94%, 95%, 96%, 97%, 98%, 99% or 100%) of the native form of the VEGFR-antibody light chain fusion protein can be detected in the formulation after at least about 6 hrs, at least about 8 hrs, at least about 10 hrs, at least about 12 hrs, at least about 14 hrs, at least about 16 hrs, at least about 18 hrs, at least about 20 hrs, at least about 22 hrs, at least about 24 hrs, at least about 26 hrs, at least about 28 hrs, at least about 30 hrs, at least about 32 hrs, at least about 34 hrs, at least about 36 hrs, at least about 38 hrs, at least about 40 hrs, at least about 42 hrs, at least about 44 hrs, at least about 46 hrs, or at least about 48 hrs under room temperature (about 25° C.).

Stability can be measured, inter alia, by determining the percentage of VEGFR-antibody light chain fusion protein that forms in an aggregate within the formulation (liquid or reconstituted) after storage for a defined amount of time at a defined temperature, wherein stability is inversely proportional to the percent aggregate that is formed. The percentage of aggregated VEGFR-antibody light chain fusion protein can be determined by, inter alia, size exclusion chromatography (e.g., size exclusion high performance liquid chromatography [SE-HPLC]). In some embodiment, there is less than about 10% (preferably less than about 5%) of the VEGFR-antibody light chain fusion protein present as an aggregate in the formulation after storage for a defined amount of time at a given temperature. In some embodiments, the VEGFR-antibody light chain fusion protein descried herein has substantially no aggregation, for example, at most about 6%, 5%, 4%, 3%, 2%, 1%, 0.5%, or 0.1% of the VEGFR-antibody light chain fusion protein can be detected in an aggregate in the formulation after storage for a defined amount of time at a given temperature, for example, after at least about 6 hrs, at least about 8 hrs, at least about 10 hrs, at least about 12 hrs, at least about 14 hrs, at least about 16 hrs, at least about 18 hrs, at least about 20 hrs, at least about 22 hrs, at least about 24 hrs, at least about 26 hrs, at least about 28 hrs, at least about 30 hrs, at least about 32 hrs, at least about 34 hrs, at least about 36 hrs, at least about 38 hrs, at least about 40 hrs, at least about 42 hrs, at least about 44 hrs, at least about 46 hrs, or at least about 48 hrs under room temperature (about 25° C.).

Measuring the binding affinity of the VEGFR-antibody light chain fusion protein to its target (antibody antigen and/or VEGF) may also be used to assess stability. For example, a VEGFR-antibody light chain fusion protein of the present invention may be regarded as stable if, after storage at e.g., room temperature (about 25° C.) for a defined amount of time (e.g., 6 hrs, 12 hrs, 24 hrs, 36 hrs, 48 hrs), both the antibody and the VEGFR component contained within VEGFR-antibody light chain fusion protein bind to antibody antigen and VEGF (respectively) with an affinity that is at least 84%, 90%, 95%, or even more of the binding affinity of the antibody prior to said storage. Binding affinity may be determined by any method, such as e.g., ELISA or plasmon resonance. Biological activity may be determined by an antigen or VEGF activity assay, such as by contacting a cell that expresses VEGF with the VEGFR-antibody light chain fusion protein. The binding of the VEGFR-antibody light chain fusion protein to such a cell may be measured directly, such as via FACS analysis. Alternatively, the downstream activity of the VEGF system may be measured in the presence of the VEGFR-antibody light chain fusion protein, and compared to the activity of the VEGF system in the absence of VEGFR-antibody light chain fusion protein. In some embodiments, the VEGF may be endogenous to the cell. In other embodiments, the VEGF may be ectopically expressed (i.e., heterologous expression) in the cell.

Antibody Fusion Protein Pharmacokinetics

In some embodiments, the serum half-life of the VEGFR-antibody light chain fusion protein of the present invention is longer than that of the corresponding antibody; e.g., the pK of the VEGFR-antibody light chain fusion protein is longer than that of the corresponding antibody. In some embodiments, the serum half-life of the VEGFR-antibody light chain fusion protein is similar to that of the corresponding antibody. In some embodiments, the serum half-life of the VEGFR-antibody light chain fusion protein is at least about 15 days, about 14 days, about 13 days, about 12 days, about 11 days, about 10 days, about 9 days, about 8 days, about 7 days, about 6 days, about 5 days, about 4 days, about 3 days, about 2 days, about 24 hrs, about 24 hrs, about 20 hrs, about 18 hrs, about 16 hrs, about 14 hrs, about 12 hrs, about 10 hrs, about 8 hrs, about 6 hrs, about 4 hrs, about 3 hrs, about 2 hrs, or about 1 hr when administered to an organism.

Antibody Fusion Protein Clinical Properties

In some embodiments, the VEGFR-antibody light chain fusion protein described herein has improved clinical properties relative to VEGFR-antibody fusion protein comprising an antibody with VEGFR component fused to the C-terminus of the heavy chain, and/or VEGFR-antibody fusion protein comprising an antibody with VEGFR component fused to the N-terminus of the heavy chain, and/or VEGFR-antibody fusion protein comprising an antibody with VEGFR component fused to the N-terminus of the light chain. In some embodiments, the VEGFR-antibody light chain fusion protein described here retain both ADCC and CDC effector functions of the antibody despite the presence of the bulky VEGFR component attached to the C-terminus of the antibody light chain (e.g., C-terminus of antibody VL-CL domain). In some embodiments, the VEGFR-antibody light chain fusion protein described here exhibit improved ADCC and/or CDC effector functions of the antibody, compared to that of the corresponding antibody.

ADCC of the VEGFR-antibody light chain fusion protein can be tested as described in Example 2. Briefly, cancer cell line expressing the antigen that can be recognized by the VEGFR-antibody light chain fusion protein (e.g., SKBR3 human breast cancer cell line, which expresses HER2 that can be recognized by the anti-HER2 antibody moiety within the VEGFR-anti-HER2 light chain fusion protein) and effector cells (e.g., CD16+ NK92 cells) are mixed together in a 96-well plate. The cancer cell line can be engineered to express a reporter gene, e.g., luciferase. Varying concentrations of VEGFR-antibody light chain fusion protein is added into each well. After incubation, the reporter gene (e.g., luciferase) activity can be measured using a microplate reader. EC50 (representing ADCC activity) can then be calculated.

C-terminal heavy chain fusion sometimes alters the structure of the Fc region, even when a flexible peptide linker is used. As a result, antibody fusion protein having a heavy chain fusion exhibit low CDC relative to intact antibodies. In addition, heavy chain fusions are characterized by high Fc receptor (FcR) binding in the absence of antigen binding. This results in a relatively short half-life. These properties of heavy chain fusions can be altered, for example, to reduce or eliminate FcR binding by deglycosylating the fusing moiety and/or to prevent intracellular proteolysis by modifying the linker. However, deglycosylation results in loss of ADCC and CDC, and linker modified constructs still have relatively low CDC and sub-optimal pharmacokinetic properties.

When fusing a large moiety (e.g. a VEGFR component) to the C-terminus of an antibody light chain, the folding of the bulky moiety, as well as the antibody light chain itself, might be affected, leading to unpredictability of the 3D structure of the antibody fusion protein, which in turn might reduce or abolish the binding specificity of the antibody to its target antigen(s), and the biological activity of the bulky moiety (e.g. binding specificity of VEGFR component to VEGF). However, it is surprisingly found in the present invention that a bulky VEGFR component (e.g. about 23.2 kDa) can be fused to the C-terminus of an antibody light chain, while still maintain the binding specificities of VEGFR to VEGF, and the binding specificities of the antibody to its antigen target(s), even when two bulky VEGFR components are fused to the C-terminus of both antibody light chains (e.g., C-terminus of antibody VL-CL domain).

Figure 2:
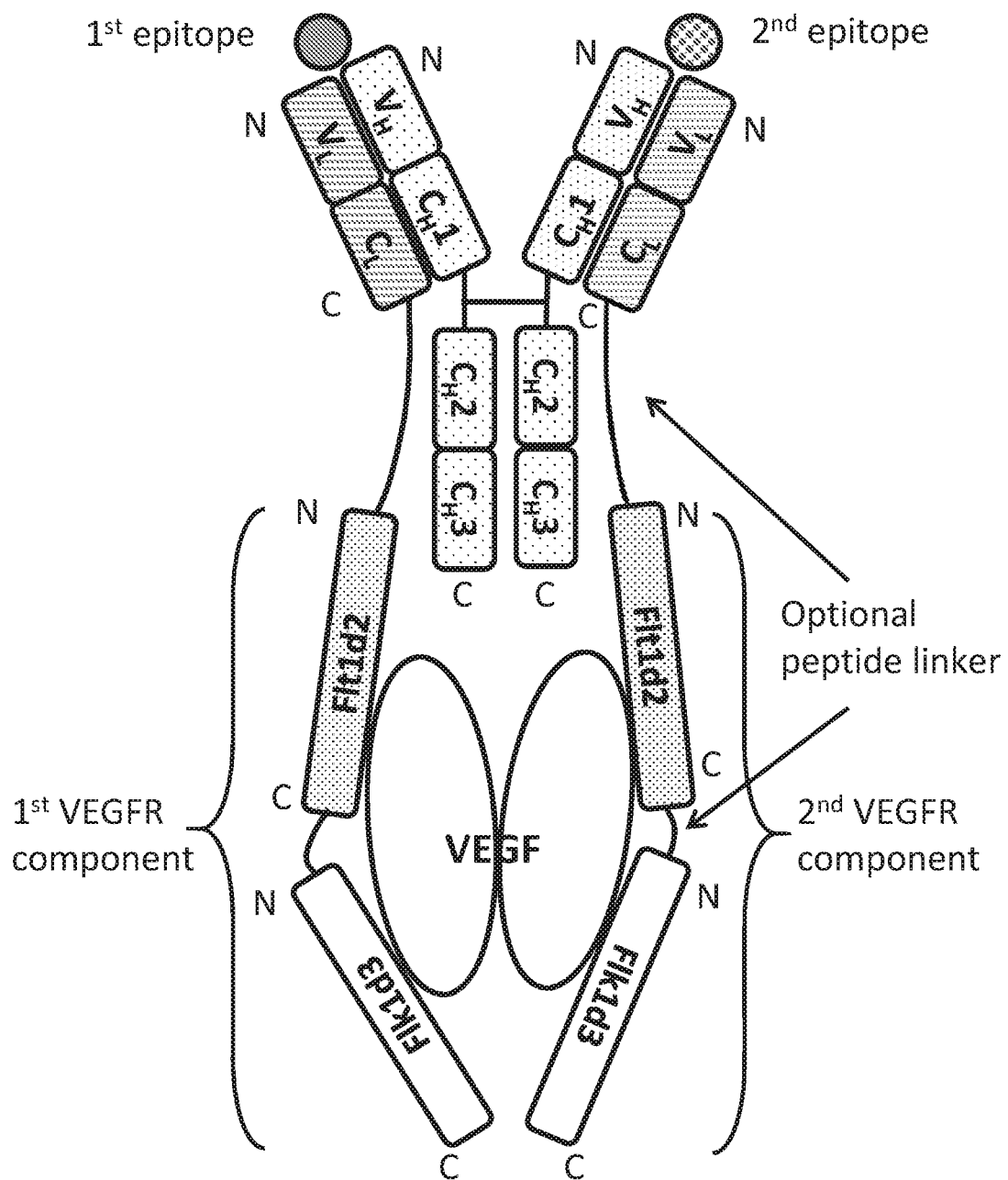
FIG. 2 depicts an exemplary VEGFR-antibody light chain fusion protein, comprising a bispecific full-length antibody and two VEGFR components, wherein each VEGFR component is fused to the C-terminus of each light chain of the antibody light chain. In alternative formats, the two VEGFR components can be different, can comprise three or more Ig-like domains, and/or can comprise any Ig-like domains of either Flt-1 or Flk-1.
Figure 3:
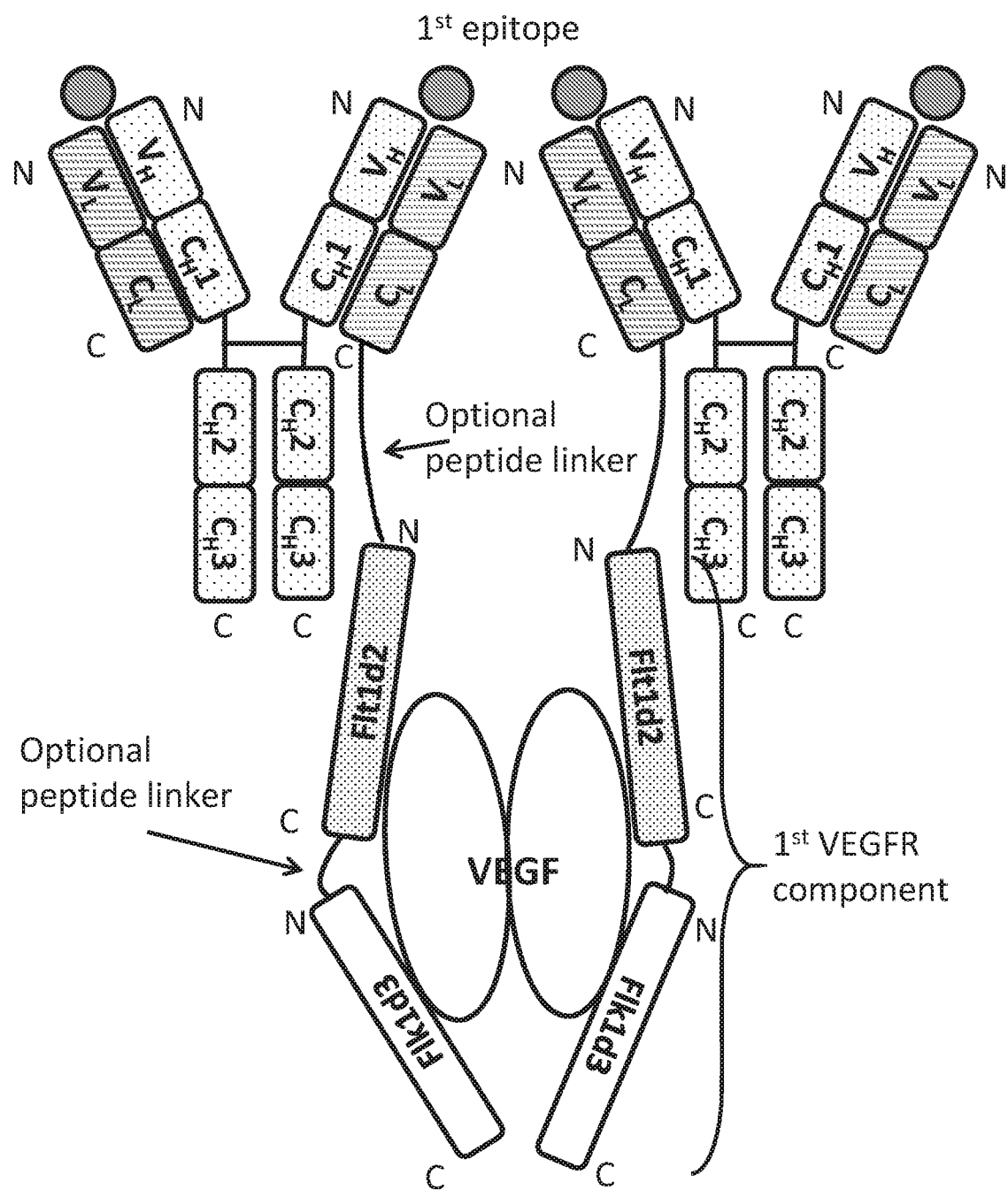
FIG. 3 depicts an exemplary of two VEGFR-antibody light chain fusion proteins, each comprising a monospecific full-length antibody and one VEGFR component fused to the C-terminus of one light chain of the antibody. Binding to VEGF dimer brings two VEGFR-antibody light chain fusion proteins in proximity. In alternative formats, the two VEGFR-antibody light chain fusion proteins can be different, each can comprise three or more Ig-like domains, and/or can comprise any Ig-like domains of either Flt-1 or Flk-1.
Figure 4:
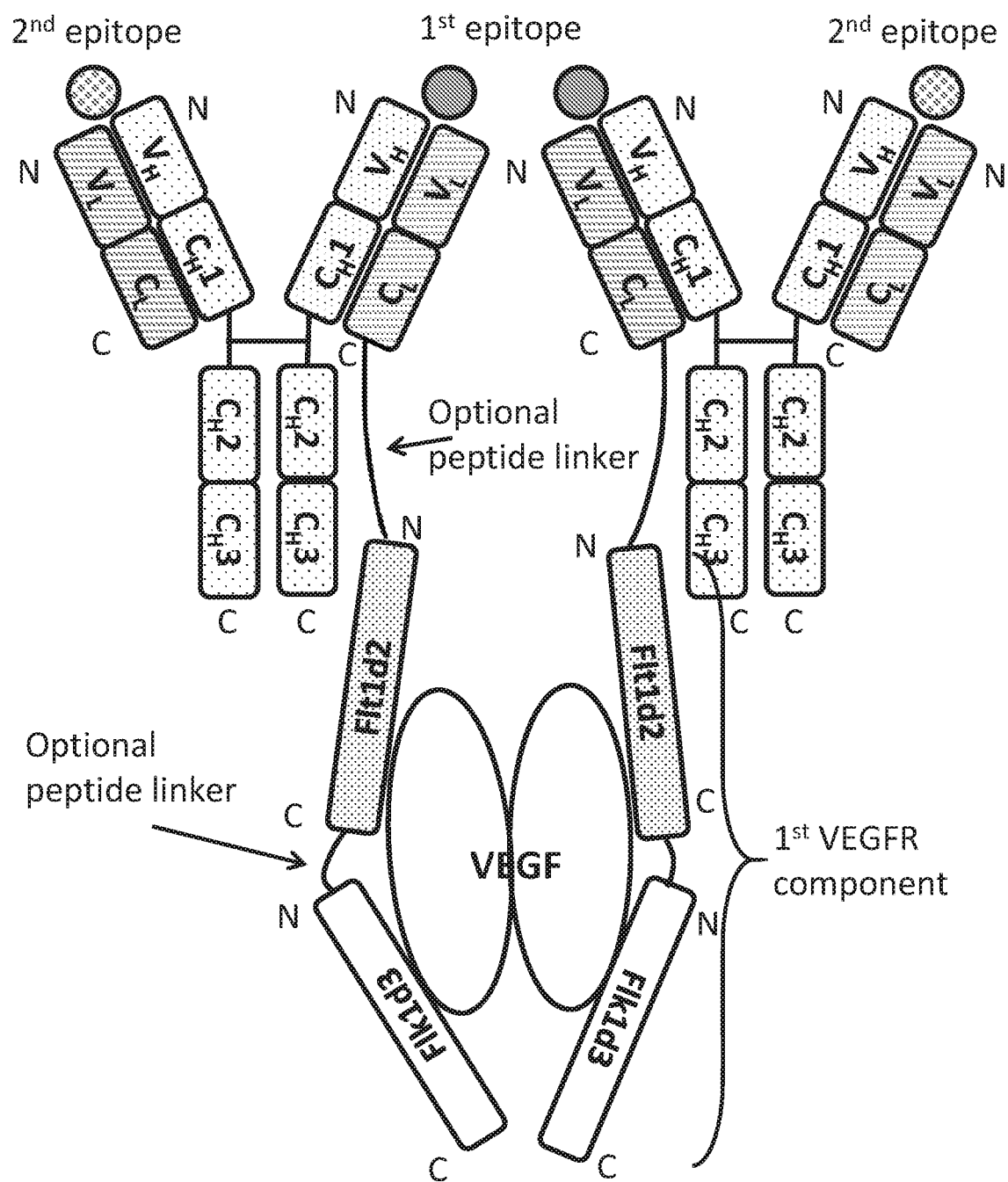
FIG. 4 depicts an exemplary of two VEGFR-antibody light chain fusion proteins, each comprising a bispecific full-length antibody and one VEGFR component fused to the C-terminus of one light chain of the antibody. Binding to VEGF dimer brings two VEGFR-antibody light chain fusion proteins in proximity. In alternative formats, the two VEGFR-antibody light chain fusion proteins can be different, each can comprise three or more Ig-like domains, and/or can comprise any Ig-like domains of either Flt-1 or Flk-1.
Figure 5:
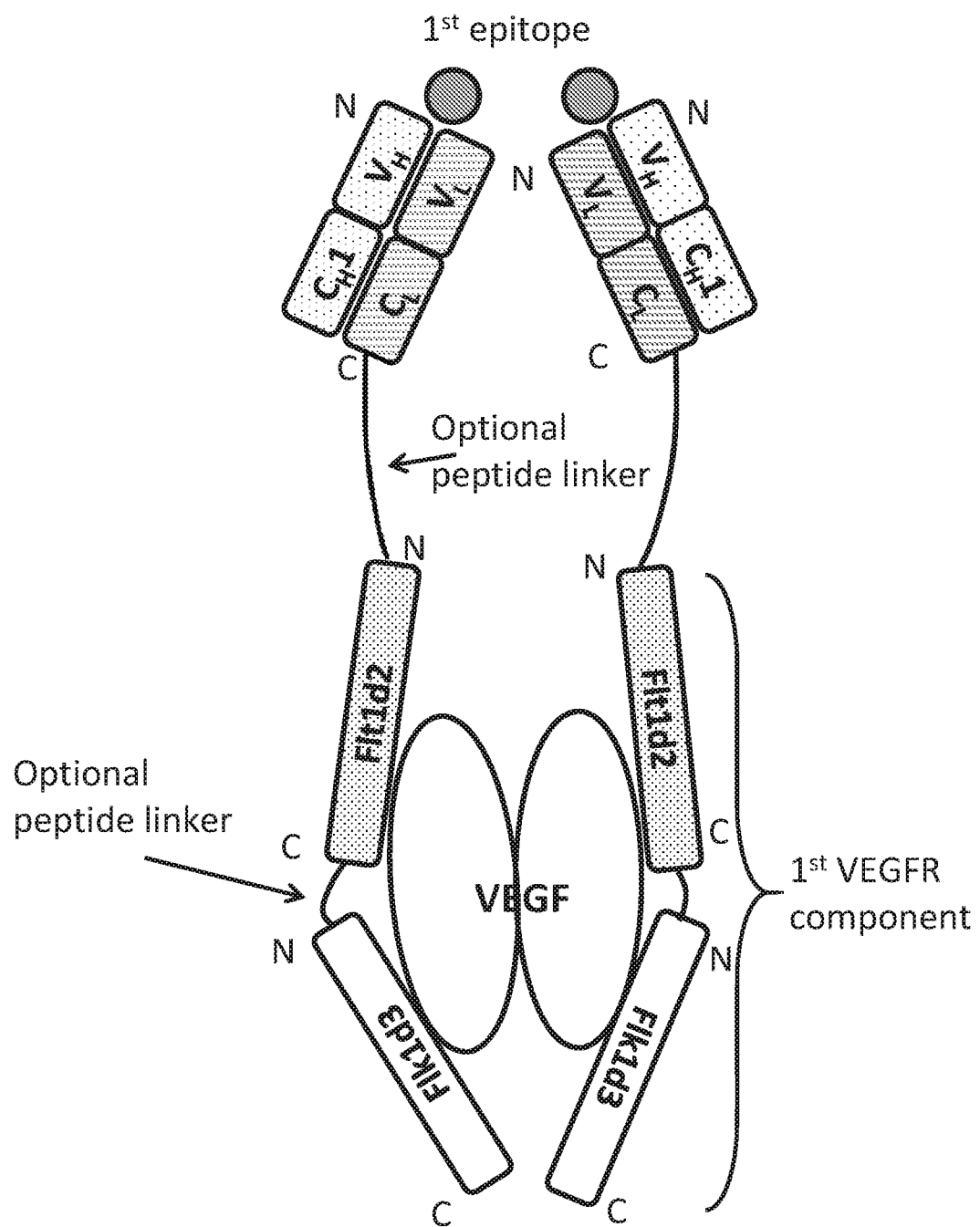
FIG. 5 depicts an exemplary of two VEGFR-antibody light chain fusion proteins, each comprising a Fab and one VEGFR component fused to the C-terminus of the light chain of the Fab. Binding to VEGF dimer brings two VEGFR-antibody light chain fusion proteins in proximity. In alternative formats, the two VEGFR-antibody light chain fusion proteins can be different, each can comprise three or more Ig-like domains, and/or can comprise any Ig-like domains of either Flt-1 or Flk-1.

In some embodiments, the VEGFR-antibody light chain fusion protein described herein can increase antibody cellular specificity by reducing antibody activity in the absence of binding to a target cell or interest (e.g. cancer cells or tissues overexpressing VEGF). This feature will be particularly useful to selectively mask or reduce cytotoxicity of the antibody fusion protein, thereby protecting non-target or normal cells from toxic effects while only exposing target cells (e.g. cancer cells or tissues overexpressing VEGF) to toxic effects. In some embodiments, the VEGFR-antibody light chain fusion protein comprising VEGFR components may stabilize VEGF dimer binding within the same antibody fusion protein (see examples shown in FIG. 1 and FIG. 2). In some embodiments, one VEGFR-antibody light chain fusion protein may pair with another one nearby, forming a dimer of the VEGFR components from two parties and stabilizing VEGF binding (see examples shown in FIGS. 3-5).

In some embodiments, the VEGFR-antibody light chain fusion protein described herein retains the functions of the intact antibody and the VEGFR component (e.g. binding to VEGF), with or without a linker peptide. In some embodiments, the VEGFR-antibody light chain fusion protein does not affect the structure of the antibody Fc region. In some embodiments, the VEGFR-antibody light chain fusion protein does not interfere with binding of the Fc portion of the antibody to Fc receptors (such as FcγR and FcRn) or binding of the antibody to its respective target(s). In some embodiments, the VEGFR-antibody light chain fusion protein does not affect the interaction between the antibody portion and the immune system (effector function). In some embodiments, the VEGFR-antibody light chain fusion protein avoids heavy chain distortions, resulting in decreased degradation after uptake by FcR bearing cells, followed by recycling out of the cell. In some embodiments, the VEGFR-antibody light chain fusion protein retains high binding affinity to both VEGF and the antigen recognized by the parental IgG.

VEGFR Component

VEGF and VEGFR

Many key players in the neovascularization process have been identified, and the VEGF family has a predominant role. The human VEGF family consists of 6 members: VEGF-A VEGF-B, VEGF-C, VEGF-D, VEGF-E, and placental growth factor (PIGF). In addition, multiple isoforms of VEGF-A. VEGF-B. and PIGF are generated through alternative RNA splicing (Sullivan et al., MAbs, 2002, 2(2): 165-75). VEGF-A is the primary factor involved with angiogenesis; it binds to both VEGFR-1 and VEGFR-2. The strategy of inhibiting angiogenesis by obstructing VEGF-A signaling has established successful therapies for treatment of specific cancers as well as retinal neovascular and ischemic diseases (Major et al., J Pharmacol Exp Then, 1997, 283(1):402-10: Willet et al., Nat. Med. 2004, 10:145-7; Papadopoulos et al., Angiogenesis, 2012, 15(2):171-85; Aiello et al., PNAS, 1995, 92:10457-61).

Compared to other growth factors that contribute to the processes of vascular formation, VEGF is unique in its high specificity for endothelial cells within the vascular system.

In addition to being an angiogenic factor in angiogenesis and vasculogenesis, VEGF, as a pleiotropic growth factor, exhibits multiple biological effects in other physiological processes, such as endothelial cell survival, vessel permeability and vasodilation, monocyte chemotaxis and calcium influx (Ferrara and Davis-Smyth (1997) *Endocrine Rev.* 18:4-25). Moreover, VEGF was also reported to have mitogenic effects on a few non-endothelial cell types, such as retinal pigment epithelial cells, pancreatic duct cells and Schwann cells. See, e.g., Guerrin et al. (1995) J. Cell Physiol. 164:385-394; Oberg-Welsh et al. (1997) Mol. Cell. Endocrinol. 126:125-132: Sondell et al. (1999) J. Neurosci. 19:5731-5740.

Substantial evidence also implicates VEGF's critical role in the development of conditions or diseases that involve pathological angiogenesis. The VEGF mRNA is overexpressed by the majority of human tumors examined (Berkman et al. *J Clin Invest* 91:153-159 (1993); Brown et al. *Human Pathol.* 26:86-91 (1995); Brown et al. *Cancer Res.* 53:4727-4735 (1993): Mattern et al. *Brit. J. Cancer.* 73:931-934 (1996); and Dvorak et al. *Am J. Pathol.* 146:1029-1039 (1995)). Also, the concentration of VEGF in eye fluids are highly correlated to the presence of active proliferation of blood vessels in patients with diabetic and other ischemia-related retinopathies (Aiello et al. *N. Engl. J. Med.* 331: 1480-1487 (1994)). Furthermore, studies have demonstrated the localization of VEGF in choroidal neovascular membranes in patients affected by AMD (Lopez et al. *Invest. Ophalmo. Vis. Sci.* 37:855-868 (1996)).

Anti-VEGF monoclonal antibodies are promising candidates for the treatment of solid tumors and various intraocular neovascular disorders. Although the VEGF molecule is upregulated in tumor cells, and its receptors are upregulated in tumor infiltrated vascular endothelial cells, the expression of VEGF and its receptors remain low in normal cells that are not associated with angiogenesis. Anti-VEGF antibodies include, but are not limited to, Bevacizumab (Avastin®), Brolucizumab, Vanucizumab (RG7221), and Ranibizumab (Lucentis®).

VEGF is a dimer with an apparent molecular mass of about 46 kDa with each subunit having an apparent molecular mass of about 23 kDa. The endothelial proliferative activity of VEGF is known to be mediated by two high affinity tyrosine kinase receptors, VEGFR-1 (Flt-1) and VEGFR-2 (KDR/Flk-1), which exist only on the surface of vascular endothelial cells. DeVries, et al., Science 225:989-991 (1992) and Terman, et al., Oncogene 6:1677-1683 (1991). Both the Flt-1 and KDR tyrosine kinase receptors have seven immunoglobulin-like (Ig-like) domains which form the extracellular ligand-binding regions of the receptors, a transmembrane domain which serves to anchor the receptor on the surface of cells in which it is expressed and an intracellular catalytic tyrosine kinase domain which is interrupted by a "kinase insert". While the KDR receptor binds only the VEGF protein with high affinity, the Flt-1 receptor also binds placenta growth factor (PLGF), a molecule having significant structural homology with VEGF. An additional member of the receptor tyrosine kinases having seven Ig-like domains in the extracellular ligand-binding region is VEGFR-3 (Flt-4), which is not a receptor for either VEGF or PLGF, but instead binds to a different ligand; VH1.4.5. The VH1.4.5 ligand has been reported in the literature as VEGF-related protein (VRP) or VEGF-C.

In addition to being known as an endothelial cell specific mitogen, VEGF is unique among angiogenic growth factors in its ability to induce a transient increase in blood vessel permeability to macromolecules (hence its original and alternative name, vascular permeability factor, VPF) (see Dvorak et al., (1979) *J. Immunol.* 122:166-174; Senger et al., (1983 *Science* 219:983-985; Senger et al., (1986) *Cancer Res.* 46:5629-5632). Increased vascular permeability and the resulting deposition of plasma proteins in the extravascular space assists the new vessel formation by providing a provisional matrix for the migration of endothelial cells (Dvorak et al., (1995) *Am. J. Pathol.* 146:1029-1039). Hyperpermeability is indeed a characteristic feature of new vessels, including those associated with tumors.

In some embodiments, the VEGFR component of the present invention comprises Ig-like domain or domains derived from either Flt-1 or KDR receptor (or the murine homologue of the KDR receptor, Flk-1) extracellular ligand-binding region which mediates binding to the VEGF protein. In some embodiments, the VEGFR component of the present invention comprises Ig-like domains derived from extracellular ligand-binding regions of both Flt-1 and KDR receptor (or the murine homologue of the KDR receptor, Flk-1), or functional equivalents thereof, forming a "chimeric VEGFR" component.

The term "Ig-like domain" of Flt-1, Flt-4, or Flk-1 is intended to encompass not only the complete wild-type domain, but also insertional, deletional, and/or substitutional variants thereof which substantially retain the functional characteristics of the intact domain. It will be readily apparent to one of skill in the art that numerous variants of the Ig domains can be obtained which will retain substantially the same functional characteristics as the wild-type domain.

The term "functional equivalents" when used in reference to an Ig-like domain "X", is intended to encompass the Ig-like domain "X" with at least one alteration, e.g., a deletion, addition, and/or substitution, which retains substantially the same functional characteristics as does the wild type Ig domain "X", that is, a substantially equivalent binding to VEGF. It will be appreciated that various amino acid substitutions can be made in an Ig domain "X" without departing from the spirit of the invention with respect to the ability of these receptor components to bind and inactivate VEGF. Thus, point mutational and other broader variations may be made in the Ig-like domain or domains of the VEGFR component of the present invention so as to impart interesting properties that do not substantially affect the VEGFR component's ability to bind to and inhibit the activity of VEGF. The functional characteristics of the VEGFR components of the invention may be determined by any suitable screening assay known to the art for measuring the desired characteristic. Other assays, for example, a change in the ability to specifically bind to VEGF can be measured by a competition-type VEGF binding assay. Modifications of protein properties such as thermal stability, hydrophobicity, susceptibility to proteolytic degradation, or tendency to aggregate may be measured by methods known to those of skill in the art. Also see subsection "1. Amino acid sequence variants" under section "V. Methods of preparation."

In some embodiments, the VEGFR component described herein comprises an Ig-like domain of either Flt-1 or Flk-1. In some embodiments, the VEGFR component comprises an Ig-like domain 1 of Flt-1 (hereinafter referred to as Flt1d1), a Flt1d2, a Flt1d3, a Flt1d4, a Flt1d5, a Flt1d6, a Flt1 d7, an Ig-like domain 1 of Flk-1 (hereinafter referred to as Flk1d1), a Flk1d2, a Flk1d3, a Flk1d4, a Flk1d5, a Flk1d6, or a Flk1d7.

In some embodiments, the VEGFR component described herein comprises 1, 2, 3, 4, 5, 6, or 7 Ig-like domains of either Flt-1 or Flk-1. In some embodiments, the VEGFR component comprises 2, 3, 4, 5, 6, or 7 Ig-like domains, comprising a mixture of Ig-like domains from Flt-1 and Flk-1. For example, in some embodiments, the VEGFR component comprises one Ig-like domain from Flk-1, and two Ig-like domains from Flt-1. In some embodiments, the VEGFR component comprises 2, 3, 4, 5, 6, or 7 Ig-like domains all from Flt-1. In some embodiments, the VEGFR component comprises 2, 3, 4, 5, 6, or 7 Ig-like domains all from Flk-1.

In some embodiments, the VEGFR component comprises 2, 3, 4, 5, 6, or 7 Ig-like domains from either Flt-1 or Flk-1 connected directly to each other. In some embodiments, the VEGFR component comprises 2, 3, 4, 5, 6, or 7 Ig-like domains from either Flt-1 or Flk-1 connected via domain linkers, such as those from either Flt-1 or Flk-1, e.g., the domain linker that connects Flt1d2 and Flt1d3. In some embodiments, the Ig-like domains within the VEGFR component are connected by peptide linkers (see, e.g. peptide linker section below), such as (GGGGS)$_n$(SEQ ID NO: 4), wherein n is an integer between 1 and 8, e.g., (GGGGS)$_3$ (SEQ ID NO: 6), or (GGGGS)$_6$ (SEQ ID NO: 7). In some embodiments, the Ig-like domains within the VEGFR component are connected by non-peptide linkers (see, e.g. non-peptide linker section below), such as thioesters.

In some embodiments, the VEGFR component consists of 1, 2, 3, 4, 5, 6, or 7 Ig-like domains of either Flt-1 or Flk-1. In some embodiments, the VEGFR component consists essentially of 1, 2, 3, 4, 5, 6, or 7 Ig-like domains of either Flt-1 or Flk-1. In some embodiments, the VEGFR component comprises a moiety that is not Ig-like domains from either Flt-1 or Flk-1.

In some embodiments, the VEGFR component described herein comprises an Ig-like domain 2 of a first VEGFR Flt-1 (Flt1d2). In some embodiments, the VEGFR component further comprises an Ig-like domain 3 of a second VEGFR Flk-1 (Flk d3). In some embodiments, the VEGFR component further comprises an Ig-like domain of a third VEGFR, and/or an Ig-like domain of a fourth VEGFR, wherein the Ig-like domain is selected from the group consisting of Ig-like domain 4 of Flk-1 (Flk1d4), Ig-like domain 1 of Flk-1 (Flk1d1), Ig-like domain 5 of Flk-1 (Flk1d5), Ig-like domain 4 of Flt-1 (Flt1d4), and Ig-like domain 5 of Flt-1 (Flt1d5). In some embodiments, the VEGFR component further comprises an Ig-like domain 4 of a third VEGFR Flk-1 (Flk1d4). In some embodiments, the VEGFR component comprises Flt1d2 and Flk1d3. In some embodiments, the VEGFR component consists essentially of Flt1d2 and Flk1d3. In some embodiments, the VEGFR component consists of Flt1d2 and Flk1d3. In some embodiments, the VEGFR component comprises the amino acid sequence of SEQ ID NO: 8. In some embodiments, the VEGFR component comprises Flt1d2, Flk1d3, and Flk1d4. In some embodiments, the VEGFR component consists essentially of Flt1d2, Flk1d3, and Flk1d4. In some embodiments, the VEGFR component consists of Flt1d2, Flk1d3, and Flk1d4.

In some embodiments, the VEGFR-antibody light chain fusion protein of the present invention comprises (and in some embodiments consists of or consists essentially of) a light chain-VEGFR component fusion protein of the following configurations (from N-terminus to C-terminus), wherein L is an optional linker (such as non-peptide linker or peptide linker):

FP1: light chain-L-Flk1d3-Flt1d2
FP2: light chain-L-Flk1d4-Flk1 d3-Flt1 d2
FP3: light chain-L-Flk1d3-Flt1d2-Flk1d1
FP4: light chain-L-Flt1d4-Flk1d3-Flt1d2
FP5: light chain-L-Flk1d5-Flk1d4-Flk d3-Flt1d2
FP6: light chain-L-Flt1d5-Flt1d4-Flk1d3-Flt1d2
FP1': light chain-L-Flt1d2-Flk1d3
FP2': light chain-L-Flt1d2-Flk1d3-Flk1d4
FP3': light chain-L-Flk1d1-Flt1 d2-Flk1d3
FP4': light chain-L-Flt1d2-Flk1d3-Fit 1d4
FP5': light chain-L-Flt1d2-Flk1d3-Flk d4-Flk d5
FP6': light chain-L-Flt1d2-Flk1d3-Flt1d4-Flt1d5

In some embodiments, the Ig-like domain(s) of either Flt-1 or Flk-1 described herein are the only Ig-like domain(s) of the VEGFR component. In some embodiments, Flt1d2 is the only Ig-like domain of the VEGFR component. In some embodiments, Flt1d2 and Flk1d3 are the only Ig-like domains of the VEGFR component. In some embodiments, Flt1d2, Flk1d3, and Flk1d4 are the only Ig-like domains of the VEGFR component. In some embodiments, Flk1d1, Flt1d2, and Flk1d3 are the only Ig-like domains of the VEGFR component. In some embodiments, Flt1d2, Flk1d3, and Fit 1 d4 are the only Ig-like domains of the VEGFR component. In some embodiments, Flt1d2, Flk1d3, and Flt1d4 are the only Ig-like domains of the VEGFR component. In some embodiments, Flt1d2, Flk1d3, Flk1d4, and Flk1d5 are the only Ig-like domains of the VEGFR component. In some embodiments, Flt1d2, Flk1d3, Flt1d4, and Flt1d5 are the only Ig-like domains of the VEGFR component.

The linker sequence may be provided to decrease steric hindrance such that the VEGFR component and the antibody light chain may assume their optimal tertiary structure and/or interact appropriately with its target molecule. In some embodiments, the linker L is a peptide linker (see "peptide linkers" section below). In some embodiments, the linker L comprises amino acid sequence of $(GGGGS)_n$, wherein n is an integer between 1 and 8, e.g., $(GGGGS)_3$ (SEQ ID NO: 6), or $(GGGGS)_6$ (SEQ ID NO: 7).

In some embodiments, the VEGFR-antibody light chain fusion protein comprises a first VEGFR component and a second VEGFR component. In some embodiments, the first VEGFR component and a second VEGFR component are the same. In some embodiments, the first VEGFR component and the second VEGFR component each comprises a first VEGFR Flt1d2. In some embodiments, the first VEGFR component and the second VEGFR component each comprises a first VEGFR Flt1d2, and a second VEGFR Flk1d3. In some embodiments, the first VEGFR component and the second VEGFR component each comprises from N-terminus to C-terminus: Flt1d2-Flk1d3, wherein the N-terminus of the VEGFR component is fused to the C-terminus of antibody light chain. In some embodiments, the first and/or second VEGFR component comprises an amino acid sequence of SEQ ID NO: 8. In some embodiments, the first VEGFR component and the second VEGFR component each comprises a first VEGFR Flt1d2, a second VEGFR Flk1d3, and a third VEGFR Flk1d4. In some embodiments, the first VEGFR component and the second VEGFR component each comprises from N-terminus to C-terminus: Flt1d2-Flk1d3-Flk1d4, wherein the N-terminus of the VEGFR component is fused to the C-terminus of antibody light chain. In some embodiments, the first VEGFR component and a second VEGFR component are different. In some embodiments, the first VEGFR component comprises 2 Ig-like domains of either Flt-1 or Flk-1, the second VEGFR component comprises 3 Ig-like domains of either Flt-1 or Flk-1. In some embodiments, the first VEGFR component comprises 3 Ig-like domains of either Flt-1 or Flk-1, the second VEGFR component comprises 4 Ig-like domains of either Flt-1 or Flk-1. In some embodiments, the first VEGFR component comprises 4 Ig-like domains of either Flt-1 or Flk-1, the second VEGFR component comprises 5 Ig-like domains of either Flt-1 or Flk-1. In some embodiments, the first VEGFR component comprises from N-terminus to C-terminus Flt1d2-Flk1d3, and the second VEGFR component comprises from N-terminus to C-terminus Flt1d2-Flk1d3-Flk1d4. In some embodiments, the first VEGFR component and the second VEGFR component comprises the same number of Ig-like domains with different sequences. For example, in some embodiments, the first VEGFR component comprises from N-terminus to C-terminus Flt1d2-Flk1d3-Flk1d4, the second VEGFR component comprises from N-terminus to C-terminus Flk1d1-Flt1d2-Flk1d3. In some embodiments, the first VEGFR component comprises from N-terminus to C-terminus Flt1d2-Flk1d3-Flk1d4, the second VEGFR component comprises from N-terminus to C-terminus Flt1d2-Flk1d3-Flt1d4.

VEGFR Component Size

The VEGFR component of the present invention is at least about 4 kDa. In some embodiments, the VEGFR component of the present invention is about 4 kDa to about 95 kDa, about 4 kDa to about 10 kDa, about 10 kDa to about 15 kDa, about 15 kDa to about 20 kDa, about 20 kDa to about 25 kDa, about 25 kDa to about 30 kDa, about 30 kDa to about 35 kDa, about 35 kDa to about 40 kDa, about 40 kDa to about 45 kDa, about 45 kDa to about 50 kDa, about 50 kDa to about 55 kDa, about 55 kDa to about 60 kDa, about 60 kDa to about 65 kDa, about 65 kDa to about 70 kDa, about 70 kDa to about 75 kDa, about 75 kDa to about 80 kDa, about 80 kDa to about 85 kDa, about 85 kDa to about 90 kDa, about 90 kDa to about 95 kDa, about 4 kDa to about 15 kDa, about 4 kDa to about 30 kDa, about 4 kDa to about 43 kDa, about 4 kDa to about 56 kDa, about 4 kDa to about 69 kDa, about 4 kDa to about 82 kDa, about 15 kDa to about 30 kDa, about 15 kDa to about 43 kDa, about 15 kDa to about 56 kDa, about 15 kDa to about 69 kDa, about 15 kDa to about 82 kDa, about 15 kDa to about 95 kDa, about 25 kDa to about 43 kDa, about 25 kDa to about 56 kDa, about 25 kDa to about 69 kDa, about 25 kDa to about 82 kDa, about 25 kDa to about 95 kDa, about 40 kDa to about 56 kDa, about 40 kDa to about 69 kDa, about 40 kDa to about 82 kDa, about 40 kDa to about 95 kDa, about 50 kDa to about 69 kDa, about 50 kDa to about 75 kDa, about 50 kDa to about 82 kDa, about 50 kDa to about 95 kDa, about 65 kDa to about 75 kDa, about 65 kDa to about 82 kDa, about 65 kDa to about 95 kDa, about 75 kDa to about 82 kDa, or about 75 kDa to about 95 kDa. In some embodiments, the VEGFR component is about 23.2 kDa.

The VEGFR component of the present invention is at least about 36 amino acid (aa) in length. In some embodiments, the VEGFR component of the present invention is about 36 aa to about 864 aa, about 36 aa to about 91 aa, about 91 aa to about 136 aa, about 136 aa to about 182 aa, about 182 aa to about 227 aa, about 227 aa to about 273 aa, about 273 aa to about 318 aa, about 318 aa to about 364 aa, about 364 aa to about 409 aa, about 409 aa to about 455 aa, about 455 aa to about 500 aa, about 500 aa to about 545 aa, about 545 aa to about 591 aa, about 591 aa to about 636 aa, about 636 as to about 682 aa, about 682 as to about 727 aa, about 727 aa to about 773 aa, about 773 as to about 818 aa, about 818 aa to about 864 aa, about 36 aa to about 136 aa, about 36 aa to about 273 aa, about 36 aa to about 391 aa, about 36 aa to about 509 aa, about 36 aa to about 627 aa, about 36 aa to about 745 aa, about 36 aa to about 745 aa, about 136 aa to about 273 aa, about 136 aa to about 391 aa, about 136 aa to about 509 aa, about 136 aa to about 627 aa, about 136 aa to about 745 aa, about 136 aa to about 864 aa, about 227 aa to about 391 aa, about 227 aa to about 509 aa, about 227 aa to about 627 aa, about 227 aa to about 745 aa, about 227 aa to about 864 aa, about 364 aa to about 509 aa, about 364 aa to about 627 aa, about 364 aa to about 745 aa, about 364 aa to about 864 aa, about 455 aa to about 627 aa, about 455 aa to about 682 aa, about 455 aa to about 745 aa, about 455 aa to about 864 aa, about 591 aa to about 682 aa, about 591 aa to about 745 aa, about 591 aa to about 864 aa, about 682 aa to about 745 aa, or about 682 aa to about 864 aa in length. In some embodiments, the VEGFR component is about 211 aa in length.

VEGFR Binding Affinity

Binding specificity of the VEGFR component described herein to VEGF can be determined experimentally by methods known in the art. Such methods comprise, but are not limited to Western blots, ELISA-, RIA-, ECL-, IRMA-, EIA-, BIAcore-tests and peptide scans.

The ELISA-based binding assay can be performed as described in Example 2. Briefly, the ELISA plate can be coated with VEGF (or antigen to be tested, e.g., PD-1), then varying concentrations of VEGFR-antibody light chain fusion proteins (or any antibody to be tested) is added into each well. After incubation and washing, a secondary antibody such as HRP conjugated anti-IgG Fc antibody can be added in to detect VEGFR-antibody light chain fusion protein (or any antibody to be tested) bound to VEGF (or the antigen to be tested). HRP substrate is added to each well. Optical density (OD) of each well can be measured using a microplate reader at 450 nm. $EC_{50}$ can then be calculated.

In some embodiments, the $K_D$ or $EC_{50}$ of the binding between the VEGFR component described herein and VEGF is about $10^{-5}$ M to about $10^{-15}$ M. In some embodiments, the $K_D$ of the binding between the VEGFR component described herein and VEGF is about $10^{-5}$ M to about $10^{-6}$ M, about $10^{-6}$ M to about $10^{-7}$ M, about $10^{-7}$ M to about $10^{-8}$ M, about $10^{-8}$ M to about $10^{-9}$ M, about $10^{-9}$ M to about $10^{-10}$ M, about $10^{-10}$ M to about $10^{-11}$ M, about $10^{-11}$ M to about $10^{-12}$ M, about $10^{-12}$ M to about $10^{-13}$ M, about $10^{-13}$ M to about $10^{-14}$ M, about $10^{-14}$ M to about $10^{-15}$ M, about $10^{-5}$ M to about $10^{-15}$ M, about $10^{-6}$ M to about $10^{-15}$ M, about $10^{-7}$ M to about $10^{-15}$ M, about $10^{-8}$ M to about $10^{-15}$ M, about $10^{-9}$ M to about $10^{-15}$ M, about $10^{-10}$ M to about $10^{-15}$ M, about $10^{-11}$ M to about $10^{-15}$ M, about $10^{-12}$ M to about $10^{-15}$ M, about $10^{-13}$ M to about $10^{-15}$ M, about $10^{-5}$ M to about $10^{-14}$ M, about $10^{-7}$ M to about $10^{-14}$ M, about $10^{-8}$ M to about $10^{-14}$ M, about $10^{-9}$ M to about $10^{-14}$ M, about $10^{-10}$ M to about $10^{-14}$ M, about $10^{-11}$ M to about $10^{-14}$ M, about $10^{-12}$ M to about $10^{-14}$ M, about $10^{-5}$ M to about $10^{-13}$ M, about $10^{-7}$ M to about $10^{-13}$ M, about $10^{-8}$ M to about $10^{-13}$ M, about $10^{-9}$ M to about $10^{-12}$ M, about $10^{-10}$ M to about $10^{-12}$ M, about $10^{-5}$ M to about $10^{-11}$ M, about $10^{-6}$ M to about $10^{-11}$ M, about $10^{-7}$ M to about $10^{-11}$ M, about $10^{-8}$ M to about $10^{-11}$ M, about $10^{-9}$ M to about $10^{-11}$ M, about $10^{-5}$ M to about $10^{-10}$ M, about $10^{-6}$ M to about $10^{-10}$ M, about $10^{-7}$ M to about $10^{-10}$ M, about $10^{-8}$ M to about $10^{-10}$ M, about $10^{-5}$ M to about $10^{-9}$ M, about $10^{-6}$ M to about $10^{-9}$ M, about $10^{-7}$ M to about $10^{-9}$ M, about $10^{-5}$ M to about $10^{-8}$ M, $10^{-6}$ M to about $10^{-8}$ M, or $10^{-5}$ M to about or $10^{-7}$ M. In some embodiments, the antibody fusion protein binds to VEGF with an affinity of around 0.5 pM. In some embodiments, the antibody fusion protein binds to VEGF with an $EC_{50}$ of about 10 nM to about 40 nM.

In some embodiments, the VEGFR-antibody light chain fusion protein comprises a first VEGFR component and a second VEGFR component fused to the C-terminus of both antibody light chains (e.g., C-terminus of antibody VL-CL domain). In some embodiments, the first VEGFR component and the second VEGFR component has similar binding affinities. In some embodiments, the first VEGFR component and the second VEGFR component has different binding affinities.

In some embodiments, the $K_D$ of the binding between the second VEGFR component and VEGF is more than the $K_D$ of the binding between the first VEGFR component and VEGF. For example, the $K_D$ of the binding between the second VEGFR component and VEGF can be about 1-10 times, about 10-20 times, about 20-30 times, about 30-40 times, about 40-50 times, about 50-60 times, about 60-70 times, about 70-80 times, about 80-90 times, about 90-100 times, about 100-500 times, or about 500-1000 times of the $K_D$ of the binding between the first VEGFR component and VEGF.

In some embodiments, the fusion of VEGFR component to the C-terminus of the antibody light chain does not affect the binding affinity of the VEGFR component to VEGF. In some embodiments, the fusion of VEGFR component to the C-terminus of the antibody light chain reduces the binding affinity of the VEGFR component to VEGF such that the $K_D$ of the binding between the fused VEGFR component and VEGF can be about 1-10 times, about 10-20 times, about 20-30 times, about 30-40 times, about 40-50 times, about 50-60 times, about 60-70 times, about 70-80 times, about 80-90 times, about 90-100 times, about 100-500 times, or about 500-1000 times of the $K_D$ of the binding between the non-fused VEGFR component and VEGF.

In some embodiments, the fusion of VEGFR component to the C-terminus of the antibody light chain does not affect the binding affinity of the antibody to its target antigen. In some embodiments, the fusion of VEGFR component to the C-terminus of the antibody light chain reduces the binding affinity of the antibody to its target antigen such that the $K_D$ of the binding between the VEGFR-fused antibody to its target antigen can be about 1-10 times, about 10-20 times, about 20-30 times, about 30-40 times, about 40-50 times, about 50-60 times, about 60-70 times, about 70-80 times, about 80-90 times, about 90-100 times, about 100-500 times, or about 500-1000 times of the $K_D$ of the binding between the non-fused antibody to its target antigen.

In some embodiments, the fusion of VEGFR component to the C-terminus of the antibody light chain increases the binding affinity of the antibody to its target antigen (e.g. by stabilizing the binding of antibody-antigen via the binding of VEGFR-VEGF at the same cell) such that the $K_D$ of the binding between the VEGFR-fused antibody to its target antigen can be about 1-10 times, about 10-20 times, about 20-30 times, about 30-40 times, about 40-50 times, about 50-60 times, about 60-70 times, about 70-80 times, about 80-90 times, about 90-100 times, about 100-500 times, or about 500-1000 times lower of the $K_D$ of the binding between the non-fused antibody to its target antigen.

Thus in some embodiments, the $K_D$ of the binding between the VEGFR-fused antibody and the antibody target antigen is about $10^{-5}$ M to about $10^{-13}$ M. In some embodiments, the $K_D$ of the binding between the VEGFR-fused antibody and the antibody target antigen is about $10^{-5}$ M to about $10^{-6}$ M, about $10^{-6}$ M to about $10^{-7}$ M, about $10^{-7}$ M to about $10^{-8}$ M, about $10^{-8}$ M to about $10^{-9}$ M, about $10^{-9}$ M to about $10^{-10}$ M, about $10^{-10}$ M to about $10^{-11}$ M, about $10^{-11}$ M to about $10^{-12}$ M, about $10^{-12}$ M to about $10^{-13}$ M, about $10^{-5}$ M to about $10^{-13}$ M, about $10^{-6}$ M to about $10^{-13}$ M, about $10^{-7}$ M to about $10^{-13}$ M, about $10^{-8}$ M to about $10^{-13}$ M, about $10^{-9}$ M to about $10^{-13}$ M, about $10^{-10}$ M to about $10^{-13}$ M, about $10^{-11}$ M to about $10^{-13}$ M, about $10^{-5}$ M to about $10^{-12}$ M, about $10^{-6}$ M to about $10^{-12}$ M, about $10^{-7}$ M to about $10^{-12}$ M, about $10^{-8}$ M to about $10^{-12}$ M, about $10^{-9}$ M to about $10^{-12}$ M, about $10^{-10}$ M to about $10^{-12}$ M, about $10^{-5}$ M to about $10^{-11}$ M, about $10^{-7}$ M to about $10^{-11}$ M, about $10^{-8}$ M to about $10^{-11}$ M, about $10^{-9}$ M to about $10^{-11}$ M, about $10^{-5}$ M to about $10^{-10}$ M, about $10^{-7}$ to about $10^{-10}$ M, about $10^{-8}$ M to about $10^{-10}$ M, about $10^{-5}$ M to about $10^{-9}$ M, about $10^{-7}$ M to about $10^{-9}$ M, about $10^{-5}$ M to about $10^{-8}$ M, or about $10^{-6}$ M to about $10^{-8}$ M. In some embodiments, the $K_D$ of the binding between the VEGFR-fused antibody and the antibody target antigen is about $10^{-8}$ M to about $10^{-16}$ M. In some embodiments, the $K_D$ of the binding between the VEGFR-fused antibody and the antibody target antigen is about $10^{-5}$ M to about $10^{-6}$ M, about $10^{-6}$ M to about $10^{-7}$ M, about $10^{-7}$ M to about $10^{-8}$ M, about $10^{-8}$ M to about $10^{-9}$ M, about $10^{-9}$ M to about $10^{-10}$ M, about $10^{-10}$ M to about $10^{-11}$ M, about $10^{-11}$ M to about $10^{-12}$ M, about $10^{-12}$ M to about $10^{-13}$ M, about $10^{-13}$ M to about $10^{-14}$ M, about $10^{-14}$ M to about $10^{-15}$ M, about $10^{-15}$ M to about $10^{-16}$ M, about $10^{-8}$ M to about $10^{-16}$ M, about $10^{-9}$ M to about $10^{-16}$ M, about $10^{-10}$ M to about $10^{-16}$ M, about $10^{-11}$ M to about $10^{-16}$ M, about $10^{-12}$ M to about $10^{-16}$ M, about $10^{-13}$ M to about $10^{-16}$ M, about $10^{-14}$ M to about $10^{-16}$ M, about $10^{-8}$ M to about $10^{-15}$ M, about $10^{-9}$ M to about $10^{-15}$ M, about $10^{-10}$ M to about $10^{-15}$ M, about $10^{-11}$ M to about $10^{-15}$ M, about $10^{-12}$ M to about $10^{-15}$ M, about $10^{-13}$ M to about $10^{-15}$ M, about $10^{-8}$ M to about $10^{-14}$ M, about $10^{-9}$ M to about $10^{-14}$ M, about $10^{-10}$ M to about $10^{-14}$ M, about $10^{-11}$ M to about $10^{-14}$ M, about $10^{-12}$ M to about $10^{-14}$ M, about $10^{-8}$ M to about $10^{-13}$ M, about $10^{-9}$ M to about $10^{-13}$ M, about $10^{-10}$ M to about $10^{-13}$ M, about $10^{-11}$ M to about $10^{-13}$ M, about $10^{-8}$ M to about $10^{-12}$ M, about $10^{-9}$ M to about $10^{-12}$ M, about $10^{-10}$ M to about $10^{-12}$ M, about $10^{-8}$ M to about $10^{-11}$ M, about $10^{-9}$ M to about $10^{-11}$ or about $10^{-8}$ M to about $10^{-10}$ M. In some embodiments, the $EC_{50}$ of the binding between the VEGFR-fused antibody and the antibody target antigen is about 1 nM to about 30 nM.

Antibody Platform

The antibody of the VEGFR-antibody light chain fission protein of the present invention can be of any possible format.

In some embodiments, the antibody comprises a single polypeptide chain. In some embodiments, the antibody comprises more than one (such as any of 2, 3, 4, or more polypeptide chains. The polypeptide chain(s) may be of any length, such as at least about any of 10, 20, 50, 100, 200, 300, 500, or more amino acids long. In the cases of multi-chain antibodies, the nucleic acid sequences encoding the polypeptide chains may be operably linked to the same promoter or to different promoters.

Native antibodies, such as monoclonal antibodies, are immunoglobulin molecules that are immunologically reactive with a particular antigen. In some embodiments, the antibody is an agonistic antibody. In some embodiments, the antibody is an antagonistic antibody. In some embodiments, the antibody is a monoclonal antibody. In some embodiments, the antibody is a full-length antibody. In some embodiments, the antibody is an antigen-binding fragment selected from the group consisting of Fab, Fab', F(ab')$_2$, minibody, and other antigen-binding subsequences of the full length antibody or engineered combinations thereof that comprise a light chain constant domain. In some embodiments, the antibody is a human antibody, a humanized antibody, or a chimeric antibody. In some embodiments, the antibody is a monovalent antibody. In some embodiments, the antibody is a multivalent antibody, such as a divalent antibody or a tetravalent antibody. In some embodiments, the antibody is a bispecific antibody. In some embodiments, the antibody is a multispecific antibody.

The antibody of the present invention (such as anti-PD-1, anti-PD-L1, anti-CTLA-4, anti-HER2, anti-EGFR, anti-Ang2 antibody, anti-TNFα antibody, or anti-IL-17A antibody) comprises a heavy chain and a light chain. In some embodiments, the heavy chain comprises a $V_H$ domain. In some embodiments, the heavy chain further comprises one or more constant domains, such as $C_H1$, $C_H2$, $C_H3$, or any combination thereof. In some embodiments, the light chain comprises a $V_L$ domain. In some embodiments, the light chain further comprises a constant domain, such as $C_L$. In some embodiments, the heavy chain and the light chain are connected to each other via a plurality of disulfide bonds. In some embodiments, the antibody comprises an Fc, such as an Fc fragment of the human IgG1, IgG2, IgG3, or IgG4. In some embodiments, the antibody does not comprise an Fc fragment. In some embodiments, the antibody is an antigen binding fragment, which is a Fab.

Antibody Formats

The antibody of the VEGFR-antibody light chain fusion protein described herein can be of any antibody or antibody fragment format that comprise a light chain (e.g. a light chain comprising $V_L$-$C_L$ domain), such as a fill-length antibody, IgG-IgG, IgG-derived molecules, a Fab, a Fab', a F(ab')2, a F(ab')2-scFv2, a Fab-scFv-Fc, a minibody, Dock and Lock, scFv, diabody, Diabody-Fc, Diabody-CH$_3$, intrabody, and other antigen-binding subsequences of the full length antibody or engineered combinations thereof. In some embodiments, the light chain comprises a $V_L$ and a $C_L$ domain. In some embodiments, the antibody fragment comprising light chain comprises $V_L$-L-$C_L$ (L is an optional linker). In some embodiments, the antibody fragment comprising light chain comprises $V_H$-L1-$V_1$-L2-$C_L$ (L1 and L2 are optional linkers). In some embodiments, the antibody fragment comprising light chain comprises $V_{L1}$-L1-$C_L$-L2-$V_{L2}$-L3-$V_{H2}$, or $V_{L1}$-L1-$C_L$-L2-$V_{H2}$-L3-$V_{L2}$, (L1, L2, L3 are optional linkers). For a review of certain antibody fragments, see Hudson et al. Nat. Med. 9:129-134 (2003). For discussion of Fab and F(ab')$_2$ fragments comprising salvage receptor binding epitope residues and having increased in vivo half-life, see U.S. Pat. No. 5,869,046. For a review of multispecific antibodies, see Weidle et al., Cancer Genomics Proteomics, 10(1):1-18, 2013; Geering and Fussenegger, Trends Biotechnol., 33(2):65-79, 2015; Stamova et al., Antibodies, 1(2):172-198, 2012. Antibody fragments can be made by various techniques, including but not limited to proteolytic digestion of an intact antibody as well as production by recombinant host cells (e.g. E. coli or phage), as described herein.

In some embodiments, the antibody of the present invention is a full length antibody (e.g. having a human immunoglobulin constant region), such as IgA, IgD, IgE, IgG, IgM, or immunoglobulin derivatives. In some embodiments, the antibody is monospecific. In some embodiments, the antibody is multispecific (such as bispecific). Multispecific antibodies have binding specificities for at least two different antigens or epitopes (e.g., bispecific antibodies have binding specificities for two antigens or epitopes).

Multivalent and/or Multispecific Antibodies

The antibody of the VEGFR-antibody light chain fusion protein described herein can be in any format known in the art (see, e.g., Weidle et al., Cancer Genomics Proteomics, 10(1):1-18, 2013; Geering and Fussenegger, Trends Biotechnol., 33(2):65-79, 2015; Stamova et al., Antibodies, 1(2):172-198, 2012; Spiess et al., Mol. Immunol., 2015 October; 67(2 Pt A):95-106). The antibody may be a format class of "IgG-derived molecules" comprising Fc regions. For example, the antibody can be in the format of, but are not limited to, IgG-IgG, Cov-X-Body, Common LC (light chain), DAF (dual acting Fab, which comprises evolved Fvs with dual specificity), CrossMab, DutaMab™, Triomab®, LUZ-Y, Fcab, Kappa-Lambda body, Orthogonal Fab, DT-IgG (dual-targeting IgG), IgG-dsscFv2 (disulfide-stabilized scFv2), IgG(H)-scFv, scFv-(H)IgG, scFv-(L)IgG, IgG(L)-scFv, DVD (dual variable domain), IgG-dsFv (disulfide-stabilized Fv), processed IgG-dsFv, IgG(L,H)-Fv, V(H)-IgG, V(L)-IgG, IgG(H)-V, IgG(L)-V, Knobs-into-holes, charge pair, Fab-arm exchange, SEEDbody (strand-exchange engineered domain), IgG-scFab (single chain Fab), scFab-dsscFv, 2scFv-IgG, IgG-2scFv, scFv4-Ig, Zybody™, or DVI-IgG. Knobs-into-holes technologies can be used for heterodimerization of different H-chains in, for example, common LC, CrossMab, IgG-dsFv, or IgG-scFab. The antibody may also be an "Fc-less bispecific" format class, which usually comprises individual Fabs of different specificities fused together via linkers. For example, the antibody can be in the format of, but are not limited to, F(ab')2, F(ab')2-scFv2, Fab-scFv2, Fab-scFv, Fab-scFv-Fc, DNL-F(ab)$_3$ (dock-and-lock trivalent Fab), say; scFv-scFv (e.g. BiTE®), Diabody, scBsDb (single-chain bispecific diabody), DART (dual-affinity retargeting molecule). TandAb (tetravalent tandem antibody), scBsTaFv (single-chain bispecific tandem variable domain), Diabody-CH$_3$, Fab-say. Bi- or trivalent Fab-scFv or Fab-scFv2 formats are generated by fusion of VH-CH1 and/or L chains to scFvs. The antibody to be employed in accordance with the disclosure can be chemically modified derivative of any of the aforementioned antibody formats, or it may comprise ligands, peptides, or combinations thereof. The antibody to be employed in accordance with the disclosure can be further modified using conventional techniques known in the art, for example, by using amino acid deletion(s), insertion(s), substitution(s), addition(s), and/or recombination(s) and/or any other modification(s) (e.g. posttranslational and chemical modifications, such as glycosylation and phosphorylation) known in the art either alone or in combination. Chemical/biochemical or molecular biological methods for such modifications are known in the art and described inter alia in laboratory manuals (see Sambrook et al.; Molecular Cloning: A Laboratory Manual; Cold Spring Harbor Laboratory Press, 2nd edition 1989 and 3rd edition 2001; Gerhardt et al.; Methods for General and Molecular Bacteriology; ASM Press, 1994; Lefkovits; immunology Methods Manual: The Comprehensive Sourcebook of Techniques; Academic Press, 1997; Golemis; Protein-Protein Interactions: A Molecular Cloning Manual; Cold Spring Harbor Laboratory Press. 2002).

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168), Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); and preparing trispecific antibodies as described, e.g., in Tutt et al. J. Immunol. 147: 60 (1991). Engineered antibodies with three or more functional antigen binding sites, including "Octopus antibodies," are also included herein (see, e.g., US 2006/0025576A1).

Linkers

In some embodiments, the VEGFR-antibody light chain fusion protein may comprise a linker between the VEGFR component and the C-terminus of the antibody light chain (e.g., C-terminus of antibody VL-CL domain). The length, the degree of flexibility and/or other properties of the linker(s) used in the VEGFR-antibody light chain fusion protein may have some influence on properties, including but not limited to the affinity, specificity or avidity for one or more particular antigens or epitopes, as well as for the VEGFR component. For example, longer linkers may be selected to ensure that two adjacent domains do not sterically interfere with one another. In some embodiment, a linker (such as peptide linker) comprises flexible residues (such as glycine and serine) so that the adjacent domains are free to move relative to each other. For example, a glycine-serine doublet can be a suitable peptide linker. In some embodiments, the linker is a non-peptide linker. In some embodiments, the linker is a peptide linker. In some embodiments, the linker is a non-cleavable linker. In some embodiments, the linker is a cleavable linker.

Other linker considerations include the effect on physical or pharmacokinetic properties of the resulting compound, such as solubility, lipophilicity, hydrophilicity, hydrophobicity, stability (more or less stable as well as planned degradation), rigidity, flexibility, immunogenicity, modulation of antibody binding, the ability to be incorporated into a micelle or liposome, and the like.

In some embodiments, the VEGFR-antibody light chain fusion protein comprises two VEGFR components, wherein the first VEGFR component and the C-terminus of the first antibody light chain (e.g., C-terminus of antibody VL-CL domain) are connected by a first linker, and the second VEGFR component and the C-terminus of the second antibody light chain (e.g., C-terminus of antibody VL-CL domain) are connected by a second linker. In some embodiments, the first and second linkers are the same. In some embodiments, the first and second linkers are different. In some embodiments, the VEGFR-antibody light chain fusion protein comprises two VEGFR components, wherein only one VEGFR component and one C-terminus of the antibody light chain (e.g., C-terminus of antibody VL-CL domain) are connected by a linker.

Non-Peptide Linkers

Coupling of the VEGFR component and the C-terminus of the antibody light chain (e.g., C-terminus of antibody VL-CL domain) may be accomplished by any chemical reaction that will bind the two molecules so long as the antibody and the VEGFR component retain their respective activities, i.e. binding to specific antigen and VEGF, respectively. This linkage can include many chemical mechanisms, for instance covalent binding, affinity binding, intercalation, coordinate binding and complexation. In some embodiments, the binding is covalent binding. Covalent binding can be achieved either by direct condensation of existing side chains or by the incorporation of external bridging molecules. Many bivalent or polyvalent linking agents are useful in coupling protein molecules, such as the VEGFR component to the antibody of the present invention. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents (see Killen and Lindstrom, Jour. Immun. 133:1335-2549 (1984); Jansen et al., Immunological Reviews 62:185-216 (1982); and Vitetta et al., Science 238:1098 (1987)).

Linkers the can be applied in the present application are described in the literature (see, for example, Ramakrishnan, S. et al., Cancer Res. 44:201-208 (1984) describing use of MBS (M-maleimidobenzoyl-N-hydroxysuccinimide ester). In some embodiments, non-peptide linkers used herein include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to VEGFR-antibody fusion proteins with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form antibody fusion protein with increased stability. Disulfide linkages, are in general, less stable than other linkages because the disulfide linkage is cleaved in vitro, resulting in less antibody fusion protein available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Peptide Linkers

The peptide linker may have a naturally occurring sequence, or a non-naturally occurring sequence. For example, a sequence derived from the hinge region of heavy chain only antibodies may be used as the linker. See, for example, WO1996/34103.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acids to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

An essential technical feature of such peptide linker is that said peptide linker does not comprise any polymerization activity. The characteristics of a peptide linker, which comprise the absence of the promotion of secondary structures, are known in the art and described, e.g., in Dall'Acqua et al. (Biochem. (1998) 37, 9266-9273), Cheadle et al. (Mol Immunol (1992) 29, 21-30) and Raag and Whitlow (FASEB (1995) 9(1), 73-80). A particularly preferred amino acid in context of the "peptide linker" is Gly. Furthermore, peptide linkers that also do not promote any secondary structures are preferred. The linkage of the domains to each other can be provided by, e.g., genetic engineering. Methods for preparing fused and operatively linked bispecific single chain constructs and expressing them in mammalian cells or bacteria are well-known in the art (e.g. WO 99/54440, Ausubel, Current Protocols in Molecular Biology, Green Publishing Associates and Wiley Interscience, N. Y. 1989 and 1994 or Sambrook et al., Molecular Cloning: A Laboratory Manual, Cold Spring Harbor Laboratory Press, Cold Spring Harbor, N.Y., 2001).

The peptide linker can be a stable linker, which is not cleavable by protease, especially by Matrix metalloproteinases (MMPs).

The linker can also be a flexible linker. Exemplary flexible linkers include glycine polymers $(G)_n$ (SEQ ID NO: 1), glycine-serine polymers (including, for example, $(GS)_n$ (SEQ ID NO: 2), $(GSGGS)_n$ (SEQ ID NO: 3), $(GGGGS)_n$ (SEQ ID NO: 4), and $(GGGS)_n$ (SEQ ID NO: 5), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11 173-142 (1992)). The ordinarily skilled artisan will recognize that design of an antibody fusion protein can include linkers that are all or partially flexible, such that the linker can include a flexible linker portion as well as one or more portions that confer less flexible structure to provide a desired antibody fusion protein structure.

In some embodiments, the VEGFR component and the C-terminus of the antibody light chain are linked together by a linker of sufficient length to enable the VEGFR component-light chain to fold in such a way as to permit binding to VEGF, as well as to the antigen specifically recognized by the antibody. Further to this embodiment, such a linker may comprise, for example, the amino acid sequence of such as (GGGGS)$_n$, wherein n is an integer between 1 and 8, e.g. (GGGGS)$_3$ (SEQ ID NO: 6; hereinafter referred to as "(G4S)3" or "GS3"), or (GGGGS)$_6$ (SEQ ID NO: 7; hereinafter referred to as "(G4S)6" or "GS6"). In some embodiments, the peptide linker comprise the amino acid sequence of (GSTSGSGKPGSGEGS)$_n$ (SEQ ID NO: 44), wherein n is an integer between 1 and 3.

Antibodies Specifically Recognizing Immune Checkpoint Molecules

In some embodiments, the antibody fusion protein of the present invention comprises an antibody specifically recognizing an immune checkpoint molecule (such as anti-PD-1, anti-PD-L1, or anti-CTLA-4 full-length antibody), and VEGFR component fused to the C-terminus of the antibody light chain (e.g., C-terminus of antibody VL-CL domain). The antibody that specifically recognizes an immune checkpoint molecule is interchangeably referred herein as "immune checkpoint modulator."

Immune checkpoints are molecules in the immune system that either turn up (stimulatory molecules) or turn down a signal (inhibitory molecules). Immune checkpoint proteins regulate and maintain self-tolerance and the duration and amplitude of physiological immune responses. Stimulatory checkpoint molecules include, but are not limited to, CD27, CD40, OX40, GITR and CD137, which belong to tumor necrosis factor (TNF) receptor superfamily, as well as CD28 and ICOS, which belong to the B7-CD28 superfamily. Inhibitory checkpoint molecules include, but are not limited to, program death 1 (PD-1), Cytotoxic T-Lymphocyte-Associated protein 4 (CTLA-4), Lymphocyte Activation Gene-3 (LAG-3), T-cell Immunoglobulin domain and Mucin domain 3 (TIM-3, HAVCR2), V-domain Ig suppressor of T cell activation (VISTA, B7-H5), B7-H3, B7-H4 (VTCN1), HHLA2 (B7-H7), B and T Lymphocyte Attenuator (BTLA), Indoleamine 2,3-dioxygenase (IDO), Killer-cell Immunoglobulin-like Receptor (KIR), adenosine A2A receptor (A2AR), T cell immunoreceptor with Ig and ITIM domains (TIGIT), 2B4 (CD244) and ligands thereof. Numerous checkpoint proteins have been studied extensively, such as CTLA-4 and its ligands CD80 (B7-1) and CD86, and PD-1 (CD279) with its ligands PD-L1 (B7-H1, CD274) and PD-L2 (B7-DC, CD273) (See, for example, Pardoll. Nature Reviews Cancer 12: 252-264 (2012)).

The antibody specifically recognizing an immune checkpoint molecule, or the "immune checkpoint modulator" of the present invention, can be immune checkpoint inhibitors (inhibitors of inhibitory immune checkpoint molecules) or activators of stimulatory immune checkpoint molecules. Immune checkpoint inhibitors (inhibitors of inhibitory immune checkpoint molecules), are of particular interest in the present invention, such as inhibitors of PD-1 (CD279), PD-L1 (B7-H1, CD274), PD-L2 (B7-DC, CD273), LAG-3, TIM-3 (HAVCR2), BTLA, CTLA-4, TIGIT, VISTA (B7-H5), B7-H4 (VTCN1), CD160 (BY55), HHLA2 (B7-H7), 2B4 (CD244), CD73, B7-1 (CD80), B7-H3 (CD276), KIR, or IDO.

In some embodiments, the antibody specifically recognizing an immune checkpoint molecule is an activator of a stimulatory immune checkpoint molecule, such as an agonist antibody, e.g. anti-CD28, anti-OX40, anti-ICOS, anti-GITR, anti-4-1BB, anti-CD27, anti-CD40, anti-CD3, and anti-HVEM.

In some embodiments, the antibody specifically recognizing an immune checkpoint molecule is an immune checkpoint inhibitor. In some embodiments, the immune checkpoint inhibitor targets T cells. In some embodiments, immune checkpoint inhibitor targets tumor cells. For example, in some cases, tumor cells can turn off activated T cells, when they attach to specific T-cell receptors. However, immune checkpoint inhibitors may prevent tumor cells from attaching to T cells so that T cells stay activated (see, for example, Howard West, JAMA Oncol. 1(1):115 (2015)). In some embodiments, the immune checkpoint inhibitor is an antibody (such as antagonist antibody) that targets an inhibitory immune checkpoint protein, including but not limited to, anti-CTLA-4, anti-TIM-3, anti-LAG-3, anti-KIR, anti-PD-1, anti-PD-L1, anti-CD73, anti-B7-H3, anti-CD47, anti-BTLA, anti-VISTA, anti-A2AR, anti-B7-l, anti-B7-H4, anti-CD52, anti-IL-10, anti-IL-35, and anti-TGF-β. In some embodiments, the immune checkpoint inhibitor is an inhibitor of an inhibitory checkpoint molecule selected from the group consisting of PD-1, PD-L1, LAG-3, TIM-3, HHLA2, CD160, CD73, BLTA, B7-H4, TIGIT, and VISTA. In some embodiments, the immune checkpoint inhibitor is an antibody specifically recognizing PD-1. In some embodiments, the immune checkpoint inhibitor is an antibody specifically recognizing PD-L1. In some embodiments, the immune checkpoint inhibitor is an antibody specifically recognizing CTLA-4. In some embodiments, the immune checkpoint inhibitor is an antibody specifically recognizing at least two different inhibitory immune checkpoint molecules (e.g. bispecific antibody).

CTLA-4

Cytotoxic T-Lymphocyte-Associated protein 4 (CTLA-4, or CD152) is a homolog of CD28, and is known as an inhibitory immune checkpoint molecule up-regulated on activated T-cells. CTLA-4 also binds to B7- and B7-2, but with greater affinity than CD28. The interaction between B7 and CTLA-4 dampens T cell activation, which constitutes an important mechanism of tumor immune escape. Anti-CTLA-4 antibody therapy (such as Ipilimumab, e.g., Yervoy®) has shown promise in a number of cancers, such as melanoma.

Exemplary anti-CTLA-4 antibodies that can be applied in the present application include, but are not limited to, Ipilimumab (e.g., YERVOY®), and Tremelimumab (formerly ticilimumab, CP-675,206).

Ipilimumab (e.g., YERVOY®) is a fully human anti-CTLA-4 immunoglobulin G1 (IgG1) monoclonal antibody (mAb) that blocks the down-regulation of T-cell activation. Ipilimumab is a CTLA-4 immune checkpoint inhibitor that blocks T-cell inhibitory signals induced by the CTLA-4 pathway, and increases the number of tumor reactive T effector cells.

In some embodiments, the VEGFR-antibody light chain fusion protein comprises an antibody (such as a full-length antibody) specifically recognizing CTLA-4 (herein after referred to as "anti-CTLA-4 antibody"). In some embodiments, the anti-CTLA-4 antibody comprises HC-CDR1, HC-CDR2, and HC-CDR3 of a heavy chain comprising the amino acid sequence of SEQ ID NO: 9; and/or LC-CDR1, LC-CDR2, and LC-CDR3 of a light chain comprising the amino acid sequence of SEQ ID NO: 10. In some embodiments, the anti-CTLA-4 antibody comprises a heavy chain comprising the amino acid sequence of SEQ ID NO: 9, and a light chain comprising the amino acid sequence of SEQ ID NO: 10. In some embodiments, the anti-CTLA-4 antibody is ipilimumab (e.g., Yervoy®) or antigen-binding fragments thereof. In some embodiments, the anti-CTLA-4 antibody binds to CTLA-4 competitively with any of the anti-CTLA-4 antibodies described herein.

PD-1

PD-1 is a part of the B7/CD28 family of co-stimulatory molecules that regulate T-cell activation and tolerance, and thus antagonistic anti-PD-1 antibodies can be useful for overcoming tolerance. PD-1 has been defined as a receptor for B74. B7-4 can inhibit immune cell activation upon binding to an inhibitory receptor on an immune cell. Engagement of the PD-1/PD-L1 pathway results in inhibition of T-cell effector function, cytokine secretion and proliferation. (Tumis et al., OncoImmunology 1(7):1172-1174, 2012). High levels of PD-1 are associated with exhausted or chronically stimulated T cells. Moreover, increased PD-1 expression correlates with reduced survival in cancer patients. Agents for down modulating PD-1, B7-4, and the interaction between B7-4 and PD-1 inhibitory signal in an immune cell can result in enhancement of the immune response. Exemplary anti-PD-1 antibodies that can be applied in the present application include, but are not limited to, Keytruda® (pembrolizumab, MK-3475) and Opdivo® (nivolumab).

Pembrolizumab (e.g., KEYTRUDA®) is a humanized antibody used in cancer immunotherapy. It targets the programmed cell death 1 (PD-1) receptor. The drug was initially used in treating metastatic melanoma. On Sep. 4, 2014 the US Food and Drug Administration (FDA) approved KEYTRUDA® under the FDA Fast Track Development Program. It is approved for use in advanced melanoma. On Oct. 2, 2015, the US FDA approved KEYTRUDA® for the treatment of metastatic non-small cell lung cancer in patients whose tumors express PD-L1 and who have failed treatments with other chemotherapeutic agents.

Nivolumab (e.g., OPDIVO®) is a human IgG4 anti-PD-1 monoclonal antibody. It was used in combination with Ipilimumab (e.g., YERVOY®) to investigate the effects of concurrent inhibition of the PD-1 and CTLA-4 receptors in nonhuman primates. OPDIVO® has demonstrated clinical efficacy either as monotherapy or in combination with ipilimumab in treating several tumor types, including renal cell carcinoma, melanoma, NSCLC, and some lymphomas. BMS recently announced the treatment results of immune combination therapy OPDIVO® and ipilimumab for treating melanoma.

In some embodiments, the VEGFR-antibody light chain fusion protein comprises an antibody (such as a full-length antibody) specifically recognizing PD-1 (herein after referred to as "anti-PD-1 antibody"). In some embodiments, the anti-PD-1 antibody comprises HC-CDR, HC-CDR2, and HC-CDR3 of a heavy chain comprising the amino acid sequence of SEQ ID NO: 12; and/or LC-CDR1, LC-CDR2, and LC-CDR3 of a light chain comprising the amino acid sequence of SEQ ID NO: 13. In some embodiments, the anti-PD-1 antibody comprises a heavy chain comprising the amino acid sequence of SEQ ID NO: 12, and a light chain comprising the amino acid sequence of SEQ ID NO: 13. In some embodiments, the anti-PD-1 antibody is pembrolizumab (e.g., Keytruda®) or antigen-binding fragments thereof. In some embodiments, the anti-PD-1 antibody comprises HC-CDR1, HC-CDR2, and HC-CDR3 of a heavy chain comprising the amino acid sequence of SEQ ID NO: 15; and/or LC-CDR1, LC-CDR2, and LC-CDR3 of a light chain comprising the amino acid sequence of SEQ ID NO: 16. In some embodiments, the anti-PD-1 antibody comprises a heavy chain comprising the amino acid sequence of SEQ ID NO: 15, and a light chain comprising the amino acid sequence of SEQ ID NO: 16. In some embodiments, the anti-PD-1 antibody is nivolumab (e.g., Opdivo®) or antigen-binding fragments thereof. In some embodiments, the anti-PD-1 antibody specifically binds to PD-1 competitively with any of the anti-PD-1 antibodies described herein.

PD-L1

PD-L1 (Programmed cell death-ligand 1) is also known as cluster of differentiation 274 (CD274) or B7 homolog 1 (B7-H1). PD-L1 serves as a ligand for PD-1 to play a major role in suppressing the immune system during particular events such as pregnancy, tissue allographs, autoimmune disease and other disease states such as hepatitis and cancer. The formation of PD-1 receptor/PD-L1 ligand complex transmits an inhibitory signal which reduces the proliferation of CD8+ T cells at the lymph nodes. Exemplary anti-PD-L1 antibodies that can be applied in the present application include, but are not limited to, atezolizumab (e.g., Tecentriq®) and Durvalumab (e.g., MEDI4736, IMFINZI®).

Atezolizumab (e.g., Tecentriq®) is a fully humanized, engineered monoclonal antibody of IgG1 isotype against PD-L1. It is an FDA-approved immunotherapy for progressive advanced urothelial carcinoma (e.g., bladder cancer) after platinum-containing chemotherapy, and non-small cell lung cancer (NSCLC).

Durvalumab (e.g., IMFINZI™) is a human immunoglobulin G1 kappa (IgG1κ) monoclonal antibody that blocks the interaction of PD-L1 with the PD-1 and CD80 (B7.1) molecules. It is an FDA-approved immunotherapy for locally advanced or metastatic urothelial carcinoma.

In some embodiments, the VEGFR-antibody light chain fusion protein comprises an antibody (such as a full-length antibody) specifically recognizing PD-L1 (herein after referred to as "anti-PD-L1 antibody"). In some embodiments, the anti-PD-L1 antibody comprises HC-CDR1, HC-CDR2, and HC-CDR3 of a heavy chain comprising the amino acid sequence of SEQ ID NO: 18; and/or LC-CDR1, LC-CDR2, and LC-CDR3 of a light chain comprising the amino acid sequence of SEQ ID NO: 19. In some embodiments, the anti-PD-L1 antibody comprises a heavy chain comprising the amino acid sequence of SEQ ID NO: 18, and a light chain comprising the amino acid sequence of SEQ ID NO: 19. In some embodiments, the anti-PD-L1 antibody is atezolizumab (e.g., Tecentriq®) or antigen-binding fragments thereof. In some embodiments, the anti-PD-L1 antibody comprises HC-CDR1, HC-CDR2, and HC-CDR3 of a heavy chain comprising the amino acid sequence of SEQ ID NO: 21; and/or LC-CDR1, LC-CDR2, and LC-CDR3 of a light chain comprising the amino acid sequence of SEQ ID NO: 22. In some embodiments, the anti-PD-L1 antibody comprises a heavy chain comprising the amino acid sequence of SEQ ID NO: 21, and a light chain comprising the amino acid sequence of SEQ ID NO: 22. In some embodiments, the anti-PD-L1 antibody is Durvalumab or antigen-binding fragments thereof. In some embodiments, the anti-PD-L1 antibody specifically binds to PD-L1 competitively with any of the anti-PD-L1 antibodies described herein.

Antibodies Specifically Recognizing a Tumor Antigen

In some embodiments, the antibody fusion protein of the present invention comprises an antibody specifically recognizing a tumor antigen (such as anti-HER2 or anti-EGFR full-length antibody), and VEGFR component fused to the C-terminus of the antibody light chain (e.g., C-terminus of antibody VL-CL domain).

In some embodiments, the antigen specifically recognized by the antibody is a tumor-associated antigen (TAA) or a tumor-specific antigen (TSA). In some embodiment, the TAA or TSA is expressed on a cancer cell. In some embodiments, the TAA or TSA is expressed on a blood cancer cell. In some embodiments, the TAA or TSA is expressed on a cell of a solid tumor. Certain forms of solid tumor cancer include, by way of non-limiting example, a glioblastoma, a non-small cell lung cancer, a lung cancer other than a non-small cell lung cancer, breast cancer, ovarian cancer, prostate cancer, pancreatic cancer, liver cancer, colorectal cancer, stomach cancer, a cancer of the spleen, skin cancer (such as melanoma), a brain cancer other than a glioblastoma, a kidney cancer, a thyroid cancer, head and neck tumors, bladder cancer, esophageal cancer, or the like. In some embodiments, the TAA or TSA is one or more of EphA2, HER2, GD2, Glypican-3, 5T4, 8H9, $\alpha_v\beta_6$ integrin, B7-H3, B7-H6, CAIX, CA9, CD19, CD20, CD22, kappa light chain, CD30, CD33, CD38, CD44, CD44v6, CD44v7/8, CD70, CD123, CD138, CD171, CEA, CSPG4, EGFR, EGFRvIII, EGP2, EGP40, EPCAM, ERBB3, ERBB4, ErbB3/4, FAP, FAR, FBP, fetal AchR, Folate Receptor a, GD2, GD3, HLA-AI MAGE A1, HLA-A2, IL11Ra, IL13Ra2, KDR, Lambda, Lewis-Y, MCSP, Mesothelin, Muc1, Muc16, NCAM, NKG2D ligands, NY-ESO-1, PRAME, PSCA, PSC, PSMA, ROR1, SURVIVIN, TAG72, TEM1, TEM8, VEGFR2, carcinoembryonic antigen, HMW-MAA, VEGF receptors, and other exemplary antigens that are present with in the extracellular matrix of tumors, such as oncofetal variants of fibronectin, tenascin, or necrotic regions of tumors.

In some embodiments, the tumor antigen specifically recognized by the antibody is HER2, or EGFR (HER1).

HER2

The HER family of receptor tyrosine kinases are important mediators of cell growth, differentiation and survival. The receptor family includes four distinct members including epidermal growth factor receptor (EGFR, ErbB1, or HER1), HER2 (ErbB2 or p185$^{new}$), HER3 (ErbB3) and HER4 (ErbB4 or tyro2).

HER2 (human epidermal growth factor receptor 2, receptor tyrosine-protein kinase erbB-2, CD340, p185$^{neu}$) is a protein encoded by the proto-oncogene ERBB2 in human. It contains an extracellular ligand binding domain, a transmembrane domain, and an intracellular domain that can interact with a multitude of signaling molecules and exhibit both ligand-dependent and ligand-independent activity. HER2 can heterodimerize with any of the other three receptors ErbB1, ErbB3, and ErbB4, and is considered to be the preferred dimerization partner of the other ErbB receptors. Dimerization results in the autophosphorylation of tyrosine residues within the cytoplasmic domain of the receptors and initiates a variety of signaling pathways that promote cell proliferation and oppose apoptosis, such as mitogen-activated protein kinase (MAPK), signal transducer and activator of transcription (STAT), protein kinase C (PKC), and phosphoinositide 3-kinase (PI3K/Akt) pathways.

p185$^{neu}$ was originally identified as the product of the transforming gene from neuroblastomas of chemically treated rats. The activated form of the neu proto-oncogene results from a point mutation (valine to glutamic acid) in the transmembrane region of the encoded protein, leading to constitutive dimerization of this protein in the absence of a ligand. Amplification of the human homolog of neu is observed in breast and ovarian cancers and correlates with a poor prognosis (Slamon et al. *Science*, 235:177-182 (1987); Slamon et al., *Science*. 244:707-712 (1989); and U.S. Pat. No. 4,968,603). To date, no point mutation analogous to that in the neu proto-oncogene has been reported for human tumors. Overexpression of HER2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science*, 229:974 (1985); Yokota et al., *Lancet:* 1:765-767 (1986); Fukushige et al., *Mol Cell Biol.*, 6:955-958 (1986); Guerin et al., *Oncogene Res.*, 3:21-31 (1988); Cohen et al., *Oncogene*, 4:81-88 (1989); Yonemura et al., *Cancer Res.*, 51:1034 (1991); Borst et al., *Gynecol. Oncol.* 38:364 (1990); Weiner et al., *Cancer Res.*, 50:421425 (1990); Kern et al., *Cancer Res.*, 50:5184 (1990); Park et al., *Cancer Res.*, 49:6605 (1989); Zhau et al., *Mol. Carcinog.*, 3:254-257 (1990); Aasland et al. *Br. J. Cancer* 57:358-363 (1988); Williams et al. *Pathobiology* 59:46-52 (1991); and McCann et al., *Cancer,* 65:88-92 (1990). HER2 may be overexpressed in prostate cancer (Gu et al. *Cancer Lett.* 99:185-9 (1996); Ross et al. *Hum. Pathol.* 28:827-33 (1997); Ross et al. *Cancer* 79:2162-70 (1997); and Sadasivan et al. *J. Urol.* 150:126-31 (1993)).

Exemplary HER2 antibodies that can be applied in the present application include, but are not limited to, Trastuzumab (Herceptin®), Trastuzumab emtansine (Kadcyla®), Ertumaxomab (Rexomun®), and Pertuzumab (Omnitarg®).

Trastuzumab (HERCEPTIN®), one of the five top selling therapeutic antibodies, is a humanized anti-HER2 receptor monoclonal antibody that has significantly increased the survival rate in patients with HER2-positive breast cancer. The HER receptors are proteins that are embedded in the cell membrane and communicate molecular signals from outside the cell (molecules called EGFs) to inside the cell, and turn genes on and off. The HER protein, Human Epidermal Growth Factor Receptor (EGFR), binds Human Epidermal Growth Factor. and stimulates cell proliferation. In some cancers, notably certain types of breast cancer, HER2 is over-expressed, and causes cancer cells to reproduce uncontrollably.

In some embodiments, the VEGFR-antibody light chain fusion protein comprises an antibody (such as a full-length antibody) specifically recognizing HER2 (herein after referred to as "anti-HER2 antibody"). In some embodiments, the anti-HER2 antibody comprises HC-CDR1, HC-CDR2, and HC-CDR3 of a heavy chain comprising the amino acid sequence of SEQ ID NO: 24; and/or LC-CDR1, LC-CDR2, and LC-CDR3 of a light chain comprising the amino acid sequence of SEQ ID NO: 25. In some embodiments, the anti-HER2 antibody comprises a heavy chain comprising the amino acid sequence of SEQ ID NO: 24, and a light chain comprising the amino acid sequence of SEQ ID NO: 25. In some embodiments, the anti-HER2 antibody is trastuzumab (e.g., Herceptin®) or antigen-binding fragments thereof. In some embodiments, the anti-HER2 antibody specifically binds to HER2 competitively with any of the anti-HER2 antibodies described herein.

EGFR (HER1)

Epidermal growth factor receptor (EGFR, HER1, or ErbB-1) is the transmembrane receptor for members of the epidermal growth factor family (EGF family). EGFR is a member of the ErbB family of receptors EGFR (ErbB1 or HER1), HER2 (ErbB2 or p185$^{neu}$), HER3 (ErbB3) and HER4 (ErbB4 or tyro2), which are receptor tyrosine kinases mediating cell growth, differentiation and survival. Mutations affecting EGFR expression or activity may result in cancer. EGFR can be activated by binding of its specific ligands, e.g., EGF, transforming growth factor α (TGFα). Upon activation, EGFR dimerization stimulates its intrinsic intracellular protein-tyrosine kinase activity, the autophosphorylation at the C-terminal domain of EGFR leads to a series of signal transduction cascades, mainly the MAPK, Akt, and JNK pathways, leaving to DNA synthesis and cell proliferation.

Exemplary anti-EGFR antibodies that can be applied in the present application include, but are not limited to, Cetuximab (e.g., Erbitux®), and Panitumumab (e.g., ABX-EGF, Vectibix®).

Cetuximab (e.g., Erbitux®) is a recombinant, human/mouse chimeric monoclonal antibody that binds specifically to the extracellular domain of the human EGFR. Cetuximab is composed of the Fv regions of a murine anti-EGFR antibody with human IgG1 heavy and kappa light chain constant regions. Erbitux® is indicated in combination with radiation therapy for the initial treatment of locally or regionally advanced squamous cell carcinoma of the head and neck. Erbitux® is also indicated for the treatment of K-Ras wild-type, EGFR-expressing, metastatic colorectal cancer (mCRC).

In some embodiments, the VEGFR-antibody light chain fusion protein comprises an antibody (such as a full-length antibody) specifically recognizing EGFR (herein after referred to as "anti-EGFR antibody"). In some embodiments, the anti-EGFR antibody comprises HC-CDR1, HC-CDR2, and HC-CDR3 of a heavy chain comprising the amino acid sequence of SEQ ID NO: 29; and/or LC-CDR1, LC-CDR2, and LC-CDR3 of a light chain comprising the amino acid sequence of SEQ ID NO: 30. In some embodiments, the anti-EGFR antibody comprises a heavy chain comprising the amino acid sequence of SEQ ID NO: 29, and a light chain comprising the amino acid sequence of SEQ ID NO: 30. In some embodiments, the anti-EGFR antibody is Cetuximab or antigen-binding fragments thereof. In some embodiments, the anti-EGFR antibody specifically binds to EGFR competitively with any of the anti-EGFR antibodies described herein.

Antibodies Specifically Recognizing an Angiogenic Factor

In some embodiments, the antibody fusion protein of the present invention comprises an antibody specifically recognizing an angiogenic factor (such as anti-Ang2, anti-TNFα, or anti-IL-17A full-length antibody), and VEGFR component fused to the C-terminus of the antibody light chain (e.g., C-terminus of antibody VL-CL domain). In some embodiments, the antibody that specifically recognizes an angiogenic factor inhibits or antagonizes the angiogenic factor function, and is interchangeably referred herein as "angiogenic inhibitor."

As mentioned earlier, angiogenesis is the process of growing new blood vessels from the existing vasculature. It plays an important role in several physiological processes, including embryonic development, as well as tissue and wound repair (Folkman J et al., Angiogenic factors. Science 1987; 235:442-7). The physiologic steps of angiogenesis are well characterized, and involve proteolysis of the extracellular matrix, proliferation, migration, and assembly of the endothelial cells into a tubular channel, mural cell recruitment and differentiation, and extracellular matrix production (Carmeliet P et al., Nature. 2011; 473:298-307). Pathologic angiogenesis may occur in tumor formation, ocular disorders (e.g., diabetic retinopathy, diabetic macular edema or macular degeneration), arthritis, psoriasis, fibrotic diseases, inflammatory diseases, and arteriosclerosis (Polverini P J. Crit Rev Oral Biol Med. 1995; 6(3):230-47).

In some embodiments, the angiogenic factor of the present invention comprises Angiopoietin (ANG, such as Ang1, Ang2. Ang3), Ephrin (Eph), Fibroblast Growth Factor (FGF, such as aFGF, bFGF), Neuropilin (NRP), Plasminogen Activators (such as uPA, tPA), angiogenin, Platelet-Derived Growth Factor (PDGF), platelet-derived endothelial cell growth factor (PD-ECGF), Tumor Growth Factor beta (TGF-β). TGF-α, Vascular Endothelial Growth Factor (VEGF), Vascular Endothelial cadherin (VE-cadherin), Epidermal Growth Factors (EGFs), Nerve Growth Factors (NGFs), Hypoxia-induced Factor (HIF), Connective-Tissue Growth Factor (CTGF), Granulocyte Macrophage Colony-Stimulating Factor (GM-CSF), Insulin-like Growth Factor (IGF), Del-1, follistatin, granulocyte colony-stimulating factor (G-CSF), Hepatocyte Growth Factors/Scatter Factor (HGF/SF), leptin, midkine, placental growth factor, pleiotrophin (PTN), progranulin, proliferin, Tumor Necrosis Factor alpha (TNF-α), Interleukin 1 (IL-1), Interleukin 6 (IL-6), Interleukin 8 (IL-8). Interleukin 17 (IL-17), Interleukin 18 (IL-18), Interleukin 20 (IL-20), Interleukin 23 (IL-23), Chemoattractants such as C-C motif Ligand (CCL28, CCL21), C-X-C motif Ligand (CXCL1, CXCL5), Macrophage migration Inhibitory Factor (MIF), immune cell surface protein such as Clusters of Differentiation (CDs), and receptors thereof. These factors are reported to be overexpressed and play key roles in angiogenesis-related diseases (Elshabrawy et al., Angiogenesis (2015) 18:433-448; Brian P. Eliceiri, Circ. Res. 2001 Dec. 7; 89(12):1104-10).

Angiogenesis is a complex biological process which involves various growth factors and signaling receptors, and targeting single molecules in the signaling cascade may not provide an effective clinical treatment for uncontrolled angiogenesis in diseases such as cancer. Therefore, there is a growing need to develop innovative therapeutics capable of binding several key angiogenic factors in a cooperative manner to effectively inhibit angiogenesis and progression of the disease, as provided in the present application.

In some embodiments, the antibody specifically recognizing an angiogenic factor, or an angiogenic inhibitor, may be an anti-VEGF antibody that binds to the VEGF ligand (see, for example, U.S. Pat. Nos. 5,730,977, 6,884,879, and 8,975,381). In some embodiments, the angiogenic inhibitor may be an anti-Ang2 antibody (see, for example, U.S. Pat. Nos. 6,166,185, 7,521,053, and 7,973,140).

Angiopoietin-2 (Ang2)

Angiopoietin-2 (Ang2) is an antagonistic ligand of a receptor Tie2 present at vascular endothelial cells. It is believed to suppress signaling by Tie2 by competing with Angiopoietin-1 (Ang1), which is an agonist of Tie2, to bind to Tie2. Ang1, which is a ligand activating the Tie2 receptor, functions as a key regulator of maintaining the stabilization of blood vessels by maintaining the barrier function of vascular endothelial cells. The vascular endothelial cells are activated, demonstrated by the overexpression of VEGF or inflammation, and vascular permeability is increased. It is thought that Ang1 induces the stabilization of vascular endothelial cells and reduces vascular permeability by accelerating the junctional integrity of the vascular endothelial cells whereas Ang2 which is increased in the activated vascular endothelial cells serves to suppress the stabilization of the vascular endothelial cells by Ang1 by competing with Ang1. Therefore, Ang2 inhibits Ang1-Tie2 binding, which maintains the stability of the vascular endothelial cells and signaling thereby, thus ultimately accelerating angiogenesis via the dynamic rearrangement of blood vessels.

In the normal adult, the three main sites of angiogenesis are the ovary, placenta, and uterus: these are the primary tissues in normal (i.e., non-cancerous) tissues in which Ang2 mRNA has been detected. Numerous published studies have purportedly demonstrated vessel-selective Ang2 expression in disease states associated with angiogenesis. These pathological conditions include, for example, psoriasis, macular degeneration, and cancer (Bunone, G., et al., *American Journal of Pathology,* 155:1967-1976 (1999); Etoh, T., et al., *Cancer Research,* 61:2145-2153 (2001); Hangai, M., et al., *Investigative Ophthalmology & Visual Science,* 42:1617-1625 (2001); Holash, J., et al., *Investigative Ophthalmology & Visual Science,* 42:1617-1625 (1999); Kuroda. K., et al., *Journal of Investigative Dermatology,* 116:713-720 (2001); Otani, A., et al., *Investigative Ophthalmology & Visual Science.* 40:1912-1920 (1999); Stratmann, A., et al., *American Journal of Pathology,* 153:1459-1466 (1998): Tanaka, S., et al., *J Clin Invest.* 103:34-345 (1999): Yoshida, Y., et al., *International Journal of Oncology,* 15:1221-1225 (1999); Yuan, K., et al., *Journal of Periodontal Research,* 35:165-171 (2000); Zagzag, D., et al., *Experimental Neurology,* 159:391400 (1999)). Most of these studies have focused on cancer, in which many tumor types appear to display vascular Ang-2 expression. In contrast with its expression in pathological angiogenesis, Ang-2 expression in normal tissues is extremely limited (Maisonpierre, P. C., et al., *Science,* 277:55-60 (1997); Mezquita, J., et al., *Biochemical and Biophysical Research Communications,* 260:492498 (1999)). Various publications have suggested Ang-1, Ang-2 and/or Tie-2 as a possible target for anti-cancer therapy.

Exemplary anti-Ang2 antibodies that can be applied in the present application include, but are not limited to, Nesvacumab and Vanucizumab (RG7221).

Nesvacumab (e.g., REGN910) is an experimental monoclonal antibody originally designed for the treatment of cancer, which targets Ang2. As of May 2017, it is in Phase II clinical trials for treating diabetic macular edema.

In some embodiments, the VEGFR-antibody light chain fusion protein comprises an antibody (such as a full-length antibody) specifically recognizing Ang2 (herein after referred to as "anti-Ang2 antibody"). In some embodiments, the anti-Ang2 antibody comprises HC-CDR1, HC-CDR2, and HC-CDR3 of a heavy chain comprising the amino acid sequence of SEQ ID NO: 35; and/or LC-CDR1, LC-CDR2, and LC-CDR3 of a light chain comprising the amino acid sequence of SEQ ID NO: 36. In some embodiments, the anti-Ang2 antibody comprises a heavy chain comprising the amino acid sequence of SEQ ID NO: 35, and a light chain comprising the amino acid sequence of SEQ ID NO: 36. In some embodiments, the anti-Ang2 antibody is Nesvacumab or antigen-binding fragments thereof. In some embodiments, the anti-Ang2 antibody specifically binds to Ang2 competitively with any of the anti-Ang2 antibodies described herein.

TNFα

Tumor necrosis factor (TNF, TNFα, cachexin, or cachectin) is a cytokine involved in systemic inflammation and is one of the cytokines that make up the acute phase reaction. It is mainly produced by activated macrophages, and also by other cell types such as CD4+ lymphocytes, NK cells, neutrophils, mast cells, eosinophils, and neurons. TNFα is primarily involved in the regulation of immune cells. It can induce fever, apoptotic cell death, cachexia, inflammation and to inhibit tumorigenesis and viral replication and respond to sepsis via IL1 and IL6 producing cells. TNF-α can promote angiogenesis in vivo. In the cornea TNFα appears to stimulate vessel growth.

Exemplary anti-TNFα antibodies that can be applied in the present application include, but are not limited to, Adalimumab (e.g., Humira®), Infliximab (e.g., Remicade®, Remsima®, Inflectra®), certolizumab pegol (e.g., Cimzia®), Golimumab (e.g., CNTO148, Simponi®), and Etanercept (e.g., Enbrel®).

Adalimumab (e.g., Humira®) is a recombinant DNA-derived human IgG1 monoclonal antibody specific for TNFα, used to treat rheumatoid arthritis (RA), psoriatic arthritis (PsA), ankylosing spondylitis (AS), Crohn's disease (CD), ulcerative colitis, plaque psoriasis (Ps), hidradenitis suppurativa, and juvenile idiopathic arthritis (JIA).

In some embodiments, the VEGFR-antibody light chain fusion protein comprises an antibody (such as a full-length antibody) specifically recognizing TNFα (herein after referred to as "anti-TNFα antibody"). In some embodiments, the anti-TNFα antibody comprises HC-CDR1 HC-CDR2, and HC-CDR3 of a heavy chain comprising the amino acid sequence of SEQ ID NO: 32; and/or LC-CDR1, LC-CDR2, and LC-CDR3 of a light chain comprising the amino acid sequence of SEQ ID NO: 33. In some embodiments, the anti-TNFα antibody comprises a heavy chain comprising the amino acid sequence of SEQ ID NO: 32, and a light chain comprising the amino acid sequence of SEQ ID NO: 33. In some embodiments, the anti-TNFα antibody is Adalimumab or antigen-binding fragments thereof. In some embodiments, the anti-TNFα antibody specifically binds to TNFα competitively with any of the anti-TNFα antibodies described herein.

IL-17A

Interleukin-17A (IL-17, CTLA8) is a proinflammatory cytokine produced by activated T cells, and regulates the activities of NF-κB and mitogen-activated protein kinases (MAPKs). High levels of IL-17A are associated with several chronic inflammatory diseases including rheumatoid arthritis, psoriasis and multiple sclerosis. There has also been found a positive correlation between IL-17A production and asthma severity. IL-17A can enhance tumor growth in vivo through the induction of IL-6, which in turn activates oncogenic transcription factor STAT3 and promote tumor survival and angiogenesis. For examples, IL-17A seems to facilitate development of colorectal carcinoma by promoting VEGF production from cancer cells, thus facilitating angiogenesis.

Exemplary anti-IL-17A antibodies that can be applied in the present application include, but are not limited to, Ixekizumab (e.g., Taltz®), and Secukinumab (e.g., Cosentyx®).

Ixekizumab (e.g., Taltz®) is a humanized monoclonal antibody that blocks IL-17A and reduces inflammation. It has been approved for the treatment of moderate-to-severe plaque psoriasis.

In some embodiments, the VEGFR-antibody light chain fusion protein comprises an antibody (such as a full-length antibody) specifically recognizing IL-17A (herein after referred to as "anti-IL-17A antibody"). In some embodiments, the anti-IL-17A antibody comprises HC-CDR1, HC-CDR2, and HC-CDR3 of a heavy chain comprising the amino acid sequence of SEQ ID NO: 38; and/or LC-CDR1, LC-CDR2, and LC-CDR3 of a light chain comprising the amino acid sequence of SEQ ID NO: 39. In some embodiments, the anti-IL-17A antibody comprises a heavy chain comprising the amino acid sequence of SEQ ID NO: 38, and a light chain comprising the amino acid sequence of SEQ ID NO: 39. In some embodiments, the anti-IL-17A antibody is Ixekizumab or antigen-binding fragments thereof. In some embodiments, the anti-IL-17A antibody specifically binds to IL-17A competitively with any of the anti-IL-17A antibodies described herein.

Antibody Variants

In some embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleic acid sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, Deletion and Variants

In some embodiments, antibody variants having one or more amino acid substitutions are provided. Sites of interest for substitutional mutagenesis include the HVRs and FRs. Conservative substitutions are shown in Table 1 under the heading of "Preferred substitutions." More substantial changes are provided under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC. Also see subsection "1. Amino acid sequence variants" under section "V. Methods of preparation."

TABLE 1

Amino acid substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Tsp; Phe; Thr; Ser | Phe |
| Val (V) | Ile; Leu; Met; Phe; Ala; Norleucine | Leu |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly. Pro; (6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In some embodiments, the antibody within the VEGFR-antibody light chain fusion protein provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the present application may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See. e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108: WO 2000/61739; US 2004/0132140; US 2004/0110704; US 2004/0110282; US 2004/0109865: WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In some embodiments, one or more amino acid modifications may be introduced into the Fc region of the antibody within the VEGFR-antibody light chain fusion protein provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates an antibody variant that possesses some but not all effector functions, which make it a desirable candidate for applications in which the half-life of the VEGFR-antibody light chain fusion protein in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and U.S. Pat. No. 5,821,337 (see Bruggemann, M. et al., J. Exp. Med. 166:1351-1361 (1987)). Alternatively, non-radioactive assays methods may be employed (see, e.g., ACTI™ non-radioactive cytotoxicity assay for flow cytometry (CellTechnology, Inc. Mountain View, CA)). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See. e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); and Cragg, M. S. and M. J. Glennie, Blood 103:2738-2743 (2004)). FcRn binding and in vivo clearance/half-life determinations can also be performed using methods known in the art (see. e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See. e.g., U.S. Pat. No. 6,737,056; WO 2004/056312, and Shields et al., *J. Bio. Chem.* 9(2): 6591-6604 (2001))

In some embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or CDC, e.g., as described in U.S. Pat. No. 6,194,551, WO 99/51642, and Idusogie et al. *J. Immunol.* 164: 41784184 (2000).

In some embodiments, the antibody variant comprises a variant Fc region comprising one or more amino acid substitutions which increase half-life and/or improve binding to the FcRn. Antibodies with increased half-lives and improved binding to the FcRn, which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988): U.S. Pat. Nos. 5,648,260; 5,624,821; and WO 94/29351 concerning other examples of Fc region variants.

VEGFR-antibody light chain fusion protein (such as VEGFR component fused to a full-length antibody) comprising any of the Fc variants described herein, or combinations thereof, are contemplated.

d) Cysteine Engineered Antibody Variants

In some embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In some embodiments, any one or more of the following residues may be substituted with cysteine: A118 (EU numbering) of the heavy chain; and S400 (EU numbering) of the heavy chain Fc region. Cysteine engineered antibody may be generated as described, e.g., in U.S. Pat. No. 7,521,541.

III. Pharmaceutical Compositions

Further provided by the present application are pharmaceutical compositions comprising any one of the antibody fusion protein comprising VEGFR component fused to C-terminus of the antibody light chain (such as C-terminus of the antibody CL domain) as described herein (such as VEGFR-anti-PD-1, VEGFR-anti-PD-L1, VEGFR-anti-CTLA-4, VEGFR-anti-HER2, VEGFR-anti-EGFR, VEGFR-anti-Ang2, VEGFR-anti-TNFα, or VEGFR-anti-IL-17A antibody light chain fusion protein), and optionally a pharmaceutically acceptable carrier. Pharmaceutical compositions can be prepared by mixing a VEGFR-antibody light chain fusion protein described herein having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

The pharmaceutical composition is preferably to be stable, in which the VEGFR-antibody light chain fusion protein described herein essentially retains its physical and chemical stability and integrity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month, and/or stable at 2-8° C. for at least 2 years. Where the formulation is to be stored at 30° C., generally the formulation should be stable for at least 2 years at 30° C., and/or stable at 40° C. for at least 6 months. For example, the extent of aggregation during storage can be used as an indicator of protein stability. In some embodiments, the stable formulation of VEGFR-antibody light chain fusion protein described herein may comprise less than about 10% (preferably less than about 5%) of the VEGFR-antibody light chain fusion protein present as an aggregate in the formulation.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers (e.g. sodium chloride), stabilizers, metal complexes (e.g. Zn-protein complexes); chelating agents such as EDTA and/or non-ionic surfactants.

Examples of physiologically acceptable carriers include buffers such as phosphate, citrate, and other organic acids; antioxidants including ascorbic acid and methionine; preservatives (such as octadecyldimethylbenzyl ammonium chloride; hexamethonium chloride: benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA: sugars such as sucrose, mannitol, trehalose or sorbitol; salt-forming counterions such as sodium; metal complexes (e.g. Zn-protein complexes); and/or nonionic surfactants such as TWEEN™, polyethylene glycol (PEG), and PLURONICS™ or polyethylene glycol (PEG).

Buffers are used to control the pH in a range which optimizes the therapeutic effectiveness, especially if stability is pH dependent. Buffers are preferably present at concentrations ranging from about 50 mM to about 250 mM. Suitable buffering agents for use in the present application include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives are added to retard microbial growth, and are typically present in a range from 0.2%-1.0% (w/v). The addition of a preservative may, for example, facilitate the production of a multi-use (multiple-dose) formulation. Suitable preservatives for use in the present application include octadecyldimethylbenzyl ammonium chloride; hexamethonium chloride; benzalkonium halides (e.g., chloride, bromide, iodide), benzethonium chloride thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjustor maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1% to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, omithine, leucine, 2-phenylalanine, glutamic acid, threonine, etc.: organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC™ polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intra-arterial, intralesional or intraarticular routes, topical administration, inhalation or by sustained release or extended-release means. In some embodiments, the pharmaceutical composition is administered locally, such as intratumorally, or intravitreally.

Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The pharmaceutical compositions herein may also contain more than one active compound as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition.

The antibody fusion protein disclosed herein can be formulated as immunoliposomes. Liposomes containing the antibody fusion protein are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

In some embodiments, the pharmaceutical composition is contained in a single-use vial, such as a single-use sealed vial. In some embodiments, the pharmaceutical composition is contained in a multi-use vial. In some embodiments, the pharmaceutical composition is contained in bulk in a container. In some embodiments, the pharmaceutical composition is cryopreserved.

Pharmaceutical Compositions for Treating Ocular Neovascular Disorder

Particularly, for treating ocular neovascular disorders such as diabetic retinopathy and AMD, the administration of the pharmaceutical composition comprising the VEGFR-antibody light chain fusion protein (such as VEGFR-anti-Ang2, VEGFR-anti-TNFα, or VEGFR-anti-IL-17A antibody light chain fusion protein) will be directly to the eye, e.g., topically. Topical methods of administration include, but are not limited to, eye drops, subconjunctival injection, subconjunctival implant, intravitreal injection, intravitreal implant, sub-Tenon's injection, or sub-Tenon's implant. In some embodiments, the pharmaceutical compositions comprising the VEGFR-antibody light chain fusion protein, and optionally a pharmaceutical acceptable carrier, is administered by intravitreal injection.

Compositions suitable for topical administration are known to the art (see, for example, US Patent Application 2005/0059639). In various embodiments, compositions of the invention can comprise a liquid comprising an active agent in solution, in suspension, or both. As used herein, liquid compositions include gels. Preferably the liquid composition is aqueous. Alternatively, the composition can take form of an ointment. In a preferred embodiment, the composition is an in situ gellable aqueous composition, more preferably an in situ gellable aqueous solution. Such a composition can comprise a gelling agent in a concentration effective to promote gelling upon contact with the eye or lacrimal fluid in the exterior of the eye. Aqueous compositions of the invention have ophthalmically compatible pH and osmolality. The composition can comprise an ophthalmic depot formulation comprising an active agent for subconjunctival administration. The microparticles comprising active agent can be embedded in a biocompatible pharmaceutically acceptable polymer or a lipid encapsulating agent. The depot formulations may be adapted to release all or substantially all the active material over an extended period of time. The polymer or lipid matrix, if present, may be adapted to degrade sufficiently to be transported from the site of administration after release of all or substantially all the active agent. The depot formulation can be a liquid formulation, comprising a pharmaceutical acceptable polymer and a dissolved or dispersed active agent. Upon injection, the polymer forms a depot at the injections site, e.g. by gelifying or precipitating. The composition can comprise a solid article that can be inserted in a suitable location in the eye, such as between the eye and eyelid or in the conjunctival sac, into a chamber of the eye, such as the anterior or posterior chambers or may be implanted in or on the sclera, choroidal space, or an avascularized region exterior to the vitreous, where the article releases the active agent. Solid articles suitable for implantation in the eye in such fashion generally comprise polymers and can be bioerodible or non-bioerodible. The implants may be permeable or impermeable to the active agent. In some embodiments, the implant may be positioned over an avascular region, such as on the sclera, so as to allow for transcleral diffusion of the drug to the desired site of treatment, e.g., the intraocular space and macula of the eye. Furthermore, the site of transcleral diffusion may be proximity to a site of neovascularization such as a site proximal to the macula.

A number of polymeric delivery vehicles for providing sustained release have been used in an ocular context and can be used to administer the compositions of the invention. Various polymers, e.g., biocompatible polymers, which may be biodegradable, can be used. The polymers may be homopolymers, copolymers (including block copolymers), straight, branched-chain, or cross-linked. Useful polymers include, but are not limited to, poly-lactic acid (PLA), poly-glycolic acid (PGA), poly-lactide-co-glycolide (PLGA), poly(phosphazine), poly (phosphate ester), poly-caprolactones, polyanhydrides, ethylene vinyl acetate, polyorthoesters, polyethers, and poly (beta amino esters). Peptides, proteins such as collagen or albumin, polysaccharides such as chitosan, alginate, hyaluronic acid (or derivatives of any of these) and dendrimers (e.g., PAMAM dendrimers) are also of use. Methods for preparation of such formulations will be apparent to those skilled in the art. Certain of the materials can also be obtained commercially, e.g., from Alza Corporation Any of these polymers, or combinations thereof, can be used in various embodiments of the invention.

Additional exemplary polymers include cellulose derivatives such as carboxymethylcellulose, polycarbamates or polyureas, cross-linked poly(vinyl acetate) and the like, ethylene-vinyl ester copolymers having an ester content of 4 to 80% such as ethylene-vinyl acetate (EVA) copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer, or mixtures thereof.

Poly(ortho esters) have been introduced into the eye and demonstrated favorable properties for sustained release ocular drug delivery (Einmahl, S., *Invest. Opthalmo. Vis. Sci.*, 43(5), 2002). Polylactide particles have been used to target an agent to the retina and RPE following intravitreous injection of a suspension of such particles (Bourges, J-L. et al. *Invest. Opthalmol. Vis. Sci.*, 44(8), 2003).

A method of making a sustained release formulation involves combining or mixing the VEGFR-antibody light chain fusion protein with a polymeric component to form a mixture. The mixture may then be extruded, compressed, molded, etc., to form a single composition. Optionally, heat and/or pressure can be used. The single composition may then be processed to form individual implants or particles suitable for placement in an eye of a patient. Additional methods for incorporating therapeutically active agents into polymeric matrices are known in the art. The polymeric matrix can be formed into various shapes such as rods, disks, wafers, etc., which may have a range of different dimensions (e.g., length, width, etc.) and volumes. Exemplary shapes include spherical, cylindrical, helical, coil-shaped or helical, screw-shaped, cubical, conical, ellipsoidal, biconvex, hemispherical or near-hemispherical etc.

IV. Methods of Treating Diseases

While vascular endothelial proliferation is desirable under certain circumstances, vascular endothelial proliferation and angiogenesis are also important components of a variety of diseases and disorders including tumor growth and metastasis, rheumatoid arthritis, psoriasis, atherosclerosis, diabetic retinopathy, retrolental fibroplasia, neovascular glaucoma, AMD, hemangiomas, immune rejection of transplanted corneal tissue and other tissues, and chronic inflammation.

The VEGFR-antibody light chain fusion protein as described herein (such as VEGFR-anti-PD-1, VEGFR-anti-PD-L1, VEGFR-anti-CTLA-4, VEGFR-anti-HER2, VEGFR-anti-EGFR, VEGFR-anti-Ang2, VEGFR-anti-TNFα, or VEGFR-anti-IL-17A antibody light chain fusion protein), and the compositions (such as pharmaceutical compositions) thereof are useful for a variety of applications, such as in diagnosis, molecular assays, and therapy.

One aspect of the invention provides a method of treating a disease or a condition in an individual in need thereof, comprising administering to the individual an effective amount of a pharmaceutical composition comprising the VEGFR-antibody light chain fusion protein described herein, and optionally a pharmaceutical acceptable carrier. In some embodiments, the disease is cancer. In some embodiments, the disease is non-neoplastic disease or neovascular disorder. In some embodiments, the disease is ocular neovascular disorder, such as AMD or diabetic retinopathy.

The present invention contemplates, in part, VEGFR-antibody light chain fusion protein, nucleic acid molecules and/or vectors encoding thereof, host cells comprising nucleic acid molecules and/or vectors encoding thereof, that can be administered either alone or in any combination with another therapy, and in at least some aspects, together with a pharmaceutically acceptable carrier or excipient. In some embodiments, prior to administration of the VEGFR-antibody light chain fusion protein, they may be combined with suitable pharmaceutical carriers and excipients that are well known in the art. The compositions prepared according to the disclosure can be used for the treatment or delaying of worsening of cancer or ocular neovascular disorders.

Cancer

In some embodiments, there is provided a method of treating cancer (such as solid tumor, or cancer with aberrant VEGF expression, activity and/or signaling) comprising administering to the individual an effective amount of a pharmaceutical composition comprising an antibody fusion protein comprising 1) an antibody (such as anti-PD-1, anti-PD-L1, anti-CTLA-4, anti-HER2, anti-EGFR, anti-Ang2, anti-TNFα, or anti-IL-17A full-length antibody) comprising a light chain, and 2) a VEGFR component fused to the C-terminus of the antibody light chain (e.g., C-terminus of antibody VL-CL domain); and optionally a pharmaceutically acceptable carrier. In some embodiments, the antibody fusion protein comprises a first VEGFR component fused to the C-terminus of a first antibody light chain, and a second VEGFR component fused to the C-terminus of a second antibody light chain. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the VEGFR component and the C-terminus of the antibody light chain are connected by a linker (such as a peptide linker comprising amino acid sequence of SEQ ID NO: 6 or 7). Thus in some embodiments, there is provided a method of treating cancer (such as solid tumor, or cancer with aberrant VEGF expression, activity and/or signaling) comprising administering to the individual an effective amount of a pharmaceutical composition comprising an antibody fusion protein comprising 1) an antibody (such as anti-PD-1, anti-PD-L1, anti-CTLA-4, anti-HER2, anti-EGFR, anti-Ang2, anti-TNFα, or anti-IL-17A full-length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8. In some embodiments, the antibody is selected from the group consisting of IgA, IgD, IgE, IgG, IgM, IgG-derived molecules, Fab, Fab', F(ab')2, Fab-scFv, F(ab')2-scFv2, Fab-scFv-Fc, Dock and Lock, scFv, di-scFv, diabody, Diabody-Fc, Diabody-CH$_3$, and intrabody. In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody specifically recognizes an immune checkpoint molecule. In some embodiments, the antibody specifically recognizes a stimulatory immune checkpoint molecule. In some embodiments, the antibody specifically recognizes an inhibitory immune checkpoint molecule. In some embodiments, the antibody specifically recognizes PD-1. In some embodiments, the antibody comprises HC-CDR1, HC-CDR2, and HC-CDR3 of a heavy chain comprising the amino acid sequence of SEQ ID NO: 12; and/or LC-CDR1, LC-CDR2, and LC-CDR3 of a light chain comprising the amino acid sequence of SEQ ID NO: 13. In some embodiments, the antibody comprises a heavy chain comprising the amino acid sequence of SEQ ID NO: 12, and a light chain comprising the amino acid sequence of SEQ ID NO: 13. In some embodiments, the antibody is pembrolizumab (e.g., Keytruda®) or antigen-binding fragments thereof. In some embodiments, the antibody binds to PD-1 competitively with pembrolizumab. In some embodiments, the antibody fusion protein comprises a heavy chain comprising the amino acid sequence of SEQ ID NO: 12, and a light chain fusion polypeptide comprising the amino acid sequence of SEQ ID NO: 14. In some embodiments, the antibody comprises HC-CDR1, HC-CDR2, and HC-CDR3 of a heavy chain comprising the amino acid sequence of SEQ ID NO: 15; and/or LC-CDR1, LC-CDR2, and LC-CDR3 of a light chain comprising the amino acid sequence of SEQ ID NO: 16. In some embodiments, the antibody comprises a heavy chain comprising the amino acid sequence of SEQ ID NO: 15, and a light chain comprising the amino acid sequence of SEQ ID NO: 16. In some embodiments, the antibody is nivolumab (e.g., Opdivo®) or antigen-binding fragments thereof. In some embodiments, the antibody binds to PD-1 competitively with nivolumab. In some embodiments, the antibody fusion protein comprises a heavy chain comprising the amino acid sequence of SEQ ID NO: 15, and a light chain fusion polypeptide comprising the amino acid sequence of SEQ ID NO: 17. In some embodiments, the antibody specifically recognizes PD-L1. In some embodiments, the antibody comprises HC-CDR1, HC-CDR2, and HC-CDR3 of a heavy chain comprising the amino acid sequence of SEQ ID NO: 18; and/or LC-CDR1, LC-CDR2, and LC-CDR3 of a light chain comprising the amino acid sequence of SEQ ID NO: 19. In some embodiments, the antibody comprises a heavy chain comprising the amino acid sequence of SEQ ID NO: 18, and a light chain comprising the amino acid sequence of SEQ ID NO: 19. In some embodiments, the antibody is atezolizumab (e.g., Tecentriq®) or antigen-binding fragments thereof. In some embodiments, the antibody binds to PD-L1 competitively with atezolizumab. In some embodiments, the antibody fusion protein comprises a heavy chain comprising the amino acid sequence of SEQ ID NO: 18, and a light chain fusion polypeptide comprising the amino acid sequence of SEQ ID NO: 20. In some embodiments, the antibody comprises HC-CDR1, HC-CDR2, and HC-CDR3 of a heavy chain comprising the amino acid sequence of SEQ ID NO: 21; and/or LC-CDR1, LC-CDR2, and LC-CDR3 of a light chain comprising the amino acid sequence of SEQ ID NO: 22. In some embodiments, the antibody comprises a heavy chain comprising the amino acid sequence of SEQ ID NO: 21, and a light chain comprising the amino acid sequence of SEQ ID NO: 22. In some embodiments, the antibody is Durvalumab (e.g., Imfinzi®) or antigen-binding fragments thereof. In some embodiments, the antibody binds to PD-L1 competitively with Durvalumab. In some embodiments, the antibody fusion protein comprises a heavy chain comprising the amino acid sequence of SEQ ID NO: 21, and a light chain fusion polypeptide comprising the amino acid sequence of SEQ ID NO: 23. In some embodiments, the antibody specifically recognizes CTLA-4. In some embodiments, the antibody comprises HC-CDR1, HC-CDR2, and HC-CDR3 of a heavy chain comprising the amino acid sequence of SEQ ID NO: 9; and/or LC-CDR1, LC-CDR2, and LC-CDR3 of a light chain comprising the amino acid sequence of SEQ ID NO: 10. In some embodiments, the antibody comprises a heavy chain comprising the amino acid sequence of SEQ ID NO: 9, and a light chain comprising the amino acid sequence of SEQ ID NO: 10. In some embodiments, the antibody is ipilimumab (e.g., Yervoy®) or antigen-binding fragments thereof. In some embodiments, the antibody binds to CTLA-4 competitively with ipilimumab. In some embodiments, the antibody fusion protein comprises a heavy chain comprising the amino acid sequence of SEQ ID NO: 9, and a light chain fusion polypeptide comprising the amino acid sequence of SEQ ID NO: 11. In some embodiments, the antibody specifically recognizes a tumor antigen. In some embodiments, the tumor antigen is HER2. In some embodiments, the antibody comprises HC-CDR1, HC-CDR2, and HC-CDR3 of a heavy chain comprising the amino acid sequence of SEQ ID NO: 24; and/or LC-CDR1, LC-CDR2, and LC-CDR3 of a light chain comprising the amino acid sequence of SEQ ID NO: 25. In some embodiments, the antibody comprises a heavy chain comprising the amino acid sequence of SEQ ID NO: 24, and a light chain comprising the amino acid sequence of SEQ ID NO: 25. In some embodiments, the antibody is trastuzumab (e.g., Herceptin®) or antigen-binding fragments thereof. In some embodiments, the antibody binds to HER2 competitively with trastuzumab. In some embodiments, the antibody fusion protein comprises a heavy chain comprising the amino acid sequence of SEQ ID NO: 24, and a light chain fusion polypeptide comprising the amino acid sequence of SEQ ID NO: 26, 27, or 28. In some embodiments, the tumor antigen is EGFR (HER1). In some embodiments, the antibody comprises HC-CDR1, HC-CDR2, and HC-CDR3 of a heavy chain comprising the amino acid sequence of SEQ ID NO: 29; and/or LC-CDR1, LC-CDR2, and LC-CDR3 of a light chain comprising the amino acid sequence of SEQ ID NO: 30. In some embodiments, the antibody comprises a heavy chain comprising the amino acid sequence of SEQ ID NO: 29, and a light chain comprising the amino acid sequence of SEQ ID NO: 30. In some embodiments, the antibody is Cetuximab (e.g., Erbitux®) or antigen-binding fragments thereof. In some embodiments, the antibody binds to EGFR competitively with Cetuximab. In some embodiments, the antibody fusion protein comprises a heavy chain comprising the amino acid sequence of SEQ ID NO: 29, and a light chain fusion polypeptide comprising the amino acid sequence of SEQ ID NO: 31. In some embodiments, the antibody specifically recognizes an angiogenic factor. In some embodiments, the angiogenic factor is Ang2. In some embodiments, the antibody comprises HC-CDR1, HC-CDR2, and HC-CDR3 of a heavy chain comprising the amino acid sequence of SEQ ID NO: 35; and/or LC-CDR1, LC-CDR2, and LC-CDR3 of a light chain comprising the amino acid sequence of SEQ ID NO: 36. In some embodiments, the antibody comprises a heavy chain comprising the amino acid sequence of SEQ ID NO: 35, and a light chain comprising the amino acid sequence of SEQ ID NO: 36. In some embodiments, the antibody is Nesvacumab or antigen-binding fragments thereof. In some embodiments, the antibody binds to Ang2 competitively with Nesvacumab. In some embodiments, the antibody fusion protein comprises a heavy chain comprising the amino acid sequence of SEQ ID NO: 35, and a light chain fusion polypeptide comprising the amino acid sequence of SEQ ID NO: 37. In some embodiments, the angiogenic factor is TNFα. In some embodiments, the antibody comprises HC-CDR1, HC-CDR2, and HC-CDR3 of a heavy chain comprising the amino acid sequence of SEQ ID NO: 32; and/or LC-CDR1, LC-CDR2, and LC-CDR3 of a light chain comprising the amino acid sequence of SEQ ID NO: 33. In some embodiments, the antibody comprises a heavy chain comprising the amino acid sequence of SEQ ID NO: 32, and a light chain comprising the amino acid sequence of SEQ ID NO: 33. In some embodiments, the antibody is Adalimumab (e.g., Humira®) or antigen-binding fragments thereof. In some embodiments, the antibody binds to TNFα competitively with Adalimumab. In some embodiments, the antibody fusion protein comprises a heavy chain comprising the amino acid sequence of SEQ ID NO: 32, and a light chain fusion polypeptide comprising the amino acid sequence of SEQ ID NO: 34. In some embodiments, the angiogenic factor is IL-17A. In some embodiments, the antibody comprises HC-CDR1, HC-CDR2, and HC-CDR3 of a heavy chain comprising the amino acid sequence of SEQ ID NO: 38; and/or LC-CDR1, LC-CDR2, and LC-CDR3 of a light chain comprising the amino acid sequence of SEQ ID NO: 39. In some embodiments, the antibody comprises a heavy chain comprising the amino acid sequence of SEQ ID NO: 38, and a light chain comprising the amino acid sequence of SEQ ID NO: 39. In some embodiments, the antibody is Ixekizumab (e.g., Taltz®) or antigen-binding fragments thereof. In some embodiments, the antibody binds to IL-17A competitively with Ixekizumab. In some embodiments, the antibody fusion protein comprises a heavy chain comprising the amino acid sequence of SEQ ID NO: 38, and a light chain fusion polypeptide comprising the amino acid sequence of SEQ ID NO: 40. In some embodiments, the cancer is a solid tumor (such as lung cancer, liver cancer, skin cancer (such as melanoma), breast cancer, ovarian cancer, prostate cancer, colorectal cancer, or bladder cancer). In some embodiments, the pharmaceutical composition is administered systemically (such as intravenously). In some embodiments, the pharmaceutical composition is administered locally (such as intratumorally). In some embodiments, the method further comprises subjecting the individual to an additional cancer therapy (such as surgery, radiation, chemotherapy, immunotherapy, hormone therapy, or a combination thereof). In some embodiments, the individual is a human. In some embodiments, the method of treating cancer has one or more of the following biological activities: (1) killing cancer cells (including bystander killing); (2) inhibiting proliferation of cancer cells; (3) inducing immune response in a tumor; (4) reducing tumor size; (5) alleviating one or more symptoms in an individual having cancer; (6) inhibiting tumor metastasis; (7) prolonging survival; (8) prolonging time to cancer progression; (9) preventing, inhibiting, or reducing the likelihood of the recurrence of a cancer; and (10) reducing or inhibiting tumor angiogenesis. In some embodiments, the method of killing cancer cells mediated by the pharmaceutical composition described herein can achieve a tumor cell death rate of at least about any of 40%, 50%, 60%, 70%, 80%, 90%, 95%, or more. In some embodiments, the method of reducing tumor size mediated by the pharmaceutical composition described herein can reduce at least about 10% (including for example at least about any of 20%, 30%, 40%, 60%, 70%, 80%, 90%, or 100%) of the tumor size. In some embodiments, the method of inhibiting tumor metastasis mediated by the pharmaceutical composition described herein can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the pharmaceutical composition described herein can prolongs the survival of the individual by at least any of 1, 2, 3, 4, 5, 6, 7, 8, 9, 10, 11, 12, 18, or 24 months. In some embodiments, the method of prolonging time to cancer progression mediated by the pharmaceutical composition described herein can prolongs the time to cancer progression by at least any of 1, 2, 3, 4, 5, 6, 7, 8, 9, 10, 11, or 12 weeks.

The methods described herein are suitable for treating a variety of cancers, including both solid cancer and liquid cancer. The methods are applicable to cancers of all stages, including early stage cancer, non-metastatic cancer, primary cancer, advanced cancer, locally advanced cancer, metastatic cancer, or cancer in remission. The methods described herein may be used as a first therapy, second therapy, third therapy, or combination therapy with other types of cancer therapies known in the art, such as chemotherapy, surgery, hormone therapy, radiation, gene therapy, immunotherapy (such as T-cell therapy), bone marrow transplantation, stem cell transplantation, targeted therapy, cryotherapy, ultrasound therapy, photodynamic therapy, radio-frequency ablation or the like, in an adjuvant setting or a neoadjuvant setting (i.e., the method may be carried out before the primary/definitive therapy). In some embodiments, the method is used to treat an individual who has previously been treated. In some embodiments, the cancer has been refractory to prior therapy. In some embodiments, the method is used to treat an individual who has not previously been treated.

In some embodiments, the method is suitable for treating cancers with aberrant VEGF expression, activity and/or signaling include, by way of non-limiting example, carcinomas of the breast, lung, esophagus, gastric anatomy, colon, rectum, liver, ovary, cervix, endometrium, thecomas, arrhenoblastomas, endometrial hyperplasia, endometriosis, fibrosarcomas, choriocarcinoma, head and neck cancer, nasopharyngeal carcinoma, laryngeal carcinoma, hepatoblastoma. Karposi's sarcoma, melanoma, skin carcinomas, hemangioma, cavernous hemangioma, hemangioblastoma, pancreas carcinoma, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as associated with brain tumors), and Meigs' syndrome. In some embodiments, the method is suitable for treating lung cancer, liver cancer, skin cancer (such as melanoma), breast cancer, ovarian cancer, prostate cancer, colorectal cancer, or bladder cancer.

In some embodiments, the method is suitable for treating cancers with aberrant CTLA-4 expression, activity and/or signaling include, by way of non-limiting example, melanoma, prostate cancer, lung cancer, colon cancer, gastric cancer, ovarian cancer, breast cancer, and glioblastoma.

Thus in some embodiments, there is provided a method of treating cancer with aberrant CTLA-4 or B7-1/B7-2 expression, activity and/or signaling (such as carcinoma or adenocarcinoma, solid tumor), comprising administering to the individual an effective amount of a pharmaceutical composition comprising an antibody fusion protein comprising 1) an anti-CTLA-4 antibody (such as full-length antibody) comprising a light chain, and 2) a VEGFR component fused to the C-terminus of the antibody light chain (e.g., C-terminus of antibody VL-CL domain); and optionally a pharmaceutically acceptable carrier. In some embodiments, the antibody fusion protein comprises a first VEGFR component fused to the C-terminus of a first antibody light chain, and a second VEGFR component fused to the C-terminus of a second antibody light chain. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the VEGFR component and the C-terminus of the antibody light chain are connected by a linker (such as a peptide linker comprising amino acid sequence of SEQ ID NO: 6 or 7). Thus in some embodiments, there is provided a method of treating cancer with aberrant CTLA4 or B7-1/B7-2 expression, activity and/or signaling (such as carcinoma or adenocarcinoma, solid tumor), comprising administering to the individual an effective amount of a pharmaceutical composition comprising an antibody fusion protein comprising 1) an anti-CTLA-4 antibody (such as full-length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8; and optionally a pharmaceutically acceptable carrier. In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the anti-CTLA-4 antibody comprises HC-CDR1, HC-CDR2, and HC-CDR3 of a heavy chain comprising the amino acid sequence of SEQ ID NO: 9; and/or LC-CDR1, LC-CDR2, and LC-CDR3 of a light chain comprising the amino acid sequence of SEQ ID NO: 10. In some embodiments, the anti-CTLA-4 antibody comprises a heavy chain comprising the amino acid sequence of SEQ ID NO: 9, and a light chain comprising the amino acid sequence of SEQ ID NO: 10. In some embodiments, the anti-CTLA-4 antibody is ipilimumab (e.g., Yervoy®) or antigen-binding fragments thereof. In some embodiments, the anti-CTLA-4 antibody binds to CTLA-4 competitively with ipilimumab. In some embodiments, the antibody fusion protein comprises a heavy chain comprising the amino acid sequence of SEQ ID NO: 9, and a light chain fusion polypeptide comprising the amino acid sequence of SEQ ID NO: 11.

In some embodiments, the method is suitable for treating cancers with aberrant PD-1 or PD-L1/PD-L2 expression, activity and/or signaling include, by way of non-limiting example, hematological cancer and/or solid tumors. Some cancers whose growth may be inhibited using the antibodies of the invention include cancers typically responsive to immunotherapy. Non-limiting examples of other cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth may be inhibited using the antibodies of the invention. Examples of other cancers that may be treated using the antibodies of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-L1 (Iwai et al. (2005) *Int. Immunol.* 17:133-144).

Thus in some embodiments, there is provided a method of treating cancer (such as carcinoma or adenocarcinoma, solid tumor, cancers with aberrant VEGF expression, activity and/or signaling, and/or aberrant PD-1/PD-L1/PD-L2 expression, activity and/or signaling) comprising administering to the individual an effective amount of a pharmaceutical composition comprising an antibody fusion protein comprising 1) an anti-PD-1 or anti-PD-L1 antibody (such as full-length antibody) comprising a light chain, and 2) a VEGFR component fused to the C-terminus of the antibody light chain (e.g., C-terminus of antibody $V_L$-$C_L$ domain); and optionally a pharmaceutically acceptable carrier. In some embodiments, the antibody fusion protein comprises a first VEGFR component fused to the C-terminus of a first antibody light chain, and a second VEGFR component fused to the C-terminus of a second antibody light chain. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the VEGFR component and the C-terminus of the antibody light chain are connected by a linker (such as a peptide linker comprising amino acid sequence of SEQ ID NO: 6 or 7).

Thus in some embodiments, there is provided a method of treating cancer (such as carcinoma or adenocarcinoma, solid tumor, cancers with aberrant VEGF expression, activity and/or signaling, and/or aberrant PD-1/PD-L1/PD-L2 expression, activity and/or signaling) comprising administering to the individual an effective amount of a pharmaceutical composition comprising an antibody fusion protein comprising 1) an anti-PD-1 or anti-PD-L antibody (such as full-length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8; and optionally a pharmaceutically acceptable carrier. In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody specifically recognizes PD-1. In some embodiments, the antibody comprises HC-CDR1, HC-CDR2, and HC-CDR3 of a heavy chain comprising the amino acid sequence of SEQ ID NO: 12; and/or LC-CDR1, LC-CDR2, and LC-CDR3 of a light chain comprising the amino acid sequence of SEQ ID NO: 13. In some embodiments, the antibody comprises a heavy chain comprising the amino acid sequence of SEQ ID NO: 12, and a light chain comprising the amino acid sequence of SEQ ID NO: 13. In some embodiments, the antibody is pembrolizumab (e.g., Keytruda®) or antigen-binding fragments thereof. In some embodiments, the antibody binds to PD-1 competitively with pembrolizumab. In some embodiments, the antibody fusion protein comprises a heavy chain comprising the amino acid sequence of SEQ ID NO: 12, and a light chain fusion polypeptide comprising the amino acid sequence of SEQ ID NO: 14. In some embodiments, the antibody comprises HC-CDR1, HC-CDR2, and HC-CDR3 of a heavy chain comprising the amino acid sequence of SEQ ID NO: 15; and/or LC-CDR1, LC-CDR2, and LC-CDR3 of a light chain comprising the amino acid sequence of SEQ ID NO: 16. In some embodiments, the antibody comprises a heavy chain comprising the amino acid sequence of SEQ ID NO: 15, and a light chain comprising the amino acid sequence of SEQ ID NO: 16. In some embodiments, the antibody is nivolumab (e.g., Opdivo®) or antigen-binding fragments thereof. In some embodiments, the antibody binds to PD-1 competitively with nivolumab. In some embodiments, the antibody fusion protein comprises a heavy chain comprising the amino acid sequence of SEQ ID NO: 15, and a light chain fusion polypeptide comprising the amino acid sequence of SEQ ID NO: 17. In some embodiments, the antibody specifically recognizes PD-L1. In some embodiments, the antibody comprises HC-CDR1, HC-CDR2, and HC-CDR3 of a heavy chain comprising the amino acid sequence of SEQ ID NO: 18; and/or LC-CDR1, LC-CDR2, and LC-CDR3 of a light chain comprising the amino acid sequence of SEQ ID NO: 19. In some embodiments, the antibody comprises a heavy chain comprising the amino acid sequence of SEQ ID NO: 18, and a light chain comprising the amino acid sequence of SEQ ID NO: 19. In some embodiments, the antibody is atezolizumab (e.g., Tecentriq®) or antigen-binding fragments thereof. In some embodiments, the antibody binds to PD-L1 competitively with atezolizumab. In some embodiments, the antibody fusion protein comprises a heavy chain comprising the amino acid sequence of SEQ ID NO: 18, and a light chain fusion polypeptide comprising the amino acid sequence of SEQ ID NO: 20. In some embodiments, the antibody comprises HC-CDR1, HC-CDR2, and HC-CDR3 of a heavy chain comprising the amino acid sequence of SEQ ID NO: 21; and/or LC-CDR1, LC-CDR2, and LC-CDR3 of a light chain comprising the amino acid sequence of SEQ ID NO: 22. In some embodiments, the antibody comprises a heavy chain comprising the amino acid sequence of SEQ ID NO: 21, and a light chain comprising the amino acid sequence of SEQ ID NO: 22. In some embodiments, the antibody is Durvalumab (e.g., Imfinzi®) or antigen-binding fragments thereof. In some embodiments, the antibody binds to PD-L1 competitively with Durvalumab. In some embodiments, the antibody fusion protein comprises a heavy chain comprising the amino acid sequence of SEQ ID NO: 21, and a light chain fusion polypeptide comprising the amino acid sequence of SEQ ID NO: 23.

In some embodiments, the method is suitable for treating cancers with aberrant HER2 expression, activity and/or signaling include, by way of non-limiting example, breast cancer, ovarian cancer, endometrial cancer, stomach cancer, colon cancer, bladder cancer, salivary gland cancer, non-small cell lung cancer, kidney cancer, prostate cancer, thyroid cancer, pancreatic cancer, and cervical cancer.

Thus in some embodiments, there is provided a method of treating cancer (such as carcinoma or adenocarcinoma, solid tumor, cancers with aberrant VEGF expression, activity and/or signaling, and/or aberrant HER2 expression, activity and/or signaling) comprising administering to the individual an effective amount of a pharmaceutical composition comprising an antibody fusion protein comprising 1) an anti-HER2 antibody (such as full-length antibody) comprising a light chain, and 2) a VEGFR component fused to the C-terminus of the antibody light chain (e.g., C-terminus of antibody VL-CL domain); and optionally a pharmaceutically acceptable carrier. In some embodiments, the antibody fusion protein comprises a first VEGFR component fused to the C-terminus of a first antibody light chain, and a second VEGFR component fused to the C-terminus of a second antibody light chain. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the VEGFR component and the C-terminus of the antibody light chain are connected by a linker (such as a peptide linker comprising amino acid sequence of SEQ ID NO: 6 or 7). Thus in some embodiments, there is provided a method of treating cancer (such as carcinoma or adenocarcinoma, solid tumor, cancers with aberrant VEGF expression, activity and/or signaling, and/or aberrant HER2 expression, activity and/or signaling) comprising administering to the individual an effective amount of a pharmaceutical composition comprising an antibody fusion protein comprising 1) an anti-HER2 antibody (such as full-length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8; and optionally a pharmaceutically acceptable carrier. In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody comprises HC-CDR1, HC-CDR2, and HC-CDR3 of a heavy chain comprising the amino acid sequence of SEQ ID NO: 24; and/or LC-CDR1, LC-CDR2, and LC-CDR3 of a light chain comprising the amino acid sequence of SEQ ID NO: 25. In some embodiments, the antibody comprises a heavy chain comprising the amino acid sequence of SEQ ID NO: 24, and a light chain comprising the amino acid sequence of SEQ ID NO: 25. In some embodiments, the antibody is trastuzumab (e.g., Herceptin®) or antigen-binding fragments thereof. In some embodiments, the antibody binds to HER2 competitively with trastuzumab. In some embodiments, the antibody fusion protein comprises a heavy chain comprising the amino acid sequence of SEQ ID NO: 24, and a light chain fusion polypeptide comprising the amino acid sequence of SEQ ID NO: 26, 27, or 28.

In some embodiments, the method is suitable for treating cancers with aberrant EGFR expression, activity and/or signaling. EGFR positive tumor is associated with cancer such as carcinoma, lymphoma, blastoma, sarcoma, neuroendocrine tumors, mesothelioma, schwannoma, meningioma, adenocarcinoma, melanoma, leukemia, and lymphoid malignancies. EGFR positive cancer include, by way of non-limiting example, lung cancer, hepatocellular cancer, gastric or stomach cancer, pancreatic cancer, glioblastoma, cervical cancer, ovarian cancer, liver cancer, bladder cancer, hepatoma, breast cancer, colon cancer, rectal cancer, colorectal cancer, endometrial and uterine carcinoma, salivary gland carcinoma, kidney cancer, prostate cancer, vulval cancer, thyroid cancer, hepatic carcinoma, anal carcinoma, penile carcinoma, testicular cancer, esophageal cancer, tumors of the biliary tract, and head and neck cancer.

Thus in some embodiments, there is provided a method of treating cancer (such as carcinoma or adenocarcinoma, solid tumor, cancers with aberrant EGFR (HER1) expression, activity and/or signaling, and/or aberrant EGFR expression, activity and/or signaling) comprising administering to the individual an effective amount of a pharmaceutical composition comprising an antibody fusion protein comprising 1) an anti-EGFR antibody (such as full-length antibody) comprising a light chain, and 2) a VEGFR component fused to the C-terminus of the antibody light chain (e.g., C-terminus of antibody VL-CL domain); and optionally a pharmaceutically acceptable carrier. In some embodiments, the antibody fusion protein comprises a first VEGFR component fused to the C-terminus of a first antibody light chain, and a second VEGFR component fused to the C-terminus of a second antibody light chain. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the VEGFR component and the C-terminus of the antibody light chain are connected by a linker (such as a peptide linker comprising amino acid sequence of SEQ ID NO: 6 or 7). Thus in some embodiments, there is provided a method of treating cancer (such as carcinoma or adenocarcinoma, solid tumor, cancers with aberrant EGFR (HER1) expression, activity and/or signaling, and/or aberrant EGFR expression, activity and/or signaling) comprising administering to the individual an effective amount of a pharmaceutical composition comprising an antibody fusion protein comprising 1) an anti-EGFR antibody (such as full-length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8; and optionally a pharmaceutically acceptable carrier. In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody comprises HC-CDR1, HC-CDR2, and HC-CDR3 of a heavy chain comprising the amino acid sequence of SEQ ID NO: 29; and/or LC-CDR1, LC-CDR2, and LC-CDR3 of a light chain comprising the amino acid sequence of SEQ ID NO: 30. In some embodiments, the antibody comprises a heavy chain comprising the amino acid sequence of SEQ ID NO: 29, and a light chain comprising the amino acid sequence of SEQ ID NO: 30. In some embodiments, the antibody is Cetuximab (e.g., Erbitux®) or antigen-binding fragments thereof. In some embodiments, the antibody binds to EGFR competitively with Cetuximab. In some embodiments, the antibody fusion protein comprises a heavy chain comprising the amino acid sequence of SEQ ID NO: 29, and a light chain fusion polypeptide comprising the amino acid sequence of SEQ ID NO: 31.

In some embodiments, the method is suitable for treating cancers with aberrant Ang2 expression (such as highly vascularized tumors), activity and/or signaling include, by way of non-limiting example, glioma, hepatocellular carcinoma, gastric carcinoma, thyroid tumor, lung cancer (such as non-small cell lung cancer, small cell lung cancer), colon cancer, prostate cancer, breast cancer, ovarian cancer, bladder cancer, melanoma, glioblastoma, endometrial cancer, kidney cancer, pancreatic cancer, esophageal carcinoma, head and neck cancers, mesothelioma, sarcomas, cholangiocarcinoma, small bowel adenocarcinoma, pediatric malignancies and epidermoid carcinoma.

Thus in some embodiments, there is provided a method of treating cancer (such as carcinoma or adenocarcinoma, solid tumor, cancers with aberrant VEGF expression, activity and/or signaling, and/or aberrant Ang2 expression, activity and/or signaling) comprising administering to the individual an effective amount of a pharmaceutical composition comprising an antibody fusion protein comprising 1) an anti-Ang2 antibody (such as full-length antibody) comprising a light chain, and 2) a VEGFR component fused to the C-terminus of the antibody light chain (e.g., C-terminus of antibody VL-CL domain); and optionally a pharmaceutically acceptable carrier. In some embodiments, the antibody fusion protein comprises a first VEGFR component fused to the C-terminus of a first antibody light chain, and a second VEGFR component fused to the C-terminus of a second antibody light chain. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the VEGFR component and the C-terminus of the antibody light chain are connected by a linker (such as a peptide linker comprising amino acid sequence of SEQ ID NO: 6 or 7). Thus in some embodiments, there is provided a method of treating cancer (such as carcinoma or adenocarcinoma, solid tumor, cancers with aberrant VEGF expression, activity and/or signaling, and/or aberrant Ang2 expression, activity and/or signaling) comprising administering to the individual an effective amount of a pharmaceutical composition comprising an antibody fusion protein comprising 1) an anti-Ang2 antibody (such as full-length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8; and optionally a pharmaceutically acceptable carrier. In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody comprises HC-CDR1, HC-CDR2, and HC-CDR3 of a heavy chain comprising the amino acid sequence of SEQ ID NO: 35; and/or LC-CDR1. LC-CDR2, and LC-CDR3 of a light chain comprising the amino acid sequence of SEQ ID NO: 36. In some embodiments, the antibody comprises a heavy chain comprising the amino acid sequence of SEQ ID NO: 35, and a light chain comprising the amino acid sequence of SEQ ID NO: 36. In some embodiments, the antibody is Nesvacumab or antigen-binding fragments thereof. In some embodiments, the antibody binds to Ang2 competitively with Nesvacumab. In some embodiments, the antibody fusion protein comprises a heavy chain comprising the amino acid sequence of SEQ ID NO: 35, and a light chain fusion polypeptide comprising the amino acid sequence of SEQ ID NO: 37.

In some embodiments, the method is suitable for treating cancers with aberrant TNFα expression, activity and/or signaling include, by way of non-limiting example, leukemia, ovarian cancer, breast cancer, and colon cancer.

Thus in some embodiments, there is provided a method of treating cancer (such as carcinoma or adenocarcinoma, solid tumor, cancers with aberrant VEGF expression, activity and/or signaling, and/or aberrant TNFα expression, activity and/or signaling) comprising administering to the individual an effective amount of a pharmaceutical composition comprising an antibody fusion protein comprising 1) an anti-TNFα antibody (such as full-length antibody) comprising a light chain, and 2) a VEGFR component fused to the C-terminus of the antibody light chain (e.g., C-terminus of antibody VL-CL domain); and optionally a pharmaceutically acceptable carrier. In some embodiments, the antibody fusion protein comprises a first VEGFR component fused to the C-terminus of a first antibody light chain, and a second VEGFR component fused to the C-terminus of a second antibody light chain. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the VEGFR component and the C-terminus of the antibody light chain are connected by a linker (such as a peptide linker comprising amino acid sequence of SEQ ID NO: 6 or 7). Thus in some embodiments, there is provided a method of treating cancer (such as carcinoma or adenocarcinoma, solid tumor, cancers with aberrant VEGF expression, activity and/or signaling, and/or aberrant TNFα expression, activity and/or signaling) comprising administering to the individual an effective amount of a pharmaceutical composition comprising an antibody fusion protein comprising 1) an anti-TNFα antibody (such as full-length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7) wherein each VEGFR component comprises an amino acid sequence of SEQ ID NO: 8; and optionally a pharmaceutically acceptable carrier. In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody comprises HC-CDR1, HC-CDR2, and HC-CDR3 of a heavy chain comprising the amino acid sequence of SEQ ID NO: 32; and/or LC-CDR1, LC-CDR2, and LC-CDR3 of a light chain comprising the amino acid sequence of SEQ ID NO: 33. In some embodiments, the antibody comprises a heavy chain comprising the amino acid sequence of SEQ ID NO: 32, and a light chain comprising the amino acid sequence of SEQ ID NO: 33. In some embodiments, the antibody is Adalimumab (e.g., Humira®) or antigen-binding fragments thereof. In some embodiments, the antibody binds to TNFα competitively with Adalimumab. In some embodiments, the antibody fusion protein comprises a heavy chain comprising the amino acid sequence of SEQ ID NO: 32, and a light chain fusion polypeptide comprising the amino acid sequence of SEQ ID NO: 34.

In some embodiments, the method is suitable for treating cancers with aberrant IL-17A expression, activity and/or signaling include, by way of non-limiting example, breast cancer, colon cancer, gastric cancer, glioma, hepatocellular carcinoma, kidney cancer, leukemia, lung cancer, lymphoma, melanoma, multiple myeloma, ovarian cancer, pancreatic cancer or prostate cancer.

Thus in some embodiments, there is provided a method of treating cancer (such as carcinoma or adenocarcinoma, solid tumor, cancers with aberrant VEGF expression, activity and/or signaling, and/or aberrant IL-17A expression, activity and/or signaling) comprising administering to the individual an effective amount of a pharmaceutical composition comprising an antibody fusion protein comprising 1) an anti-IL-17A antibody (such as full-length antibody) comprising a light chain, and 2) a VEGFR component fused to the C-terminus of the antibody light chain (e.g., C-terminus of antibody VL-CL domain); and optionally a pharmaceutically acceptable carrier. In some embodiments, the antibody fusion protein comprises a first VEGFR component fused to the C-terminus of a first antibody light chain, and a second VEGFR component fused to the C-terminus of a second antibody light chain. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_1$-L-Flt1d2-Flk1d3 (L is an optional linker). In some embodiments, the K of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$M, about $10^{-10}$ M to about $10^{-12}$ M). In some embodiments, the VEGFR component and the C-terminus of the antibody light chain are connected by a linker (such as a peptide linker comprising amino acid sequence of SEQ ID NO: 6 or 7). Thus in some embodiments, there is provided a method of treating cancer (such as carcinoma or adenocarcinoma, solid tumor, cancers with aberrant VEGF expression, activity and/or signaling, and/or aberrant IL-17A expression, activity and/or signaling) comprising administering to the individual an effective amount of a pharmaceutical composition comprising an antibody fusion protein comprising 1) an anti-IL-17A antibody (such as full-length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8; and optionally a pharmaceutically acceptable carrier. In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody comprises HC-CDR1, HC-CDR2, and HC-CDR3 of a heavy chain comprising the amino acid sequence of SEQ ID NO: 38; and/or LC-CDR1, LC-CDR2, and LC-CDR3 of a light chain comprising the amino acid sequence of SEQ ID NO: 39. In some embodiments, the antibody comprises a heavy chain comprising the amino acid sequence of SEQ ID NO: 38, and a light chain comprising the amino acid sequence of SEQ ID NO: 39. In some embodiments, the antibody is Ixekizumab (e.g., Taltz®) or antigen-binding fragments thereof. In some embodiments, the antibody binds to IL-17A competitively with Ixekizumab. In some embodiments, the antibody fusion protein comprises a heavy chain comprising the amino acid sequence of SEQ ID NO: 38, and a light chain fusion polypeptide comprising the amino acid sequence of SEQ ID NO: 40.

In some embodiments, the method described herein is suitable for treating lung cancer, liver cancer, skin cancer (such as melanoma), breast cancer, ovarian cancer, prostate cancer, colorectal cancer, or bladder cancer.

Dosages and desired drug concentrations of pharmaceutical compositions of the present application may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

When in vivo administration of the VEGFR-antibody light chain fusion protein described herein is used, normal dosage amounts may vary from about 10 ng/kg up to about 100 mg/kg of mammal body weight or more per day, preferably about 1 mg/kg/day to 10 mg/kg/day, such as about 1-3 mg/kg/day, about 2-4 mg/kg/day, about 3-5 mg/kg/day, about 4-6 mg/kg/day, about 5-7 mg/kg/day, about 6-8 mg/kg/day, about 6-6.5 mg/kg/day, about 6.5-7 mg/kg/day, about 7-9 mg/kg/day, or about 8-10 mg/kg/day, depending upon the route of administration. It is within the scope of the present application that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

In some embodiments, the pharmaceutical composition is administered for a single time (e.g. bolus injection). In some embodiments, the pharmaceutical composition is administered for multiple times (such as any of 2, 3, 4, 5, 6, or more times). If multiple administrations, they may be performed by the same or different routes and may take place at the same site or at alternative sites. The pharmaceutical composition may be administered twice per week, 3 times per week. 4 times per week, 5 times per week, daily, daily without break, once per week, weekly without break, once per 2 weeks, once per 3 weeks, once per month, once per 2 months, once per 3 months, once per 4 months, once per 5 months, once per 6 months, once per 7 months, once per 8 months, once per 9 months, once per 10 months, once per 11 months, or once per year. The interval between administrations can be about any one of 24 h to 48 h, 2 days to 3 days, 3 days to 5 days, 5 days to 1 week, 1 week to 2 weeks, 2 weeks to 1 month, month to 2 months, 2 month to 3 months, 3 months to 6 months, or 6 months to a year. Intervals can also be irregular (e.g. following tumor progression). In some embodiments, there is no break in the dosing schedule. In some embodiments, the pharmaceutical composition is administered every 4 days for 4 times. The optimal dosage and treatment regime for a particular patient can readily be determined by one skilled in the art of medicine by monitoring the patient for signs of disease and adjusting the treatment accordingly.

The pharmaceutical compositions of the present application, including but not limited to reconstituted and liquid formulations, are administered to an individual in need of treatment with the VEGFR-antibody light chain fusion protein described herein, preferably a human, in accord with known methods, such as intravenous administration as a bolus or by continuous infusion over a period of time, by intramuscular, intraperitoneal, intracerobrospinal, subcutaneous, intravenous (i.v.), intra-articular, intrasynovial, intrathecal, oral, topical, or inhalation routes. A reconstituted formulation can be prepared by dissolving a lyophilized VEGFR-antibody light chain fusion protein described herein in a diluent such that the protein is dispersed throughout. Exemplary pharmaceutically acceptable (safe and nontoxic for administration to a human) diluents suitable for use in the present application include, but are not limited to, sterile water, bacteriostatic water for injection (BWFI), a pH buffered solution (e.g. phosphate-buffered saline), sterile saline solution, Ringer's solution or dextrose solution, or aqueous solutions of salts and/or buffers.

In some embodiments, the pharmaceutical compositions are administered to the individual by subcutaneous (i.e. beneath the skin) administration. For such purposes, the pharmaceutical compositions may be injected using a syringe. However, other devices for administration of the pharmaceutical compositions are available such as injection devices; injector pens; auto-injector devices, needleless devices; and subcutaneous patch delivery systems.

In some embodiments, the pharmaceutical compositions are administered to the individual intravenously. In some embodiments, the pharmaceutical composition is administered to an individual by infusion, such as intravenous infusion. Infusion techniques for immunotherapy are known in the art (see, e.g., Rosenberg et al., New Eng. J. of Med. 319: 1676 (1988)).

Non-Neoplastic Disorders

In some embodiments, the non-neoplastic disorder that can be treated by the present invention is not associated with VEGF expression. In some embodiments, the non-neoplastic disorder that can be treated by the present invention is associated with VEGF expression (such as VEGF overexpression).

Overexpression of VEGF can cause non-neoplastic conditions such as rheumatoid arthritis, psoriasis, atherosclerosis, hemangiomas, immune rejection of transplanted corneal tissue and other tissues, chronic inflammation, and ocular neovascular disorders (e.g. diabetic retinopathy, retrolental fibroplasia, neovascular glaucoma, and AMD).

Thus in some embodiments, there is provided method of treating non-neoplastic disorders (such as ocular neovascular disorders, e.g. diabetic retinopathy and AMD) comprising administering to the individual an effective amount of a pharmaceutical composition comprising an antibody fusion protein comprising 1) an antibody (such as anti-PD-1, anti-PD-L1, anti-CTLA-4, anti-HER2, anti-EGFR, anti-Ang2, anti-TNFα, or anti-IL-17A full-length antibody) comprising an antibody light chain, and 2) a VEGFR component fused to the C-terminus of the antibody light chain (e.g., C-terminus of antibody VL-CL domain); and optionally a pharmaceutically acceptable carrier. In some embodiments, the antibody fusion protein comprises a first VEGFR component fused to the C-terminus of a first antibody light chain, and a second VEGFR component fused to the C-terminus of a second antibody light chain. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises an amino acid sequence of SEQ ID NO: 8. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the VEGFR component and the C-terminus of the antibody light chain are connected by a linker (such as a peptide linker comprising amino acid sequence of SEQ ID NO: 6 or 7). Thus in some embodiments, there is provided method of treating non-neoplastic disorders (such as ocular neovascular disorders, e.g. diabetic retinopathy and AMD) comprising administering to the individual an effective amount of a pharmaceutical composition comprising an antibody fusion protein comprising 1) an antibody (such as anti-PD-1, anti-PD-L1, anti-CTLA-4, anti-HER2, anti-EGFR, anti-Ang2, anti-TNFα, or anti-IL-17A full-length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8; and optionally a pharmaceutically acceptable carrier. In some embodiments, the antibody is selected from the group consisting of IgA, IgD, IgE, IgG, IgM. IgG-derived molecules, Fab, Fab', F(ab')2, Fab-scFv, F(ab')2-scFv2, Fab-scFv-Fc, Dock and Lock, scFv, di-scFv, diabody, Diabody-Fe, Diabody-$CH_3$, and intrabody. In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody specifically recognizes an immune checkpoint molecule. In some embodiments, the antibody specifically recognizes a stimulatory immune checkpoint molecule. In some embodiments, the antibody specifically recognizes an inhibitory immune checkpoint molecule. In some embodiments, the antibody specifically recognizes PD-1. In some embodiments, the antibody comprises HC-CDR1, HC-CDR2, and HC-CDR3 of a heavy chain comprising the amino acid sequence of SEQ ID NO: 12; and/or LC-CDR1, LC-CDR2, and LC-CDR3 of a light chain comprising the amino acid sequence of SEQ ID NO: 13. In some embodiments, the antibody comprises a heavy chain comprising the amino acid sequence of SEQ ID NO: 12, and a light chain comprising the amino acid sequence of SEQ ID NO: 13. In some embodiments, the antibody is pembrolizumab (e.g., Keytruda®) or antigen-binding fragments thereof. In some embodiments, the antibody binds to PD-1 competitively with pembrolizumab. In some embodiments, the antibody fusion protein comprises a heavy chain comprising the amino acid sequence of SEQ ID NO: 12, and a light chain fusion polypeptide comprising the amino acid sequence of SEQ ID NO: 14. In some embodiments, the antibody comprises HC-CDR1, HC-CDR2, and HC-CDR3 of a heavy chain comprising the amino acid sequence of SEQ ID NO: 15; and/or LC-CDR1, LC-CDR2, and LC-CDR3 of a light chain comprising the amino acid sequence of SEQ ID NO: 16. In some embodiments, the antibody comprises a heavy chain comprising the amino acid sequence of SEQ ID NO: 15, and a light chain comprising the amino acid sequence of SEQ ID NO: 16. In some embodiments, the antibody is nivolumab (e.g., Opdivo®) or antigen-binding fragments thereof. In some embodiments, the antibody binds to PD-1 competitively with nivolumab. In some embodiments, the antibody fusion protein comprises a heavy chain comprising the amino acid sequence of SEQ ID NO: 15, and a light chain fusion polypeptide comprising the amino acid sequence of SEQ ID NO: 17. In some embodiments, the antibody specifically recognizes PD-L1. In some embodiments, the antibody comprises HC-CDR1, HC-CDR2, and HC-CDR3 of a heavy chain comprising the amino acid sequence of SEQ ID NO: 18; and/or LC-CDR1. LC-CDR2, and LC-CDR3 of a light chain comprising the amino acid sequence of SEQ ID NO: 19. In some embodiments, the antibody comprises a heavy chain comprising the amino acid sequence of SEQ ID NO: 18, and a light chain comprising the amino acid sequence of SEQ ID NO: 19. In some embodiments, the antibody is atezolizumab (e.g., Tecentriq®) or antigen-binding fragments thereof. In some embodiments, the antibody binds to PD-L1 competitively with atezolizumab. In some embodiments, the antibody fusion protein comprises a heavy chain comprising the amino acid sequence of SEQ ID NO: 18, and a light chain fusion polypeptide comprising the amino acid sequence of SEQ ID NO: 20. In some embodiments, the antibody comprises HC-CDR1, HC-CDR2, and HC-CDR3 of a heavy chain comprising the amino acid sequence of SEQ ID NO: 21; and/or LC-CDR1, LC-CDR2, and LC-CDR3 of a light chain comprising the amino acid sequence of SEQ ID NO: 22. In some embodiments, the antibody comprises a heavy chain comprising the amino acid sequence of SEQ ID NO: 21, and a light chain comprising the amino acid sequence of SEQ ID NO: 22. In some embodiments, the antibody is Durvalumab (e.g., Imfinzi®) or antigen-binding fragments thereof. In some embodiments, the antibody binds to PD-L1 competitively with Durvalumab. In some embodiments, the antibody fusion protein comprises a heavy chain comprising the amino acid sequence of SEQ ID NO: 21, and a light chain fusion polypeptide comprising the amino acid sequence of SEQ ID NO: 23. In some embodiments, the antibody specifically recognizes CTLA-4. In some embodiments, the antibody comprises HC-CDR1, HC-CDR2, and HC-CDR3 of a heavy chain comprising the amino acid sequence of SEQ ID NO: 9; and/or LC-CDR1, LC-CDR2, and LC-CDR3 of a light chain comprising the amino acid sequence of SEQ ID NO: 10. In some embodiments, the antibody comprises a heavy chain comprising the amino acid sequence of SEQ ID NO: 9, and a light chain comprising the amino acid sequence of SEQ ID NO: 10. In some embodiments, the antibody is ipilimumab (e.g., Yervoy®) or antigen-binding fragments thereof. In some embodiments, the antibody binds to CTLA4 competitively with ipilimumab. In some embodiments, the antibody fusion protein comprises a heavy chain comprising the amino acid sequence of SEQ ID NO: 9, and a light chain fusion polypeptide comprising the amino acid sequence of SEQ ID NO: 11. In some embodiments, the antibody specifically recognizes a tumor antigen. In some embodiments, the tumor antigen is HER2. In some embodiments, the antibody comprises HC-CDR1, HC-CDR2, and HC-CDR3 of a heavy chain comprising the amino acid sequence of SEQ ID NO: 24; and/or LC-CDR1, LC-CDR2, and LC-CDR3 of a light chain comprising the amino acid sequence of SEQ ID NO: 25. In some embodiments, the antibody comprises a heavy chain comprising the amino acid sequence of SEQ ID NO: 24, and a light chain comprising the amino acid sequence of SEQ ID NO: 25. In some embodiments, the antibody is trastuzumab (e.g., Herceptin®) or antigen-binding fragments thereof. In some embodiments, the antibody binds to HER2 competitively with trastuzumab. In some embodiments, the antibody fusion protein comprises a heavy chain comprising the amino acid sequence of SEQ ID NO: 24, and a light chain fusion polypeptide comprising the amino acid sequence of SEQ ID NO: 26, 27, or 28. In some embodiments, the tumor antigen is EGFR (HER). In some embodiments, the antibody comprises HC-CDR1, HC-CDR2, and HC-CDR3 of a heavy chain comprising the amino acid sequence of SEQ ID NO: 29; and/or LC-CDR1, LC-CDR2, and LC-CDR3 of a light chain comprising the amino acid sequence of SEQ ID NO: 30. In some embodiments, the antibody comprises a heavy chain comprising the amino acid sequence of SEQ ID NO: 29, and a light chain comprising the amino acid sequence of SEQ ID NO: 30. In some embodiments, the antibody is Cetuximab (e.g., Erbitux®) or antigen-binding fragments thereof. In some embodiments, the antibody binds to EGFR competitively with Cetuximab.

In some embodiments, the antibody fusion protein comprises a heavy chain comprising the amino acid sequence of SEQ ID NO: 29, and a light chain fusion polypeptide comprising the amino acid sequence of SEQ ID NO: 31. In some embodiments, the antibody specifically recognizes an angiogenic factor. In some embodiments, the angiogenic factor is Ang2. In some embodiments, the antibody comprises HC-CDR1, HC-CDR2, and HC-CDR3 of a heavy chain comprising the amino acid sequence of SEQ ID NO: 35; and/or LC-CDR1, LC-CDR2, and LC-CDR3 of a light chain comprising the amino acid sequence of SEQ ID NO: 36. In some embodiments, the antibody comprises a heavy chain comprising the amino acid sequence of SEQ ID NO: 35, and a light chain comprising the amino acid sequence of SEQ ID NO: 36. In some embodiments, the antibody is Nesvacumab or antigen-binding fragments thereof. In some embodiments, the antibody binds to Ang2 competitively with Nesvacumab. In some embodiments, the antibody fusion protein comprises a heavy chain comprising the amino acid sequence of SEQ ID NO: 35, and a light chain fusion polypeptide comprising the amino acid sequence of SEQ ID NO: 37. In some embodiments, the angiogenic factor is TNFα. In some embodiments, the antibody comprises HC-CDR1, HC-CDR2, and HC-CDR3 of a heavy chain comprising the amino acid sequence of SEQ ID NO: 32, and/or LC-CDR1, LC-CDR2, and LC-CDR3 of a light chain comprising the amino acid sequence of SEQ ID NO: 33. In some embodiments, the antibody comprises a heavy chain comprising the amino acid sequence of SEQ ID NO: 32, and a light chain comprising the amino acid sequence of SEQ ID NO: 33. In some embodiments, the antibody is Adalimumab (e.g., Humira®) or antigen-binding fragments thereof. In some embodiments, the antibody binds to TNFα competitively with Adalimumab. In some embodiments, the antibody fusion protein comprises a heavy chain comprising the amino acid sequence of SEQ ID NO: 32, and a light chain fusion polypeptide comprising the amino acid sequence of SEQ ID NO: 34. In some embodiments, the angiogenic factor is IL-17A. In some embodiments, the antibody comprises HC-CDR1, HC-CDR2, and HC-CDR3 of a heavy chain comprising the amino acid sequence of SEQ ID NO: 38; and/or LC-CDR1, LC-CDR2, and LC-CDR3 of a light chain comprising the amino acid sequence of SEQ ID NO: 39. In some embodiments, the antibody comprises a heavy chain comprising the amino acid sequence of SEQ ID NO: 38, and a light chain comprising the amino acid sequence of SEQ ID NO: 39. In some embodiments, the antibody is Ixekizumab (e.g., Taltz®) or antigen-binding fragments thereof. In some embodiments, the antibody binds to IL-17A competitively with Ixekizumab. In some embodiments, the antibody fusion protein comprises a heavy chain comprising the amino acid sequence of SEQ ID NO: 38, and a light chain fusion polypeptide comprising the amino acid sequence of SEQ ID NO: 40. In some embodiments, the non-neoplastic disorder is associated with VEGF overexpression. In some embodiments, the non-neoplastic disorder is selected from rheumatoid arthritis, psoriasis, atherosclerosis, hemangiomas, immune rejection of transplanted corneal tissue and other tissues, chronic inflammation, and ocular neovascular disorders (e.g. diabetic retinopathy, retrolental fibroplasia, neovascular glaucoma, and AMD). In some embodiments, the pharmaceutical composition is administered systemically (such as intravenously). In some embodiments, the individual is a human.

In some embodiments, the disease to be treated by the present invention is rheumatoid arthritis. Rheumatoid arthritis is a chronic disease which can exhibit a variety of systemic manifestations. This disease has an unknown etiology and characteristically exhibits a persistent inflammatory synovitis which usually involves peripheral joints in a symmetric distribution. Complement-mediated inflammation which causes cartilage destruction, bone erosions and, ultimately, joint deformities is the most important feature of this disease. Methods provided herein are thus useful for treatment of rheumatoid arthritis.

In some embodiments, the disease to be treated by the present invention is Psoriasis. Psoriasis (psoriasis vulgaris) is a chronic inflammatory skin disease characterized by red, scaly, raised plaques. The disease process is driven by T-cell infiltration and associated elevation in cytokine levels leading to increased cell division and aberrant differentiation, resulting in the psoriatic phenotype. Plaque psoriasis has a worldwide prevalence of 2-3%, and is a chronic, recurrent skin condition with varying degrees of severity. Psoriasis can profoundly impact a patient's quality of life, causing disability of physical and mental functioning comparable to other major medical diseases such as type 2 diabetes, hypertension, myocardial infarction, depression, and arthritis, it is also associated with serious co-morbidities, including psoriatic arthritis, depression, malignancy, metabolic syndrome, cardiovascular morbidity and mortality and autoimmune diseases, such as inflammatory bowel disease (iBD).

In some embodiments, the disease to be treated by the present invention is atherosclerosis. Atherosclerosis is a disease of the arterial wall in which the layer thickens, causing narrowing of the channel and thus, impairing blood flow. Atherosclerosis may occur in any area of the body, but can be most damaging to a subject when it occurs in the heart, brain or blood vessels leading to the brain stem. Atherosclerosis includes thickening and hardening of artery walls or the accumulation of fat, cholesterol and other substances that form atheromas or plaques. Atherosclerosis may result also from calcification, hemorrhage, ulceration, thrombosis, and/or trauma.

In some embodiments, the disease to be treated by the present invention is hemangiomas. Hemangiomas are non-cancerous growths that form due to an abnormal collection of blood vessels. They are often found on the skin or internal organs, particularly the liver, and are usually congenital.

In some embodiments, the disease to be treated by the present invention is chronic inflammation, including but are not limited to, asthma, chronic peptic ulcer, tuberculosis, rheumatoid arthritis, chronic periodontitis, ulcerative colitis and Crohn's disease, chronic sinusitis, and chronic active hepatitis. Chronic inflammation can result from failure to eliminate whatever was causing an acute inflammation, an autoimmune response to a self-antigen, or a chronic irritant of low intensity that persists.

Ocular Neovascular Disorder

In some embodiments, there is provided a method of treating ocular neovascular disorders (such as diabetic retinopathy and AMD) comprising administering to the individual an effective amount of a pharmaceutical composition comprising an antibody fusion protein comprising 1) an antibody (such as anti-Ang2, anti-TNFα, or anti-IL-17A full-length antibody) comprising an antibody light chain, and 2) a VEGFR component fused to the C-terminus of the antibody light chain (e.g., C-terminus of antibody VL-CL domain); and optionally a pharmaceutically acceptable carrier. In some embodiments, the antibody fusion protein comprises a first VEGFR component fused to the C-terminus of a first antibody light chain, and a second VEGFR component fused to the C-terminus of a second antibody light chain. In some embodiments, the first VEGFR component and the second VEGFR component are the same. In some embodiments, the first VEGFR component and the second VEGFR component are different. In some embodiments, the VEGFR component comprises an Flt1d2. In some embodiments, the VEGFR component further comprises an Flk1d3. In some embodiments, the VEGFR component further comprises an Flk1d4. In some embodiments, the VEGFR component comprises from N-terminus to C-terminus: Flt1d2-Flk1d3, wherein the N-terminus of the VEGFR component is fused to the C-terminus of antibody light chain. In some embodiments, the VEGFR component comprises from N-terminus to C-terminus: Flt1d2-Flk1d3-Flk1d4, wherein the N-terminus of the VEGFR component is fused to the C-terminus of antibody light chain. In some embodiments, the VEGFR component is at least about 4 kDa (such as at least about any of 4 kDa, 8 kDa, 12 kDa, 17 kDa, 20 kDa, 25 kDa, 27 kDa, or 30 kDa). In some embodiments, the VEGFR component-antibody light chain fusion polypeptide comprises from N-terminus to C-terminus: $V_L$-$C_L$-L-Flt1d2-Flk1d3 (L is an optional linker). In some embodiments, the $K_D$ of the binding between the VEGFR component and VEGF is about $10^{-8}$ M to about $10^{-13}$ M (such as about $10^{-8}$ M to about $10^{-13}$ M, about $10^{-8}$ M to about $10^{-12}$ M, about $10^{-9}$ M to about $10^{-12}$ M, about $10^{-10}$ M to about $10^{-12}$ M). In some embodiments, the VEGFR component and the C-terminus of the antibody light chain are connected by a linker (such as a peptide linker comprising amino acid sequence of SEQ ID NO: 6 or 7). Thus in some embodiments, there is provided a method of treating ocular neovascular disorders (such as diabetic retinopathy and AMD) comprising administering to the individual an effective amount of a pharmaceutical composition comprising an antibody fusion protein comprising 1) an antibody (such as anti-Ang2, anti-TNFα, or anti-IL-17A full-length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8; and optionally a pharmaceutically acceptable carrier. In some embodiments, the antibody is selected from the group consisting of IgA, IgD, IgE, IgG, IgM, IgG-derived molecules, Fab, Fab', F(ab')2, Fab-scFv, F(ab')2-scFv2, Fab-scFv-Fc, Dock and Lock, scFv, di-scFv, diabody, Diabody-Fc, Diabody-CH₃, and intrabody. In some embodiments, the antibody is a full length antibody. In some embodiments, the antibody is an IgG antibody (such as IgG1 or IgG4 antibody, or variants thereof). In some embodiments, the antibody is monospecific. In some embodiments, the antibody is multispecific (e.g., bispecific). In some embodiments, the antibody specifically recognizes an angiogenic factor. In some embodiments, the angiogenic factor is Ang2. In some embodiments, the antibody comprises HC-CDR1, HC-CDR2, and HC-CDR3 of a heavy chain comprising the amino acid sequence of SEQ ID NO: 35; and/or LC-CDR1, LC-CDR2, and LC-CDR3 of a light chain comprising the amino acid sequence of SEQ ID NO: 36. In some embodiments, the antibody comprises a heavy chain comprising the amino acid sequence of SEQ ID NO: 35, and a light chain comprising the amino acid sequence of SEQ ID NO: 36. In some embodiments, the antibody is Nesvacumab or antigen-binding fragments thereof. In some embodiments, the antibody binds to Ang2 competitively with Nesvacumab. In some embodiments, the antibody fusion protein comprises a heavy chain comprising the amino acid sequence of SEQ ID NO: 35, and a light chain fusion polypeptide comprising the amino acid sequence of SEQ ID NO: 37. In some embodiments, the angiogenic factor is TNFα. In some embodiments, the antibody comprises HC-CDR1, HC-CDR2, and HC-CDR3 of a heavy chain comprising the amino acid sequence of SEQ ID NO: 32, and/or LC-CDR1, LC-CDR2, and LC-CDR3 of a light chain comprising the amino acid sequence of SEQ ID NO: 33. In some embodiments, the antibody comprises a heavy chain comprising the amino acid sequence of SEQ ID NO: 32, and a light chain comprising the amino acid sequence of SEQ ID NO: 33. In some embodiments, the antibody is Adalimumab (e.g., Humira®) or antigen-binding fragments thereof. In some embodiments, the antibody binds to TNFα competitively with Adalimumab. In some embodiments, the antibody fusion protein comprises a heavy chain comprising the amino acid sequence of SEQ ID NO: 32, and a light chain fusion polypeptide comprising the amino acid sequence of SEQ ID NO: 34. In some embodiments, the angiogenic factor is IL-17A. In some embodiments, the antibody comprises HC-CDR1, HC-CDR2, and HC-CDR3 of a heavy chain comprising the amino acid sequence of SEQ ID NO: 38; and/or LC-CDR1, LC-CDR2, and LC-CDR3 of a light chain comprising the amino acid sequence of SEQ ID NO: 39. In some embodiments, the antibody comprises a heavy chain comprising the amino acid sequence of SEQ ID NO: 38, and a light chain comprising the amino acid sequence of SEQ ID NO: 39. In some embodiments, the antibody is Ixekizumab (e.g., Taltz®) or antigen-binding fragments thereof. In some embodiments, the antibody binds to IL-17A competitively with Ixekizumab. In some embodiments, the antibody fusion protein comprises a heavy chain comprising the amino acid sequence of SEQ ID NO: 38, and a light chain fusion polypeptide comprising the amino acid sequence of SEQ ID NO: 40. In some embodiments, the ocular neovascular disorder is AMD. In some embodiments the ocular neovascular disorder is associated with choroidal neovascularization, vascular leak, and/or retinal edema. In some embodiments, the pharmaceutical composition is administered topically, such as eye drops, subconjunctival injection, subconjunctival implant, intravitreal injection, intravitreal implant, sub-Tenon's injection, and sub-Tenon's implant. In some embodiments, the pharmaceutical composition is administered by intravitreal injection. In some embodiments, the method further comprises subjecting the individual to an additional ocular therapy. In some embodiments, the individual is a human. In some embodiments, the method of treating ocular neovascular disorders has one or more of the following biological activities: (1) inhibiting or preventing drusen formation; (2) causing a reduction in drusen number and/or size (drusen regression); (3) causing a reduction in or prevent lipofuscin deposits; (4) inhibiting or preventing visual loss or slow the rate of visual loss; (5) inhibiting choroidal neovascularization or slowing the rate of choroidal neovascularization; (6) causing a reduction in size and/or number of lesions characterized by choroidal neovascularization; (7) inhibiting choroidal neovascularization or slow the rate of retinal neovascularization; (8) causing a reduction in size and/or number of lesions characterized by retinal neovascularization; (9) improving visual acuity and/or contrast sensitivity; (10) reducing macular edema and/or reducing abnormal macular thickness; (11) inhibiting or preventing photoreceptor or RPE cell atrophy or apoptosis, or reducing the rate of photoreceptor or RPE cell atrophy or apoptosis; (12) inhibiting or preventing progression of non-exudative macular degeneration to exudative macular degeneration.

Several ocular disorders involve alterations in angiogenesis. Non-limiting examples of ocular neovascular disorders that may be treated according to the methods of the invention include exudative AMD, diabetic retinopathy, angiod streaks, pathological myopia, ocular histoplasmosis syndrome, breaks in Bruch's membrane, macular edema (including diabetic macular edema), sarcoidosis and uveitis. Additional examples of disorders that may be treated by the disclosed methods include atrophic AMD, keratoconus, Sjogren's syndrome, myopia, ocular tumors, corneal graft rejection, corneal injury, neovascular glaucoma, corneal ulceration, corneal scarring, proliferative vitreoretinopathy, retinopathy of prematurity, retinal degeneration, chronic glaucoma, retinal detachment, and sickle cell retinopathy.

Diabetic retinopathy, the third leading cause of adult blindness (accounting for almost 7% of blindness in the USA), is associated with extensive angiogenic events. Nonproliferative retinopathy is accompanied by the selective loss of pericytes within the retina, and their loss results in dilation of associated capillaries dilation and a resulting increase in blood flow. In the dilated capillaries, endothelial cells proliferate and form outpouchings, which become microaneurysms, and the adjacent capillaries become blocked so that the area of retina surrounding these microaneurysms is not perfused. Eventually, shunt vessels appear between adjacent areas of micro aneurysms, and the clinical picture of early diabetic retinopathy with micro aneurysms and areas of nonperfused retina is seen. The microaneurysms leak and capillary vessels may bleed, causing exudates and hemorrhages. Once the initial stages of background diabetic retinopathy are established, the condition progresses over a period of years, developing into proliferative diabetic retinopathy and blindness in about 5% of cases. Proliferative diabetic retinopathy occurs when some areas of the retina continue losing their capillary vessels and become nonperfused, leading to the appearance of new vessels on the disk and elsewhere on the retina. These new blood vessels grow into the vitreous and bleed easily, leading to preretinal hemorrhages. In advanced proliferative diabetic retinopathy, a massive vitreous hemorrhage may fill a major portion of the vitreous cavity. In addition, the new vessels are accompanied by fibrous tissue proliferation that can lead to traction retinal detachment.

Diabetic retinopathy is associated primarily with the duration of diabetes mellitus; therefore, as the population ages and diabetic patients live longer, the prevalence of diabetic retinopathy will increase. Laser therapy is currently used in both nonproliferative and proliferative diabetic retinopathy. Focal laser treatment of the leaking microaneurysms surrounding the macular area reduces visual loss in 50% of patients with clinically significant macular edema. In proliferative diabetic retinopathy, panretinal photocoagulation results in several thousand tiny burns scattered throughout the retina (sparing the macular area); this treatment reduces the rate of blindness by 60 percent. Early treatment of macular edema and proliferative diabetic retinopathy prevents blindness for 5 years in 95% of patients, whereas late treatment prevents blindness in only 50 percent. Therefore, early diagnosis and treatment are essential.

Another ocular disorder involving neovascularization is AMD, a disease that affects approximately one in ten Americans over the age of 65. AMD is characterized by a series of pathologic changes in the macula, the central region of the retina, which is accompanied by decreased visual acuity, particularly affecting central vision. AMD involves the single layer of cells called the retinal pigment epithelium that lies immediately beneath the sensory retina. These cells nourish and support the portion of the retina in contact with them, i.e., the photoreceptor cells that contain the visual pigments. The retinal pigment epithelium lies on the Bruch membrane, a basement membrane complex which, in AMD, thickens and becomes sclerotic. New blood vessels may break through the Bruch membrane from the underlying choroid, which contains a rich vascular bed. These vessels may in turn leak fluid or bleed beneath the retinal pigment epithelium and also between the retinal pigment epithelium and the sensory retina. Subsequent fibrous scarring disrupts the nourishment of the photoreceptor cells and leads to their death, resulting in a loss of central visual acuity. This type of age-related maculopathy is called the "wet" type because of the leaking vessels and the subretinal edema or blood. The wet type accounts for only 10% of age-related maculopathy cases but results in 90% of cases of legal blindness from macular degeneration in the elderly. The "dry" type of age-related maculopathy involves disintegration of the retinal pigment epithelium along with loss of the overlying photoreceptor cells. The dry type reduces vision but usually only to levels of 20/50 to 20/100.

AMD is accompanied by distortion of central vision with objects appearing larger or smaller or straight lines appearing distorted, bent, or without a central segment. In the wet type of AMD, a small detachment of the sensory retina may be noted in the macular area, but the definitive diagnosis of a subretinal neovascular membrane requires fluorescein angiography. In the dry type, drusen may disturb the pigmentation pattern in the macular area. Drusen are excrescences of the basement membrane of the retinal pigment epithelium that protrude into the cells, causing them to bulge anteriorly; their role as a risk factor in age-related maculopathy is unclear. No treatment currently exists for the dry type of age-related maculopathy. Laser treatment is used in the wet type of age-related maculopathy and initially obliterates the neovascular membrane and prevents further visual loss in about 50% of patients at 18 months. By 60 months, however, only 20% still have a substantial benefit.

Macular edema is associated with a variety of eye disorders including AMD, diabetic retinopathy, inflammatory conditions such as anterior or posterior uveitis, etc. The macula becomes thickened as a result of the accumulation of fluid that leaks from weakened or otherwise abnormal blood vessels into nearby tissues. Leakage of blood or other fluids and the resulting increase in macular thickness can lead to acute alterations in visual acuity, color perception, etc. Thus macular edema can contribute to the visual disturbances and loss experienced by individuals suffering from AMD and a variety of other eye disorders.

In some embodiments, the present invention provides a method of treating or preventing one or more aspects or symptoms of AMD or diabetic retinopathy, including, but not limited to, neovascularization (such as choroidal neovascularization or CNV), vascular leak, and/or retinal edema, formation of ocular drusen, inflammation in the eye or eye tissue, loss of photoreceptor cells, loss of vision (including for example visual acuity and visual field), and retinal detachment, by administering to the individual an effective amount of a pharmaceutical composition comprising an antibody fusion protein comprising 1) an antibody (such as anti-Ang2, anti-TNFα, or anti-IL-17A full-length antibody) comprising an antibody light chain, and 2) a VEGFR component fused to the C-terminus of the antibody light chain; and optionally a pharmaceutically acceptable carrier. In some embodiments, the present invention provides a method of treating or preventing one or more aspects or symptoms of AMD or diabetic retinopathy by administering to the individual an effective amount of a pharmaceutical composition comprising an antibody fusion protein comprising 1) an antibody (such as anti-Ang2, anti-TNFα, or anti-IL-17A full-length antibody) comprising a first light chain and a second light chain, and 2) a first VEGFR component and a second VEGFR component, wherein the first VEGFR component is fused to the C-terminus of the first antibody light chain (e.g., C-terminus of antibody $V_L$-$C_L$ domain) optionally via a linker X (such as peptide linker of SEQ ID NO: 6 or 7), and the second VEGFR component is fused to the C-terminus of the second antibody light chain (e.g., C-terminus of antibody $V_L$-$C_L$ domain) optionally via a linker Y (such as peptide linker of SEQ ID NO: 6 or 7); wherein each VEGFR component comprises an amino acid sequence of SEQ ID NO: 8; and optionally a pharmaceutically acceptable carrier. Treatments of other aspects of AMD are also contemplated, such as photoreceptor degeneration, RPE degeneration, retinal degeneration, chorioretinal degeneration, cone degeneration, retinal dysfunction, retinal damage in response to light exposure (such as constant light exposure), damage of the Bruch's membrane, loss of RPE function, loss of integrity of the histoarchitecture of the cells and/or extracellular matrix of the normal macular, loss of function of the cells in the macula, photoreceptor dystrophy, mucopolysaccharidoses, rod-cone dystrophies, cone-rod dystrophies, anterior and posterior uvitis, and diabetic neuropathy.

Suppression of a neovascular disorder can be evaluated by any accepted method of measuring whether angiogenesis is slowed or diminished. This includes direct observation and indirect evaluation such as by evaluating subjective symptoms or objective physiological indicators. Treatment efficacy, for example, may be evaluated based on the prevention or reversal of neovascularization, microangiopathy, vascular leakage or vascular edema or any combination thereof. Treatment efficacy for evaluating suppression of an ocular neovascular disorder may also be defined in terms of stabilizing or improving visual acuity.

In some embodiments of the method of the invention, a human subject with at least one visually impaired eye is treated with about 25-4000 μg of a VEGFR-antibody light chain fusion protein described herein via intravitreal injection. Improvement of clinical symptoms are monitored by one or more methods known to the art, for example, indirect ophthalmoscopy, fundus photography, fluorescein angiopathy, electroretinography, external eye examination, slit lamp biomicroscopy, applanation tonometry, pachymetry, and autorefaction. Subsequent doses may be administered weekly or monthly, e.g., with a frequency of 2-8 weeks or 1-12 months apart.

V. Methods of Preparation

The VEGFR-antibody light chain fusion protein (such as VEGFR component fused to C-terminus of a full-length antibody CL domain) described herein may be prepared using any methods known in the art or as described herein.

An isolated DNA is understood herein to mean chemically synthesized DNA, cDNA, chromosomal, or extrachromosomal DNA with or without the 3'- and/or 5'-flanking regions. Preferably, the desired VEGFR-antibody light chain fusion protein described herein is made by synthesis in recombinant cell culture.

For such synthesis, it is first necessary to secure nucleic acid that encodes a VEGFR component of the present invention. DNA encoding a Flt-/, KDR, or Flt-4 receptor may be obtained from vascular endothelial cells by (a) preparing a cDNA library from these cells, (b) conducting hybridization analysis with labeled DNA encoding the Flt-1 or KDR receptor or fragments thereof (up to or more than 100 base pairs in length) to detect clones in the library containing homologous sequences, and (c) analyzing the clones by restriction enzyme analysis and nucleic acid sequencing to identify fill-length clones. If fill-length clones are not present in a cDNA library, then appropriate fragments may be recovered from the various clones using the nucleic acid and amino acid sequence information known for the Flt-1 and KDR receptors and ligated at restriction sites common to the clones to assemble a full-length clone encoding the Flt-1 or KDR domain. Alternatively, genomic libraries may provide the desired DNA.

Once this DNA has been identified and isolated from the library, this DNA may be ligated into an appropriate expression vector operably connected to appropriate control sequences. Moreover, once cloned into an appropriate vector, the DNA can be altered in numerous ways as described above to produce functionally equivalent variants thereof. Additionally, DNA encoding various domains, such as the intracellular, transmembrane and/or various Ig-like domains can be deleted and/or replaced by DNA encoding corresponding domains from other receptors. DNA encoding antibody amino acid sequences, such as the light chain of an immunoglobulin molecule, may also be fused in-frame to the DNA encoding some or all of the VEGFR, thereby producing a VEGFR-light chain C-terminus fusion molecule (hereinafter referred to as "hybrid light chain").

Many vectors are available. The choice of vector depends in part on the host cell to be used. Generally, preferred host cells are of either prokaryotic or eukaryotic (generally mammalian) origin. In general, of course, prokaryotes are preferred for the initial cloning of DNA sequences and construction of the vectors useful in the invention.

1. Amino Acid Sequence Variants

It will be appreciated that various amino acid substitutions can be made in the Ig-like domain or domains of the VEGFR component of the present invention without departing from the spirit of the present invention with respect to the VEGFR component's ability to bind to and inhibit the activity of VEGF. Thus, point mutational and other broader variations may be made in the Ig-like domain or domains of the VEGFR component of the present invention so as to impart interesting properties that do not substantially affect the VEGFR component's ability to bind to and inhibit the activity of VEGF. Various amino acid substitutions can also be made in the antibody portion of the VEGFR-antibody light chain fusion protein described herein to produce desired activities (also see. "Antibody variants" section). These variants may be made by means generally known well in the art.

a) Covalent Modifications

Covalent modifications may be made to various amino acid residues of the Ig-like domain or domains present in the VEGFR component, thereby imparting new properties to that Ig-like domain or domains without eliminating the capability to bind to and inactivate VEGF. Covalent modifications may also be made to the antibody portion of the VEGFR-antibody light chain fusion protein described herein to produce desired activities, e.g. retained/improved antigen binding, improved ADCC or CDC.

For example, cysteinyl residues most commonly are reacted with a-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, a-bromo-b-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate: pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N—C—N—R') such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for cross-linking the VEGFR-antibody light chain fusion protein described herein to a water-insoluble support matrix or surface for use in the method for purifying the VEGFR-antibody light chain fusion protein from complex mixtures. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis-(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the a-amino groups of lysine, arginine, and histidine side chains (T. E. Creighton, Proteins: Structure and Molecular Properties, W.H. Freeman & Co., San Francisco, pp. 79-86 [1983]), acetylation of the N-terminal amine, and, in some instances, amidation of the C-terminal carboxyl group.

b) DNA Mutations

Amino acid sequence variants of the Ig-like domain or domains present in the VEGFR component of the present invention, or amino acid sequence variants of the antibody portion present in the present invention, can also be prepared by creating mutations in the DNA encoding the VEGFR component or antibody, respectively. Such variants include, for example, deletions from, or insertions or substitutions of, amino acid residues within the amino acid sequence of the Ig-like domain or domains of VEGFR component, or the antibody. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP 75,444A).

At the genetic level, variants of the Ig-like domain or domains present in the VEGFR component of the present invention (or antibody variants of the present invention) ordinarily are prepared by site-directed mutagenesis of nucleotides in the DNA encoding the Ig-like domain or domains (or the antibody), thereby producing DNA encoding the variant, and thereafter expressing the DNA in recombinant cell culture. The VEGFR component variants typically exhibit the same qualitative ability to bind to the VEGF ligand as does the unaltered chimeric protein. The antibody variants typically exhibit the same qualitative ability to bind to target antigen(s), better antigen binding ability, decreased immunogenicity, or improved ADCC or CDC.

While the site for introducing an amino acid sequence variation in the Ig-like domain or domains of the VEGFR component is predetermined, the mutation per se need not be predetermined. For example, to optimize the performance of a mutation at a given site, random mutagenesis may be conducted at the target codon or region and the expressed chimeric protein variants screened for the optimal combination of desired attributes such as ability to specifically bind to the VEGF ligand, in vivo half-life, and the like. The site for introducing an amino acid sequence variation in the antibody portion of the fusion protein described herein can be at, for example, HVRs (e.g. to change antibody-antigen binding affinity), Fc fragment (e.g. to improve ADCC or CDC), or any accessible sites of the antibody (e.g. substitutes residues with cysteine for conjugation). Also see "Antibody variants" section. Techniques for making substitution mutations at predetermined sites in DNA having a known sequence are well known, for example, site-specific mutagenesis.

Preparation of variants in the Ig-like domain or domains of a VEGFR component, or the antibody portion within the fusion protein described herein, in accordance herewith is preferably achieved by site-specific mutagenesis of DNA that encodes an earlier prepared chimeric protein, or antibody. Site-specific mutagenesis allows the production of Ig-like domain variants or antibody variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., DNA 2, 183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., Third Cleveland Symposium on Macromolecules and Recombinant DNA, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., Meth. Enzymol., 153, 3 [1987]) may be employed to obtain single-stranded DNA.

In general, site-directed mutagenesis in accordance herewith is performed by first obtaining a single-stranded vector that includes within its sequence a DNA sequence that encodes the relevant VEGFR component, the antibody, or the VEGFR-antibody light chain fusion protein. An oligonucleotide primer bearing the desired mutated sequence is prepared, generally synthetically, for example, by the method of Crea et al., Proc. Natl. Acad. Sci. (USA), 75, 5765 (1978). This primer is then annealed with the single-stranded chimeric protein-sequence-containing vector, and subjected to DNA-polymerizing enzymes such as E. coli polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated DNA encoding the variant VEGFR component, antibody variant, or the VEGFR-antibody light chain fusion protein described herein may be removed and placed in an appropriate vector for protein production, generally an expression vector of the type that may be employed for transformation of an appropriate host.

c) Types of Mutations

Amino acid sequence deletions generally range from about 1 to 15 residues, more preferably 1 to 7 residues, and typically are contiguous.

Amino acid sequence insertions include amino- and/or carboxyl-terminal fusions of from one residue to polypeptides of essentially unrestricted length, as well as intrasequence insertions of single or multiple amino acid residues.

Intrasequence insertions (i.e., insertions within the Ig-like domain sequences) may range generally from about 1 to 10 residues, more preferably 1 to 5. An example of a terminal insertion includes a fusion of a signal sequence, whether heterologous or homologous to the host cell, to the N-terminus of the antibody light chain-VEGFR component fusion protein to facilitate its secretion from recombinant hosts.

The third group of mutations which can be introduced into the Ig-like domain or domains present in the VEGFR component are those in which at least one amino acid residue in the Ig-like domain or domains, and preferably only one, has been removed and a different residue inserted in its place. Such substitutions preferably are made in accordance with the following Table 2 when it is desired to modulate finely the characteristics of the Ig-like domain or domains.

TABLE 2

| Original Residue | Exemplary Substitutions |
| --- | --- |
| Ala (A) | Gly; Ser |
| Arg (R) | Lys |
| Asn (N) | Gln; His |
| Asp (D) | Glu |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in the properties of the Ig-like domains will be those in which (a) glycine and/or proline (P) is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; (e) a residue having an electronegative side chain is substituted for (or by) a residue having an electropositive charge; or (f) a residue having a bulky side chain, e.g., phenylalanine, is substituted for (or by) one not having such a side chain, e.g., glycine.

For substitutions recommended for antibody variants, see Table 1 and "Antibody variants" section.

Most deletions and insertions, and substitutions in particular, are not expected to produce radical changes in the characteristics of the Ig-like domain or domains of the VEGFR component or the antibody portion of the fusion protein described herein. However, when it is difficult to predict the exact effect of the substitution, deletion, or insertion in advance of doing so, one skilled in the art will appreciate that the effect will be evaluated by routine screening assays. For example, an Ig-like domain variant typically is made by site-specific mutagenesis of the nucleic acid encoding the intact VEGFR component, expression of the variant nucleic acid in recombinant cell culture, purification of the antibody light chain-variant VEGFR component fusion protein from the cell culture and detecting the ability of the variant VEGFR component to specifically bind to a VEGF ligand. Binding assays which can be routinely employed to determine if a particular alteration or alterations in an Ig-like domain or domains affects the capability of the VEGFR component to bind to and inhibit the activity of VEGF, are described both in Example 2 and in the article by Park et al., J. Biol. Chem. 269:25646-25654 (1994) which is expressly incorporated by reference herein. Binding specificity of the antibody or antigen-binding domain, or the VEGFR component, can be also determined experimentally by methods known in the art. Such methods comprise, but are not limited to Western blots, ELISA-, RIA-, ECL-, IRMA-, EIA-, BIAcore-tests and peptide scans.

Thus, the activity of a variant VEGFR component, or antibody variant or the VEGFR-antibody light chain fusion protein described herein may be screened in a suitable screening assay for the desired characteristic. For example, a change in the ability to specifically bind to a VEGF ligand can be measured by a competitive-type VEGF binding assay. Modifications of protein properties such as redox or thermal stability, hydrophobicity, susceptibility to proteolytic degradation, or the tendency to aggregate with carriers or into multimers are assayed by methods well known to the ordinarily skilled artisan.

2. Recombinant Production in Prokaryotic Cells a) Vector Construction

Polynucleic acid sequences encoding the VEGFR-antibody light chain fusion protein of the present application can be obtained using standard recombinant techniques. Desired polynucleic acid sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as *E. coli* LE392.

The expression vector of the present application may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the present application. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the -galactamase and lactose promoter systems, a tryptophan (trp) promoter system and hybrid promoters such as the tac or the tre promoter. However, other promoters that are functional in bacteria (such as other known bacterial or phage promoters) are suitable as well. Their nucleic acid sequences have been published, thereby enabling a skilled worker operably to ligate them to cistrons encoding the target light and heavy chains (Siebenlist et al. (1980) *Cell* 20: 269) using linkers or adaptors to supply any required restriction sites.

In one aspect, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In some embodiments of the present application, the signal sequences used in both cistrons of the expression system are STII signal sequences or variants thereof.

In some embodiments, the production of the VEGFR-antibody light chain fusion protein according to the present application can occur in the cytoplasm of the host cell, and therefore does not require the presence of secretion signal sequences within each cistron. In some embodiments, polypeptide components, such as the polypeptide encoding the antibody heavy chain, and the polypeptide encoding the antibody light chain fused with the VEGFR component, are expressed, folded and assembled to form functional antibody fusion protein within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene,* 159:203 (1995).

The present invention provides an expression system in which the quantitative ratio of expressed polypeptide components can be modulated in order to maximize the yield of secreted and properly assembled VEGFR-antibody light chain fusion protein of the present application. Such modulation is accomplished at least in part by simultaneously modulating translational strengths for the polypeptide components. One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleic acid sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each cistron therein. This limited set provides a comparison of expression levels of each chain as well as the yield of the desired protein products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the present application.

b) Prokaryotic Host Cells

Prokaryotic host cells suitable for expressing the VEGFR-antibody light chain fusion protein of the present application include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vireoscilla,* or *Paracoccus*. In some embodiments, gram-negative cells are used.

In some embodiments, E. coli cells are used as hosts for the invention. Examples of E. coli strains include strain W3110 (Bachmann, Cellular and Molecular Biology, vol. 2 (Washington, D.C.: American Society for Microbiology, 1987), pp. 1190-1219; ATCC Deposit No. 27.325) and derivatives thereof, including strain 33D3 having genotype W3110 ΔfhuA (ΔtonA) ptr3 lac Iq lacL8 ΔompT A(nmpc-fepE) degP41 kan$^R$ (U.S. Pat. No. 5,639,635). Other strains and derivatives thereof, such as E. coli 294 (ATCC 31,446), E. coli B. E. coli 1776 (ATCC 31,537) and E. coli RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, E. coli, Serratia, or Salmonella species can be suitably used as the host when well known plasmids such as pBR322, pBR325, pACYC177, or pKN410 are used to supply the replicon.

Typically the host cell should secrete minimal amounts of proteolytic enzymes, and additional protease inhibitors may desirably be incorporated in the cell culture.

c) Protein Production

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the VEGFR-antibody light chain fusion protein of the present application are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures. For E. coli growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For E. coli, the pH is preferably from about 6.8 to about 7.4, and more preferably about 7.0.

If an inducible promoter is used in the expression vector of the present application, protein expression is induced under conditions suitable for the activation of the promoter. In one aspect of the present application, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

The expressed VEGFR-antibody light chain fusion protein of the present application are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, protein production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

During the fermentation process, induction of protein expression is typically initiated after the cells have been grown under suitable conditions to a desired density. e.g., an OD$_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the VEGFR-antibody light chain fusion protein of the present application, various fermentation conditions can be modified. For example, to improve the proper assembly and folding of the secreted polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275:17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V. Protease VI and combinations thereof. Some *E. coli* protease-deficient strains are available and described in, for example, Joly et al. *Proc. Natl. Acad. Sci. USA.* 95, 2773-2777 (1998); Georgiou et al., U.S. Pat. No. 5,264,365; Georgiou et al., U.S. Pat. No. 5,508,192; Hara et al., *Microbial Drug Resistance,* 2:63-72 (1996).

*E. coli* strains deficient for proteolytic enzymes and transformed with plasmids overexpressing one or more chaperone proteins may be used as host cells in the expression system encoding the VEGFR-antibody light chain fusion protein of the present application.

d) Protein Purification

The VEGFR-antibody light chain fusion protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In some embodiments. Protein A immobilized on a solid phase is used for immunoaffinity purification of the VEGFR-antibody light chain fusion protein comprising an Fc region of the present application. Protein A is a 411(D cell wall protein from *Staphylococcus aureus* which binds with a high affinity to the Fc region of antibodies. Lindmark et al (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants. The solid phase is then washed to remove contaminants non-specifically bound to the solid phase. Finally the VEGFR-antibody light chain fusion protein is recovered from the solid phase by elution.

3. Recombinant Production in Eukaryotic Cells

For eukaryotic expression, the vector components generally include, but are not limited to, one or more of the following: a signal sequence, an origin of replication, one or more marker genes, and enhancer element, a promoter, and a transcription termination sequence.

a) Signal Sequence Component

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex virus glycoprotein D (gD) signal, are available. In some embodiments, the heavy chain and/or the VEGFR-light chain fusion polypeptide described herein can further comprise a signal peptide at the N-terminus. In some embodiments, the signal peptide comprises an amino acid sequence of SEQ ID NO: 41, 42, or 43.

The DNA for such precursor region is ligated in reading frame to DNA encoding the VEGFR-antibody light chain fusion protein of the present application.

b) Origin of Replication

Generally, the origin of replication component is not needed for mammalian expression vectors (the SV40 origin may typically be used only because it contains the early promoter).

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the antibodies of the present application, such as DHFR, thymidine kinase, metallothionein-I and -II, preferably primate metallothionein genes, adenosine deaminase, omithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with the polypeptide encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418, See U.S. Pat. No. 4,965,199.

d) Promoter Component

Expression and cloning vectors usually contain a promoter that is recognized by the host organism and is operably linked to the nucleic acid encoding the desired polypeptide sequences. Virtually all eukaryotic genes have an AT-rich region located approximately 25 to 30 based upstream from the site where transcription is initiated. Another sequence found 70 to 80 bases upstream from the start of the transcription of many genes is a CNCAAT region where N may be any nucleotide. At the 3' end of most eukaryotic is an AATAAA sequence that may be the signal for addition of the poly A tail to the 3' end of the coding sequence. All of these sequences may be inserted into eukaryotic expression vectors.

Other promoters suitable for use with prokaryotic hosts include the phoA promoter, -lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibodies.

Polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of a DNA encoding the VEGFR-antibody light chain fusion protein of the present application by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (100-270 bp), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the polypeptide encoding sequence, but is preferably located at a site 5' from the promoter.

f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the polypeptide-encoding mRNA. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/−DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for VEGFR-antibody light chain fusion protein production and cultured in conventional nutrient media modified as appropriate for inducing promoters, selecting transformants, or amplifying the genes encoding the desired sequences.

h) Culturing the Host Cells

The host cells used to produce the VEGFR-antibody light chain fusion protein of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature. pH, and the like, are those previously used with the host cell selected for expression, and will be apparent to the ordinarily skilled artisan.

i) Protein Purification

When using recombinant techniques, the VEGFR-antibody light chain fusion protein can be produced intracellularly, in the periplasmic space, or directly secreted into the medium. If the VEGFR-antibody light chain fusion protein is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the VEGFR-antibody light chain fusion protein is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify the antibodies that are based on human immunoglobulins containing 1, 2, or 4 heavy chains (Lindmark et al., *J. Immunol. Meth.* 62:1-13 (1983)). Protein G is recommended for all mouse isotypes and for human 3 (Guss et al., *EMBO J.* 5:15671575 (1986)). The matrix to which the affinity ligand is attached is most often agarose, but other matrices are available. Mechanically stable matrices such as controlled pore glass or poly(styrene-divinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the VEGFR-antibody light chain fusion protein and contaminants may be subjected to low pH hydrophobic interaction chromatography using an elution buffer at a pH between about 2.5-4.5, preferably performed at low salt concentrations (e.g., from about 0-0.25M salt).

VI. Articles of Manufacture and Kits

Further provided are kits and articles of manufacture comprising any of the VEGFR-antibody light chain fusion protein (such as VEGFR-anti-PD-1 fusion protein, VEGFR-anti-PD-L1 fusion protein, VEGFR-anti-CTLA4 fusion protein, VEGFR-anti-EGFR fusion protein, VEGFR-anti-HER2 fusion protein, VEGFR-anti-Ang2 fusion protein, VEGFR-anti-TNFα fusion protein, VEGFR-anti-IL-17A fusion protein), isolated nucleic acids or vectors encoding thereof, or isolated host cells comprising the isolated nucleic acids or vectors encoding the VEGFR-antibody light chain fusion protein. In some embodiments, a kit is provided which comprises any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder (such as cancer) described herein, and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments of the invention the article of manufacture may further comprise one or more devices or instruments for administering the pharmaceutical composition to the eye. For example, the article of manufacture may include one or more needles (e.g., a 22, 25, 27, or gauge needle) and/or one or more syringes (e.g., 0.3, 0.5, or 1.0 ml syringes). Either a needle or a syringe, or both, may contain one or more compositions comprising a unit dosage form of the VEGFR-antibody light chain fusion protein. For example, the article of manufacture may include a needle or syringe that contains a predetermined volume and/or amount of a composition comprising the VEGFR-antibody light chain fusion protein. The article of manufacture may contain a needle or syringe that contains a sustained release formulation of the VEGFR-antibody light chain fusion protein, e.g., an ocular implant. The needle and syringe may, but need not be, attached to one another. The needle and/or syringe may be provided with a removable cap. Providing one or more of the compositions already loaded into the device that will be used to administer the agent(s) may provide increased reliability, safety, and convenience.

The kits or article of manufacture may include multiple unit doses of the pharmaceutical composition and instructions for use, packaged in quantities sufficient for storage and use in pharmacies, for example, hospital pharmacies and compounding pharmacies.

EXEMPLARY EMBODIMENTS

Embodiment 1

An antibody fusion protein comprising 1) an antibody comprising a light chain, and 2) a VEGFR component, wherein the VEGFR component is fused to the C-terminus of the antibody light chain.

Embodiment 2

The antibody fusion protein of embodiment 1, comprising a first VEGFR component fused to the C-terminus of a first antibody light chain, and a second VEGFR component fused to the C-terminus of a second antibody light chain.

Embodiment 3

The antibody fusion protein of embodiment 2, wherein the first VEGFR component and the second VEGFR component are the same.

Embodiment 4

The antibody fusion protein of embodiment 2, wherein the first VEGFR component and the second VEGFR component are different.

Embodiment 5

The antibody fusion protein of any one of embodiments 1-4, wherein the VEGFR component comprises an Ig-like domain 2 of a first VEGFR Flt1 (Flt1d2).

Embodiment 6

The antibody fusion protein of embodiment 5, wherein the VEGFR component further comprises an Ig-like domain 3 of a second VEGFR Flk1 (Flk1d3).

Embodiment 7

The antibody fusion protein of embodiment 6, wherein the VEGFR component comprises an amino acid sequence of SEQ ID NO: 8.

Embodiment 8

The antibody fusion protein of embodiment 6 or 7, wherein the VEGFR component further comprises an Ig-like domain 4 of a third VEGFR Flk1 (Flk1d4).

Embodiment 9

The antibody fusion protein of any one of embodiments 1-8, wherein the VEGFR component is at least about 4 kDa.

Embodiment 10

The antibody fusion protein of any one of embodiments 1-9, wherein the $K_D$ of the binding between the VEGFR component and VEGF is about $10^{-8}$ M to about $10^{-13}$ M.

Embodiment 11

The antibody fusion protein of any one of embodiments 1-10, wherein the VEGFR component and the C-terminus of the antibody light chain are connected by a linker.

Embodiment 12

The antibody fusion protein of embodiment 11, wherein the linker is a peptide linker.

Embodiment 13

The antibody fusion protein of embodiment 12, wherein the linker comprises an amino acid sequence of SEQ ID NO: 6 or 7.

Embodiment 14

The antibody fusion protein of any one of embodiments 1-13, wherein the antibody is selected from the group consisting of IgA, IgD, IgE, IgG, IgM, IgG-derived molecules. Fab, Fab', F(ab')2, Fab-scFv, F(ab')2-scFv2, Fab-scFv-Fc, Dock and Lock, scFv, di-scFv, diabody, Diabody-Fc, Diabody-CH$_3$, and intrabody.

Embodiment 15

The antibody fusion protein of embodiment 14, wherein the antibody comprises a light chain constant domain (CL domain), and the VEGFR component is fused to the C-terminus of the antibody CL domain.

Embodiment 16

The antibody fusion protein of embodiment 14 or 15, wherein the antibody is a full length antibody.

Embodiment 17

The antibody fusion protein of embodiment 16, wherein the antibody is an IgG antibody.

Embodiment 18

The antibody fusion protein of embodiment 17, wherein the antibody is an IgG1 or IgG4 antibody, or variants thereof.

Embodiment 19

The antibody fusion protein of any one of embodiments 1-18, wherein the antibody is monospecific.

Embodiment 20

The antibody fusion protein of any one of embodiments 1-18, wherein the antibody is multispecific.

Embodiment 21

The antibody fusion protein of any one of embodiments 1-20, wherein the antibody specifically recognizes an immune checkpoint molecule.

Embodiment 22

The antibody fusion protein of embodiment 21, wherein the immune checkpoint molecule is a stimulatory immune checkpoint molecule.

Embodiment 23

The antibody fusion protein of embodiment 21, wherein the immune checkpoint molecule is an inhibitory immune checkpoint molecule.

Embodiment 24

The antibody fusion protein of embodiment 23, wherein the inhibitory immune checkpoint molecule is selected from the group consisting of PD-1, PD-L1, PD-L2, CD47, CXCR4, CSF1R. LAG-3, TIM-3, HHLA2, BTLA, CTLA-4, TIGIT, VISTA, B7-H4, CD160, 2B4, and CD73.

Embodiment 25

The antibody fusion protein of embodiment 24, wherein the inhibitory immune checkpoint molecule is PD-1.

Embodiment 26

The antibody fusion protein of embodiment 25, wherein the antibody comprises HC-CDR1, HC-CDR2, and HC-CDR3 of a heavy chain comprising the amino acid sequence of SEQ ID NO: 12; and/or LC-CDR1, LC-CDR2, and LC-CDR3 of a light chain comprising the amino acid sequence of SEQ ID NO: 13.

Embodiment 27

The antibody fusion protein of embodiment 25 or 26, wherein the antibody comprises a heavy chain comprising the amino acid sequence of SEQ ID NO: 12, and a light chain comprising the amino acid sequence of SEQ ID NO: 13.

Embodiment 28

The antibody fusion protein of embodiment 27, wherein the antibody fusion protein comprises a heavy chain comprising the amino acid sequence of SEQ ID NO: 12, and a light chain fusion polypeptide comprising the amino acid sequence of SEQ ID NO: 14.

Embodiment 29

The antibody fusion protein of embodiment 25, wherein the antibody comprises HC-CDR1, HC-CDR2, and HC-CDR3 of a heavy chain comprising the amino acid sequence of SEQ ID NO: 15; and/or LC-CDR1, LC-CDR2, and LC-CDR3 of a light chain comprising the amino acid sequence of SEQ ID NO: 16.

Embodiment 30

The antibody fusion protein of embodiment 25 or 29, wherein the antibody comprises a heavy chain comprising the amino acid sequence of SEQ ID NO: 15, and a light chain comprising the amino acid sequence of SEQ ID NO: 16.

Embodiment 31

The antibody fusion protein of embodiment 30, wherein the antibody fusion protein comprises a heavy chain comprising the amino acid sequence of SEQ ID NO: 15, and a light chain fusion polypeptide comprising the amino acid sequence of SEQ ID NO: 17.

Embodiment 32

The antibody fusion protein of embodiment 24, wherein the inhibitory immune checkpoint molecule is PD-L1.

Embodiment 33

The antibody fusion protein of embodiment 32, wherein the antibody comprises HC-CDR1, HC-CDR2, and HC-CDR3 of a heavy chain comprising the amino acid sequence of SEQ ID NO: 18 and/or LC-CDR1, LC-CDR2, and LC-CDR3 of a light chain comprising the amino acid sequence of SEQ ID NO: 19.

Embodiment 34

The antibody fusion protein of embodiment 32 or 33, wherein the antibody comprises a heavy chain comprising the amino acid sequence of SEQ ID NO: 18, and a light chain comprising the amino acid sequence of SEQ ID NO: 19.

Embodiment 35

The antibody fusion protein of embodiment 34, wherein the antibody fusion protein comprises a heavy chain comprising the amino acid sequence of SEQ ID NO: 18, and a light chain fusion polypeptide comprising the amino acid sequence of SEQ ID NO: 20.

Embodiment 36

The antibody fusion protein of embodiment 32, wherein the antibody comprises HC-CDR1, HC-CDR2, and HC-CDR3 of a heavy chain comprising the amino acid sequence of SEQ ID NO: 21; and/or LC-CDR1, LC-CDR2, and LC-CDR3 of a light chain comprising the amino acid sequence of SEQ ID NO: 22.

Embodiment 37

The antibody fusion protein of embodiment 32 or 36, wherein the antibody comprises a heavy chain comprising the amino acid sequence of SEQ ID NO: 21, and a light chain comprising the amino acid sequence of SEQ ID NO: 22.

Embodiment 38

The antibody fusion protein of embodiment 37, wherein the antibody fusion protein comprises a heavy chain comprising the amino acid sequence of SEQ ID NO: 21, and a light chain fusion polypeptide comprising the amino acid sequence of SEQ ID NO: 23.

Embodiment 39

The antibody fusion protein of embodiment 24, wherein the inhibitory immune checkpoint molecule is CTLA-4.

Embodiment 40

The antibody fusion protein of embodiment 39, wherein the antibody comprises HC-CDR1, HC-CDR2, and HC-CDR3 of a heavy chain comprising the amino acid sequence of SEQ ID NO: 9; and/or LC-CDR1, LC-CDR2, and LC-CDR3 of a light chain comprising the amino acid sequence of SEQ ID NO: 10.

Embodiment 41

The antibody fusion protein of embodiment 39 or 40, wherein the antibody comprises a heavy chain comprising the amino acid sequence of SEQ ID NO: 9, and a light chain comprising the amino acid sequence of SEQ ID NO: 10.

Embodiment 42

The antibody fusion protein of embodiment 41, wherein the antibody fusion protein comprises a heavy chain comprising the amino acid sequence of SEQ ID NO: 9, and a light chain fusion polypeptide comprising the amino acid sequence of SEQ ID NO: 11.

Embodiment 43

The antibody fusion protein of any one of embodiments 1-20, wherein the antibody specifically recognizes a tumor antigen.

Embodiment 44

The antibody fusion protein of embodiment 43, wherein the tumor antigen is HER2.

Embodiment 45

The antibody fusion protein of embodiment 44, wherein the antibody comprises HC-CDR1, HC-CDR2, and HC-CDR3 of a heavy chain comprising the amino acid sequence of SEQ ID NO: 24; and/or LC-CDR1, LC-CDR2, and LC-CDR3 of a light chain comprising the amino acid sequence of SEQ ID NO: 25.

Embodiment 46

The antibody fusion protein of embodiment 44 or 45, wherein the antibody comprises a heavy chain comprising the amino acid sequence of SEQ ID NO: 24, and a light chain comprising the amino acid sequence of SEQ ID NO: 25.

Embodiment 47

The antibody fusion protein of embodiment 46, wherein the antibody fusion protein comprises a heavy chain comprising the amino acid sequence of SEQ ID NO: 24, and a light chain fusion polypeptide comprising the amino acid sequence of SEQ ID NO: 26, 27, or 28.

Embodiment 48

The antibody fusion protein of embodiment 43, wherein the tumor antigen is EGFR (HER1).

Embodiment 49

The antibody fusion protein of embodiment 48, wherein the antibody comprises HC-CDR1, HC-CDR2, and HC-CDR3 of a heavy chain comprising the amino acid sequence of SEQ ID NO: 29; and/or LC-CDR1, LC-CDR2, and LC-CDR3 of a light chain comprising the amino acid sequence of SEQ ID NO: 30.

Embodiment 50

The antibody fusion protein of embodiment 48 or 49, wherein the antibody comprises a heavy chain comprising the amino acid sequence of SEQ ID NO: 29, and a light chain comprising the amino acid sequence of SEQ ID NO: 30.

Embodiment 51

The antibody fusion protein of embodiment 50, wherein the antibody fusion protein comprises a heavy chain comprising the amino acid sequence of SEQ ID NO: 29, and a light chain fusion polypeptide comprising the amino acid sequence of SEQ ID NO: 31.

Embodiment 52

The antibody fusion protein of any one of embodiments 1-20, wherein the antibody specifically recognizes an angiogenic factor.

Embodiment 53

The antibody fusion protein of embodiment 52, wherein the angiogenic factor is Angiopoietin-2 (Ang2).

Embodiment 54

The antibody fusion protein of embodiment 53, wherein the antibody comprises HC-CDR1. HC-CDR2, and HC-CDR3 of a heavy chain comprising the amino acid sequence of SEQ ID NO: 35; and/or LC-CDR1, LC-CDR2, and LC-CDR3 of a light chain comprising the amino acid sequence of SEQ ID NO: 36.

Embodiment 55

The antibody fusion protein of embodiment 53 or 54, wherein the antibody comprises a heavy chain comprising the amino acid sequence of SEQ ID NO: 35, and a light chain comprising the amino acid sequence of SEQ ID NO: 36.

Embodiment 56

The antibody fusion protein of embodiment 55, wherein the antibody fusion protein comprises a heavy chain comprising the amino acid sequence of SEQ ID NO: 35, and a light chain fusion polypeptide comprising the amino acid sequence of SEQ ID NO: 37.

Embodiment 57

The antibody fusion protein of embodiment 52, wherein the angiogenic factor is TNFα.

Embodiment 58

The antibody fusion protein of embodiment 57, wherein the antibody comprises HC-CDR1. HC-CDR2, and HC-CDR3 of a heavy chain comprising the amino acid sequence of SEQ ID NO: 32 and/or LC-CDR1, LC-CDR2, and LC-CDR3 of a light chain comprising the amino acid sequence of SEQ ID NO: 33.

Embodiment 59

The antibody fusion protein of embodiment 57 or 58, wherein the antibody comprises a heavy chain comprising the amino acid sequence of SEQ ID NO: 32, and a light chain comprising the amino acid sequence of SEQ ID NO: 33.

Embodiment 60

The antibody fusion protein of embodiment 59, wherein the antibody fusion protein comprises a heavy chain comprising the amino acid sequence of SEQ ID NO: 32, and a light chain fusion polypeptide comprising the amino acid sequence of SEQ ID NO: 34.

Embodiment 61

The antibody fusion protein of embodiment 52, wherein the angiogenic factor is IL-17A.

Embodiment 62

The antibody fusion protein of embodiment 61, wherein the antibody comprises HC-CDR1, HC-CDR2, and HC- CDR3 of a heavy chain comprising the amino acid sequence of SEQ ID NO: 38; and/or LC-CDR1, LC-CDR2, and LC-CDR3 of a light chain comprising the amino acid sequence of SEQ ID NO: 39.

Embodiment 63

The antibody fusion protein of embodiment 61 or 62, wherein the antibody comprises a heavy chain comprising the amino acid sequence of SEQ ID NO: 38, and a light chain comprising the amino acid sequence of SEQ ID NO: 39.

Embodiment 64

The antibody fusion protein of embodiment 63, wherein the antibody fusion protein comprises a heavy chain comprising the amino acid sequence of SEQ ID NO: 38, and a light chain fusion polypeptide comprising the amino acid sequence of SEQ ID NO: 40.

Embodiment 65

A pharmaceutical composition comprising the antibody fusion protein of any one of embodiments 1-64, and a pharmaceutical acceptable carrier.

Embodiment 66

A method of treating an individual having cancer, comprising administering to the individual an effective amount of the pharmaceutical composition of embodiment 65.

Embodiment 67

The method of embodiment 66, wherein the cancer is a solid tumor.

Embodiment 68

The method of embodiment 67, wherein the cancer is lung cancer, liver cancer, skin cancer (e.g., melanoma), breast cancer, ovarian cancer, prostate cancer, colorectal cancer, or bladder cancer.

Embodiment 69

The method of any one of embodiments 66-68, further comprising subjecting the individual to an additional cancer therapy.

Embodiment 70

The method of any one of embodiments 66-69, wherein the pharmaceutical composition is administered systemically.

Embodiment 71

The method of embodiment 70, wherein the pharmaceutical composition is administered intravenously (i.v.).

Embodiment 72

The method of any one of embodiments 66-69, wherein the pharmaceutical composition is administered locally.

Embodiment 73

The method of embodiment 72, wherein the pharmaceutical composition is administered intratumorally.

Embodiment 74

A method of treating an individual having a non-neoplastic disorder comprising administering to the individual an effective amount of the pharmaceutical composition of embodiment 65.

Embodiment 75

The method of embodiment 74, wherein the non-neoplastic disorder is associated with VEGF overexpression.

Embodiment 76

The method of embodiment 74 or 75, wherein the non-neoplastic disorder is selected from rheumatoid arthritis, psoriasis, atherosclerosis, hemangiomas, immune rejection of transplanted corneal tissue and other tissues, chronic inflammation, and ocular neovascular disorders.

Embodiment 77

The method of any one of embodiments 74-76, wherein the pharmaceutical composition is administered systemically.

Embodiment 78

The method of embodiment 77, wherein the pharmaceutical composition is administered intravenously (i.v.).

Embodiment 79

The method of any one of embodiments 74-78, wherein the non-neoplastic disorder is an ocular neovascular disorder.

Embodiment 80

The method of embodiment 79, wherein the ocular neovascular disorder is age-related macular degeneration (AMD) or diabetic retinopathy.

Embodiment 81

The method of embodiment 80, wherein the ocular non-vascular disorder is AMD.

Embodiment 82

The method of embodiment 80 or 81, wherein the ocular neovascular disorder is associated with choroidal neovascularization, vascular leak, and/or retinal edema.

Embodiment 83

The method of any one of embodiments 79-82, wherein the administration of the pharmaceutical composition is selected from one of eye drops, subconjunctival injection, subconjunctival implant, intravitreal injection, intravitreal implant, sub-Tenon's injection, and sub-Tenon's implant.

Embodiment 84

The method of embodiment 83, wherein the pharmaceutical composition is administered by intravitreal injection.

Embodiment 85

The method of any one of embodiments 66-84, wherein the individual is a human.

Embodiment 86

An isolated nucleic acid encoding the antibody fusion protein of any one of embodiments 1-64.

Embodiment 87

A vector comprising the isolated nucleic acid of embodiment 86.

Embodiment 88

An isolated host cell comprising the isolated nucleic acid of embodiment 86, or the vector of embodiment 87.

Embodiment 89

A kit comprising the antibody fusion protein of any one of embodiment 1-64, the isolated nucleic acid of embodiment 86, the vector of embodiment 87, or the isolated host cell of embodiment 88.

Embodiment 90

A method of producing an antibody fusion protein, comprising: (a) culturing a host cell comprising the isolated nucleic acid of embodiment 86 or the vector of embodiment 87, or the isolated host cell of embodiment 88 under conditions effective to express the antibody fusion protein; and (b) obtaining the expressed antibody fusion protein from said host cell.

Embodiment 91

The method of embodiment 90, wherein step (a) further comprises producing a host cell comprising the isolated nucleic acid of embodiment 86 or the vector of embodiment 87.

EXAMPLES

The examples below are intended to be purely exemplary of the invention and should therefore not be considered to limit the invention in any way. The following examples and detailed description are offered by way of illustration and not by way of limitation.

Example 1: Construction of VEGFR-Antibody Light Chain Fusion Proteins

VEGF-trap (Aflibercept) comprises Ig-like domain 2 of VEGFR-1-Ig-like domain 3 of VEGFR-2 (Flt1d2-Flk1d3) chimeric fusion to the N-terminus of an IgG Fc fragment (hereinafter referred to as "VEGFR-Fc"). This VEGFR-Fc fusion protein can capture VEGF with higher affinity (0.5 pM) than bevacizumab (VEGF neutralizing antibody, 50 pM).

To construct VEGFR-antibody light chain fusion proteins, Flt1d2-Flk1d3 fusion amino acid sequence (211 aa) was derived from Aflibercept, and fused to the C-terminus of light chains of various antibodies as described in Table 3, via an optional peptide linker, such as $(GGGGS)_3$ (SEQ ID NO: 6; "(G4S)3" or "GS3"), or $(GGGGS)_6$ (SEQ ID NO: 7; "(G4S)6" or "GS6"). The constructs were then expressed in CHO cells and purified.

TABLE 3

VEGFR-antibody light chain fusion protein constructs

| Construct name | Full-length antibody | Full-length antibody target | Linker |
|---|---|---|---|
| Her2/LC-GS3-VEGFR-IgG1 | Trastuzumab (e.g, Herceptin ®) | HER2 (ERBB2, EGFR2) | GS3 |
| Her2/LC-GS6-VEGFR-IgG1 | | | GS6 |
| Her2/LC-VEGFR-IgG1 | | | None |
| CTLA-4/LC-GS6-VEGFR-IgG1 | Ipilimumab (e.g., Yervoy ®) | CTLA-4 | GS6 |
| EGFR/LC-GS6-VEGFR-IgG1 | Cetuximab (e.g., Erbitux ®) | HER1 (ERBB1, EGFR) | GS6 |
| TNFα/LC-GS6-VEGFR-IgG1 | Adalimumab (e.g., Humira ®) | TNFα | GS6 |
| Ang2/LC-GS6-VEGFR-IgG1 | Nesvacumab (e.g., REGN910) | Ang2 | GS6 |
| mPD-1/LC-GS6-VEGFR-IgG4 | Pembrolizumab (e.g., Keytruda ®) | PD-1 | GS6 |
| bPD-1/LC-GS6-VEGFR-IgG4 | Nivolumab (e.g., Opdivo ®) | | GS6 |
| IL-17A/LC-GS6-VEGFR-IgG4 | Ixekizumab (e.g., Taltz ®) | IL-17A | GS6 |
| tPD-L1/LC-GS6-VEGFR-nIgG1 | Atezolizumab (e.g., Tecentriq ®) | PD-L1 | GS6 |
| aPD-L1/LC-GS6-VEGFR-mIgG1 | Durvalumab (e.g., IMFINZI ™) | | GS6 |

Example 2: Test of Binding Affinity and ADCC for VEGFR-Antibody Light Chain Fusion Proteins Materials Human VEGF121/VEGF-A protein (human VEGF 121 isoform (P15692-9) (121 amino acids, Ala 27-Arg 147)) with 6-His tag (Cat. #10008-HNAB) and human HER2 protein (extracellular domain of human ErbB2 (NP_004439.2), 641 amino acids. Thr 23-Thr 652) with polyhistidine tag fused at the C-terminus (Cat. #10004-H08H) were purchased from Sino Biological. Human PD-1, PD-L1, CTLA-4, EGFR (HER1), TNFα, Ang2, and IL-17A proteins were all purchased. His-tag antibody (capture antibody) was purchased from Qiagen. HRP conjugated anti-IgG Fc antibody (secondary antibody) was purchased from Birmingham SouthernBiotech. 96-well ELISA plates (immunoGrade™) were purchased from BrandTech.

ELISA-Based Binding Assay 96-well ELISA plates were coated with 100 μl His-tag antibody (capture antibody, 0.4 μg/ml) at room temperature (RT) overnight. The coated plates were washed with washing buffer (pH 7.4 PBS with 0.1% Tween 20) three times, and blocked with 3% BSA in washing buffer for 2 hours, at RT. After washing three times, these plates were coated with VEGF121 protein (3% BSA in washing buffer, containing 0.4 μg/ml VEGF121) or the target protein that can be recognized by the full-length antibody (3% BSA in washing buffer, containing 0.4 μg/ml target protein, e.g., HER2, CTLA-4, or PD-1, etc.), and incubated for 2 hours at RT. After washing three times, VEGFR-antibody light chain fusion proteins of various concentrations in washing buffer containing 3% BSA were added to the coated plates, and let incubation for 2 hours at RT. Aflibercept (VEGFR-Fc fusion protein) and the corresponding parental full-length antibody were included as positive controls. For example, trastuzumab (e.g., Herceptin®) was used as the positive anti-HER2 antibody control for Her2/LC-GS6-VEGFR-IgG1, Her2/LC-GS3-VEGFR-IgG1, and Her2/LC-VEGFR-IgG1; pembrolizumab (e.g., Keytruda®) was used as the positive anti-PD-1 antibody control for mPD-1/LC-GS6-VEGFR-IgG4; Atezolizumab (e.g., Tecentriq®) was used as the positive anti-PD-L1 antibody control for tPD-L1/LC-GS6-VEGFR-nIgG1, etc. After washing three times, HRP conjugated anti-gG Fc antibody (secondary antibody) was added (1:6000 dilution with 3% BSA in washing buffer), and incubated for 2 hours at RT. After washing four times, 100 μl HRP substrate was added to each well. After developing for 20 minutes, stop buffer was added to each well. Optical density (OD) of each well was measured immediately using a microplate reader at 450 nm. $EC_5$, was calculated if OD>2.0; otherwise, $EC_{50}$ was not calculated.

As can be seen from Table 4, VEGFR-anti-HER2 light chain fusion proteins with linkers between the VEGFR component and the light chain (Her2/LC-GS3-VEGFR-IgG1, Her2/LC-GS6-VEGFR-IgG1) showed similar binding to HER2 as the positive anti-HER2 control Herceptin®, and similar binding to VEGF (VEGF121) as the positive control Aflibercept (VEGFR-Fc). Longer linker (compare GS6 and GS3) seemed to confer better binding to both VEGF and the antigen recognized by the parental full-length antibody (HER2), likely due to the abundant space between the VEGFR component and the full-length antibody which allows each binding portion to function properly. Although VEGFR-anti-HER2 light chain fusion protein without linker (Her2/LC-VEGFR-IgG1) still maintained similar binding affinity to HER2 as that of Herceptin®, its binding to VEGF (VEGF121) significantly decreased ("not detected"), indicating that a linker (and/or linker length) is crucial for the proper binding of VEGFR component to VEGF.

TABLE 4

Binding affinities of VEGFR-anti-HER2 light chain fusion proteins to Her2 and VEGF

| Construct name | Her2 ($EC_{50}$) | VEGF121 ($EC_{50}$) |
|---|---|---|
| Herceptin (anti-Her2 antibody) | 16.9 nM | Not detected |
| Aflibercept (VEGFR-Fc) | ND | 12.2 nM |
| Her2/LC-GS3-VEGFR-IgG1 | 28 nM | 22.5 nM |
| Her2/LC-GS6-VEGFR-IgG1 | 21.5 nM | 19.5 nM |
| Her2/LC-VEGFR-IgG1 | 30 nM | Not detected |

To determine whether VEGFR-antibody light chain fusion applies for other IgG1 therapeutic antibodies besides Herceptin®, several IgG-based monoclonal antibodies were fused with Flt1d2-Flk1d3 at the C-terminus of light chains (see Example 1 for parental antibodies and construct names). Aflibercept (VEGFR-Fc) was used as a positive VEGF-binding control. As can be seen from Table 5, all VEGFR-IgG1 antibody light chain fusion proteins exhibited similar binding affinity to VEGF as their parental VEGFR-Fc fusion protein (Aflibercept), suggesting that VEGFR-antibody light chain fusion applies for different IgG1-based therapeutic antibodies.

TABLE 5

Binding affinities of VEGFR-IgG1 antibody light chain fusion proteins to VEGF

| Construct name | VEGF121 ($EC_{50}$) |
|---|---|
| Aflibercept (VEGFR-Fc) | 10.5 nM |
| CTLA-4/LC-GS6-VEGFR-IgG1 | 20.5 nM |
| EGFR/LC-GS6-VEGFR-IgG1 | 14 nM |
| TNFα/LC-GS6-VEGFR-IgG1 | 19.5 nM |
| Ang2//LC-GS6-VEGFR-IgG1 | 13 nM |

To determine whether VEGFR-antibody light chain fusion applies for IgG4-based therapeutic antibodies, such as anti-PD-1 (Pembrolizumab, e.g., Keytruda®, or Nivolumab, e.g., Opdivo®) and anti-IL-17A (Ixekizumab, e.g., Taltz®), IgG4-based monoclonal antibodies were fused with Flt1d2-Flk1d3 at the C-terminus of light chains (see Example 1 for parental antibodies and construct names). As can be seen from Table 6, mPD-1/LC-GS6-VEGFR-IgG4, bPD-1/LC-GS6-VEGFR-IgG4, and IL-17A/LC-GS6-VEGFR-IgG4 all showed similar binding affinity to VEGF (VEGF121) as that of Aflibercept (VEGFR-Fc). mPD-1/LC-GS6-VEGFR-IgG4 and bPD-1/LC-GS6-VEGFR-IgG4 showed similar binding affinities to PD-1 as their parental full-length antibody Pembrolizumab and Nivolumab, respectively. IL-17A/LC-GS6-VEGFR-IgG4 showed similar IL-17A binding affinity as its parental full-length antibody Ixekizumab.

TABLE 6

Binding affinities of VEGFR-antibody light chain fusion proteins to VEGF, PD-1, and IL-17A

| Construct name | VEGF121 ($EC_{50}$) | PD-1 ($EC_{50}$) | IL-17A ($EC_{50}$) |
|---|---|---|---|
| Aflibercept (VEGFR-Fc) | 15.3 nM | Not detected | Not detected |
| Pembrolizumab | Not detected | 4.1 nM | Not detected |
| mPD-1/LC-GS6- | 26 nM | 4.5 nM | Not detected |

TABLE 6-continued

Binding affinities of VEGFR-antibody light chain fusion proteins to VEGF, PD-1, and IL-17A

| Construct name | VEGF121 (EC$_{50}$) | PD-1 (EC$_{50}$) | IL-17A (EC$_{50}$) |
|---|---|---|---|
| VEGFR-IgG4 Nivolumab | Not detected | 23.4 nM | Not detected |
| bPD-1/LC-GS6-VEGFR-IgG4 | 21.5 nM | 25 nM | Not detected |
| Ixekizumab | Not detected | Not detected | 1.1 nM |
| IL-17A/LC-GS6-VEGFR-IgG4 | 19 nM | Not detected | 2 nM |

Therapeutic IgGs are sometimes mutated within the Fc region to reduce Fc effector functions, e.g., ADCC. For example, anti-PD-L1 antibody Atezolizumab (e.g., Tecentriq®) is mutated at the N-glycosylation site (N219A) to result in de-glycosylated IgG1, while anti-PD-L1 antibody Durvalumab (e.g., IMFINZI™) is mutated with three amino acids (E233A, E234A and F289A) to minimize the Fc effector function. To test if these IgG mutations affect the binding of VEGFR-antibody light chain fusion proteins, Flt1d2-Flk1d3 was fused to the C-terminus of the light chains of either Atezolizumab (tPD-L1/LC-GS6-VEGFR-nIgG1) or Durvalumab (aPD-L1/LC-GS6-VEGFR-mIgG1). As can be seen from Table 7, mutations in the Fc regions did not affect the binding of the VEGFR-anti-PD-L1 antibody light chain fusion proteins to either VEGF (VEGF121) or PD-L1 (compared with VEGFR-Fc and corresponding parental anti-PD-L1 antibodies).

TABLE 7

Binding affinities of VEGFR-antibody light chain fusion proteins to VEGF and PD-L1

| Construct name | VEGF121 (EC$_{50}$) | PD-L1 (EC$_{50}$) |
|---|---|---|
| Aflibercept (VEGFR-Fc) | 21.4 nM | Not detected |
| Atezolizumab | Not detected | 1.9 nM |
| tPD-L1/LC-GS6-VEGFR-nIgG1 | 26.5 nM | 2 nM |
| Durvalumab | Not detected | 3.7 nM |
| aPD-L1/LC-GS6-VEGFR-mIgG1 | 34.5 nM | 7.51 nM |

ADCC Test

We next examined if VEGFR-antibody light chain fusion proteins exhibit similar Fc effector functions as their parental full-length antibody, e.g., ADCC. SKBR3 human breast cancer cell line (Her2 positive) was used as the target cell, which was developed to carry a luciferase reporter gene. CD16+NK92 cells were used as effector cells. A 50 µl mixture of NK92 cells (~6,000 cells) and SKBR3 cells (~2,000 cells; containing the luciferase reporter gene) was placed into each well of a V-shaped 96-well plate. The mixture can be centrifuged to allow the formation of 3D tumors (breast cancer). 50 µl culture medium containing varying concentrations of VEGFR-antibody light chain fusion proteins or controls (Aflibercept or Herceptin®) were then added to each well and incubated for 24 hours at RT. The luciferase activity (OD) of each well was then measured using a microplate reader. The luciferase activity of cell mixture without adding antibody or VEGFR-Fc served as a control (100% cell viability). EC$_{50}$ (representing ADCC activity) was calculated. As can be seen from Table 8, EC$_{50}$ of Herceptin in our assay (8.6 nM) was 10 times less than those reported in other studies (373.9 nM), indicating the high sensitivity of our ADCC test. All VEGFR-anti-HER2 light chain fusion proteins retained similar ADCC activity as the parental Herceptin® antibody (Table 8).

TABLE 8

ADCC activities of VEGFR-antibody light chain fusion proteins on SKBR3 cells

| Construct name | Her2 (EC$_{50}$) |
|---|---|
| Herceptin (anti-Her2 antibody) | 8.6 nM |
| Aflibercept (VEGFR-Fc) | Not detected |
| Her2/LC-GS3-VEGFR-IgG | 16 nM |
| Her2/LC-GS6-VEGFR-IgG | 12 nM |
| Her2/LC-VEGFR-IgG | 15 nM |

To summarize, the above examples demonstrated that a VEGFR component can be fused to the C-terminus of the light chain of an IgG, which can retain high binding affinity to both VEGF and the antigen recognized by the parental IgG.

```
SEQUENCE LISTING
(linker amino acid sequence, n is an integer of at least one)
                                                         SEQ ID NO: 1
    (G)_n (linker amino acid sequence, n is an integer of at least one)
                                                         SEQ ID NO: 2
    (GS)_n (linker amino acid sequence, n is an integer of at least one)
                                                         SEQ ID NO: 3
    (GSGGS)_n (linker amino acid sequence, n is an integer of at least one)
                                                         SEQ ID NO: 4
    (GGGGS)_n (linker amino acid sequence, n is an integer of at least one)
                                                         SEQ ID NO: 5
    (GGGS)_n (GS3 linker amino acid sequence)
                                                         SEQ ID NO: 6
    GGGGSGGGSGGGGS
```

(GS6 linker amino acid sequence)
SEQ ID NO: 7
GGGGSGGGGSGGGGSGGGGSGGGGSGGGGS (VEGFR component amino acid sequence)
SEQ ID NO: 8
TGSDTGRPFVEMYSEIPEIIHMTEGRELVIPCRVTSPNITVTLKKFPLDTUPDGKRIIWDSRKGFII

SNATYKEIGLLTCEATVNGHLYKTNYLTHRQTNTIIDWLSPSHGIELSVGEKLVLNCTARTELNVGI

DFNWEYPSSKHQHKKLVLSPVNRDLKTQSGSEMKKFLSTLTIDGVTRSDQGLYTCAASSGLMTKKNS

TFVRVHEK (ipilimumab (anti-CTLA-4) heavy chain amino acid sequence)
SEQ ID NO: 9
QVQLVESGGGVVQPGRSLRLSCAASGFTFSSYTMHWVRQAPGKGLEWVTFISYDGNNKYYADSVKGR

FTISRDNSKNTLYLQMNSLRAEDTAIYYCARTGWLGPFDYWCXJGTLVTVSSASTKGPSVFPLAPSS

KSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKDTLMISRIPEVTCVVVDVS

HEDPEVKFNWYVDGVEVHNAKTKPREEQYNSTYRWSVLTVLHQDWLNGKEYKCKVSNKALPAPIEKT

ISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK (ipilimumab (anti-CTLA-4) light chain amino acid sequence)
SEQ ID NO: 10
EIVLTQSPGTLSLSPGERATLSCRASQSVGSSYLAWYQQKPGQAPRLLIYGAFSRATGIPDRFSGS

GSGTDFTLTISRLEPEDFAVYYCQQYGSSPWTFGQGTKVEIKRTVAAPSVFIFPPSDEQLKSGTAS

VVCLLNNFYPREAKVQWKVDNALQSGNSQESVTEQDSKDSTYSLSSTLTLSKADYEKHKVYACEVT

HQGLSSPVTKSFNRGEC (CTLA-4/LC-GS6-VEGFR; ipilimumab (anti-CTLA-4) light chain fusion
polypeptide amino acid sequence;
linker is bolded, VEGFR component is underlined)
SEQ ID NO: 11
EIVLTQSPGTLSLSPGERATLSCRASQSVGSSYLAWYQQKPGQAPRLLIYGAFSRATGIPDRFSGS

GSGTDFTLTISRLEPEDFAVYYCQQYGSSPVVTFGQGTKVEIKRTVAAPSVFIFPPSDEQLKSGTA

SVVCLLNNFYPREAKVQWKVDNALQSGNSQESVTEQDSKDSTYSLSSTLTLSKADYEKHKVYACEV

THQGLSSPVTKSFNRGECTGGGCSGCGGSGGGCSGCGGSGGGGSCCGGS<u>TGSDTGRPFVEMYSEIP</u>

<u>EIIHMTEGRELVIPCRVTSPNITVTLKKFPLDTLIPDGKRIIWDSRKGFIISNATYKEIGLLTCEA</u>

<u>TVNGHLYKTNYLTHRQTNTIIDVVLSPSHGIELSVGEKLVLNCTARTELNVGIDFNWEYPSSKHQH</u>

<u>KKLVLSPVNRDLKTQSGSEMKKFLSTLHDGVTRSDQGLYTCAASSGLMTKKNSTFVRVHEK</u>

(pembrolizumab (anti-PD-1) heavy chain amino acid sequence)
SEQ ID NO: 12
QVQLVQSGVEVKKPGASVKVSCKASGYTFTNYYMYWVRQAPGQGLEWMGGINPSNGGTNFNEKFKN

RVTLTTDSSTTTAYMELKSLQFDDTAVYYCARRDYRFDMGFDYWGQGTTVTVSSASTKGPSVFPLA

PCSRSTSESTAALGCLVKDYFPEPVTVSWNSGALTSGVHTFPAVLQSSGLYSLSSVYTVPSSSLGT

KTYTCNVDHKPSNTKVDKRVESKYGPPCPPCPAPEFLGGPSVFLFPPKPKDTLMISRTPEVTCVVV

DVSQEDPEVQFNWYVDGVEVNNAKTKPREEQFNSTYRVVSVLTVLHQDWLNGKEYKCKVSNKGLPS

SJEKTISKAKGQRREPQVYTLPPSQEEMTKNQVSLTCLVKGFYPSDIAVEWESNGQPENNYKTTPP

YTLDSDGSFFLYSRLTVDKSRWQEGNVFSCSVMHEALHNHYTQKSLSLSLGK (pembrolizumab (anti-PD-1) light chain amino acid sequence)
SEQ ID NO: 13
EIVLTQSPATLSLSPGERATLSCRASKGVSTSGYSYLHWYQQKPGQAPRLLIYLASYLESGVPARF

SGSGSGTDFTLTISSLEPEDFAVYYCQHSRDLPLTFGGGTKVEIKRTVAAPSVFIFPPSDEQLKSG

-continued

TASVVCLLNNFYPREAKVQWKVDNALQSGNSQESVTEQDSKDSTYSLSSTLTLSKADYEKHKVYAC

EVTHQGLSSPVTKSFNRGEC (mPD1/LC-GS6-VEGFR; pembrolizumab (anti-PD-1) light chain
fusion polypeptide amino acid sequence;
linker is bolded, VEGFR component is underlined)
SEQ ID NO: 14

EIVLTQSPATLSLSPGERATLSCRASKGVSTSGYSYLHWYQQKPGQAPRLLIYLASYLESGVPARF

SGSGSGTDFTLTISSLEPEDFAVYYCQHSRDLPLTFGGGTKVEIKRTVAAPSVFIFPPSDEQLKSG

TASWCLLNNTYPREAKVQWKVDNALQSGNSQESVTEQDSKDSTYSLSSTLTLSKADYEKHKVYACE

VTHQGLSSPVTKSFNRGECTGGGGSGGGGSGGGGSGGGGSGGGGSGGGGSTGSDTGRPFVEMYSEI

PEIIHMTEGRELVIPCRVTSPNITVTLKKFPLDTLIPDGKRHWDSRKGFIISNATYKEIGLLTCEA

TVNGHLYKTNYLTHRQTNTIIDWLSPSHGIELSVGEKLVLNCTARTELNVGIPFNWEYPSSKHQHK

KLVLSPVNRDLKTQSGSEMKKFLSTLTFDGVTRSDQGLYTCAASSGLMTKKNSTFVRVHEK (nivolumab (anti-PD-1) heavy chain amino acid sequence)
SEQ ID NO: 15

QVQLVESGGGWQPGRSLRLDCKASGITFSNSGMHWVRQAPGKGLEWVAVIWYDGSKRYYADSVKGR

FTISRDNSKNTLFLQMNSLRAEDTAVYYCATNDDYWGQGTLVTVSSASTKGPSVFPLAPCSRSTSE

STAALGCLVKDYFPEPVTVSWNSGALTSGVHTFPAVLQSSGLYSLSSVVTVPSSSLGTKTYTCNVD

HKPSNTKVDKRVESKYGPPCPPCPAPEFLGGPSYTLFPPKPKDTLMISRTPEVTCVVVDVSQEDPE

VQFNWYVDGVEVHNAKTKPREEQFNSTYRWSVLTVLHQDWLNGKEYKCKVSNKGLPSSIEKTISKA

KGQRREPQVYTLPPSQEEMTKNQVSLTCLVKGFYPSDIAVEVVESNGQPENNYKTTPPVLDSDGSF

FLYSRLTVDKSRWQEGNVFSCSVMHEALHNHYTQKSLSLSLGK (nivolumab (anti-PD-1) light chain amino acid sequence)
SEQ ID NO: 16

EIVLTQSPATLSLSPGERaTLSCRASQSVSSYLAWYQQKPGQAPRLLIYDASNRATGIPARFSGSG

SGTDFTLTISSLEPEDFAVYYCQQSSNWPRTFGQGTKVEIKRTVAAPSVFIFPPSDEQLKSGTASW

CLLNNFYPREAKVQWKVDNALQSGNSQESVTEQDSKDSTYSLSSTLTLSKADYEKHKVYACEVTHQ

GLSSPVTKSFNRGEC (bPD1/LC-GS6-VEGFR; nivolumab (anti-PD-1) light chain
fusion polypeptide amino acid sequence;
linker is bolded, VEGFR component is underlined)
SEQ ID NO: 17

EIVLTQSPATLSLSPGERATLSCRASQSVSSYLAWYQQKPGQAPRLLIYDASNRATGIPARFSGSG

SGTDFTLTISSLEPEDFAVYYCQQSSNWPRTFGQGTKVEIKRTVAAPSVFIFPPSDEQLKSGTASV

VCLLNNFYPREAKVQWKVDNALQSGNSQESVTEQDSKDSTYSLSSTLTLSKADYEKHKVYACEVTH

QGLSSPVTKSFNRGECTGGGGSGGGGSGGGGSGGGGSGGGGSGGGGSTGSDTGRPFVEMYSEIPEI

IHMTEGRELVIPCRVTSPNITVTLKKFPLDTLIPDGKRIIWDSRKGFIISNATYKEIGLLTCEATV

NGHLYKTNYLTHRQTNTIIDVVLSPSHGIELSVGEKLVLNCTARTELNVGIDFNWEYPSSKHQHKK

LVLSPVNRDLKTQSGSEMKKFLSTLTIDGVTRSDQGLYTCAASSGLMTKKNSTFVRVHEK (atezolizumab (anti-PD-L1) heavy chain amino acid sequence)
SEQ ID NO: 18

EVQLVESGGGLVQPGGSLRLSCAASGFTFSDSWIHWVRQAPGKGLEWVAWISPYGGSTYYADSVKG

RFTISADTSKNTAYLQMNSLRAEDTAVYYCARRHWPGGFDYWGQGTLVTVSSASTKGPSVFPLAPS

SKSTSGGTAALGCLVKDYFPEPVTVSWNSGALTSGVHTFPAVLQSSGLYSLSSWTVPSSSLQTQTY

ICNVNHKPSNTKVDKKVEPKSCDKTHTCPPCPAPELLQGPSVFLFPPKPKDTLMISRTPEVTCVVVD

VSHEDPEVKFNWYVDGVEVHNAKTKPREEQYASTYRVVSVLTVLHQDWLNGKEYKCKVSNKALPAP

IEKTISKAKGQPREPQVYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

-continued (atezolizumab (anti-PD-L1) light chain amino acid sequence)
SEQ ID NO: 19
DIQMTQSPSSLSASVGDRVTITCRASQDVSTAVAWYQQKPGKAPKLLIYSASFLYSGVPSRFSGSG

SGTDFTLTISSLQPEDFATYYCQQYLYHPATFGQGTKVEIKRTVAAPSVFIFPPSDEQLKSGTASV

VCLLNNFYPREAKVQWKVDNALQSGNSQESVTEQDSKDSTYSLSSTLTLSKADYEKHKVYACEVTH

QGLSSPVTKSFNRGEC (tPD-L1/LC-GS6-VEGFR; atezolizumab (anti-PD-L1) light chain fusion
polypeptide amino acid sequence; linker is bolded,
VEGFR component is underlined)
SEQ ID NO: 20
DIQMTQSPSSLSASVGDRVTITCRASQDVSTAVAWYQQKPGKAPKLLIYSASFLYSGVPSRFSGSG

SGTDFTLTISSLQPEDFATYYCQQYLYHPATFGQGTKVEIKRTVAAPSVFIFPPSDEQLKSGTASV

VCLLNNFYPREAKVQWKVDNALQSGNSQESVTEQDSKDSTYSLSSTLTLSKADYEKHKVYACEVTH

QGLSSPVTKSFNRGECTGGGGSGGGGSGGGGSGGGGSGGGGSGGGGS<u>TGSDTGRPFVEMYSEIPEI

IHMTEGRELVIPCRVTSPNITVTLKKFPLDTLIPDGKRIIWDSRKGFIISNATYKEIGLLTCEATV

NGHLYKTNYLTHRQTNTIIDWLSPSHGIELSVGEKLVLNCTARTELNVGIDFNWEYPSSKHQHKKL

VLSPVNRDLKTQSGSEMKKFLSTLTIDGVTRSDQGLYTCAASSGLMTKKNSTFVRVHEK</u>

(durvalumab (anti-PD-L1) heavy chain amino acid sequence)
SEQ ID NO: 21
EVQLVESGGGLVQPGGSLRLSCAASGFTFSRYWMSWVRQAPGKGLEWVANIKQDGSEKYYVDSVKG

RFTISRDNAKNSLYLQMNSLRAEDTAVYYCAREGGWFGELAFDYWGQGTLVTVSSASTKGPSVFPL

APSSKSTSGGTAALGCLVKDYFPEPVTVSWNSGALTSGVHTFPAVLQSSGLYSLSSWTVPSSSLGT

QTYICNVNHKPSNTKVDKRVEPKSCDKTHTCPPCPAPEFEGGPSVFLFPPKPKDTLMISRTPEVTC

VVVDVSHEDPEVKFNWYVDGWVHNAKTKPREEQYNSTYRWSVLTVLHQDWLNGKEYKCKVSNKALP

ASIEKTISKAKGQPREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK (durvalumab (anti-PD-L1) light chain amino acid sequence)
SEQ ID NO: 22
EIVLTQSPGTLSLSPGERATLSCRASQRVSSSYLAWYQQKPGQAPRLLIYDASSRATGIPDRFSGS

GSGTDFTLTISRLEPEDFAVYYCQQYGSLPWTFGQGTKVEIKRTVAAPSVFIFPPSDEQLKSGTAS

VVCLLNNFYPREAKVQWKVDNALQSGNSQESVTEQDSKDSTYSLSSTLTLSKADYEKHKVYACEVT

HQGLSSPVTKSFNRGEC (aPDL1/LC-GS6-VEGFR; durvalumab (anti-PD-L1) light chain fusion
polypeptide amino acid sequence; linker is bolded,
VEGFR component is underlined)
SEQ ID NO: 23
EIVLTQSPGTLSLSPGERATLSCRASQRVSSSYLAWYQQKPGQAPRLLIYDASSRATGIPDRFSGS

GSGTDFTLTISRLEPEDFAVYYCQQYGSLPWTFGQGTKVEIKRTVAAPSVFIFPPSDEQLKSGTAS

VVCLLNNFYPREAKVQWKVDNALQSGNSQESVTEQDSKDSTYSLSSTLTLSKADYEKHKVYACEVT

HQGLSSPVTKSFNRGECTGGGGSGGGGSGGGGSGGGGSGGGGSGGGGS<u>TGSDTGRPFVEMYSEIPE

IIHMTEGRELVIPCRVTSPNITVTLKKFPLDTLIPDGKRIIWDSRKGFIISNATYKEIGLLTCEAT

VNGHLYKTNYLTHRQTNTIIDVVLSPSHGIELSVGEKLVLNCTARTELNVGIDFNWEYPSSKHQHK

KLVLSPVNRDLKTQSGSEMKKFLSTLTIDGVTRSDQGLYTCAASSGLMTKKNSTFVRVHEK</u>

(trastuzumab (anti-HER2) heavy chain amino acid sequence)
SEQ ID NO: 24
EVQLVESGGGLVQPGGSLRLSCAASGFNIKDTYIHWVRQAPGKGLEWVARIYPTNGYTRYADSVKG

RFTISADTSKNTAYLQMNSLRAEDTAVYYCSRWGGDGFYAMDYWGQGTLVTVSSASTKGPSVFPLA

PSSKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPPKPKDTLMISRTPEVTC

VVVDVSHEDPEWFNWYVDGVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSDIAVEWESWjQPENNYKIT

PPVLDSDGSFFLYSKLTVDKSRWQQGNVFSCSVMHEALHNHYTQKSLSLSPGK (trastuzumab (anti-HER2) light chain amino acid sequence)
SEQ ID NO: 25

DIQMTQSPSSLSASVGDRVTITCRASQDVNTAVAWYQQKPGKAPKLLIYSASFLYSGVPSRFSGSR

SGTDFTLTISSLQPEDFATYYCQQHYTTPPTFGQGTKVEIKRTVAAPSVFIFPPSDEQLKSGTASW

CLLNNFYPREAKVQWKVDNALQSGNSQESVTEQDSKDSTYSLSSTLTLSKADYEKHKVYACEVTHQ

GLSSPVTKSFNRGEC (Her2/LC-GS6-VEGFR; trastuzumab (anti-HER2) light chain fusion
polypeptide amino acid sequence; linker is bolded,
VEGFR component is underlined)
SEQ ID NO: 26

DIQMTQSPSSLSASVGDRVTITCRASQDVNTAVAWYQQKPGKAPKLLIYSASFLYSGVPSRFSGSR

SGTDFTLTISSLQPEDFATYYCQQHYTTPPTFGQGTKVEIKRTVAAPSVFIFPPSDEQLKSGTASW

CLLNNFYPREAKVQWKVDNALQSGNSQESVTEQDSKDSTYSLSSTLTLSKADYEKHKVYACEVTHQ

GLSSPVTKSFNRGECTGGGGSGGGGSGGGGSGGGGSGGGGSGGGGSTGSPTGRPFVEMYSEIPEII

HMTEGRELVIPCRVTSPNITVTLKKFPLDTLIPDGKRIIWDSRKGFIJSNATYKEIGLLTCEATVN

GHLYKTNYLTHRQTNTIIDWLSPSHGIELSVGEKLVLNCTARTELNVGIPFNWEVTSSKHQHKKLV

LSPVNRDLKTQSGSEMKKFLSTLTIDGVTRSPQGLYTCAASSGLMTKKNSTFVRVHEK (Her2/LC-GS3-VEGFR; trastuzumab (anti-HER2) light chain fusion
polypeptide amino acid sequence; linker is bolded,
VEGFR component is underlined)
SEQ ID NO: 27

DIQMTQSPSSLSASVGDRVTITCRASQDVNTAVAWYQQKPGKAPKLLIYSASFLYSGVPSRFSGSR

SGTDFTLTISSLQPEDFATYYCQQHYTTPPTFGQGTKVEIKRTVAAPSVFIFPPSDEQLKSGTASW

CLLNNFYPREAKVQWKVDNALQSGNSQESVTEQDSKDSTYSLSSTLTLSKADYEKHKVYACEVTHQ

GLSSPVTKSFNRGECTGGGGSGGGGSGGGGSTGSDTGRPFVEMYSEIPEIIHMTEGRELVIPCRVT

SPNITVTLKKFPLDTLIPDGKRIIWDSRKGFIISNATYKEIGLLTCEATVNGHLYKTNYLTHRQTN

TIIDVVLSPSHGIELSVGEKLVTNCTARTELNVGIDFNWEYPSSKHQHKKLVLSPVNRDLKTQSGS

EMKKFLSTLTIDGVTRSDQGLYTCAASSGLMTKKNSTFVRVHEK (Her2/LC-VEGFR; trastuzumab (anti-HER2) light chain fusion
polypeptide amino acid sequence; linker is bolded,
VEGFR component is underlined)
SEQ ID NO: 28

DIQMTQSPSSLSASVGDRVTITCRASQDVNTAVAWYQQKPGKAPKLLIYSASFLYSGVPSRFSGSR

SGTDFTLTISSLQPEDFATYYCQQHYTTPPTFGQGTKVEIKRTVAAPSVFIFPPSDEQLKSGTASW

CLLNNFYPREAKVQWKVDNALQSGNSQESVTEQDSKDSTYSLSSTLTLSKADYEKHKVYACEVTHQ

GLSSPVTKSFNRGECTTGSDTGRPFVEMYSEIPEIIHMTEGRELVIPCRVTSPNITVTLKKFPLDT

LIPDGKRIIWDSRKGFIISNATYKEIGLLTCEATVNGHLYKTNYLTHRQTNTHDVVLSPSHGIELS

VGEKLVLNCTARTELNVGIDFNWEYPSSKHQHKKLVLSPVNRDLKTQSGSEMKKFLSTLTIDGVTR

SDQGLYTCAASSGLMTKKNSTFVRVHEK (cetuximab (anti-EGFR) heavy chain amino acid sequence)
SEQ ID NO: 29

QVQLKQSGPGLVQPSQSLSITCTVSGFSLTNYGVHWVRQSPGKGLEWLGVIWSGGNTDYNTFFTSR

LSINKDNSKSQVFFKMNSLQSNDTAIYYCARALTYYDYEFAYWGQGTLVTVSAASTKGPSVFPLAP

SSKSTSGGTAALGCLVKDYFPEPVTVSWNSGALTSGVHTFPAVLQSSGLYSLSSWTVPSSSLGTQT

YICNVNHKPSNTKVDKKVEPKSCDKTHTCPPCPAPELLGGPSVFLFPPKPKDTLMISRTPEVTCVV

```
VDVSHEDPEVKFNWYVDGVEVHNAKTKPREEQYNSTYRWSVLTVLHQDWLNGKEYKCKVSNKALPA

PIEKTISKAKGQPREPQVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPGK (cetuximab (anti-EGFR) light chain amino acid sequence)
                                                         SEQ ID NO: 30
DILLTQSPVILSVSPGERVSFSCRASQSIGTNIHWYQQRTNGSPRLLIKYASESISGIPSRFSGSG

SGTDFTLSINSVESEDIADYYCQQNNNWPTTFGAGTKLELKRTVAAPSVFIFPPSDEQLKSGTASW

CLLNNFYPREAKVQWKVDNALQSGNSQESVTEQDSKDSTYSLSSTLTLSKADYEKHKVYACEVTHQ

GLSSPVTKSFNRGEC (EGFR/LC-GS6-VEGFR; cetuximab (anti-EGFR) light chain fusion
polypeptide amino acid sequence;
linker is bolded, VEGFR component is underlined)
                                                         SEQ ID NO: 31
DILLTQSPVILSVSPGERVSFSCRASQSIGTNIHWYQQRTNGSPRLLIKYASESISGIPSRFSGSG

SGTDFTLSINSVESEDIADYYCQQNNNWPTTFGAGTKLELKRTVAAPSVFIFPPSDEQLKSGTASW

CLLNNFYPREAKVQWKVDNALQSGNSQESVTEQDSKDSTYSLSSTLTLSKADYEKHKVYACEVTHQ

GLSSPVTKSFNRGECTGGGGSGGGGSGGGGSGGGGSGGGGSGGGGSTGSPTGRPFVEMYSEIPEII

HMTEGRELVIPCRVTSPNITVTLKKFPLDTLIPDGKRIIWDSRKGFIISNATYKEIGLLTCEATVN

GHLYKTNVLTHRQTNTIIDVVLSPSHGIELSVGEKLVLNCTARTELNVGIDFNWEYPSSKHQHKKL

VLSPVNRDLKTQSGSEMKKFLSTLTIDGVTRSDQGLYTCAASSGLMTKKNSTFVRVHEK (adalimumab (anti-TNFα) heavy chain amino acid sequence)
                                                         SEQ ID NO: 32
EVQLVESGGGLVQPGRSLRLSCAASGFTFDDYAMHWVRQAPGKGLEWVSAITWNSGHIDYADSVEG

RFTISRDNAKNSLYLQMNSLRAEDTAVYYCAKVSYLSTASSLDYWGQGTLVTVSSASTKGPSVFPL

APSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFPPKPKDTLMISRTPEVT

CVVVDVSHEDPEVKFNWYVDGVEVHNAKTKPREEQYNSTYRWSVLTVLHQDWLNGKEYKCKVSNKA

LPAPIEKTISKAKGQPREPQYTTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGK (adalimumab (anti-TNFα) light chain amino acid sequence)
                                                         SEQ ID NO: 33
DIQMTQSPSSLSASVGDRVTITCRASQGIRNYLAWYQQKPGKAPKLLIYAASTLQSGVPSRFSGSG

SGTDFTLTISSLQPEDVATYYCQRYNRAPYTFGQGTKVEIKRTVAAPSVFIFPPSDEQLKSGTASV

VCLLNNFYPREAKVQWKVDNALQSGNSQESVTEQDSKDSTYSLSSTLTLSKADYEKHKVYACEVTH

QGLSSPVTKSFNRGEC (TNFα/LC-GS6-VEGFR; adalimumab (anti-TNFα) light chain
fusion polypeptide amino acid sequence; linker is bolded,
VEGFR component is underlined)
                                                         SEQ ID NO: 34
DIQMTQSPSSLSASVGDRVTITCRASQGIRNYLAWYQQKPGKAPKLLIYAASTLQSGVPSRFSGSG

SGTDFTLTISSLQPEDVATYYCQRYNRAPYTFGQGTKVEIKRTVAAPSVFIFPPSDEQLKSGTASV

VCLLNNFYPREAKVQWKVDNALQSGNSQESVTEQDSKDSTYSLSSTLTLSKADYEKHKVYACEVTH

QGLSSPVTKSFNRGECTGGGGSGGGGSGGGGSGGGGSGGGGSGGGGSTGSDTGRPFVEMYSEIPEI

IHMTEGRELVIPCRVTSPNITVTLKKFPLDTLIPDGKRIIWDSRKGFHSNATYKEIGLLTCEATVN

GHLYKTNYLTHRQTNTIIDVVLSPSHGIELSVGEKLVLNCTARTELNVGIDFNWEYPSSKHQHKKL

VLSPVNRDLKTQSGSEMKKFLSTLTIDGVTRSDQGLYTCAASSGLMTKKNSTFVRYHEK
```

-continued (nesvacumab (anti-Ang2) heavy chain amino acid sequence)
SEQ ID NO: 35
EVQLVESGGGLVQPGGSLRLSCAASGFTFSSYDIHWVRQATGKGLEWVSAIGPAGDTYYPGSVKGR

FTISRENAKNSLYLQMNSLRAGDTAVYYCARGLITFGGLIAPFDYWGQGTLVTVSSASTKGPSVFP

LAPSSKSTSGGTAALGCLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGK (nesvacumab (anti-Ang2) light chain amino acid sequence)
SEQ ID NO: 36
EIVLTQSPGTLSLSPGERATLSCRASQSVSSTYLAWYQQKPGQAPRLLIYGASSRATGIPDRFSG

SGSGTDFTLTISRLEPEDFAVYYCQHYDNSQTFGQGTKVEIKRTVAAPSVFIFPPSDEQLKSGTA

SVVCLLNNFYPREAKVQWKVDNALQSGNSQESVTEQDSKDSTYSLSSTLTLSKADYEKHKVYACE

VTHQGLSSPVTKSFNRGEC (Ang2/LC-GS6-VEGFR, nesvacumab (anti-Ang2) light chain fusion
polypeptide amino acid sequence;
linker is bolded, VEGFR component is underlined)
SEQ ID NO: 37
EIVLTQSPGTLSLSPGERATLSCRASQSVSSTYLAWYQQKPGQAPRLLIYGASSRATGIPDRFSGS

GSGTDFTLTISRLEPEDFAVYYCQHYDNSQTFGQGTKVEIKRTVAAPSVFIFPPSDEQLKSGTASV

VCLLNNFYPREAKVQWKVDNALQSGNSQESVTEQDSKDSTYSLSSTLTLSKADYEKHKVYACEVTH

QGLSSPVTKSFNRGECTGGGGSGGGGSGGGGSGGGGSGGGGSGGGGS<u>TGSDTGRPFVEIVIYSEIP</u>

<u>EIIHMTEGRELVIPCRVTSPNITVTLKKFPLDTLIPDGKRIIWDSRKGFHSNATYKEIGLLTCEAT</u>

<u>VNGHLYKTNYLTHRQTNTIIDVVLSPSHGIELSVGEKLVLNCTARTELNVGIDFNWEYPSSKHQHK</u>

<u>KLVLSPVNRDLKTQSGSEMKKFLSTLTIDGVTRSDQGLYTCAASSGLMTKKNSTFWVHEK</u>

(ixekizumab (anti-IL-17A) heavy chain amino acid sequence)
SEQ ID NO: 38
QVQLVQSGAEVKKPGSSVKVSCKASGYSFTDYHIHWVRQAPGQGLEWMGVINPMYGTTDYNQRFKG

RVTITADESTSTAYMELSSLRSEDTAVYYCARYDYFTGTGVYWGQGTLVTVSSASTKGPSVFPLAP

CSRSTSESTAALGCLVKDYFPEPVTVSWNSGALTSGVHTFPAVLQSSGLYSLSSVVTVPSSSLGTK

TYTCNVDHKPSNTKVDKRVESKYGPPCPPCPAPEFLGGPSVFLFPPKPKDTLMISRTPEVTCVVVD

VSQEDPEVQFNWYVDGVEVHNAKTKPREEQFNSTYRVVSVLTVLHQDWLNGKEYKCKVSNKGLFSS

IEKTISKAKGQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLG (ixekizumab (anti-IL-17A) light chain amino acid sequence)
SEQ ID NO: 39
DIVMTQTPLSLSVTPGQPASISCRSSRSLVHSRGNTYLHWYLQKPGQSPQLLIYKVSNRFIGVPDR

FSGSGSGTDFTKISRVEAEDVGVYYCSQSTHLPFTFGQGTKLEIKRTVAAPSVFIFPPSDEQLKSG

TASVVCLLNNFYPREAKVQWKVDNALQSGNSQESVTEQDSKDSTYSLSSTLTLSKADYEKHKVYAC

EVTHQGLSSPVTKSFNRGEC (IL17α/LC-GS6-VEGFR; ixekizumab (anti-IL-I7A) light chain fusion
polypeptide amino acid sequence; linker is bolded,
VEGFR component is underlined)
SEQ ID NO: 40
DIVMTQTPLSLSVTPGQPASISCRSSRSLVHSRGNTYLHWYLQKPGQSPQLLIYKVSNRFIGVPDR

FSGSGSGTDFTLKISRVEAEDVGVYYCSQSTHLPFTFGQGTKLEIKRTVAAPSVFIFPPSDEQLKS

GTASVVCLLNNFYPREAKVQWKVDNALQSGNSQESVTEQDSKDSTYSLSSTLTLSKADYEKHKVYA

-continued

CEVTHQGLSSPVTKSFNRGECTGGGGSGGGGSGGGGSGCGGSGGGGSGCGGSTGSDTGRPFVEMYS

EIPEIIHMTEGRELVIPCRVTSPNITVTLKKFPLDTLIPDGKRIIWDSRKGFIISNATYKEIGLLT

CEATVNGHLYKTNVLTHRQTNTIIDVVLSPSHGIELSVGEKLVLNCTARTELNVGIDFNWEYPSSK

HQHKKLVLSPVNRPLKTQSGSEMKKFLSTLTIDGVTRSDQGLVTCAASSGLMTKKNSTFVRVHEK

```
(signal peptide amino acid sequence)
                                                         SEQ ID NO: 41
MEFGLSWLFLVA1LKGVQC (signal peptide amino acid sequence)
                                                         SEQ ID NO. 42
MDMRVPAQLLGLLLLWLRGARC (signal peptide amino acid sequence)
                                                         SEQ ID NO: 43
METDTLLLWVLLLWVPGSTG (linker amino acid sequence, n is an integer of at least one)
                                                         SEQ ID NO: 44
(GSTSGSGKPGSGEGS)_n
```

---

What is claimed is:

1. An antibody fusion protein comprising 1) an antibody comprising a first light chain and a second light chain, and 2) a first vascular endothelial growth factor receptor (VEGFR) component and a second VEGFR component, wherein the first VEGFR component is fused to the C-terminus of the first light chain, and the second VEGFR component is fused to the C-terminus of the second light chain; wherein the first VEGFR component and the second VEGFR component each comprises the amino acid sequence of SEQ ID NO: 8; and wherein the antibody specifically recognizes an immune checkpoint molecule, a tumor antigen, or an angiogenic factor.

2. The antibody fusion protein of claim 1, wherein the first VEGFR component and the second VEGFR component are the same.

3. The antibody fusion protein of claim 1, wherein the first VEGFR component and the second VEGFR component are different.

4. The antibody fusion protein of claim 1, wherein the first VEGFR component and the C-terminus of the first light chain are connected by a linker, and/or wherein the second VEGFR component and the C-terminus of the second light chain are connected by a linker.

5. The antibody fusion protein of claim 4, wherein the linker comprises the amino acid sequence of SEQ ID NO: 6 or 7.

6. The antibody fusion protein of claim 1, wherein the first light chain comprises a first light chain constant domain (CL domain), wherein the second light chain comprises a second CL, wherein the first VEGFR component is fused to the C-terminus of the first CL domain, and wherein the second VEGFR component is fused to the C-terminus of the second CL domain.

7. The antibody fusion protein of claim 1, wherein the antibody is a full length antibody.

8. The antibody fusion protein of claim 1, wherein the antibody specifically recognizes an immune checkpoint molecule.

9. The antibody fusion protein of claim 8, wherein the immune checkpoint molecule is PD-1, PD-L1, or CTLA-4.

10. The antibody fusion protein of claim 8,
   (i) wherein the immune checkpoint molecule is PD-1, and wherein the antibody comprises: heavy chain-CDR1 (HC-CDR1), HC-CDR2, and HC-CDR3 of a heavy chain comprising the amino acid sequence of SEQ ID NO: 12; and/or light chain-CDR1 (LC-CDR1), LC-CDR2, and LC-CDR3 of a light chain comprising the amino acid sequence of SEQ ID NO: 13;
   (ii) wherein the immune checkpoint molecule is PD-1, and wherein the antibody comprises: HC-CDR1, HC-CDR2, and HC-CDR3 of a heavy chain comprising the amino acid sequence of SEQ ID NO: 15; and/or LC-CDR1, LC-CDR2, and LC-CDR3 of a light chain comprising the amino acid sequence of SEQ ID NO: 16;

(iii) wherein the immune checkpoint molecule is PD-L1, and wherein the antibody comprises: HC-CDR1, HC-CDR2, and HC-CDR3 of a heavy chain comprising the amino acid sequence of SEQ ID NO: 18; and/or LC-CDR1, LC-CDR2, and LC-CDR3 of a light chain comprising the amino acid sequence of SEQ ID NO: 19;

(iv) wherein the immune checkpoint molecule is PD-L1, and wherein the antibody comprises: HC-CDR1, HC-CDR2, and HC-CDR3 of a heavy chain comprising the amino acid sequence of SEQ ID NO: 21; and/or LC-CDR1, LC-CDR2, and LC-CDR3 of a light chain comprising the amino acid sequence of SEQ ID NO: 22; or (v) wherein the immune checkpoint molecule is CTLA-4, and wherein the antibody comprises: HC-CDR1, HC-CDR2, and HC-CDR3 of a heavy chain comprising the amino acid sequence of SEQ ID NO: 9; and/or LC-CDR1, LC-CDR2, and LC-CDR3 of a light chain comprising the amino acid sequence of SEQ ID NO: 10.

11. The antibody fusion protein of claim 1, wherein the antibody specifically recognizes a tumor antigen.

12. The antibody fusion protein of claim 11, wherein the tumor antigen is HER2 or EGFR.

13. The antibody fusion protein of claim 11,
(i) wherein the tumor antigen is HER2, and wherein the antibody comprises: HC-CDR1, HC-CDR2, and HC-CDR3 of a heavy chain comprising the amino acid sequence of SEQ ID NO: 24; and/or LC-CDR1, LC-CDR2, and LC-CDR3 of a light chain comprising the amino acid sequence of SEQ ID NO: 25; or
(ii) wherein the tumor antigen is EGFR (HER1), and wherein the antibody comprises: HC-CDR1, HC-CDR2, and HC-CDR3 of a heavy chain comprising the amino acid sequence of SEQ ID NO: 29; and/or LC-CDR1, LC-CDR2, and LC-CDR3 of a light chain comprising the amino acid sequence of SEQ ID NO: 30.

14. The antibody fusion protein of claim 1, wherein the antibody specifically recognizes an angiogenic factor.

15. The antibody fusion protein of claim 14, wherein the angiogenic factor is Ang2, TNFα, or IL-17A.

16. The antibody fusion protein of claim 14,
(i) wherein the angiogenic factor is Angiopoietin-2 (Ang2), and wherein the antibody comprises: HC-CDR1, HC-CDR2, and HC-CDR3 of a heavy chain comprising the amino acid sequence of SEQ ID NO: 35; and/or LC-CDR1, LC-CDR2, and LC-CDR3 of a light chain comprising the amino acid sequence of SEQ ID NO: 36;
(ii) wherein the angiogenic factor is TNFα, and wherein the antibody comprises: HC-CDR1, HC-CDR2, and HC-CDR3 of a heavy chain comprising the amino acid sequence of SEQ ID NO: 32; and/or LC-CDR1, LC-CDR2, and LC-CDR3 of a light chain comprising the amino acid sequence of SEQ ID NO: 33; or
(iii) wherein the angiogenic factor is IL-17A, and wherein the antibody comprises: HC-CDR1, HC-CDR2, and HC-CDR3 of a heavy chain comprising the amino acid sequence of SEQ ID NO: 38; and/or LC-CDR1, LC-CDR2, and LC-CDR3 of a light chain comprising the amino acid sequence of SEQ ID NO: 39.

17. A pharmaceutical composition comprising the antibody fusion protein of claim 1, and a pharmaceutical acceptable carrier.

* * * * *